(12) United States Patent
Take et al.

(10) Patent No.: US 7,166,598 B2
(45) Date of Patent: Jan. 23, 2007

(54) PIPERAZINE DERIVATIVES

(75) Inventors: Kazuhiko Take, Tondabayashi (JP);
Nobukiyo Konishi, Nagaokakyo (JP);
Shinji Shigenaga, Kobe (JP); Natsuko Kayakiri, Suita (JP); Hidenori Azami, Amagasaki (JP); Yoshiteru Eikyu, Nara (JP); Kazuo Nakai, Amagasaki (JP); Junya Ishida, Nishinomiya (JP); Masataka Morita, Nishinomiya (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/968,473

(22) Filed: Oct. 20, 2004

(65) Prior Publication Data
US 2006/0014948 A1    Jan. 19, 2006

Related U.S. Application Data

(63) Continuation of application No. 09/857,869, filed as application No. PCT/JP99/08943 on Dec. 10, 1999, now abandoned.

(30) Foreign Application Priority Data

Dec. 14, 1998 (AU) ........................ PP7706
Oct. 21, 1999 (AU) ........................ PQ3568

(51) Int. Cl.
  A61K 31/5355  (2006.01)
  C07D 413/06   (2006.01)
  A61K 31/496   (2006.01)
  C07D 401/06   (2006.01)

(52) U.S. Cl. ................ 514/235.8; 544/121; 544/360

(58) Field of Classification Search ............... 544/121, 544/360; 514/235.8, 253.01
See application file for complete search history.

(56) References Cited

U.S. PATENT DOCUMENTS

| 6,087,357 A | 7/2000 | Matsuo et al. |
| 6,924,278 B2 * | 8/2005 | Miyake et al. ............ 514/183 |
| 2002/0010182 A1 | 1/2002 | Masaaki et al. |
| 2003/0114668 A1 | 6/2003 | Miyake et al. |

FOREIGN PATENT DOCUMENTS

| EP | 0 655 442 | 5/1995 |
| WO | WO 97/08166 | 3/1997 |
| WO | WO 97/22597 | 6/1997 |
| WO | WO 98/57954 | 12/1998 |

OTHER PUBLICATIONS

Ohnmacht et al. in Annual Reports in Medicinal Chemistry, vol. 33, pp. 71-80 (1998).
U.S. Appl. No. 10/968,473, filed, Oct. 20, 2004, Take et al.
U.S. Appl. No. 10/720,021, filed Nov. 24, 2003, filed, Miyake et al.
U.S. Appl. No. 09/545,614, filed Apr. 6, 2000, Matsuo et al.

* cited by examiner

*Primary Examiner*—Emily Bernhardt
(74) *Attorney, Agent, or Firm*—Oblon, Spivak, McClelland, Maier & Neustadt, P.C.

(57) ABSTRACT

This invention relates to piperazine derivatives of the formula:

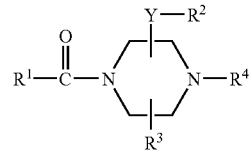

wherein each symbol is as defined in the description, and its pharmaceutically acceptable salt, to processes for preparation thereof, to pharmaceutical composition comprising the same, and to a use of the same for treating or preventing Tachykinin-mediated diseases in human being or animals.

15 Claims, No Drawings

PIPERAZINE DERIVATIVES

TECHNICAL FIELD

The present invention relates to new piperazine derivatives and a salt thereof.

More particularly, it relates to new piperazine derivatives and a salt thereof which have pharmacological activities such as Tachykinin antagonism, especially Substance P antagonism, Neurokinin A antagonism, Neurokinin B antagonism, and the like, to a process for preparation thereof, to a pharmaceutical composition comprising the same, and to a use of the same as a medicament.

Accordingly, one object of the present invention is to provide new and useful piperazine derivatives and a salt thereof which have pharmacological activities such as Tachykinin antagonism, especially Substance P antagonism, Neurokinin A antagonism, Neurokinin B antagonism, and the like.

Another object of the present invention is to provide a process for the preparation of said piperazine derivatives and a salt thereof.

A further object of the present invention is to provide a pharmaceutical composition comprising, as an active ingredient, said piperazine derivatives and a pharmaceutically acceptable salt thereof.

Still further object of the present invention is to provide a use of said piperazine derivatives or a pharmaceutically acceptable salt thereof as Tachykinin antagonist, especially Substance P antagonist, Neurokinin A antagonist or Neurokinin B antagonist, useful for treating or preventing Tachykinin-mediated diseases, for example, respiratory diseases such as asthma, bronchitis, rhinitis, couph, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

BACKGROUND ART

Some piperazine derivatives having pharmaceutical activities such as Tachykinin antagonism have been known as described in WO 97/22597 A1 and WO 98/57954 A1.

DISCLOSURE OF INVENTION

The object compound of the present invention can be represented by the following general formula (I):

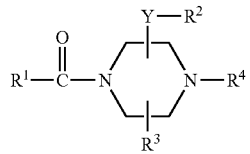

(I)

wherein
Y is bond or lower alkylene,
$R^1$ is aryl which is substituted with 1 to 3 same or different substituent(s) selected from the group consisting of halogen, lower alkyl, lower alkoxy, mono(or di or tri)halo(lower)alkyl, nitro, amino, lower alkylamino, di(lower)alkylamino, lower alkylthio, lower alkylsulfonyl, cyclo(lower)alkylsulfonyl, aminosulfonyl, lower alkylaminosulfonyl, di(lower)alkylaminosulfonyl, pyrrolidinylsulfonyl, morpholinylsulfonyl, pyrrolylsulfonyl, pyridylsulfonyl, pyrrolyl and pyridyl;

$R^2$ is aryl which is substituted with 1 to 3 same or different substituent(s) selected from the group consisting of lower alkyl, mono(or di or tri)halo(lower)alkyl, mono(or di or tri)halo(lower)alkylsulfonyloxy, halogen, lower alkylenedioxy, lower alkoxy, lower alkoxycarbonyl, lower alkoxy(lower)alkoxy(lower)alkoxy, hydroxy, diphenyl(lower)alkylsilyloxy, tri(lower)alkylsilyloxy, hydroxy(lower)alkyl, cyano, amino, [mono(or di or tri)halo(lower)alkylcarbonyl]amino, lower alkylamino, N-(lower alkyl)-[mono(or di or tri)halo(lower)alkylcarbonyl]amino, pyrrolidinyl and morpholinyl which may be substituted with lower alkoxy(lower)alkyl or lower alkyl;

$R^3$ is hydrogen or lower alkyl; and
$R^4$ is (3-pyridyl)methyl;
(3-pyridyl)ethyl;
3-(3-pyridyl)propyl;
3-(3-pyridyl)propenyl;
3-(3-pyridyl)propynyl;
thiazolyl(lower)alkyl, 1,2,4-thiadiazolyl(lower)alkyl or 1,2,4-oxadiazolyl(lower)alkyl, each of which is substituted with halogen, amino, lower alkylamino or di(lower)alkylamino;
pyrazolylmethyl which may be substituted with triphenyl(lower)alkyl or hydroxy(lower)alkyl; pyrazolyl(lower)alkyl which is substituted with lower alkyl, lower alkoxy(lower)alkylmorpholinyl(lower)alkyl or lower alkoxy(lower)alkylmorpholinylcarbonyl(lower)alkyl;
pyrrolidinyl(lower)alkyl which is substituted with 1 or 2 same or different substituent(s) selected from the group consisiting of hydroxy, hydroxy(lower)alkyl, lower alkoxy and lower alkoxy(lower)alkyl; piperidylmethyl;
piperidyl(lower)alkyl which is substituted with 1 or 2 same or different substituent(s) selected from the group consisting of halogen, lower alkyl and lower alkoxy(lower)alkyl;
[2,6-di[hydroxy(lower)alkyl]piperidyl](lower)alkyl;
(2,6-dimethylmorpholino)(lower)alkyl;
(2,2-dimethylmorpholino)(lower)alkyl;
(3,3-dimethylmorpholino)(lower)alkyl;
(cis-3,5-dimethylmorpholino)(lower)alkyl;
((3S,5S)-3,5-dimethylmorpholino)(lower)alkyl;
((3S,5R)-3,5-dimethylmorpholino)(lower)alkyl;
(2-methoxymethylmorpholino)(lower)alkyl;
(3-methoxymethylmorpholino)(lower)alkyl;
(2-methoxymethyl-5-methylmorpholino)(lower)alkyl;
(2-methoxymethyl-5,5-dimethylmorpholino)(lower)alkyl;
(3,5-dimethoxymethylmorpholino)(lower)alkyl;
(2,2-dimethoxymethylmorpholino)(lower)alkyl;
(2,3-dimethoxymethylmorpholino)(lower)alkyl;
(2,6-dimethoxymethylmorpholino)(lower)alkyl;
(2-methoxymethylmorpholino)(lower)alkenyl;
(3,3-dimethylmorpholino)(lower)alkynyl;
(2-methoxymethylmorpholino)(lower)alkynyl;
(2-methoxymethyl-5-methylmorpholino)(lower)alkynyl;
quinoly (lower)alkyl;
[1H-pyrrolo[3,2-b]pyridinyl](lower)alkyl;
[4,5,6,7-tetrahydrothieno[3,2-c]pyridinyl](lower)alkyl;
[3,4-dihydro-2H-pyrido[3,2-b]-1,4-oxazinyl](lower)alkyl;

(5,6,7,8-tetrahydro-1,6-naphthyridin-6-yl)(lower)alkyl; or lower alkyl which is substituted with a saturated heterocyclic group of the formula:

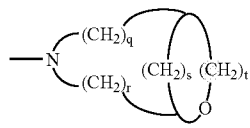

(wherein
r, s and t are each integer of 1 to 2, and
q is integer of 0 to 2) which may be substituted with one or two lower alkyl, provided that when $R^4$ is 3-(3-pyridyl)propyl;
3-(3-pyridyl)propenyl;
pyrazolylmethyl which may be substituted with hydroxy(lower)alkyl;
(2-methoxymethylmorpholino)(lower)alkyl;
(3-methoxymethylmorpholino)(lower)alkyl; or
(2-methoxymethylmorpholino)(lower)alkynyl, then
$R^2$ is not di(lower)alkylphenyl.

It is to be noted that the object compound (I) may include one or more stereoisomers due to asymmetric carbon atom(s) and double bond, and all of such isomers and a mixture thereof are included within the scope of the present invention.

It is further to be noted that isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

According to the present invention, the object compound (I) or a salt thereof can be prepared by processes which are illustrated in the following schemes.

Process 1

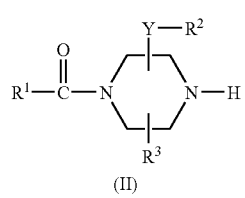

(II)
or its reactive derivative at the imino group or a salt thereof

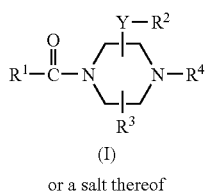

(I)
or a salt thereof

Process 2

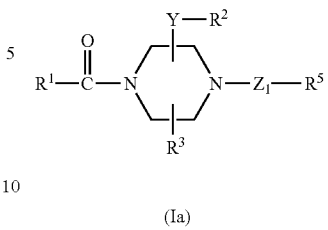

(Ia)
or a salt thereof

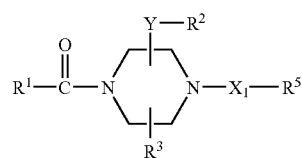

(Ib)
or a salt thereof wherein
Y, $R^1$, $R^2$, $R^3$ and $R^4$ are each as defined above,
$X_1$ is lower alkylene,
$Z_1$ is lower alkynylene,
$R^5$ is 3-pyridyl, and
$W_1$ is a leaving group.

As to the starting compounds (II) and (III), some of them are novel and can be prepared by the procedures described in the Preparations and Examples mentioned later or similar manners thereto.

Suitable salts of the starting and object compounds are conventional non-toxic and pharmaceutically acceptable salt and include an acid addition salt such as an organic acid salt (e.g. acetate, trifluoroacetate, fumarate, maleate, tartrate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention intends to include within the scope thereof are explained in detail as follows.

The term "lower" is intended to mean 1 to 6, preferably 1 to 4, carbon atom(s), unless otherwise indicated.

Suitable "lower alkylene" may include straight or branched one having 1 to 6, preferably 1 to 4, carbon atom(s), such as methylene, ethylene, trimethylene, propylene, tetramethylene, methylmethylene, methyltrimethylene, hexamethylene, and the like, in which the preferred one is methylene, ethylene, trimethylene or methylmethylene.

Suitable "lower alkynylene" may include one having 2 to 6 carbon atoms, such as ethynylene, propynylene, butynylene, and the like, in which the preferred one is propynylene or butynylene.

Suitable "halogen" and "halogen" moiety in the terms "mono(or di or tri)halo(lower)alkyl", "mono(or di or tri)halo($C_1$–$C_4$)alkyl", etc. may include fluorine, chlorine, bromine and iodine.

Suitable "lower alkyl" and "lower alkyl" moiety in the terms "hydroxy(lower)alkyl", "pyrazolyl(lower)alkyl", etc. may include straight or branched one having 1 to 6 carbon atom(s), such as methyl, ethyl, propyl, isopropyl, butyl, isobutyl, pentyl, hexyl and the like, in which the preferred one is $C_1$–$C_4$ alkyl and the most preferred one is methyl, ethyl or propyl.

Suitable "lower alkenyl" moiety in the term "(2-methoxymethylmorpholino)(lower)alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1- (or 2- or 3-)butenyl, and the like, in which more preferable example may be $C_2$–$C_4$ alkenyl.

Suitable "aryl" may include phenyl, naphthyl, and the like, in which the preferred one is $C_6$–$C_{10}$ aryl and the most preferred one is phenyl or naphthyl.

Suitable "lower alkoxy" and "lower alkoxy" moiety in the terms "lower alkoxy(lower)alkylmorpholinyl(lower)alkyl", "lower alkoxy(lower)alkylmorpholinylcarbonyl(lower)alkyl", etc. may include methoxy, ethoxy, propoxy, isopropoxy, butoxy, isobutoxy, t-butoxy, pentyloxy, t-pentyloxy, hexyloxy and the like, in which the preferred one is $C_1$–$C_4$ alkoxy and the most preferred one is methoxy.

Suitable "leaving group" may include lower alkoxy (e.g. methoxy, ethoxy, propoxy, isopropoxy, butoxy, isobutoxy, t-butoxy, pentoxy, etc.), aryloxy (e.g., phenoxy, naphthoxy, etc.), an acid residue or the like.

Suitable "acid residue" may be halogen (e.g., chlorine, bromine, iodine, etc.), sulfonyloxy (e.g., methanesulfonyloxy, phenylsulfonyloxy, mesitylenesulfonyloxy, toluenesulfonyloxy, etc.) or the like.

Preferred embodiments of the object compound (I) are as follows:

Y is lower alkylene (more preferably $C_1$–$C_4$ alkylene, most preferably methylene);

$R^1$ is phenyl which is substituted with 1 or 2 same or different substituent(s) selected from the group consisting of halogen (more preferably fluorine or chlorine), lower alkyl (more preferably $C_1$–$C_4$ alkyl, most preferably methyl), lower alkoxy (more preferably $C_1$–$C_4$ alkoxy, most preferably methoxy), mono(or di or tri)halo(lower) alkyl (more preferably trihalo(lower)alkyl, most preferably trifluoromethyl), nitro, amino, lower alkylamino (more preferably $C_1$–$C_4$ alkylamino, most preferably methylamino), di(lower)alkylamino (more preferably di($C_{1-C4}$)alkylamino, most preferably dimethylamino), lower alkylthio (more preferably $C_1$–$C_4$ alkylthio, most preferably methylthio), lower alkylsulfonyl (more preferably $C_1$–$C_4$ alkylsulfonyl, most preferably methanesulfonyl), cyclo(lower)alkylsulfonyl (more preferably cyclo($C_1$–$C_6$)alkylsulfonyl, most preferably cyclopentylsulfonyl), aminosulfonyl, lower alkylaminosulfonyl (more preferably $C_1$–$C_4$ alkylaminosulfonyl, most preferably methylaminosulfonyl), di(lower)alkylaminosulfonyl (more preferably di($C_1$–$C_4$)alkylaminosulfonyl, most preferably dimethylaminosulfonyl), pyrrolidinylsulfonyl (more preferably pyrrolidinosulfonyl), morpholinylsulfonyl (more preferably morpholinosulfonyl), pyrrolylsulfonyl (more preferably 1-pyrrolylsulfonyl), pyridylsulfonyl (more preferably 4-pyridylsulfonyl), pyrrolyl (more preferably 1-pyrrolyl) and pyridyl (more preferably 4-pyridyl);

$R^2$ is phenyl which is substituted with 1 or 2 same or different substituent(s) selected from the group consisting of lower alkyl (more preferably $C_1$–$C_4$ alkyl, most preferably methyl or isopropyl), mono(or di or tri)halo(lower) alkyl (more preferably mono(or di or tri)halo($C_1$–$C_4$) alkyl, most preferably trifluoromethyl), mono(or di or tri)halo(lower)alkylsulfonyloxy (more preferably mono (or di or tri)halo($C_1$–$C_4$)alkylsulfonyl, most preferably trifluoromethylsulfonyloxy), halogen (more preferably chlorine or fluoride), lower alkylenedioxy (more preferably $C_1$–$C_4$ alkylenedioxy, most preferably methylenedioxy or ethylenedioxy), lower alkoxy (more preferably $C_1$–$C_4$ alkoxy, most preferably methoxy), lower alkoxycarbonyl (more preferably $C_1$–$C_4$ alkoxycarbonyl, most preferably methoxycarbonyl), lower alkoxy(lower)alkoxy (lower)alkoxy (more preferably $C_1$–$C_4$ alkoxy($C_1$–$C_4$) alkoxy($C_1$–$C_4$)alkoxy, most preferably (2-methoxyethoxy)methoxy), hydroxy, diphenyl(lower)alkylsilyloxy (more preferably diphenyl($C_1$–$C_4$)alkylsilyloxy, most preferably diphenyl(tert-butyl)silyloxy), tri(lower)alkylsilyloxy (more preferably tri($C_1$–$C_4$)alkylsilyloxy, most preferably dimethyl(tert-butyl)silyloxy), hydroxy(lower) alkyl (more preferably hydroxy($C_1$–$C_4$)alkyl, most preferably hydroxymethyl or 1-hydroxy-1-methylethyl), cyano, amino, [mono(or di or tri)halo(lower)alkylcarbonyl]amino (more preferably [mono(or di or tri)halo ($C_1$–$C_4$)alkylcarbonyl]amino, most preferably (trifluoromethylcarbonyl)amino), lower alkylamino (more preferably $C_1$–$C_4$ alkylamino, methylamino), N-(lower alkyl)-[mono(or di or tri)halo(lower)alkylcarbonyl]amino (more preferably N—($C_1$–$C_4$ alkyl)-[mono(or di or tri) halo($C_1$–$C_4$)alkylcarbonyl]amino, most preferably N-methyl-(trifluoro-methylcarbonyl)amino), pyrrolidinyl (more preferably pyrrolidino) and morpholinyl (more preferably morpholino) which may be substituted with lower alkoxy(lower)alkyl (more preferably $C_1$–$C_4$ alkoxy ($C_1$–$C_4$)alkyl, most preferably methoxymethyl) or lower alkyl (more preferably $C_1$–$C_4$ alkyl, most preferably methyl);

$R^3$ is hydrogen; and $R^4$ is (3-pyridyl)methyl;

(3-pyridyl)ethyl (more preferably 2-(3-pyridyl)ethyl);

3-(3-pyridyl)propyl;

3-(3-pyridyl)propenyl (more preferably 3-(3-pyridyl)-2-propenyl);

3-(3-pyridyl)propynyl (more preferably 3-(3-pyridyl)-2-propynyl);

thiazolyl(lower)alkyl (more preferably thiazolyl($C_1$–$C_4$) alkyl, most preferably 4-thiazolymethyl), 1,2,4-thiadiazolyl(lower)alkyl (more preferably 1,2,4-thiadiazolyl ($C_1$–$C_4$)alkyl, most preferably 1,2,4-thiadiazolyl-3-ylmethyl) or 1,2,4-oxadiazolyl(lower)-alkyl (more preferably 1,2,4-oxadiazolyl($C_1$–$C_4$)alkyl, most preferably 1,2,4-oxadiazolyl-5-ylmethyl), each of which is substituted with halogen (more preferably bromine), amino, lower alkylamino (more preferably $C_1$–$C_4$ alkylamino, most preferably methylamino) or di(lower) alkylamino (more preferably di($C_1$–$C_4$)alkylamino, most preferably dimethylamino); pyrazolylmethyl (more preferably (4-pyrazolyl)methyl or (5-pyrazolyl) methyl) which may be substituted with triphenyl(lower)alkyl (more preferably triphenyl($C_1$–$C_4$)alkyl, most preferably triphenylmethyl) or hydroxy(lower)alkyl (more preferably hydroxy($C_1$–$C_4$)-alkyl, most preferably 2-hydroxyethyl);

pyrazolyl(lower)alkyl (more preferably pyrazolyl-($C_1$–$C_4$)alkyl, most preferably (4-pyrazolyl)methyl, (5-pyrazolyl)methyl or 3-(4-pyrazolyl)propyl) which is substituted with lower alkyl (more preferably $C_1$–$C_4$ alkyl, most preferably methyl), (lower)alkoxy(lower)-alkylmorpholinyl(lower)alkyl (more preferably ($C_1$–$C_4$)-alkoxy($C_1$–$C_4$)alkylmorpholinyl($C_1$–$C_4$) alkyl, most preferably 2-(2-methoxymethylmorpholino)ethyl) or (lower)alkoxy(lower)alkylmorpholinylcarbonyl(lower)alkyl (more preferably ($C_1$–$C_4$) alkoxy($C_1$–$C_4$)-alkylmorpholinylcarbonyl($C_1$–$C_4$) alkyl, most preferably (2-methoxymethylmorpholino)carbonylmethyl);

pyrrolidinyl(lower)alkyl (more preferably pyrrolidinyl ($C_1$–$C_4$)alkyl, most preferably 2-pyrrolidinoethyl) which is substituted with 1 or 2 same or different substituent(s) selected from the group consisiting of hydroxy, hydroxy(lower)alkyl (more preferably hydroxy($C_1$–$C_4$)alkyl, most preferably hydroxymethyl), lower alkoxy (more preferably $C_1$–$C_4$ alkoxy, most preferably methoxy) and lower alkoxy(lower) alkyl (more preferably $C_1$–$C_4$ alkoxy($C_1$–$C_4$)alkyl, most preferably methoxymethyl);

piperidylmethyl (more preferably (4-piperidyl)methyl);

piperidyl(lower)alkyl (more preferably piperidyl($C_1$–$C_4$)-alkyl, most preferably 2-piperidinoethyl) which is substituted with 1 or 2 same or different substituent(s) selected from the group of halogen (more preferably fluorine), lower alkyl (more preferably $C_1$–$C_4$ alkyl, most preferably methyl) and lower alkoxy(lower)alkyl (more preferably $C_1$–$C_4$ alkoxy($C_1$–$C_4$)alkyl, most preferably methoxymethyl);

[2,6-di[hydroxy(lower)alkyl]piperidyl](lower)alkyl (more preferably [2,6-di[hydroxy($C_1$–$C_4$)alkyl]piperidyl]($C_1$-$C_4$)alkyl, most preferably 2-[2,6-di(hydroxymethyl)piperidino]ethyl);

(2,6-dimethylmorpholino)(lower)alkyl (more preferably (2,6-dimethylmorpholino)($C_1$–$C_4$)alkyl, most preferably 2-(2,6-dimethylmorpholino)ethyl);

(2,2-dimethylmorpholino)(lower)alkyl (more preferably (2,2-dimethylmorpholino)($C_1$–$C_4$)alkyl, most preferably 2-(2,2-dimethylmorpholino)ethyl);

(3,3-dimethylmorpholino)(lower)alkyl (more preferably (3,3-dimethylmorpholino)($C_1$–$C_4$)alkyl, most preferably 2-(3,3-dimethylmorpholino)ethyl);

(cis-3,5-dimethylmorpholino)(lower)alkyl (more preferably (cis-3,5-dimethylmorpholino)($C_1$–$C_4$)alkyl, most preferably 2-(cis-3,5-dimethylmorpholino)ethyl);

((3S,5S)-3,5-dimethylmorpholino)(lower)alkyl (more preferably ((3S,5S)-3,5-dimethylmorpholino)($C_1$–$C_4$) alkyl, most preferably 2-((3S,5S)-3,5-dimethylmorpholino)-ethyl);

((3S,5R)-3,5-dimethylmorpholino)(lower)alkyl (more preferably ((3S,5R)-3,5-dimethylmorpholino)($C_1$–$C_4$) alkyl, most preferably 2-((3S,5R)-3,5-dimethylmorpholino)-ethyl);

(2-methoxymethylmorpholino)(lower)alkyl (more preferably (2-methoxymethylmorpholino)($C_1$–$C_4$)alkyl, most preferably 3-(2-methoxymethylmorpholino)propyl or 2-(2-methoxymethylmorpholino)ethyl);

(3-methoxymethylmorpholino)(lower)alkyl (more preferably (3-methoxymethylmorpholino)($C_1$–$C_4$)alkyl, most preferably 2-(3-methoxymethylmorpholino) ethyl);

(2-methoxymethyl-5-methylmorpholino)(lower)alkyl (more preferably (2-methoxymethyl-5-methylmorpholino)-($C_1$–$C_4$)alkyl, most preferably 2-(2-methoxymethyl-5-methylmorpholino)ethyl);

(2-methoxymethyl-5,5-dimethylmorpholino)(lower)alkyl (more preferably (2-methoxymethyl-5,5-dimethylmorpholino)($C_1$–$C_4$)alkyl, most preferably 2-(2-methoxymethyl-5,5-dimethylmorpholino)ethyl);

(3,5-dimethoxymethylmorpholino)(lower)alkyl (more preferably (3,5-dimethoxymethylmorpholino)($C_1$–$C_4$) alkyl, most preferably 2-(3,5-dimethoxymethylmorpholino)ethyl);

(2,2-dimethoxymethylmorpholino)(lower)alkyl (more preferably (2,2-dimethoxymethylmorpholino)($C_1$–$C_4$) alkyl, most preferably 2-(2,2-dimethoxymethylmorpholino)ethyl);

(2,3-dimethoxymethylmorpholino)(lower)alkyl (more preferably (2,3-dimethoxymethylmorpholino)($C_1$–$C_4$) alkyl, most preferably 2-(2,3-dimethoxymethylmorpholino)ethyl);

(2,6-dimethoxymethylmorpholino)(lower)alkyl (more preferably (2,6-dimethoxymethylmorpholino)($C_1$–$C_4$) alkyl, most preferably 2-(2,6-dimethoxymethylmorpholino)ethyl);

(2-methoxymethylmorpholino)(lower)alkenyl (more preferably (2-methoxymethylmorpholino)($C_2$–$C_4$)alkenyl, most preferably 4-(2-methoxymethylmorpholino)-2-butenyl);

(3,3-dimethylmorpholino)(lower)alkynyl (more preferably (3,3-dimethylmorpholino)($C_2$–$C_4$)alkynyl, most preferably 4-(3,3-dimethylmorpholino)-2-butynyl);

(2-methoxymethylmorpholino)(lower)alkynyl (more preferably (2-methoxymethylmorpholino)($C_2$–$C_4$) alkynyl, most preferably 4-(2-methoxymethylmorpholino)-2-butynyl);

(2-methoxymethyl-5-methylmorpholino)(lower)alkynyl (more preferably (2-methoxymethyl-5-methylmorpholino)($C_2$–$C_4$)alkynyl, most preferably 4-(2-methoxymethyl-5-methylmorpholino)-2-butynyl);

quinolyl(lower)alkyl (more preferably quinolyl($C_1$–$C_4$) alkyl, most preferably (6-quinolyl)methyl);

[1H-pyrrolo[3,2-b]pyridinyl](lower)alkyl (more preferably [1H-pyrrolo[3,2-b]pyridinyl]($C_1$–$C_4$)alkyl, most preferably [1H-pyrrolo[3,2-b]pyridin-3-yl]methyl);

[4,5,6,7-tetrahydrothieno[3,2-c]pyridinyl](lower)alkyl (more preferably [4,5,6,7-tetrahydrothieno[3,2-c]-pyridinyl]($C_1$–$C_4$)alkyl, most preferably 2-[4,5,6,7-tetrahydrothieno[3,2-c]pyridin-5-yl]ethyl);

[3,4-dihydro-2H-pyrido[3,2-b]-1,4-oxazinyl](lower)alkyl (more preferably [3,4-dihydro-2H-pyrido[3,2-b]-1,4-oxazinyl]($C_1$–$C_4$)alkyl, most preferably 2-[3,4-dihydro-2H-pyrido[3,2-b]-1,4-oxazin-4-yl]ethyl);

(5,6,7,8-tetrahydro-1,6-naphthyridin-6-yl)(lower)alkyl (more preferably (5,6,7,8-tetrahydro-1,6-naphthyridin-6-yl)($C_1$–$C_4$)alkyl, most preferably 2-(5,6,7,8-tetrahydro-1,6-naphthyridin-6-yl)ethyl); or lower alkyl (more preferably $C_1$–$C_4$ alkyl, most preferably ethyl) which is substituted with a saturated heterocyclic group of the formula:

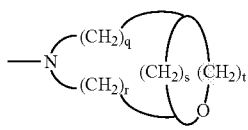

(wherein
r, s and t are each integer of 1 to 2, and
q is integer of 0 to 2) (more preferably (1S,4S)-2-aza-5-oxabicyclo[2.2.1]-heptan-2-yl) which may be substituted with one or two lower alkyl (more preferably $C_1$–$C_4$ alkyl, most preferably methyl)).

More preferred embodiments of the object compound (I) are as follows:

Y is lower alkylene (more preferably $C_1$–$C_4$ alkylene, most preferably methylene);

$R^1$ is phenyl which is substituted with 1 or 2 same or different substituent(s) selected from the group consisting of halogen, lower alkyl, lower alkoxy, mono(or di or tri)halo(lower)alkyl, nitro, amino, lower alkylamino, di(lower)alkylamino, lower alkylthio, lower alkylsulfonyl, cyclo(lower)alkylsulfonyl, aminosulfonyl, lower alkylaminosulfonyl, di(lower alkyl)aminosulfonyl, pyrrolidinylsulfonyl, morpholinylsulfonyl, pyrrolylsulfonyl, pyridylsulfonyl, pyrrolyl and pyridyl [more preferably dihalophenyl, bis(trihalo(lower)alkyl)phenyl, (trihalo(lower)alkyl)(halo)phenyl, (trihalo(lower)alkyl)((lower)alkyl)phenyl, (trihalo(lower)alkyl)((lower)alkoxy)phenyl, (trihalo(lower)alkyl)(nitro)phenyl, (trihalo(lower)alkyl)(lower alkylamino)phenyl, (trihalo(lower)alkyl)(di(lower)alkylamino)phenyl, (trihalo(lower)alkyl)((lower)alkylthio)phenyl, (trihalo(lower)alkyl)((lower)alkylsulfonyl)phenyl, (trihalo(lower)alkyl)(cyclo(lower)alkylsulfonyl)phenyl, (trihalo(lower)alkyl)(aminosulfonyl)phenyl, (trihalo(lower)alkyl)(lower alkylaminosulfonyl)phenyl, (trihalo(lower)alkyl)(di(lower)alkylaminosulfonyl)-phenyl, (trihalo(lower)alkyl)(pyrrolidinylsulfonyl)-phenyl, (trihalo(lower)alkyl)(morpholinylsufonyl)phenyl, (trihalo(lower)alkyl)(pyridylsulfonyl)phenyl, (trihalo(lower)alkyl)(pyrrolyl)phenyl or (trihalo(lower)alkyl)(pyridyl)phenyl, most preferably 3,5-dichlorophenyl, 3,5-bis(trifluoromethyl)phenyl, 3-fluoro-5-trifluoromethylphenyl, 3-chloro-5-trifluoromethylphenyl, 3-methyl-5-trifluoromethylphenyl, 3-methoxy-5-trifluoromethylphenyl, 3-nitro-5-trifluoromethylphenyl, 3-methylamino-5-trifluoromethylphenyl, 3-dimethylamino-5-trifluoromethylphenyl, 3-methylthio-5-trifluoromethylphenyl, 3-methanesulfonyl-5-trifluoromethylphenyl, 3-cyclopentylsulfonyl-5-trifluoromethylphenyl, 3-aminosulfonyl-5-trifluoromethylphenyl, 3-methylaminosulfonyl-5-trifluoromethylphenyl, 3-dimethylaminosulfonyl-5-trifluoromethylphenyl, 3-pyrrolidinosulfonyl-5-trifluoromethylphenyl, 3-morpholinosulfonyl-5-trifluoromethylphenyl, 3-(4-pyridyl)sulfonyl-5-trifluoromethylphenyl, 3-(1-pyrrolyl)-5-trifluoromethylphenyl or 3-(4-pyridyl)-5-trifluoromethylphenyl];

$R^2$ is phenyl which is substituted with 1 or 2 same or different substituent(s) selected from the group consisting of lower alkyl, mono(or di or tri)halo(lower)alkyl, mono(or di or tri)halo(lower)alkylsulfonyloxy, halogen, lower alkylenedioxy, lower alkoxy, lower alkoxycarbonyl, lower alkoxy(lower)alkoxy(lower)alkoxy, hydroxy, diphenyl(lower)alkylsilyloxy, tri(lower)alkylsilyloxy, hydroxy(lower)alkyl, cyano, amino, [mono(or di or tri)halo(lower)alkylcarbonyl]amino, lower alkylamino, N-(lower alkyl)-[mono(or di or tri)halo(lower)alkylcarbonyl]amino, pyrrolidinyl and morpholinyl which may be substituted with lower alkoxy(lower)alkyl or lower alkyl [more preferably ((lower)alkylenedioxy)phenyl, (lower alkoxy)phenyl, halophenyl, dihalophenyl, (trihalo(lower)alkyl)phenyl, (trihalo(lower)alkyl)(lower alkyl)phenyl, (halo) (lower alkyl)phenyl, (halo)(lower alkoxy)phenyl, (halo)(hydroxy)phenyl, (halo)(diphenyl(lower)alkylsilyloxy)phenyl, (trihalo(lower)alkyl)(hydroxy)-phenyl, (hydroxy(lower)alkyl)(hydroxy)phenyl, (cyano)(hydroxy)phenyl, (dihalo(lower)alkyl)(hydroxy)phenyl, (lower alkyl)(amino)phenyl, (lower alkyl)(lower alkylamino)phenyl, (lower alkyl)(mono(or di or tri)halo(lower)alkylsulfonyloxy)phenyl, (lower alkyl)[[mono(or di or tri)halo(lower)alkylcarbonyl]-amino]phenyl, (lower alkyl)[N-(lower alkyl)-[mono(or di or tri)halo(lower)alkylcarbonyl]amino]phenyl, (lower alkyl)(diphenyl(lower)alkylsilyloxy)phenyl, (lower alkyl)(lower alkoxy(lower)alkoxy(lower)alkoxy)phenyl, (lower alkyl)(tri(lower)alkylsilyloxy)phenyl, (lower alkoxycarbonyl)(tri(lower)alkylsilyloxy)phenyl, (hydroxy(lower)alkyl)(tri(lower)alkylsilyloxy)phenyl, (lower alkyl)(hydroxy)phenyl, (lower alkyl)(pyrrolidinyl)phenyl, (lower alkyl)(morpholinyl)phenyl, (lower alkyl)(lower alkoxy-(lower)alkylmorpholinyl)phenyl or (lower alkyl)(lower alkyl)morpholinyl)phenyl, most preferably 1,4-benzodioxan-6-yl, 4-methoxyphenyl, 4-fluorophenyl, 4-chlorophenyl, 3,4-difluorophenyl, 4-(trifluoromethyl)-phenyl, 3-methoxy-4-trifluoromethylphenyl, 4-fluoro-3-methylphenyl, 4-fluoro-3-methoxy-phenyl, 3-fluoro-4-methylphenyl, 4-fluoro-3-hydroxyphenyl, 4-chloro-3-methoxyphenyl, 4-chloro-3-(dimethyl(tert-butyl)silyloxy)phenyl, 4-chloro-3-hydroxy-phenyl, 3-hydroxy-4-(trifluoromethyl)phenyl, 3-hydroxy-4-(hydroxymethyl)phenyl, 3-hydroxy-4-methylphenyl, 3-hydroxy-4-(1-hydroxy-1-methylethyl)phenyl, 4-cyano-3-hydroxyphenyl, 3-hydroxy-4-(difluoromethyl)phenyl, 3-hydroxy-4-isopropylphenyl, 3-amino-4-methylphenyl, 4-methyl-3-methylaminophenyl, 4-methyl-3-(trifluoromethylsulfonyloxy)phenyl, 4-methyl-3-[(trifluoromethylcarbonyl)amino]phenyl, 4-methyl-3-[N-methyl-(trifluoromethylcarbonyl)amino]phenyl, 3-diphenyl(tert-butyl)silyloxy-4-methylphenyl, 4-methyl-3-[(2-methoxyethoxy)methoxy]phenyl, 3-dimethyl(tert-butyl)silyloxy-4-methylphenyl, 3-dimethyl(tert-butyl)silyloxy-4-methoxycarbonylphenyl, 3-dimethyl(tert-butyl)silyloxy-4-(1-hydroxy-1-methylethyl)phenyl, 4-methyl-3-pyrrolidinophenyl or 4-methyl-3-morpholinophenyl];

$R^3$ is hydrogen; and $R^4$ is (2,6-dimethylmorpholino)(lower)alkyl (more preferably (2,6-dimethylmorpholino)($C_1$–$C_4$)alkyl, most preferably 2-(2,6-dimethylmorpholino)ethyl);

(2,2-dimethylmorpholino)(lower)alkyl (more preferably (2,2-dimethylmorpholino)($C_1$–$C_4$)alkyl, most preferably 2-(2,2-dimethylmorpholino)ethyl);

(3,3-dimethylmorpholino)(lower)alkyl (more preferably (3,3-dimethylmorpholino)($C_1$–$C_4$)alkyl, most preferably 2-(3,3-dimethylmorpholino)ethyl);

(cis-3,5-dimethylmorpholino)(lower)alkyl (more preferably (cis-3,5-dimethylmorpholino)($C_1$–$C_4$)alkyl, most preferably 2-(cis-3,5-dimethylmorpholino)ethyl);

((3S,5S)-3,5-dimethylmorpholino)(lower)alkyl (more preferably ((3S,5S)-3,5-dimethylmorpholino)($C_1$–$C_4$) alkyl, most preferably 2-((3S,5S)-3,5-dimethylmorpholino)ethyl);

((3S,5R)-3,5-dimethylmorpholino)(lower)alkyl (more preferably ((3S,5R)-3,5-dimethylmorpholino)($C_1$–$C_4$) alkyl, most preferably 2-((3S,5R)-3,5-dimethylmorpholino)-ethyl);

(2-methoxymethylmorpholino)(lower)alkyl (more preferably (2-methoxymethylmorpholino)($C_1$–$C_4$)alkyl, most preferably 3-(2-methoxymethylmorpholino)propyl or 2-(2-methoxymethylmorpholino)ethyl);

(3-methoxymethylmorpholino)(lower)alkyl (more preferably (3-methoxymethylmorpholino)($C_1$–$C_4$)alkyl, most preferably 2-(3-methoxymethylmorpholino)ethyl);

(2-methoxymethyl-5-methylmorphblino)(lower)alkyl (more preferably (2-methoxymethyl-5-methylmorpholino)($C_1$–$C_4$)-alkyl, most preferably 2-(2-methoxymethyl-5-methylmorpholino)ethyl);

(2-methoxymethyl-5,5-dimethylmorpholino)(lower)alkyl (more preferably (2-methoxymethyl-5,5-dimethylmorpholino)($C_1$–$C_4$)alkyl, most preferably 2-(2-methoxymethyl-5,5-dimethylmorpholino)ethyl);

(3,5-dimethoxymethylmorpholino)(lower)alkyl (more preferably (3,5-dimethoxymethylmorpholino)($C_1$–$C_4$) alkyl, most preferably 2-(3,5-dimethoxymethylmorpholino)ethyl);

(2,2-dimethoxymethylmorpholino)(lower)alkyl (more preferably (2,2-dimethoxymethylmorpholino)($C_1$–$C_4$) alkyl, most preferably 2-(2,2-dimethoxymethylmorpholino)ethyl);

(2,3-dimethoxymethylmorpholino)(lower)alkyl (more preferably (2,3-dimethoxymethylmorpholino)($C_1$–$C_4$) alkyl, most preferably 2-(2,3-dimethoxymethylmorpholino)ethyl);

(2,6-dimethoxymethylmorpholino)(lower)alkyl (more preferably (2,6-dimethoxymethylmorpholino)($C_1$–$C_4$) alkyl, most preferably 2-(2,6-dimethoxymethylmorpholino)ethyl);

(2-methoxymethylmorpholino)(lower)alkenyl (more preferably (2-methoxymethylmorpholino)($C_2$–$C_4$)alkenyl, most preferably 4-(2-methoxymethylmorpholino)-2-butenyl);

(3,3-dimethylmorpholino)(lower)alkynyl (more preferably (3,3-dimethylmorpholino)($C_2$–$C_4$)alkynyl, most preferably 4-(3,3-dimethylmorpholino)-2-butynyl);

(2-methoxymethylmorpholino)(lower)alkynyl (more preferably (2-methoxymethylmorpholino)($C_2$–$C_4$) alkynyl, most preferably 4-(2-methoxymethylmorpholino)-2-butynyl); or (2-methoxymethyl-5-methylmorpholino)(lower)alkynyl (more preferably (2-methoxymethyl-5-methylmorpholino)($C_2$–$C_4$)alkynyl, most preferably 4-(2-methoxymethyl-5-methylmorpholino)-2-butynyl).

The Processes 1 and 2 for preparing the object compound (I) of the present invention are explained in detail in the following.

Process 1

The object compound (I) or a salt thereof can be prepared by reacting the compound (II) or its reactive derivative at the imino group or a salt thereof with the compound (III) or a salt thereof.

Suitable reactive derivative at the imino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl)acetamide, bis(trimethylsilyl)urea or the like; a derivative formed by reaction of the compound (II) with phosphorus trichloride or phosgene and the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

The reaction may also be carried out in the presence of an inorganic or organic base such as alkali metal carbonate (e.g. potassium carbonate, etc.), alkali metal bicarbonate, tri (lower)alkylamine, pyridine, N-(lower)alkyl-morpholine, N,N-di(lower)alkylethylamine (e.g. N,N-diisopropylethylamine, etc.), N,N-di(lower)alkylbenzylamine, or the like.

The reaction temperature is not critical, and the reaction is usually carried out under cooling to heating.

Process 2

The object compound (Ib) or a salt thereof can be prepared by subjecting the compound (Ia) or a salt thereof to a reduction reaction.

The reaction can be carried out in the manner disclosed in Example 8 mentioned later or similar manners thereto.

The object compound (I) and a pharmaceutically acceptable salt thereof have pharmacological activities such as Tachykinin antagonism, especially Substance P antagonism, Neurokinin A antagonism or Neurokinin B antagonism, and therefore are useful for treating or preventing Tachykinin-mediated diseases, particularly Substance P-mediated diseases, for example, respiratory diseases such as asthma, bronchitis (e.g. chronic bronchitis, acute bronchitis and diffuse panbronchiolitis, etc.), rhinitis, couph, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, cluster headache, toothache, cancerous pain, back pain, neuralgia, etc.); and the like.

Further, it is expected that the object compound (I) and a pharmaceutically acceptable salt thereof of the present invention are useful for treating or preventing ophthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, Raynaud's disease, and the like; epilepsy; spastic paralysis; pollakiuria; cystitis; bladder detrusor hyperreflexia; urinary incontinence; Parkinson diseases; dimentia; AIDS related dementia; Alzheimer's diseases; Down's syndrome; Huntington's chorea; carcinoid syndrome; disorders related to immune enhancement or suppression; disorders caused by *Helicobacter pylori* or another spiral urease-positive gram-negative bacterium; sunburn; angiogenesis or diseases caused by angiogenesis; and the like.

It is furthermore expected that the object compound (I) and a pharmaceutically acceptable salt thereof of the present invention are useful for treating or preventing chronic obstructive pulmonary diseases, particularly chronic pulmonary emphysema; iritis; proliferative vitreoretinopathy; psoriasis; inflammatory intestinal diseases, particularly Crohn's diseases; hepatitis; superficial pain on congelation, burn, herpes zoster or diabetic neuropathy; telalgia attended to hyperlipidemia; postoperative neuroma, particularly of mastectomy; vulvar vestibulitis; hemodialysis-associated itching; lichen planus; laryngopharyngitis; bronchiectasis; coniosis; whooping cough; pulmonary tuberculosis; cystic fibrosis; emesis (e.g., nausea, retching, vomiting, acute emesis, delayed emesis, anticipatory emesis, past operative nausea and vomiting (PONV), acute and/or delayed emesis induced by drugs such as cancer chemotherapeutic agents, etc.); mental diseases, particularly anxiety disorders, stress-related disorders, affective disorders, psychological development disorders and schizophrenia; demyelinating diseases such as multiple sclerosis and amyotrophic lateral sclerosis; attenuation of morphine withdrawal; oedema, such as oedema caused by thermal injury; small cell carcinomas, particularly small cell lung cancer (SCLC); hypersensitivity disorders such as poison ivy; fibrosing and collagen diseases such as scleroderma and eosinophilic fascioliasis; reflex sympathetic dystrophy such as shoulder/hand syndrome; addiction disorders such as alcoholism; stress related somatic disorders; rheumatic diseases such as fibrositis; aggressive behaviour, optionally taking an antipsychotic agent together; mania or hypomania, optionally taking an antipsychotic agent together; symptoms associated with Premenstrual Syndrome (PMS) (PMS is also now referred to as Late Luteal Phase Syndrome (LLS); psychosomatic disoredrs; psychoimmunologic disoredrs; attetion deficit disoredrs (ADD) with or without hyperactivity; and the like.

Furthermore, the object compound (I) and a pharmaceutically acceptable salt thereof of the present invention are Central Nervous System (CNS) penetrant.

For therapeutic purpose, the compound (I) and a pharmaceutically acceptable salt thereof of the present invention can be used in a form of pharmaceutical preparation containing one of said compound, as an active ingredient, in admixture with a pharmaceutically acceptable carrier such as an organic or inorganic solid or liquid excipient suitable for oral, parenteral, external including topical, enternal, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms, gels, tapes, eye drops, solution, syrups, aerosols, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of a patient, an average single dose of about 0.1 mg, 1 mg, 10 mg, 50 mg, 100 mg, 250 mg, 500 mg and 1000 mg of the compound (I) may be effective for treating Tachykinin-mediated diseases such as asthma and the like. In general, amounts between 0.1 mg/body and about 1,000 mg/body may be administered per day.

In order to show the utility of the object compound (I) and a pharmaceutically acceptable salt thereof, the pharmacological test data of some representative compounds of the present invention is shown in the following.

A. Evaluation of $NK_1$ Antagonist Transport Efficiency to the Central Nervous System Using a h-$NK_1$ Receptor Binding Assay

[1] Test Method (1) Administration of Test Compound and Extraction of the Compound from Brain Male SD rats were given an i.v. injection of a solution containing a test compound (1 mg/kg). 5 Min later the animals were anesthetized by ether, bled and perfused through the aorta asscendens with 20 ml of saline. The brain was rapidly removed, weighed and homogenized in 4 vol. ice-cold distilled water by using Polytoron (KINEMATICA). To extract the test compound, 500 µl of the homogenate, 100 µl of methanol, 500 µl of 0.1 N NaOH and 4 ml of ethyl acetate were mixed by shaking for 10 min at room temperature. The organic phase (2.5 ml) was recovered by centrifugation at 3,000 rpm for 10 min, dried and dissolved in dimethyl sulfoxide.

(2) h-$NK_1$ Receptor Binding Assay (a) Crude CHO Cell Membrane Preparation

CHO cells permanently expressing h-$NK_1$ receptors were harvested and homogenized with a Dounce homogenizer at 4° C. in a buffer (0.25 M sucrose, 25 mM Tris-HCl (pH 7.4), 10 mM $MgCl_2$, 1 mM EDTA, 5 µg/ml p-APMSF). The homogenate was centrifuged (500×g, 10 min), and the pellet was resuspended in the same buffer, homogenized, and centrifuged. The two supernatants were combined and centrifuged (100,000×g, 1 hour). The crude cell membranes thus isolated were resuspended in a buffer (25 mM Tris-HCl (pH 7.4), 10 mM $MgCl_2$, 1 mM EDTA, 5 µg/ml p-APMSF) and stored at −80° until use.

(b) $^{125}$I-BH-Substance P Binding to the Prepared Membrane

Cell membranes (6 µg/ml) were incubated with $^{125}$I-BH-Substance P (0.1 nM) with or without the extracted compounds in 0.25 ml of a medium (50 mM Tris-HCl (ph 7.4), 5 mM $MnCl_2$, 20 µg/ml chymostatin, 40 µg/ml bacitracin, 4 µg/ml leupeptin, 5 µg/ml p-APMSF, 200 µg/ml BSA) at 22° C. for 90 min. At the end of the incubation period, the contents were quickly filtered through a Blue Mat 11740 filter (pretreated with 0.1% polyethylenimine for 3 hours prior to use) by using SKATRON Cell Harvester. The filter was then washed with a washing buffer (50 mM Tris-HCl (pH 7.4), 5 mM $MnCl_2$). The radioactivity was counted by using an auto gamma counter (Packard RIASTAR 5420A). All data presented are specific binding defined as that displaceable by 3 µM unlabeled Substance P.

[II] Test Result

All of the following Test Compounds showed more than 80% inhibition rate of $^{125}$I-BH-Substance P binding to h-$NK_1$ receptors at the dose of 1 mg/kg.

Test Compounds: The object compounds of the Examples 4-(1), 4-(2), 7 and 8

B. Emesis in the Dog

[I] Test Method

Individually housed adult female dogs (8 to 15 kg) were given an i.v. injection of a solution containing a test compound. 5 Min later the emetic responses (retching and vomiting) were induced by administration of subcutaneous apomorphine (0.1 mg/0.5 ml/kg) and observed for the next 60 min. The timing and number of retches and vomits observed were recorded for each animal. An individual animal was tested with at least 10 days between experiments.

[II] Test Result

The following Test Compound showed 100% inhibition rate of emesis in the dog at the dose of 0.32 mg/kg.

Test compound: The object compound of the Example 4-(1)

The following Preparations and Examples are given for the purpose of illustrating this invention.

Preparation 1

(2-Methoxyethoxy)methyl chloride (4.87 ml) was added to a solution of 3-hydroxy-4-methylbenzoic acid (2.16 g) and N,N-diisopropylethylamine (9.2 ml) in 1,2-dichloroethane (40 ml) at room temperature. The mixture was stirred under reflux for 24 hours. After removal of the solvent by evaporation, the residue was partitioned between aqueous diluted hydrochloric acid solution and ethyl acetate. The organic layer was separated and washed with brine, dried over magnesium sulfate and evaporated under reduced pressure. The crude oil was purified by column chromatography on silica gel using mixed solvents of hexane and ethyl acetate (3:1). The fractions containing the objective compound were collected and evaporated under reduced pressure to give (2-methoxyethoxy)methyl 3-[((2-methoxyethoxy)methoxy]-4-methylbenzoate (4.82 g) as an oil.

IR (Neat): 1725, 1595 cm$^{-1}$

NMR (CDCl$_3$, δ): 2.29 (3H, s), 3.37 (3H, s), 3.39 (3H, s), 3.54–3.90 (8H, m), 5.35 (2H, s), 5.60 (2H, s), 7.21 (1H, d, J=8.0 Hz), 7.65 (1H, dd, J=1.6 and 8.0 Hz), 7.74 (1H, d, J=1.4 Hz)

MASS (API-ES): 351 (M+Na)$^+$

Preparation 2

Lithium aluminum hydride (0.35 g) was added by small portions over 12 minutes to an ice-cooled solution of (2-methoxyethoxy)methyl 3-[(2-methoxyethoxy)methoxy]-4-methylbenzoate (3.5 g) in tetrahydrofuran (20 ml) below 5° C. under nitrogen atmosphere. After the mixture was stirred at the same temperature for 30 minutes, 2N sodium hydroxide (0.5 ml) was added to the mixture. After the mixture was stirred for 30 minutes, the insoluble materials were removed by filtration and washed with tetrahydrofuran. The filtrate and the washing were combined, and evaporated under reduced pressure. The residue was dissolved into ethyl acetate, and manganese (IV) oxide (3.5 g) was added to the solution. After being stirred under reflux for 2 hours, the reaction mixture was filtered through Celite® and the insoluble mass was washed with ethyl acetate. The filtrate and the washing were combined and evaporated under reduced pressure. The resulting residue was purified by column chromatography on silica gel using mixed solvents of hexane and ethyl acetate (10:1). The fractions containing the objective compound were collected and evaporated under reduced pressure to give 3-[(2-methoxyethoxy)methoxy]-4-methylbenzaldehyde (1.7 g) as an oil.

IR (Neat): 1687, 1407 cm$^{-1}$

NMR (CDCl$_3$, δ): 2.31 (3H, s), 3.38 (3H, s), 3.55–3.60 (2H, m), 3.82–3.87 (2H, m), 5.37 (2H, s), 7.30 (1H, d, J=7.7 Hz), 7.44 (1H, dd, J=1.4 and 7.7 Hz), 7.58 (1H, d, J=1.4 Hz), 9.92 (1H, s)

MASS (API-ES): 279 (M+Na+MeOH)$^+$, 247 (M+Na)$^+$

Preparation 3

To a stirred mixture of 3-[(2-methoxyethoxy)methoxy]-4-methylbenzaldehyde (1.70 g) and 1,4-diacetyl-2,5-piperazinedione (1.6 g) in a mixture of N,N-dimethylformamide (17 ml) and tert-butanol (17 ml) was added potassium tert-butoxide (900 mg) at 5° C. The mixture was stirred for 24 hours at room temperature and then poured into water (300 ml). The aqueous mixture was adjusted to pH 4–5 with aqueous diluted hydrochloric acid solution and extracted with ethyl acetate. The extract was washed with brine, dried over sodium sulfate and evaporated under reduced pressure. The resulting residue was purified by column chromatography on silica gel using mixed solvents of toluene and ethyl acetate (3:1). The fractions containing the objective compound were collected and evaporated under reduced pressure to give 1-acetyl-3-[3-[(2-methoxyethoxy)methoxy]-4-methylphenyl]-methylene-2,5-piperazinedione (2.05 g) as a powder.

IR (KBr): 3208, 1700, 1627, 1598, 1455, 1375 cm$^{-1}$

NMR (CDCl$_3$, δ): 2.26 (3H, s), 2.65 (3H, s), 3.27 (3H, s), 3.58–3.62 (2H, m), 3.81–3.86 (2H, m), 4.49 (2H, s), 5.32 (2H, s), 6.94 (1H, dd, J=1.5 and 7.8 Hz), 7.15 (1H, d, J=7.8 Hz), 7.23 (1H, d, J=1.5 Hz), 7.27 (1H, s), 8.34 (1H, br s)

MASS (API-ES): 417 (M+MeOH+Na)$^+$

Preparation 4

A solution of 1-acetyl-3-[[3-[(2-methoxyethoxy)methoxy]-4-methylphenyl]methylene]-2,5-piperazinedione (2.0 g) in tetrahydrofuran (20 ml) was hydrogenated over 10% palladium-carbon (50% wet, 0.2 g) at room temperature under atmospheric pressure for 3 hours. After removal of the catalyst by filtration, the filtrate was concentrated under reduced pressure. The resulting residue was dissolved into tetrahydrofuran (30 ml) and thereto was added hydrazine monohydride (1.5 ml). After being stirred for 1 hour at room temperature, the mixture was concentrated under reduced pressure. The residue was triturated with isopropyl alcohol and the resulting solid was collected by filtration to give 3-[3-[(2-methoxyethoxy)methoxy]-4-methylbenzyl]-2,5-piperazinedione (1.75 g).

IR (KBr): 3183, 3060, 1675, 1454 cm$^{-1}$

NMR (CDCl$_3$, δ): 2.21 (3H, s), 2.95–4.00 (8H, m), 3.36 (3H, s), 4.20–4.27 (1H, m), 5.19 (1H, d, J=7.0 Hz), 5.38 (1H, d, J=7.0 Hz), 6.50 (1H, br s), 6.72 (1H, br s), 6.75 (1H, dd, J=1.4 and 7.9 Hz), 6.97 (1H, d, J=1.4 Hz), 7.08 (1H, d, J=7.9 Hz)

MASS (APCI): 323 (M+H)$^+$, 247, 235

Preparation 5

Lithium aluminum hydride (0.62 mg) was added to an ice-cooled solution of 3-[3-[(2-methoxyethoxy)methoxy]-4-methyl]-benzyl-2,5-piperazinedione (1.7 g) in tetrahydrofuran (17 ml) below 5° C. under nitrogen atmosphere. The mixture was stirred under reflux for 3.5 hours. After the mixture was cooled below 5° C., 2N sodium hydroxide was added to the mixture. After the mixture was stirred for 30 minutes at the same temperature, the insoluble materials were removed by filtration and washed with tetrahydrofuran. The filtrate and the washing were combined and evaporated under reduced pressure. The residue was dissolved into ethyl acetate, and the solution was dried over sodium sulfate and evaporated under reduced pressure to give 2-[3-[(2-methoxyethoxy)-methoxy]-4-methylbenzyl]piperazine (1.27 g) as an oil.

A solution of benzyloxycarbonyl chloride (0.75 g) in dichloromethane (1 ml) was added dropwise over 5 minutes to an ice-cooled solution of 2-[3-[(2-methoxyethoxy)methoxy]-4-methylbenzyl]piperazine (1.27 g) obtained by above procedure and triethylamine (2.2 ml) in dichloromethane (10 ml) below 5° C. After the mixture was stirred for 30 minutes at the same temperature, a solution of 3,5-bis(trifluoromethyl)-benzoyl chloride (0.93 ml) in dichloromethane (1.0 ml) was added dropwise to the mixture over 10 minutes below 5° C. After being stirred for 30 minutes at the same temperature, the reaction mixture was washed with brine, dried over magnesium sulfate and evaporated under reduced pressure. The residue was purified by column chromatography on silica gel using mixed solvents of toluene and ethyl acetate (5:1). The fractions containing the objective compound were collected and evaporated under reduced pressure to give 1-[3,5-bis(trifluoromethyl)benzoyl]-4-(benzyloxycarbonyl)-2-[3-[(2-methoxyethoxy)methoxy]-4-methylbenzyl]piperazine (1.61 g) as an oil.

IR (Neat): 2879, 1700, 1645 cm$^{-1}$

NMR (CDCl$_3$, δ): 2.19 (3H, s), 3.35 (3H, s), 2.40–5.40 (17H, m), 6.40–8.10 (10H, m), 7.82 (1H, br s)

MASS (APCI): 669 (M+H)$^+$

Preparation 6

A solution of 1-[3,5-bis(trifluoromethyl)benzoyl]-4-(benzyloxycarbonyl)-2-[3-[(2-methoxyethoxy)methoxy]-4-methylbenzyl]piperazine (1.6 g) in methanol (20 ml) was hydrogenated over 10% palladium-carbon (50% wet, 0.2 g) at room temperature under atmospheric pressure for 4 hours. After removal of the catalyst by filtration, the filtrate was concentrated under reduced pressure. The residue was purified by column chromatography on silica gel using mixed solvents of dichloromethane and methanol (40:1). The fractions containing the objective compound were collected and evaporated under reduced pressure to give 1-[3,5-bis(trifluoromethyl)benzoyl]-2-[3-[(2-methoxyethoxy)methoxy]-4-methylbenzyl]piperazine (0.89 g) as an oil.

IR (Neat): 1732, 1714, 1705, 1647, 1431 cm$^{-1}$

NMR (CDCl$_3$, δ): 2.20 (3H, s), 2.50–5.20 (16H, m), 3.00 (3H, s), 6.40–7.40 (5H, m), 7.80 (1H, s)

MASS (API-ES): 557 (M+Na)$^+$, 535 (M+H)$^+$

Preparation 7

To a mixed solution of (3R)-3-(methoxymethyl)morpholine hydrochloride (4.71 g) and triethylamine (4.11 ml) in methanol (110 ml) was added 5.8M ethylene oxide (22 ml) in toluene solution at room temperature. After the reaction mixture was stirred at the same temperature for two days, it was evaporated under reduced pressure. The residue was purified by column chromatography on silica gel using mixed solvents of dichloromethane and methanol (20:1). The fractions containing the objective compound were collected and evaporated under reduced pressure to give 2-[(3R)-3-methoxymethylmorpholino]ethanol (4.67 g) as an oil.

IR (Neat): 3433, 2860, 1454, 1119, 1055 cm$^{-1}$

NMR (CDCl$_3$, δ): 2.38–3.05 (5H, m), 3.33 (3H, s), 3.40–3.80 (8H, m)

MASS (APCI): 176 (M+H)$^+$

Preparation 8

The following compounds were obtained according to a similar manner to that of Preparation 8.

(1) 2-[cis-2,6-Dimethylmorpholino]ethanol

IR (Neat): 3431, 3402, 1456, 1373, 1325, 1146 cm$^{-1}$

NMR (CDCl$_3$, δ): 1.17 (6H, d, J=6.3 Hz), 1.84 (2H, dd, J=10.2 and 11.4 Hz), 2.5.2 (2H, t, J=5.5 Hz), 2.71–2.78 (2H, m), 3.65 (2H, t, J=5.6 Hz), 3.49–3.76 (2H, m)

MASS (APCI): 160 (M+H)$^+$ (2) 2-[(2S,5S)-2-Methoxymethyl-5-methylmorpholino]ethanol IR (Neat): 3433, 3400, 1456, 1379, 1327, 1086, 1051 cm$^{-1}$ NMR (CDCl$_3$, δ): 1.19 (3H, d, J=6.3 Hz), 1.88 (1H, d, J=10.8 Hz), 1.96 (1H, t, J=10.5 Hz), 2.54 (2H, t, J=5.5 Hz), 2.72–2.83 (2H, m), 3.38 (3H, s), 3.36–3.45 (2H, m), 3.63 (2H, t, J=5.2 Hz), 3.60–3.90 (2H, m)

MASS (APCI): 190 (M+H)$^+$ (3) 2-[(2S)-2-(Methoxymethyl)morpholino]ethanol

IR (Neat): 3435, 1456, 1354, 1302 cm$^{-1}$

NMR (CDCl$_3$, δ): 2.06 (1H, t, J=10.7 Hz), 2.27 (1H, td, J=10.7 and 3.3 Hz), 2.53–2.58 (2H, m), 2.68–2.84 (2H, m), 3.38 (3H, s), 3.38–3.44 (2H, m), 3.61–3.75 (4H, m), 3.89–3.98 (1H, m)

MASS (API-ES): 176 (M+H)$^+$, 198 (M+Na)$^+$

Preparation 9

To an ice-cooled solution of 2-[(3R)-3-methoxymethylmorpholino]ethanol (505 mg) in toluene (2.5 ml) was added dropwise a solution of thionyl chloride (429 mg) in toluene (1.5 ml) below 5° C. under nitrogen atmosphere. The mixture was stirred at 70° C. for 1.5 hours. After the mixture was cooled at room temperature, ethyl acetate was added to the mixture, and resulting suspension was evaporated under reduced pressure. Diisopropyl ether was added to the residue, and after the mixture was stirred at room temperature for 15 minutes, the resulting precipitates were collected by filtration, washed with diisopropyl ether and dried at 40° C. under reduced pressure to give (3R)-4-(2-chloroethyl)-3-(methoxymethyl)morpholine hydrochloride (620 mg) as a light yellowish powder.

mp: 162–163° C.

IR (KBr): 2945, 1140, 1109, 1084 cm$^{-1}$

NMR (DMSO-d$_6$, δ): 3.31 (3H, s), 3.10–4.10 (13H, m)

MASS (APCI): 194 (M+H)$^+$ (free)

Preparation 10

The following compounds were obtained according to a similar manner to that of Preparation 9.

(1) cis-2,6-Dimethyl-4-(2-chloroethyl)morpholine hydrochloride

IR (KBr): 1513, 1458, 1394, 1336, 1143 cm$^{-1}$

NMR (DMSO-d$_6$, δ): 1.12 (6H, d, J=6.3 Hz), 2.60–2.80 (2H, m), 3.44–3.50 (4H, m), 3.95–4.10 (4H, m)

MASS (APCI): 178 (M+H)$^+$ (free)

(2) (2S,5S)-4-(2-Chloroethyl)-2-methoxymethyl-5-methylmorpholine hydrochloride

IR (KBr): 2613, 1456, 1390, 1124, 1082 cm$^{-1}$

NMR (DMSO-d$_6$, δ): 1.13 (3H, d, J=6.3 Hz), 2.50–3.00 (3H, m), 3.27 (3H, s), 3.34–3.51 (7H, m), 4.03–4.10 (4H, m)

MASS (APCI): 208 (M+H)$^+$ (free)

(3) (2S)-4-(2-Chloroethyl)-2-(methoxymethyl)morpholine hydrochloride

NMR (DMSO-d$_6$, δ): 3.00 (2H, m), 3.27 (3H, s), 3.47 (4H, m), 3.75–4.12 (7H, m), 11.91 (1H, m)

MASS (APCI): 194 (M+H)$^+$ (free)

Preparation 11

Sodium triacetoxyborohydride (36.7 g) was added portionwisely to a mixture of (2S)-2-amino-1-propanol (10.0 g) and benzaldehyde (13.53 ml) in a mixture of dichloromethane (140 ml) and acetic acid (8.38 ml) at 0° C. and the whole was stirred at room temperature overnight. The mixture was washed successively with 2N sodium hydroxide and brine, and dried over sodium sulfate. The solution was evaporated under reduced pressure and the resulting residue was purified by column chromatography on silica gel using a mixed solvent of dichloromethane and methanol (30:1). The fractions containing the objective compound were collected and evaporated under reduced pressure to give (2S)-2-benzylamino-1-propanol (15.96 g).

IR (KBr): 2843, 1496, 1454, 1377, 1340, 1065 cm$^{-1}$

NMR (CDCl$_3$, δ): 1.10 (3H, d, J=6.4 Hz), 2.77–2.93 (1H, m), 3.28 (1H, dd, J=10.6 and 6.9 Hz), 3.61 (1H, dd, J=10.6 and 4.0 Hz), 3.75, 3.87 (2H, ABq, J=13 Hz), 7.21–7.34 (5H, m)

MASS (API-ES): 166 (M+H)$^+$

Preparation 12

(s)-(+)-Methyl glycidyl ether (8.25 ml) was added dropwise to a solution of (2S)-2-benzylamino-1-propanol (7.6 g) in methanol (7.6 ml) at room temperature. After being stirred at 40–50° for 24 hours, the solution was concentrated under reduced pressure. The residue was purified by column chromatography on silica gel using mixed solvents of dichloromethane and methanol (30:1). The fractions containing the objective compound were collected and evaporated under reduced pressure to give (2S)-2-[(N-benzyl-N-[(2S)-2-hydroxy-3-methoxypropyl]amino]-1-propanol (10.4 g) as an oil.

IR (Neat): 3400, 2929, 1452, 1414, 1373, 1329 cm$^{-1}$

NMR (CDCl$_3$, δ): 0.96 (3H, d, J=6.7 Hz), 2.50–2.60 (1H, m), 2.57 (1H, dd, J=13.4 and 6.2 Hz), 2.67 (1H, dd, J=13.4 and 6.5 Hz), 2.95–3.10 (1H, m), 3.21–3.52 (4H, m), 3.30 (3H, s), 3.49 (1H, d, J=13.6 Hz), 3.71–3.75 (1H, m), 3.83 (1H, d, J=13.6 Hz), 7.21–7.37 (5H, m)

MASS (APCI): 254 (M+H)$^+$

Preparation 13

Triphenylphosphine (10.09 g) was added to a solution of (2S)-2-[N-benzyl-N-[(2S)-2-hydroxy-3-methoxypropyl]amino]-1-propanol (8.86 g) in tetrachloromethane (4.06 ml) at room temperature. After being stirred at room temperature for 2 days, the solution was concentrated under reduced pressure. The residue was triturated with diisopropyl ether (200 ml) three times, and the soluble portions were separated by decantation and evaporated under reduced pressure. The residue was purified by column chromatography on silica gel using mixed solvents of dichloromethane and methanol (40:1). The fractions containing the objective compound were collected and evaporated under reduced pressure to give (2S)-1-[N-benzyl-N-[(1S)-2-chloro-1-methylethyl]amino]-3-methoxy-2-propanol (4.90 g) as an oil.

IR (Neat): 3463, 1452, 1362 cm$^{-1}$

NMR (CDCl$_3$, δ): 1.43 (3H, d, J=6.6 Hz), 2.53–2.82 (4H, m), 3.30–3.39 (2H, m), 3.36 (3H, s), 3.59 (1H, d, J=13.6 Hz), 3.83 (1H, d, J=13.6 Hz), 3.79–3.87 (1H, m), 4.01–4.09 (1H, m), 7.21–7.33 (5H, m)

MASS (APCI): 272 (M+H)$^+$

Preparation 14

A solution of (2S)-1-[N-benzyl-N-[(1S)-2-chloro-1-methylethyl]amino]-3-methoxy-2-propanol (1.90 g) in N,N-dimethylformamide (10 ml) was added to an ice-cooled suspension of sodium hydride (0.45 g, 60% in mineral oil) in N,N-dimethylformamide (10 ml) at 0° C. After being stirred for 1 hour at the same temperature, the mixture was poured into ice-water and extracted with ethyl acetate. The extract was washed with brine, dried over magnesium sulfate and evaporated under reduced pressure. The residue was purified is by column chromatography on silica gel using mixed solvents of hexane and ethyl acetate (10:1). The fractions containing the objective compound were collected and evaporated under reduced pressure to give (2S,5S)-4-benzyl-2-methoxymethyl-5-methylmorpholine (0.86 g) as an oil.

IR (Neat): 2875, 1452, 1362, 1325, 1130, 1082 cm$^{-1}$

NMR (CDCl$_3$, δ): 1.15 (3H, d, J=6.3 Hz), 1.73–1.93 (2H, m), 2.68–2.77 (2H, m), 3.35 (3H, s), 3.49 (2H, s), 3.31–3.49 (2H, m), 3.68–3.81 (2H, m), 7.25–7.32 (5H, m)

MASS (APCI): 236 (M+H)$^+$

Preparation 15

A solution of (2S,5S)-4-benzyl-2-methoxymethyl-5-methylmorpholine (0.86 g) in a mixture of concentrated hydrochloric acid (0.31 ml) and methanol (8.6 ml) was hydrogenated over 10% palladium-carbon (50% wet, 0.2 g) at room temperature under atmospheric pressure for 3 hours. After removal of the catalyst by filtration through Celite®, the filtrate was concentrated under reduced pressure to give (2S,5S)-2-methoxymethyl-5-methylmorpholine hydrochloride (0.71 g) as an oil.

IR (Neat): 3433, 3402, 2939, 1597, 1456, 1392, 1331, 1107 cm$^{-1}$

NMR (DMSO-d$_6$, δ): 1.12 (3H, d, J=6.3 Hz), 2.49–2.75 (2H, m), 3.13–3.19 (2H, m), 3.27 (3H, s), 3.38 (2H, d, J=4.8 Hz), 3.80–4.00 (2H, m)

MASS (APCI): 146 (M+H)$^+$ (free)

Preparation 16

N-Acetyl-3-methoxy-4-methyl-DL-phenylalanine (7.28 g) was dissolved into a mixture of water (36.5 ml) and 1N sodium hydroxide solution (29 ml). Cobalt(II) chloride hexahydrate (36.5 mg) and acylase (Acylase Amano, 365 mg) were added to the solution and the mixture was stirred at 37° C. for 15.5 hours with controlling the pH of the reaction mixture to 7.5 with 1N sodium hydroxide solution. The insoluble material was removed by filtration and the pH of the filtrate was made to 3 with 6N hydrochloric acid, extracted with ethyl acetate, washed with water, dried over sodium sulfate, and evaporated in vacuo to give crude N-acetyl-3-methoxy-4-methyl-D-phenylalanine (3.17 g). The crude product was again subjected to the acylase reaction (cobalt(II) chloride hexahydrate 15.2 mg, acylase 152 mg, 37° C., pH 7.5, 20 hours) to give pure N-acetyl-3-methoxy-4-methyl-D-phenylalanine (2.70 g) as a viscous oil.

$[α]_D^{26.8}$: −36.16° (C=0.424, MeOH)

IR (Neat): 3350, 1740, 1725 cm$^{-1}$

NMR (CDCl$_3$, δ): 1.99 (3H, s), 2.17 (3H, s), 3.00–3.30 (2H, m), 3.78 (3H, s), 4.75–4.90 (1H, m), 6.00–7.10 (3H, m), 6.36 (2H, br s)

MASS (APCI): 252 (M+H)$^+$

Preparation 17

A mixture of N-acetyl-3-methoxy-4-methylphenyl-D-alanine (2.55 g) in a mixture of 6N hydrochloric acid (25.5 ml) and toluene (18 ml) was stirred under reflux for 4 hours. After being cooled to room temperature, the aqueous layer was separated and the organic layer was washed with water (10 ml) twice. The aqueous layer and the washings were combined and evaporated under reduced pressure. The resulting crystals were collected by filtration and washed with ice-water to give 3-methoxy-4-methyl-D-phenylalanine hydrochloride (1.35 g) as colorless crystals. The filtrate was evaporated under reduced pressure to give crude 3-methoxy-4-methyl-D-phenylalanine hydrochloride (0.6 g).

mp: 207–211° C.

[α]$_D^{27.2}$: +20.2° (C=0.5, H$_2$O)

IR (KBr): 1735, 1610, 1508 cm$^{-1}$

NMR (D$_2$O, δ): 2.18 (3H, s), 3.17 (1H, dd, J=7.6 and 14.6 Hz), 3.32 (1H, dd, J=6.0 and 14.6 Hz), 3.85 (3H, s), 4.27 (1H, dd, J=6.0 and 7.0 Hz), 6.85 (1H, d, J=7.3 Hz), 6.91 (1H, s), 7.21 (1H, d, J=8.0 Hz)

MASS (APCI): 210 (M+H)$^+$ (free)

Preparation 18

Thionyl chloride (0.7 ml) was added dropwise to a solution of 3-methoxy-4-methyl-D-phenylalanine hydrochloride (1.75 g) in methanol (8 ml) over 10 minutes at room temperature. The whole was stirred at 40–50° C. for 2 hours and then an additional thionyl chloride (0.7 ml) was added to the mixture. The whole mixture was stirred for further 1 hour and evaporated under reduced pressure. The resulting solid was triturated with diisopropyl ether and collected by filtration to give colorless crystals of 3-methoxy-4-methyl-D-phenylalanine methyl ester hydrochloride (1.70 g).

mp: 196–197° C.

[α]$_D^{30}$: −4.60° (C=0.5, MeOH)

IR (Nujol): 3400, 1741, 1583, 1465, 1446, 1249 cm$^{-1}$

NMR (D$_2$O, δ): 2.19 (3H, s), 3.21 (1H, dd, J=7.4 and 14.5 Hz), 3.32 (1H, dd, J=6.0 and 14.5 Hz), 3.85 (6H, s), 4.43 (1H, dd, J=6.0 and 7.4 Hz), 6.82 (1H, dd, J=1.4 and 7.6 Hz), 6.87 (1H, d, J=1.4 Hz), 7.22 (1H, d, J=7.6 Hz)

MASS (APCI): 224 (M+H)$^+$ (free), 207, 164

Preparation 19

Potassium carbonate (1.70 g) was added by small portions with ice-cooling to a mixture of 3-methoxy-4-methyl-D-phenylalanine methyl ester hydrochloride (1.60 g) in mixed solvents of dichloromethane (7 ml) and water (9 ml). Chloroacetyl chloride (0.66 ml) was added to the mixture below 5° C. over 15 minutes and then the whole was stirred for 30 minutes. The organic layer was separated, washed with brine, dried over magnesium sulfate and evaporated under reduced pressure to give an oil of (2R)-2-[N-(chloroacetyl)-amino]-3-(3-methoxy-4-methylphenyl)propionic acid methyl ester.

IR (Neat): 3305, 1737, 1643, 1583 cm$^{-1}$

Preparation 20

Benzylamine (1.65 g) and potassium carbonate (1.28 g) were added successively to a solution of (2R)-2-[N-(chloroacetyl)amino]-3-(3-methoxy-4-methylphenyl)propionic acid methyl ester (1.85 g) in N,N-dimethylformamide (15 ml) at 20° C. After being stirred at 35° C. for 1.5 hours, the mixture was poured into a mixture of ice-water (20 ml) and dichloromethane (20 ml). After the mixture was adjusted to pH 9 with diluted aqueous hydrochloric acid under stirring, the organic layer was separated, washed with brine (20 ml), dried over magnesium sulfate and evaporated under reduced pressure to give an oil of (2R)-2-[N-(benzylaminoacetyl)-amino]-3-(3-methoxy-4-methylphenyl)propionic acid methyl ester. A solution of (2R)-2-[N-(benzylaminoacetyl) amino]-3-(3-methoxy-4-methylphenyl)propionic acid methyl ester obtained by above procedure and acetic acid (0.18 ml) in isopropyl alcohol (10 ml) was stirred for 12 hours under reflux.

After the mixture was cooled to room temperature, isopropyl ether was added to the mixture. The resulting precipitates were collected by filtration and washed with isopropyl ether to give colorless crystals of (3R)-1-benzyl-3-(3-methoxy-4-methylbenzyl)piperazine-2,5-dione (1.45 g).

mp: 205–209° C.

[α]$_D^{30}$: +11.12° (C=0.4, DMF)

IR (KBr): 3237, 1677, 1656, 1465, 1446, 1442 cm$^{-1}$

NMR (DMSO-d$_6$, δ): 2.08 (3H, s), 2.76 (1H, d, J=17.2 Hz), 2.87 (1H, dd, J=4.8 and 13.4 Hz), 3.11 (1H, dd, J=4.8 and 13.4 Hz), 3.46 (1H, d, J=17.2 Hz), 3.69 (3H, s), 4.25 (1H, d, J=14.6 Hz), 4.20–4.30 (1H, m), 4.52 (1H, d, J=14.6 Hz), 6.54 (1H, dd, J=1.4 and 7.4 Hz), 6.69 (1H, d, J=1.4 Hz), 6.87 (1H, d, J=7.4 Hz), 7.04–7.11 (2H, m), 7.24–7.30 (3H, m), 8.33 (1H, d, J=2.2 Hz)

MASS (APCI): 339 (M+H)$^+$

Preparation 21

Lithium aluminum hydride (0.378 g) was added to an ice-cooled suspension of (3R)-1-benzyl-3-(3-methoxy-4-methylphenyl)-2,5-piperazinedione (1.35 g) in tetrahydrofuran (22 ml) below 5° C. under nitrogen atmosphere. The mixture was stirred under reflux for 3 hours. After the mixture was cooled below 5° C., 2N sodium hydroxide was added to the mixture. After the mixture was stirred for 30 minutes, the insoluble materials were removed by filtration and washed with tetrahydrofuran. The filtrate and the washing were combined and evaporated under reduced pressure to give (3R)-1-benzyl-3-(3-methoxy-4-methylphenyl)piperazine as an oil. A solution of 3,5-bis(trifluoromethyl) benzoyl chloride (0.80 ml) in dichloromethane (1 ml) was added dropwise over 5 minutes to an ice-cooled solution of (3R)-1-benzyl-3-(3-methoxy-4-methylphenyl)piperazine obtained by above procedure and triethylamine (0.84 ml) in dichloromethane (10 ml) below 5° C. After being stirred for 30 minutes at the same temperature, the reaction mixture was washed with brine, dried over magnesium sulfate and evaporated under reduced pressure. The residue was purified by column chromatography on silica gel using mixed solvents of hexane and ethyl acetate (4:1). The fractions containing the objective compound were collected and evaporated under reduced pressure to give (2R)-4-benzyl-1-[3,5-bis(trifluoromethyl)benzoyl]-2-(3-methoxy-4-methylbenzyl)piperazine (1.92 g) as an oil.

IR (Neat): 2950, 2850, 1640, 1590, 1515 cm$^{-1}$

NMR (CDCl$_3$, δ): 2.16 (3H, s), 2.00–5.20 (14H, m), 6.25–6.32 (1H, m), 6.70–6.90 (2H, m), 7.20–7.44 (7H, m), 7.80 (1H, br s)

MASS (APCI): 551 (M+H)$^+$, 573 (M+Na)$^+$

Preparation 22

A solution of boron tribromide in dichloromethane (1M solution, 3.7 ml) was added dropwise over 20 minutes to an ice-cooled solution of (2R)-4-benzyl-1-[3,5-bis(trifluoromethyl)benzoyl]-2-(3-methoxy-4-methylbenzyl)-piperazine (0.68 g) in dichloromethane (5 ml). After being stirred at the same temperature for 2 hours, followed by further stirring at room temperature for 12 hours, the mixture was poured into aqueous saturated sodium hydrogen carbonate solution. The organic layer was separated, dried over magnesium sulfate and evaporated under reduced pressure. The residue was purified by column chromatography on silica gel using mixed solvents of hexane and ethyl acetate (4:1). The fractions containing the objective compound were collected and evaporated under reduced pressure to give (2R)-4-benzyl-1-[3,5-bis(trifluoromethyl)benzoyl]-2-(3-hydroxy-4-methylbenzyl)piperazine (0.56 g) as a red foam.

IR (Neat): 1630, 1430 cm$^{-1}$

NMR (CDCl$_3$, δ): 2.00–5.20 (14H, m), 5.61 (1H, br s), 6.20–6.25 (1H, m), 6.60–7.70 (2H, m), 7.20–7.60 (7H, m), 7.80–7.85 (1H, m)

MASS (API-ES): 519 (M−H$_2$O+H)$^+$, 537 (M+H)$^+$, 559 (M+Na)$^+$

Preparation 23

Sodium hydride (60% in mineral oil, 18 mg) was added by small portions to an ice-cooled solution of (2R)-4-benzyl-1-[3,5-bis(trifluoromethyl)benzoyl]-2-(3-hydroxy-4-methylbenzyl)piperazine (0.20 g) in N,N-dimethylformamide (2 ml) below 5° C. under nitrogen atmosphere. After the mixture was stirred for 5 minutes, (2-methoxyethoxy)methyl chloride (0.064 ml) was added to the mixture. The whole was stirred at room temperature for 2.5 hours, and thereto water was added. The whole was extracted with ethyl acetate. The extract was dried over magnesium sulfate and evaporated under reduced pressure. The residue was purified by column chromatography on silica gel using mixed solvents of hexane and ethyl acetate (7:3). The fractions containing the objective compound were collected and evaporated under reduced pressure to give (2R)-4-benzyl-1-[3,5-bis(trifluoromethyl)benzoyl]-2-[3-[(2-methoxyethoxy)methoxy]-4-methylbenzyl]piperazine (0.21 g) as an oil.

IR (Neat): 2950, 1645, 1435 cm$^{-1}$

NMR (CDCl$_3$, δ): 2.19 (3H, s), 3.34 (3H, s), 2.00–5.20 (17H, m), 6.60–7.40 (10H, m), 7.70–7.80 (1H, m)

MASS (API-ES): 625 (M+H)$^+$, 647 (M+Na)$^+$

Preparation 24

A mixture of (2R)-4-benzyl-1-[3,5-bis(trifluoromethyl)benzoyl]-2-[3-[(2-methoxyethoxy)methoxy]-4-methylbenzyl]-piperazine (0.38 g) in methanol (6 ml) was hydrogenated over 20% palladium hydroxide-carbon (0.06 g) at room temperature under atmospheric pressure for 8 hours. After removal of the catalyst by filtration through Celite®, the filtrate was concentrated under reduced pressure. The residue was purified by column chromatography on silica gel using mixed solvents of dichloromethane and methanol (30:1). The fractions containing the objective compound were collected and evaporated under reduced pressure to give (2R)-1-[3,5-bis(trifluoromethyl)benzoyl]-2-[3-[(2-methoxyethoxy)methoxy]-4-methylbenzyl]piperazine (0.32 g) as an oil.

IR (KBr): 3000–2700, 1629, 1513, 1444 cm$^{-1}$

NMR (CDCl$_3$, δ): 2.20 (3H, s), 2.50–5.30 (16H, m), 3.36 (3H, s), 6.40–7.50 (5H, m), 7.80 (1H, s)

MASS (API-ES): 535 (M+H)$^+$, 557 (M+Na)$^+$

EXAMPLE 1

To a solution of 1-[3,5-bis(trifluoromethyl)benzoyl]-2-[3-[(2-methoxyethoxy)methoxy]-4-methylbenzyl]piperazine (440 mg) in N,N-dimethylformamide (2.2 ml) were added (3R)-4-(2-chloroethyl)-3-(methoxymethyl)morpholine hydrochloride (289 mg), potassium carbonate (434 mg) and potassium iodide (149 mg) at room temperature. The whole was stirred at 73° C. for 2 hours. After being cooled to room temperature, the mixture was poured into ice-water and the aqueous mixture was made alkaline with saturated aqueous sodium hydrogen carbonate solution. The resulting mixture was extracted with ethyl acetate. The extract was washed with brine, dried over sodium sulfate and evaporated under reduced pressure. The residue was purified by column chromatography on silica gel using mixed solvents of dichloromethane and methanol (40:1). The fractions containing the objective compound were collected and evaporated under reduced pressure to give 1-[3,5-bis(trifluoromethyl)benzoyl]-2-[3-[(2-methoxyethoxy)-methoxy]-4-methylbenzyl]-4-[2-[(3R)-3-methoxymethyl-morpholino]ethyl]piperazine (450 mg) as a light yellowish oil.

IR (Neat): 2879, 1639, 1437, 1281, 1136, 1009 cm$^{-1}$

NMR (CDCl$_3$, δ): 2.20 (3H, s), 1.95–5.40 (34H, m), 6.40–8.10 (6H, m)

MASS (APCI): 692 (M+H)$^+$

EXAMPLE 2

The following compounds were obtained according to a similar manner to that of Example 1.

(1) 1-[3,5-Bis(trifluoromethyl)benzoyl]-4-[2-(cis-2,6-dimethylmorpholino)ethyl]-2-[3-[((2-methoxyethoxy)-methoxy]-4-methylbenzyl]piperazine IR (Neat): 1680, 1643, 1508, 1435 cm$^{-1}$ NMR (CDCl$_3$, δ): 1.17 (6H, d, J=6.3 Hz), 1.78 (2H, t, J=10.8 Hz), 2.20 (3H, br s), 2.20–5.30 (23H, m), 3.36 (3H, s), 6.42–8.02 (6H, m)

MASS (APCI): 676 (M+H)$^+$ (2) 1-[3,5-Bis(trifluoromethyl)benzoyl]-2-[3-[(2-methoxyethoxy)methoxy]-4-methylbenzyl]-4-[2-[(2S,5S)-2-methoxymethyl-5-methylmorpholino]ethyl]piperazine IR (Neat): 2933, 2881, 1643, 1439, 1281, 1086, 1012 cm$^{-1}$ NMR (CDCl$_3$, δ): 1.18 (3H, d, J=6.2 Hz), 1.78–1.96 (2H, m), 2.20 (3H, br s), 2.20–5.30 (25H, m), 3.37 (3H, s), 3.36 (3H, s), 6.66–7.80 (6H, m)

MASS (API-ES): 706.3 (M+H)$^+$, 728.3 (M+Na)$^+$

EXAMPLE 3

1-[3,5-Bis(trifluoromethyl)benzoyl]-2-[3-[(2-methoxyethoxy)methoxy]-4-methylbenzyl]-4-[2-[(3R)-3-(methoxymethyl)morpholino]ethyl]piperazine (430 mg) was dissolved in methanol (10 ml) at room temperature, and methanesulfonic acid (0.215 ml) was added to the solution. After being stirred at the same temperature for 18 hours, the reaction mixture was concentrated until one third of original volume under reduced pressure, and poured into iced water. The aqueous mixture was made alkaline with 15% aqueous sodium hydroxide solution, and the resulting mixture was extracted with ethyl acetate. The extract was washed with brine, dried over sodium sulfate and evaporated under reduced pressure. The residue was purified by column chromatography on silica gel using mixed solvents of dichloromethane and methanol (30:1). The fractions containing the objective compound were collected and evaporated under reduced pressure, and the residue was treated with 4N hydrogen chloride in ethyl acetate solution to give 1-[3,5-bis(trifluoromethyl)benzoyl]-2-[3-hydroxy-4-methylbenzyl]-4-[2-[(3R)-3-(methoxymethyl)-morpholino]ethyl]piperazine dihydrochloride (280 mg) as a colorless powder.

mp: 167–172° C.

$[α]_D^{28}$: −8.50° (C=0.20, MeOH)

IR (KBr): 3400, 1645, 1429, 1282, 1184, 1138 cm$^{-1}$

NMR (DMSO-d$_6$, δ): 2.08 (3H, s), 2.60–5.10 (25H, m), 6.18–7.10 (3H, m), 7.36–8.22 (3H, m), 9.25 (1H, br)

MASS (APCI): 604 (M+H)$^+$ (free)

EXAMPLE 4

The following compounds were obtained according to a similar manner to that of Example 3.

(1) 1-[3,5-Bis(trifluoromethyl)benzoyl]-4-[2-(cis-2,6-dimethylmorpholino)ethyl]-2-(3-hydroxy-4-methylbenzyl)piperazine dihydrochloride mp: 188–200° C.
$[\alpha]_D^{29}$:+0.70° (C=0.25, MeOH)
IR (KBr): 3402, 1643, 1516, 1429 cm$^{-1}$
NMR (DMSO-d$_6$, δ): 1.15 (6H, d, J=6.0 Hz), 2.08 (3H, br s), 2.00–5.10 (19H, m), 6.19–8.21 (6H, m)
MASS (APCI): 588 (M+H)$^+$ (free)

(2) 1-[3,5-Bis(trifluoromethyl)benzoyl]-2-(3-hydroxy-4-methylbenzyl)-4-[2-[(2S,5S)-2-methoxymethyl-5-methylmorpholino]ethyl]piperazine dihydrochloride mp: 214–218° C.
$[\alpha]_D^{29}$: +0.80° (C=0.25, MeOH)
IR (KBr): 3433, 3398, 1645, 1516, 1429, 1371, 1281, 1182, 1140 cm$^{-1}$
NMR (DMSO-d$_6$, δ): 1.16 (3H, d, J=6.0 Hz), 2.08 (3H, br s), 2.50–5.10 (21H, m), 3.27 (3H, s), 6.20–8.20 (6H, m), 9.00–9.20 (1H, m)
MASS (APCI): 618 (M+H)$^+$ (free)

(3) 1-[3,5-Bis(trifluoromethyl)benzoyl]-2-(3-hydroxy-4-methylbenzoy)-4-[3-(3-pyridyl)-2-propynyl]piperazine NMR (CDCl$_3$, δ): 0.60–5.30 (14H, m), 5.77 (1H, br s), 6.20–8.90 (10H, m)
MASS (APCI): 562 (M+H)$^+$

EXAMPLE 5

The following compounds were obtained according to a similar manner to that of Example 1 and then a similar manner to that of Example 3.

(1) (2R)-1-[3,5-Bis(trifluoromethyl)benzoyl]-4-[2-[(2S)-2-(methoxymethyl)morpholino]ethyl]-2-(3-hydroxy-4-methylbenzyl)piperazine dihydrochloride mp: 207–210° C.
$[\alpha]_D^{26.2}$: -6.40° (C=0.4, MeOH)
IR (KBr): 3300, 3000, 2700, 1644, 1428 cm$^{-1}$
NMR (DMSO-d$_6$, δ): 2.18 (3H, s), 2.20–5.20 (22H, m), 6.10–8.20 (6H, m), 9.00–9.40 (1H, br s), 11.00–12.00 (2H, m)
MASS (APCI): 604 (M+H)$^+$ (free)

(2) 1-[3,5-Bis(trifluoromethyl)benzoyl]-4-[2-[(2S)-2-(methoxymethyl)morpholino]ethyl]-2-(3-hydroxy-4-methylbenzyl)piperazine dihydrochloride IR (KBr): 1645, 1516, 1458, 1425, 1369 cm$^{-1}$
NMR (DMSO-d$_6$, δ): 2.08 (3H, br s), 3.28 (3H, br s), 2.40–5.10 (22H, m), 6.19–8.22 (6H, m)
MASS (APCI): 604 (M+H)$^+$ (free)

EXAMPLE 6

A mixture of 1-[3,5-bis(trifluoromethyl)benzoyl]-2-[3-[(2-methoxyethoxy)methyl]-4-methylbenzyl]piperazine (0.4 g), 1-chloro-3-(3-pyridyl)-2-propyne hydrochloride (0.17 g), potassium carbonate (0.52 g) and a trace of potassium iodide in N,N-dimethylformamide (7 ml) was stirred for 4 hours at 80° C. After cooling, the solvent was removed by evaporation, and ethyl acetate and aqueous sodium hydrogen carbonate solution were added thereto. The organic layer was separated, dried over magnesium sulfate, and evaporated under reduced pressure. The residue was purified by column chromatography on silica gel using ethyl acetate. The fractions containing the objective compound were collected and evaporated under reduced pressure to give 1-[3,5-bis(trifluoromethyl)benzoyl]-2-[3-[(2-methoxyethoxy)methyl]-4-methylbenzyl]-4-[3-(3-pyridyl)-2-propynyl]piperazine (0.44 g) as an oil.
NMR (CDCl$_3$, δ): 0.60–5.60 (23H, m), 6.30–8.90 (10H, m)
MASS (APCI): 650 (M+H)$^+$

EXAMPLE 7

A solution of 1-[3,5-bis(trifluoromethyl)benzoyl]-2-(3-hydroxy-4-methylbenzyl)-4-[3-(3-pyridyl)-2-propynyl]piperazine (0.11 g) in methanol (10 ml) was treated with 4N hydrogen chloride in ethyl acetate (1 ml) and the mixture was evaporated under reduced pressure. The residue was triturated with a mixture of dichloromethane and ethyl acetate and the resulting powder was collected by filtration to give 1-[3,5-bis(trifluoromethyl)benzoyl]-2-(3-hydroxy-4-methylbenzyl)-4-[3-(3-pyridyl)-2-propynyl]piperazine dihydrochloride (0.07 g).
mp: 180–190° C.
IR (KBr): 1693, 1676, 1645, 1549, 1531, 1516, 1460, 1456, 1427, 1392, 1367, 1317, 1281, 1217, 1188, 1066 cm$^{-1}$
NMR (DMSO-d$_6$, δ): 1.60–5.20 (14H, m), 6.10–9.00 (10H, m)
MASS (APCI): 562 (M+H)$^+$ (free)

EXAMPLE 8

A solution of 1-[3,5-bis(trifluoromethyl)benzoyl]-2-(3-hydroxy-4-methylbenzyl)-4-[3-(3-pyridyl)-2-propynyl]piperazine (0.16 g) in a mixed solvent of methanol (10 ml) and tetrahydrofuran (10 ml) was hydrogenated over 10% palladium-charcoal (20 mg) at room temperature for 1.5 hours. After removal of catalyst by filtration, the filtrate was concentrated under reduced pressure. The residue was purified by column chromatography on silica gel using ethyl acetate as an eluent. The fractions containing the objective compound were collected and evaporated under reduced pressure and the resulting residue was treated with 4N hydrogen chloride in ethyl acetate to give 1-[3,5-bis(trifluoromethyl)benzoyl]-2-(3-hydroxy-4-methylbenzyl)-4-[3-(3-pyridyl)propyl]piperazine dihydrochloride (0.17 g) as a colorless solid.
mp: 60–70° C.
IR (KBr): 1707, 1693, 1676, 1645, 1628, 1558, 1550, 1541, 1516, 1466, 1456, 1427, 1387, 1365, 1329, 1319, 1281, 1182, 1136, 1039 cm$^{-1}$
NMR (DMSO-d$_6$, δ): 1.80–5.20 (18H, m), 6.00–9.00 (10H, m)
MASS (APCI): 566 (M+H)$^+$ (free)

Preparation 25

A solution of 3-methoxy-p-toluic acid (45.32 g) in tetrahydrofuran (280 ml) was added to a suspension of sodium borohydride (9.29 g) in tetrahydrofuran (45 ml) with ice bath cooling under nitrogen atmosphere. After 10 minutes stirring, boron trifluuoride diethyl etherate (41.5 ml) was added to the mixture at 3 to 15° C. and the whole was stirred at room temperature overnight. Water (210 ml) and diisopropyl ether (60 ml) were added to the mixture. The organic layer was separated and the aqueous layer was extracted with diisopropyl ether (100 ml). The combined organic layer was washed successively with 1N sodium hydroxide solution and brine, dried over sodium sulfate, and evaporated in vacuo to give 3-methoxy-4-methylbenzylalcohol (41.63 g) as an oil.

IR (Neat): 3330, 1615, 1590, 1510, 1465, 1418, 1255 cm$^{-1}$

NMR (CDCl$_3$, δ): 1.70 (1H, br s), 2.21 (3H, s), 3.84 (3H, s), 4.65 (2H, s), 6.80–7.16 (3H, m)

Preparation 26

A mixture of 3-methoxy-4-methylbenzylalcohol (41.61 g), conc. hydrochloric acid (125 ml) and toluene (83 ml) was stirred at 90° C. for 1 hour. After cooling, ice-water (125 ml) and diisopropyl ether (80 ml) were added to the mixture, and the organic layer was separated, and the aqueous layer was extracted with diisopropyl ether (160 ml). The combined organic layer was washed with saturated sodium hydrogen carbonate solution and brine, dried over sodium sulfate, and evaporated in vacuo to give 3-methoxy-4-methylbenzyl chloride (46.35 g) as an oil.

IR (Neat): 1615, 1590, 1510, 1470, 1415, 1255 cm$^{-1}$

NMR (CDCl$_3$, δ): 2.21 (3H, s), 3.85 (3H, s), 4.57 (2H, s), 6.82–7.15 (3H, m)

Preparation 27

3-Methoxy-4-methylbenzyl chloride (46.35 g) and ethyl acetamidomalonate (71.16 g) were added successively into a solution of sodium ethoxide (24.34 g) in ethanol (230 ml). The mixture was stirred under reflux for 2 hours, poured into ice-water (690 ml) and the pH of the mixture was adjusted to 7 with 6N hydrochloric acid. The resulting precipitates were collected by filtration, washed with aqueous ethanol (3:1, 100 ml) and dried to give crude 2-acetylamino-2-(3-methoxy-4-methylbenzyl)malonic acid diethyl ester (85.03 g). A suspension of the crude product (80.66 g) in heptane (400 ml) was stirred at 50° C. for 1 hour and cooled to room temperature. The resulting precipitates were collected by filtration, washed with heptane, and dried to give pure product (74.57 g) as a colorless crystals.

mp: 123–125° C.

IR (KBr): 3251, 1747, 1643, 1518, 1267, 1213, 1190, 1051 cm$^{-1}$

NMR (CDCl$_3$, δ): 1.30 (6H, t, J=7.1 Hz), 2.03 (3H, s), 2.16 (3H, s), 3.61 (2H, s), 3.76 (3H, s), 4.28 (4H, q, J=7.1 Hz), 6.44–7.06 (4H, m)

Preparation 28

A mixture of 2-acetylamino-2-(3-methoxy-4-methylbenzyl)-malonic acid diethyl ester (10.0 g), potassium hydroxide solution (1.88 g) in water (25 ml) and ethanol (25 ml) were stirred under reflux for 1 hour. Another potassium hydroxide solution (1.88 g) in water (10 ml) was added to the mixture and the whole was stirred under reflux for 2 hours. After being cooled to room temperature, the reaction mixture was concentrated under reduced pressure. Water (50 ml) and ethyl acetate (50 ml) were added to the resulting aqueous solution. The aqueous layer was separated and was adjusted to pH 1.5 with 6N hydrochloric acid. The solution was extracted with ethyl acetate, washed with brine, dried over sodium sulfate and evaporated under reduced pressure to give N-acetyl-3-methoxy-4-methyl-DL-phenylalanine (7.58 g) as a viscous oil.

IR (Neat): 3350, 1740, 1725 cm$^{-1}$

NMR (CDCl$_3$, δ): 1.99 (3H, s), 2.17 (3H, s), 3.00–3.30 (2H, m), 3.78 (3H, s), 4.75–4.90 (1H, m), 6.00–7.10 (3H, m), 6.37 (2H, br s)

Preparation 29

The following compounds were obtained according to a similar manner to that of Preparation 27.

(1) 2-Acetylamino-2-(4-chloro-3-methoxybenzyl)malonic acid diethyl ester mp: 122–123° C.

IR (KBr): 3247, 2977, 1749, 1643, 1523, 1309, 1205 cm$^{-1}$

NMR (CDCl$_3$, δ): 1.30 (6H, t, J=7.1 Hz), 2.03 (3H, s), 3.64 (2H, s), 3.83 (3H, s), 4.16–4.35 (4H, m), 6.53 (1H, dd, J=2.0 and 8.0 Hz), 6.56 (1H, d, J=2.0 Hz), 6.56 (1H, s), 7.23 (1H, d, J=8.0 Hz)

MASS (APCI): 372 (M+H)$^+$, 330, 282

(2) 2-Acetylamino-2-(4-fluoro-3-methoxybenzyl)malonic acid diethyl ester mp: 128–131° C.

IR (KBr): 2981, 1747, 1641, 1520, 1269, 1211 cm$^{-1}$

NMR (CDCl$_3$, δ): 1.30 (6H, t, J=7.1 Hz), 2.04 (3H, s), 3.62 (2H, s), 3.82 (3H, s), 4.27 (4H, q, J=7.1 Hz), 6.48–7.09 (4H, m)

MASS (APCI): 356 (M+H)$^+$ (3) 2-Acetylamino-2-(3,4-difluorobenzyl)malonic acid diethyl ester IR (Nujol): 3259, 1749, 1645, 1518, 1317, 1277, 1205, 1051, 1016 cm$^{-1}$ NMR (DMSO-d$_6$, δ): 1.16 (6H, t, J=7.1 Hz), 1.91 (3H, s), 3.42 (2H, s), 4.15 (4H, q, J=7.1 Hz), 6.76–7.45 (3H, m), 8.19 (1H, s)

MASS (APCI): 344 (M+H)$^+$, 302

(4) 2-Acetylamino-2-[3-methoxy-4-(trifluoromethyl)benzyl]-malonic acid diethyl ester mp: 119–120° C.

IR (KBr): 3500–3150, 2700–2300, 1637, 1631, 1461, 1348, 1238, 1172 cm$^{-1}$

NMR (CDCl$_3$, δ): 1.31 (6H, t, J=7.2 Hz), 2.04 (3H, s), 3.70 (2H, s), 3.84 (3H, s), 4.21–4.36 (4H, m), 6.57–6.64 (2H, m), 7.44 (1H, d, J=8.2 Hz)

MASS (APCI): 406 (M+H)$^+$, 316

(5) 2-Acetylamino-2-(4-fluoro-3-methylbenzyl)malonic acid diethyl ester

IR (Neat): 3250, 1740, 1640, 1510, 1460, 1370, 1270, 1210, 1185 cm$^{-1}$

NMR (CDCl$_3$, δ): 1.30 (6H, t, J=7.1 Hz), 2.03 (3H, s), 2.22 (3H, s), 3.58 (2H, s), 4.27 (4H, q, J=7.1 Hz), 6.53 (1H, s), 6.70–6.95 (3H, m)

MASS (APCI): 340 (M+H)$^+$

Preparation 30

The following compounds were obtained according to a similar manner to that of Preparation 28.

(1) N-Acetyl-4-chloro-3-methoxy-DL-phenylalanine mp: 177–179° C.
IR (KBr): 3351, 3200–2500, 1735, 1629, 1548 cm$^{-1}$
MASS (APCI): 272 (M+H)$^+$, 230

(2) N-Acetyl-4-fluoro-3-methoxy-DL-phenylalanine mp: 150–152° C.
IR (KBr): 3340, 2947, 1718, 1603, 1514, 1259, 1215 cm$^{-1}$
NMR (DMSO-d$_6$, δ): 1.79 (3H, s), 2.74–3.07 (2H, m), 3.81 (3H, s), 4.41 (1H, m), 6.77 (1H, m), 7.01–7.14 (2H, m), 8.17 (1H, d, J=8.1 Hz), 12.68 (1H, br)
MASS (APCI): 256 (M+H)$^+$ (3) N-Acetyl-3,4-difluorophenyl-DL-alanine IR (KBr): 3360, 1710, 1615, 1550, 1530 cm$^{-1}$
NMR (DMSO$_6$, δ): 1.78 (3H, s), 2.50–2.88 (2H, m), 4.35–4.47 (1H, m), 7.07–7.41 (3H, m), 8.19 (1H, d, J=8.2 Hz)
MASS (APCI): 244 (M+H)$^+$, 202

(4) N-Acetyl-3-methoxy-4-trifluoromethyl-DL-phenylalanine mp: 156–160° C.
IR (KBr): 3326, 3200–2300, 1716, 1621, 1552, 1459 cm$^{-1}$
NMR (DMSO-d$_6$, δ): 1.80 (3H, s), 2.85–3.50 (2H, m), 3.87 (3H, s), 4.23–4.54 (1H, m), 6.94 (1H, d, J=8.0 Hz), 7.13 (1H, s), 7.52 (1H, d, J=8.0 Hz), 8.23 (1H, d, J=8.1 Hz), 12.82 (1H, br s)
MASS (APCI): 306 (M+H)$^+$ (free)

(5) N-Acetyl-4-fluoro-3-methyl-DL-phenylalanine

IR (Neat): 3350, 1720, 1600, 1540, 1500, 1345 cm$^{-1}$
NMR (DMSO-d$_6$, δ): 1.78 (3H, s), 2.20 (3H, s), 2.71–3.03 (2H, m), 4.31–4.42 (1H, m), 6.97–8.19 (3H, m), 12.68 (1H, br s)
MASS (APCI): 240 (M+H)$^+$ (6) N-Acetyl-3-fluoro-4-methyl-DL-phenylalanine IR (Neat): 3300, 1740, 1720, 1600, 1540 cm$^{-1}$ Preparation 31

The following compounds were obtained according to a similar manner to that of Preparation 16.

(1) N-Acetyl-4-chloro-3-methoxy-D-phenylalanine mp: 116–117° C.
$[\alpha]_D^{27}$: −36.6° (C=0.37, MeOH)
IR (KBr): 3500–3150, 2700–2300, 1733, 1623 cm$^{-1}$
MASS (APCI): 272 (M+H)$^+$, 230

(2) N-Acetyl-4-fluoro-3-methoxy-D-phenylalanine

IR (Neat): 3330, 2940, 1728, 1618, 1518, 1275, 1223 cm$^{-1}$
NMR (DMSO-d$_6$, δ): 1.79 (3H, s), 2.70–3.10 (2H, m), 3.81 (3H, s), 4.40 (1H, m), 6.78 (1H, m), 7.01–7.14 (2H, m), 8.18 (1H, d, J=8.1 Hz), 12.63 (1H, br)
MASS (APCI): 256 (M+H)$^+$ (3) N-Acetyl-3,4-difluoro-D-phenylalanine IR (KBr): 3395, 1720, 1615, 1545, 1515 cm$^{-1}$ (4) N-Acetyl-3-methoxy-4-trifluoromethyl-D-phenylalanine mp: 156–160° C.
IR (KBr): 3326, 3200–2300, 1716, 1621, 1552, 1459 cm$^{-1}$
NMR (DMSO-d$_6$, δ): 1.80 (3H, s), 2.85–3.50 (2H, m), 3.87 (3H, s), 4.23–4.54 (1H, m), 6.94 (1H, d, J=8.0 Hz), 7.13 (1H, s), 7.52 (1H, d, J=8.0 Hz), 8.23 (1H, d, J=8.1 Hz), 12.82 (1H, br s)
MASS (APCI): 306 (M+H)$^+$ (free)

(5) N-Acetyl-4-fluoro-3-methyl-D-phenylalanine $[\alpha]_D^{28}$: −34.60° (C=0.5, MeOH)
IR (Nujol): 3400, 1715, 1605, 1530, 1500, 1450, 1240, 1200, 1120 cm$^{-1}$
NMR (DMSO-d$_6$, δ): 1.78 (3H, s), 2.20 (3H, s), 2.71–3.03 (2H, m), 4.31–4.42 (1H, m), 6.97–8.19 (3H, m), 12.68 (1H, br s)
MASS (APCI): 240 (M+H)$^+$ (6) N-Acetyl-3-fluoro-4-methyl-D-phenylalanine $[\alpha]_D^{29}$: −46.10° (C=0.5, MeOH)
IR (Nujol): 3300, 1705, 1600, 1560 cm$^{-1}$ Preparation 32

The following compounds were obtained according to a similar manner to that of Preparation 17.

(1) 4-Chloro-3-methoxy-D-phenylalanine hydrochloride mp: 218–222° C.
$[\alpha]_D^{27}$: +3.17° (C=0.52, MeOH)
IR (KBr): 3500–3150, 2700–2300, 1739, 1589, 1488 cm$^{-1}$
NMR (D$_2$O, δ): 3.19 (1H, dd, J=7.5 and 14.5 Hz), 3.33 (1H, dd, J=5.7 and 14.5 Hz), 3.91 (3H, s), 4.28 (1H, dd, J=5.7 and 7.5 Hz), 6.89 (1H, dd, J=1.8 and 8.1 Hz), 7.03 (1H, d, J=1.8 Hz), 7.42 (1H, d, J=8.1 Hz)
MASS (APCI): 230 (M+H)$^+$ (2) 4-Fluoro-3-methoxy-D-phenylalanine hydrochloride mp: 210–220° C. (decomp.)
IR (KBr): 1738, 1606, 1520, 1487, 1462, 1417, 1274, 1223, 1209, 1157, 1128 cm$^{-1}$
NMR (DMSO-d$_6$, δ): 3.13 (2H, m), 3.83 (3H, s), 4.00–4.40 (1H, m), 6.70–6.90 (1H, m), 7.00–7.30 (2H, m)
MASS (APCI): 214 (M+H)$^+$ (free)

(3) 3-Methoxy-4-trifluoromethyl-D-phenylalanine hydrochloride mp: 156–160° C.
IR (KBr): 3326, 3200–2300, 1716, 1621, 1552, 1459 cm$^{-1}$
NMR (D$_2$O, δ): 3.19 (1H, dd, J=7.5 and 14.4 Hz), 3.33 (1H, dd, J=5.7 and 14.4 Hz), 3.86 (3H, s), 4.20–4.26 (1H, m), 6.97 (1H, d, J=8.0 Hz), 7.07 (1H, s), 7.58 (1H, d, J=8.0 Hz)

MASS (APCI): 264 (M+H)+ (free)

(4) 4-Fluoro-3-methyl-D-phenylalanine hydrochloride

IR (Nujol): 1735, 1485, 1460, 1375, 1210 cm$^{-1}$

MASS (APCI): 198 (M+H)+ (free)

(5) 3-Fluoro-4-methyl-D-phenylalanine hydrochloride

IR (Nujol): 1730, 1480, 1555, 1250, 1220, 1200 cm$^{-1}$

Preparation 33

The following compounds were obtained according to a similar manner to that of Preparation 18.

(1) 4-Chloro-3-methoxy-D-phenylalanine methyl ester hydrochloride mp: 165–168° C.
IR (KBr): 3200–2500, 1745, 1583, 1494 cm$^{-1}$
NMR (D$_2$O, δ): 3.22 (1H, dd, J=7.5 and 14.5 Hz), 3.35 (1H, dd, J=6.8 and 14.5 Hz), 3.85 (3H, s), 3.92 (3H, s), 4.44 (1H, dd, J=6.8 and 7.5 Hz), 6.89 (1H, dd, J=1.9 and 8.1 Hz), 7.02 (1H, d, J=1.9 Hz), 7.44 (1H, d, J=8.1 Hz)
MASS (APCI): 244 (M+H)+

(2) 4-Fluoro-3-methoxy-D-phenylalanine methyl ester hydrochloride mp: 172–173° C.
IR (KBr): 1745, 1610, 1581, 1518, 1452, 1398, 1294, 1273, 1242, 1215, 1163, 1120, 1061, 1028 cm$^{-1}$
NMR (DMSO-d$_6$, δ): 3.13 (2H, d, J=6.3 Hz), 3.71 (3H, s), 3.83 (3H, s), 4.31 (1H, t, J=6.3 Hz), 6.70–6.90 (1H, m), 7.00–7.30 (2H, m)
MASS (APCI): 228 (M+H)+ (free)

(3) 3-Methoxy-4-trifluoromethyl-D-phenylalanine methyl ester hydrochloride mp: 158–165° C.
IR (KBr): 3326, 3200–2300, 1739, 1617, 1504, 1328 cm$^{-1}$
NMR (D$_2$O, δ): 3.29 (1H, dd, J=7.5 and 14.4 Hz), 3.42 (1H, dd, J=5.7 and 14.4 Hz), 3.85 (3H, s), 3.90 (3H, s), 4.46–4.55 (1H, m), 7.00 (1H, d, J=8.0 Hz), 7.12 (1H, s), 7.65 (1H, d, J=8.0 Hz)
MASS (APCI): 277 (M+H)+ (free)

(4) 4-Fluoro-3-methyl-D-phenylalanine methyl ester hydrochloride

IR (Nujol): 3200, 1740, 1490, 1450, 1240 cm$^{-1}$
NMR (DMSO-d$_6$, δ): 2.22 (3H, s), 3.00–3.17 (2H, m), 3.68 (3H, s), 4.21–4.28 (1H, m), 7.07–7.18 (3H, m), 8.67 (3H, s)
MASS (APCI): 212 (M+H)+ (free)

(5) 3-Fluoro-4-methyl-D-phenylalanine methyl ester hydrochloride

IR (Nujol): 1740, 1580, 1510, 1450 cm$^{-1}$
NMR (DMSO-d$_6$, δ): 2.21 (3H, s), 3.13 (2H, d, J=6.0 Hz), 3.69 (3H, s), 4.29 (1H, t, J=6.0 Hz), 6.95–7.28 (3H, m), 8.70 (3H, s)
MASS (APCI): 212 (M+H)+ (free)

(6) 4-Fluoro-D-phenylalanine methyl ester hydrochloride mp: 197.3–197.8° C.
IR (KBr): 2989, 2956, 2910, 1745, 1741, 1504, 1490, 1450, 1240, 825 cm$^{-1}$
NMR (DMSO-d$_6$, δ): 3.10 (1H, dd, J=7.0 and 14.0 Hz), 3.18 (1H, dd, J=6.4 and 14.0 Hz), 3.67 (3H, s), 4.26 (1H, dd, J=6.4 and 7.0 Hz), 7.11–7.33 (4H, m), 8.67 (3H, br s)
MASS: 198 (M+H)+ (free)

(7) 4-Chloro-D-phenylalanine methyl ester hydrochloride mp: 210–211° C.
IR (KBr): 1743, 1707, 1693, 1645, 1547, 1541, 1514, 1495, 1454, 1240, 1186, 1147, 1126, 1099, 1061, 1024 cm$^{-1}$
NMR (DMSO-d$_6$, δ): 3.00–3.30 (2H, m), 3.68 (3H, s), 4.28 (1H, t, J=6.5 Hz), 7.28 (2H, d, J=8.4 Hz), 7.40 (2H, d, J=8.4 Hz)
MASS (APCI): 214 (M+H)+ (free)

(8) 4-Trifluoromethyl-D-phenylalanine methyl ester hydrochloride mp: 198–199° C.
IR (KBr): 3199, 2864, 1741 cm$^{-1}$
NMR (DMSO-d$_6$, δ): 3.10–3.30 (2H, m), 3.69 (3H, s), 4.35 (1H, t, J=6.4 Hz), 7.51 (2H, d, J=8.1 Hz), 7.71 (2H, d, J=8.1 Hz)
MASS (APCI): 248 (M+H)+ (free)

Preparation 34

The following compounds were obtained according to a similar manner to that of Preparation 19.

(1) (2R)-2-(2-Chloroacetylamino)-3-(4-chloro-3-methoxyphenyl)propionic acid methyl ester mp: 68–69° C.
IR (KBr): 3303, 2954, 1739, 1654, 1538 cm$^{-1}$
NMR (CDCl$_3$, δ): 3.13 (2H, d, J=6.0 Hz), 3.75 (3H, s), 3.88 (3H, s), 4.05 (2H, s), 4.84–4.93 (1H, m), 6.65 (1H, dd, J=1.8 and 8.1 Hz), 6.67 (1H, d, J=1.8 Hz), 7.28 (1H, d, J=8.1 Hz)
MASS (APCI): 320 (M+H)+, 288, 260

(2) (2R)-2-(2-Chloroacetylamino)-3-(4-fluoro-3-methoxyphenyl)propionic acid methyl ester mp: 86–87° C.
IR (KBr): 1726, 1687, 1649, 1614, 1550, 1518, 1454, 1423, 1419, 1362, 1331, 1273, 1227, 1213, 1186 cm$^{-1}$
NMR (CDCl$_3$, δ): 3.12 (2H, d, J=5.8 Hz), 3.75 (3H, s), 3.87 (3H, s), 4.05 (2H, s), 4.87 (1H, dt, J=8.0 and 5.8 Hz), 6.40–7.20 (3H, m)
MASS (APCI): 304 (M+H)+

(3) (2R)-2-(2-Chloroacetylamino)-3-(3,4-difluorophenyl)-propionic acid methyl ester IR (Neat): 3305, 1470, 1675, 1660, 1515 cm$^{-1}$
NMR (DMSO-d$_6$, δ): 2.87–3.11 (2H, m), 3.63 (2H, s), 4.03 (3H, s), 4.48–4.57 (1H, m), 7.03–7.41 (3H, m), 8.68 (1H, d, J=7.8 Hz)
MASS (APCI): 292 (M+H)$^+$

(4) (2R)-2-(2-Chloroacetylamino)-3-[3-methoxy-4-(trifluoromethyl)phenyl]propionic acid methyl ester mp: 108–109° C.
IR (KBr): 3315, 2965, 1751, 1648, 1536, 1459, 1421 cm$^{-1}$
NMR (CDCl$_3$, δ): 3.10–3.29 (2H, m), 3.76 (3H, s), 3.89 (3H, s), 4.05 (2H, s), 4.87–4.97 (1H, m), 6.73–6.77 (2H, m), 7.00–7.05 (1H, m), 7.75 (1H, d, J=8.3 Hz)
MASS (APCI): 354 (M+H)$^+$ 312

(5) (2R)-2-(2-Chloroacetylamino)-3-(4-fluoro-3-methylphenyl)propionic acid methyl ester IR (Nujol): 3300, 1730, 1540, 1500, 1450 cm$^{-1}$
NMR (DMSO-d$_6$, δ): 2.19 (3H, s), 2.82–3.06 (2H, m), 3.62 (3H, s), 4.06 (2H, s), 4.32–4.53 (1H, m), 6.97–7.13 (3H, m), 8.66 (1H, d, J=7.8 Hz)
MASS (APCI): 288 (M+H)$^+$

(6) (2R)-2-(2-Chloroacetylamino)-3-(3-fluoro-4-methylphenyl)propionic acid methyl ester IR (Nujol): 3300, 1740, 1660, 1540, 1450, 1360 cm$^{-1}$
NMR (DMSO-d$_6$, δ): 2.19 (3H, s), 2.85–3.10 (2H, m), 3.63 (3H, s), 4.06 (2H, s), 4.45–4.56 (1H, m), 6.92–7.22 (3H, m), 8.68 (1H, d, J=7.8 Hz)
MASS (APCI): 288 (M+H)$^+$

(7) (2R)-2-(2-Chloroacetylamino)-3-(4-fluorophenyl)-propionic acid methyl ester IR (KBr): 3330, 1735, 1646, 1538, 1509, 1448, 1367, 1226, 1151 cm$^{-1}$
NMR (CDCl$_3$, δ): 3.09 (1H, dd, J=5.8 and 14.0 Hz), 3.16 (1H, dd, J=5.8 and 14.0 Hz), 3.74 (3H, s), 4.03 (2H, s), 4.85 (1H, ddd, J=5.8, 5.8 and 7.9 Hz), 6.95–7.12 (5H, m)
MASS: 274 (M+H)$^+$

(8) (2R)-2-(2-Chloroacetylamino)-3-(4-chlorophenyl)-propionic acid methyl ester mp: 87–88° C.
IR (KBr): 1738, 1662, 1537, 1495, 1491, 1446, 1408, 1363, 1265, 1209, 1119, 1090, 1036, 1016 cm$^{-1}$
NMR (CDCl$_3$, δ): 2.90–3.30 (3H, m), 3.75 (3H, s), 4.03 (2H, s), 4.70–5.00 (1H, m), 7.05 (2H, d, J=8.0 Hz), 7.28 (2H, d, J=8.0 Hz)
MASS (APCI): 290 (M+H)$^+$

(9) (2R)-2-(2-Chloroacetylamino)-3-[4-(trifluoromethyl)-phenyl]propionic acid methyl ester mp: 83–84° C.
IR (KBr): 3294, 1741, 1655, 1547 cm$^{-1}$
NMR (DMSO-d$_6$, δ): 3.12–3.32 (2H, m), 3.76 (3H, s), 4.04 (2H, s), 4.86–4.96 (1H, m), 7.25 (2H, d, J=8.1 Hz), 7.57 (2H, d, J=8.1 Hz)
MASS (APCI): 324 (M+H)$^+$ Preparation 35

The following compounds were obtained according to a similar manner to that of Preparation 20.

(1) (3R)-1-Benzyl-3-(4-chloro-3-methoxybenzyl)piperazine-2,5-dione mp: 149–150° C.
[α]$_D^{27}$: +6.38° (C=0.47, MeOH)
IR (KBr): 3253, 1658, 1461 cm$^{-1}$
NMR (DMSO-d$_6$, δ): 2.94 (1H, dd, J=4.7 and 13.4 Hz), 2.96 (1H, d, J=17.4 Hz), 3.14 (1H, dd, J=4.5 and 13.4 Hz), 3.56 (1H, d, J=17.4 Hz), 3.76 (3H, s), 4.21 (1H, d, J=14.6 Hz), 4.30–4.35 (1H, m), 4.61 (1H, d, J=14.6 Hz), 6.66 (1H, dd, J=1.8 and 8.0 Hz), 6.91 (1H, d, J=1.8 Hz), 7.04–7.11 (2H, m), 7.17 (1H, d, J=8.0 Hz), 7.26–7.33 (3H, m), 8.38 (1H, br s)
MASS (APCI): 359 (M+H)$^+$

(2) (3R)-1-Benzyl-3-(4-fluoro-3-methoxybenzyl)piperazine-2,5-dione mp: 177–179° C.
IR (KBr): 3240, 1658, 1516, 1464 cm$^{-1}$
NMR (CDCl$_3$, δ): 3.00–3.30 (3H, m), 3.61 (1H, d, J=17.7 Hz), 3.84 (3H, s), 4.20–4.60 (3H, m), 6.29 (1H, br s), 6.60–7.50 (8H, m)
MASS (APCI): 343 (M+H)$^+$

(3) (3R)-1-Benzyl-3-(3,4-difluorobenzyl)piperazine-2,5-dione

IR (KBr): 3313, 3255, 1650, 1515, 1465, 1275 cm$^{-1}$
NMR (DMSO-d$_6$, δ): 2.90–4.70 (7H, m), 6.94–7.32 (8H, m), 8.35 (1H, s)
MASS (APCI): 331 (M+H)$^+$

(4) (3R)-1-Benzyl-3-[3-methoxy-4-(trifluoromethyl)benzyl]-piperazine-2,5-dione IR (KBr): 3315, 1751, 1648, 1536, 1459, 1421 cm$^{-1}$
NMR (DMSO-d$_6$, δ): 2.89–3.25 (2H, m), 3.19 (1H, d, J=17.5 Hz), 3.62 (1H, d, J=17.5 Hz), 3.77 (3H, s), 4.15 (1H, d, J=14.5 Hz), 4.30–4.35 (1H, m), 4.68 (1H, d, J=14.5 Hz), 6.80 (1H, d, J=8.0 Hz), 7.00–7.41 (7H, m), 8.41 (1H, br s)
MASS (APCI): 393 (M+H)$^+$, 351

(5) (3R)-1-Benzyl-3-(4-fluoro-3-methylbenzyl)piperazine-2,5-dione

[α]$_D^{28}$: −15.60° (C=0.5, DMF)
IR (Nujol): 3250, 3225, 1650, 1430, 1320, 1250 cm$^{-1}$
NMR (DMSO-d$_6$, δ): 2.13 (3H, s), 2.81–4.65 (7H, m), 6.83–7.34 (8H, m), 8.33 (1H, s)
MASS (APCI): 327 (M+H)$^+$

(6) (3R)-1-Benzyl-3-(3-fluoro-3-methylbenzyl)piperazine-2,5-dione

[α]$_D^{27}$: −16.90° (C=0.5, DMF)
IR (Nujol): 3250, 1680, 1640, 1460, 1320 cm$^{-1}$
NMR (DMSO-d$_6$, δ): 2.17 (3H, s), 2.84–4.69 (7H, m), 6.80–7.34 (8H, m), 8.35 (1H, s)
MASS (APCI): 327 (M+H)$^+$ (7) (2R)-2-[N-(Benzylaminoacetyl)amino]-3-(4-fluorophenyl)-propionic acid methyl ester

MASS: 345 (M+H)+

(8) (3R)-1-Benzyl-3-(4-fluorobenzyl)piperazine-2,5-dione mp: 190.1–190.8° C.
IR (KBr): 1671, 1656, 1509, 1448, 1334, 1162 cm$^{-1}$
NMR (CDCl$_3$, δ): 3.08 (1H, d, J=4.4 and 14.0 Hz), 3.19 (1H, d, J=5.9 and 14.0 Hz), 3.05 (1H, d, J=17.7 Hz), 3.56 (1H, d, J=17.7 Hz), 4.33 (1H, m), 4.41 (1H, d, J=14.3 Hz), 4.54 (1H, d, J=14.3 Hz), 6.38–7.35 (10H, m)
MASS: 313 (M+H)+

(9) (3R)-1-Benzyl-3-(4-chlorobenzyl)piperazine-2,5-dione mp: 181–182° C.
IR (KBr): 1678, 1649, 1564, 1550, 1516, 1489, 1462, 1433, 1408, 1325, 1273, 1178, 1112, 1090, 1063 cm$^{-1}$
NMR (CDCl$_3$, δ): 2.80–3.30 (3H, m), 3.57 (1H, d, J=17.6 Hz), 4.20–4.40 (2H, m)), 4.60 (1H, d, J=14.3 Hz), 6.80–7.50 (9H, m)
MASS (APCI): 329 (M+H)+

(10) (3R)-1-Benzyl-3-[4-(trifluoromethyl)benzyl]piperazine-2,5-dione mp: 180–181° C.
IR (KBr): 3257, 1678, 1651 cm$^{-1}$
NMR (DMSO-d$_6$, δ): 2.86 (1H, d, J=17.3 Hz), 3.00 (1H, dd, J=4.8 and 13.5 Hz), 3.25 (1H, d, J=4.5 and 13.5 Hz), 3.59 (1H, d, J=17.3 Hz), 4.08 (1H, d, J=14.3 Hz), 4.30–4.40 (1H, m), 4.73 (1H, d, J=14.3 Hz), 7.05–7.32 (7H, m), 7.47 (2H, d, J=8.2 Hz)
MASS (APCI): 363 (M+H)+

Preparation 36

The following compounds were obtained according to a similar manner to that of Preparation 21.

(1) (2R)-4-Benzyl-1-[3,5-bis(trifluoromethyl)benzoyl]-2-(4-chloro-3-methoxybenzyl)piperazine IR (Neat): 1643, 1517 cm$^{-1}$
NMR (CDCl$_3$, δ): 2.00–5.20 (14H, m), 6.20–8.00 (11H, m)
MASS (APCI): 571 (M+H)+

(2) (2R)-1-[3,5-Bis(trifluoromethyl)benzoyl]-2-(3,4-difluorobenzyl)-4-benzylpiperazine IR (Neat): 1645, 1515, 1435, 1280, 1180, 1140 cm$^{-1}$
NMR (DMSO-d$_6$, δ): 2.06–4.82 (11H, m), 6.61–8.19 (11H, m)
MASS (APCI): 543 (M+H)+

Preparation 37

A solution of (2R)-4-benzyl-1-[3,5-bis(trifluoromethyl)-benzoyl]-2-(4-chloro-3-methoxybenzyl)piperazine (2.23 g) and 1-chloroethyl chloroformate (0.61 ml) in 1,2-dichloroethane (10 ml) was stirred under reflux for 15 hours. After cooling, the reaction mixture was concentrated under reduced pressure. The resulting syrup was dissolved into methanol (10 ml) and the solution was stirred under reflux for 2 hours. After cooling, the reaction mixture was concentrated under reduced pressure and the resulting powder was collected by filtration to give a yellow powder of (2R)-1-[3,5-bis(trifluoromethyl)benzoyl]-2-(4-chloro-3-methoxybenzyl)piperazine hydrochloride (2.00 g).

mp: 70–71° C.

MASS (APCI): 481 (M+H)+

Preparation 38

A solution of boron tribromide in dichloromethane (1M solution, 6.0 ml) was added dropwise over 20 minutes to an ice-cooled solution of (2R)-1-[3,5-bis(trifluoromethyl)-penzoyl]-2-(4-chloro-3-methoxybenzyl)piperazine hydrochloride (0.98 g) in dichloromethane (5 ml). After being stirred at the same temperature for 2 hours, followed by at room temperature for 12 hours, an additional solution of boron tribromide in dichloromethane (1M solution, 4.0 ml) was added, and the whole was stirred at room temperature for further 4 hours. The resulting mixture was poured into aqueous saturated sodium hydrogen carbonate solution and the whole was stirred for 1 hour. The organic layer was separated, dried over magnesium sulfate and evaporated under reduced pressure. The residue was purified by column chromatography on silica gel using a mixed solvent of dichloromethane and methanol (20:1). The fractions containing the objective compound were collected and evaporated under reduced pressure to give (2R)-1-[3,5-bis-(trifluoromethyl)benzoyl]-2-(4-chloro-3-hydroxybenzyl)-piperazine (0.67 g) as a foam.

IR (Neat): 3400–3000, 1635 cm$^{-1}$
NMR (DMSO-d$_6$, δ): 2.60–4.80 (10H, m), 6.28–7.20 (3H, m), 7.41 (1H, s), 7.75 (1H, s), 8.14 (1H, d, J=8.2 Hz), 10.00 (1H, br s)
MASS (APCI): 467 (M+H)+

Preparation 39

The following compounds were obtained according to a similar manner to that of Preparation 38.

(1) (2R)-4-Benzyl-2-(4-chloro-3-hydroxybenzyl)piperazine mp: 65–68° C.
IR (KBr): 2939, 2813, 1444, 1429, 1294, 1236, 1136, 1047 cm$^{-1}$
NMR (DMSO-d$_6$, δ): 1.60–4.00 (11H, m), 6.60 (1H, dd, J=1.6 and 8.0 Hz), 6.78 (1H, d, J=1.6 Hz), 7.16–7.40 (6H, m)

(2) (2R)-1-[3,5-Bis(trifluoromethyl)benzoyl]-2-(4-fluoro-3-hydroxybenzyl)piperazine mp: 82–86° C.
IR (KBr): 3282, 1637, 1282, 1182, 1136 cm$^{-1}$
NMR (CDCl$_3$, δ): 2.20–5.20 (10H, m), 6.10–8.10 (6H, m)
MASS (APCI): 451 (M+H)+

(3) (3R)-1-Benzyl-3-(3-hydroxy-4-methylbenzyl)piperazine

IR (KBr): 1649, 1516 cm$^{-1}$
NMR (CDCl$_3$, δ): 1.95–2.20 (2H, m), 2.20 (3H, s), 2.57–3.06 (7H, m), 3.51 (1H, d, J=13.1 Hz), 3.52 (1H, d, J=13.1 Hz), 6.60 (1H, d, J=7.4 Hz), 6.61 (1H, s), 7.03 (1H, d, J=7.4 Hz), 7.20–7.35 (5H, m)
MASS (APCI): 297 (M+H)+

Preparation 40

To a solution of (2R)-2-(4-chloro-3-hydroxybenzyl)-4-benzylpiperazine (3.78 g) and triethylamine (5.71 ml) in dichloromethane was added 4-dimethylaminopyridine (0.29 g) and tert-butyldimethylsilyl chloride (5.30 g) successively with ice bath cooling under nitrogen atmosphere. After stirring overnight at room temperature, water (50 ml) was added to the mixture and the organic layer was separated, washed with brine, dried over sodium sulfate, and evaporated in vacuo. The residue was purified by column chromatography on silica gel with a mixture of dichloromethane and methanol (10:1) as eluent to give (2R)-4-benzyl-2-[4-chloro-3-(tert-butyldimethylsilyloxy)benzyl]piperazine (4.11 g) as an oil.

IR (Neat): 1600, 1575, 1485, 1420, 1295, 1250, 1170, 1140 cm$^{-1}$

NMR (CDCl$_3$, δ): 0.15 (6H, s), 0.96 (9H, s), 1.80 (1H, t, J=10.0 Hz), 1.94–2.98 (8H, m), 3.40 (1H, d, J=13.0 Hz), 3.48 (1H, d, J=13.0 Hz), 6.60–7.34 (8H, m)

MASS (APCI): 431 (M+H)$^+$, 397

Preparation 41

1-[3-(Dimethylamino)propyl]-3-ethylcarbodiimide hydrochloride (1.93 g) was added to a mixture of (2R)-4-benzyl-2-[4-chloro-3-(tert-butyldimethylsilyloxy)benzyl]-piperazine (2.90 g) and 3-methoxy-5-(trifluoromethyl)benzoic acid (1.48 g), 1-hydroxybenzotriazole (1.14 g) in dichloromethane (18 ml) at room temperature. After being stirred for 6 hours at the same temperature, the reaction mixture was poured into a mixed solvent of water (25 ml) and dichloromethane (15 ml). The aqueous layer was adjusted to pH 9 with aqueous sodium hydrogen carbonate solution. The organic layer was separated, washed with brine, dried over sodium sulfate, and concentrated under reduced pressure. The resulting residue was purified by column chromatography on silica gel (52 g) using a mixed solvent of hexane and ethyl acetate (2:1). The fractions containing the objective compound was collected and evaporated under reduced pressure to give a syrup of (2R)-1-[3-methoxy-5-(trifluoromethyl)-benzoyl]-2-[4-chloro-3-(tert-butyldimethylsilyloxy)benzyl]-4-benzylpiperazine (3.3 g).

IR (Neat): 2937, 1639, 1603, 1421, 1250, 1173, 1132, 847 cm$^{-1}$

NMR (CDCl$_3$, δ): 0.13 (6H, s), 1.00 (9H, s), 1.60–5.10 (11H, m), 3.81 (3H, s), 6.30–8.20 (11H, m)

MASS (APCI): 633 (M)$^+$

Preparation 42

The following compounds were obtained according to a similar manner to that of Preparation 37.

(1) (2R)-1-[3-Methoxy-5-(trifluoromethyl)benzoyl]-2-(4-chloro-3-hydroxybenzyl)piperazine mp: 154–157° C.
IR (KBr): 3265, 2956, 1624, 1427, 1173, 1128 cm$^{-1}$
NMR (DMSO-d$_6$, δ): 2.20–4.90 (10H, m), 3.82 (3H, s), 6.20–7.30 (6H, m), 10.02 (1H, br)
MASS (APCI): 429 (M+H)$^+$ (2) (2R)-1-[3-Trifluoromethyl-5-(methylthio)benzoyl]-2-[4-chloro-3-(tert-butyldimethylsilyloxy)benzyl]piperazine IR (Neat): 1645, 1630, 1420, 1170, 1130 cm$^{-1}$
NMR (CDCl$_3$, δ): 0.18 (6H, s), 1.02 (9H, s), 2.48 (3H, s), 2.60–5.10 (10H, m), 6.28–8.26 (6H, m)
MASS (APCI): 559 (M+H)$^+$ (3) (2R)-1-[3,5-Bis(trifluoromethyl)benzoyl]-2-[4-fluoro-3-methoxybenzyl]piperazine hydrochloride mp: 127–134° C.
IR (KBr): 2970, 2947, 1645, 1520, 1281, 1184, 1136 cm$^{-1}$
NMR (DMSO-d$_6$, δ): 2.60–5.20 (12H, m), 6.50–8.30 (6H, m), 9.60 (2H, br)
MASS (APCI): 465 (M+H)$^+$ (free)

(4) (2R)-2-(4-Fluoro-3-methoxybenzyl)-1-[3-methoxy-5-(trifluoromethyl)benzoyl]piperazine hydrochloride IR (KBr): 1643, 1606, 1518, 1464, 1423, 1377, 1350, 1321, 1242, 1215, 1173, 1126, 1053, 1038 cm$^{-1}$
NMR (DMSO-d$_6$, δ): 2.30–5.30 (16H, m), 6.30–7.50 (6H, m)
MASS (APCI): 427 (M+H)$^+$ (free)

(5) (2R)-1-[3,5-Bis(trifluoromethyl)benzoyl]-2-(3,4-difluorobenzyl)piperazine hydrochloride IR (KBr): 3435, 2940, 2800, 1645, 1520, 1435, 1365, 1280, 1185, 1135 cm$^{-1}$
NMR (DMSO-d$_6$, δ): 2.50–5.17 (9H, m), 6.60–8.45 (6H, m), 9.63 (2H, br s)
MASS (APCI): 453 (M+H)$^+$ (free)

(6) (2R)-1-[3,5-Bis(trifluoromethyl)benzoyl]-2-[3-methoxy-4-(trifluoromethyl)benzyl]piperazine IR (Neat): 2952, 1639, 1623, 1461, 1423, 1124 cm$^{-1}$
NMR (CDCl$_3$, δ): 2.60–5.20 (13H, m), 6.40–8.00 (6H, m)
MASS (APCI): 515 (M+H)$^+$ (7) (2R)-1-[3-Methoxy-5-(trifluoromethyl)benzoyl]-2-[3-methoxy-4-(trifluoromethyl)benzyl]piperazine IR (Neat): 2950, 1637, 1461, 1423, 1317 cm$^{-1}$
NMR (CDCl$_3$, δ): 2.60–5.20 (15H, m), 6.60–7.60 (6H, m)
MASS (APCI): 477 (M+H)$^+$ (8) (2R)-1-[3,5-Bis(trifluoromethyl)benzoyl]-2-(4-fluoro-3-methylbenzyl)piperazine IR (Neat): 3350, 1640, 1500, 1430, 1380, 1350, 1275 cm$^{-1}$
NMR (DMSO-d$_6$, δ): 2.00–4.84 (12H, m), 6.69–8.34 (7H, m)
MASS (APCI): 449 (M+H)$^+$ (9) (2R)-1-[3,5-Bis(trifluoromethyl)benzoyl]-2-(3-fluoro-4-methylbenzyl)piperazine IR (Neat): 3300, 1625, 1425, 1275, 1120 cm$^{-1}$
NMR (DMSO-d$_6$, δ): 2.18 (3H, s), 2.40–4.86 (9H, m), 6.62–8.20 (6H, m)
MASS (APCI): 449 (M+H)$^+$

(10) (2R)-2-(4-Fluorobenzyl)-1-[3-methoxy-5-(trifluoromethyl)benzoyl]piperazine hydrochloride mp: 78.8–80.3° C.
IR (KBr): 1513, 1423, 1349, 1172, 1126, 1054 cm$^{-1}$
NMR (DMSO-d$_6$, δ): 2.50–5.03 (9H, m), 3.82 (3H, s), 6.94–7.25 (8H, m), 9.56 (1H, br s)
MASS (APCI): 397 (M+H)$^+$ (free)

(11) (2R)-1-[3,5-Bis(trifluoromethyl)benzoyl]-2-(4-chlorobenzyl)piperazine hydrochloride mp: 240–260° C.
IR (Neat): 1658, 1496, 1437, 1387, 1362, 1331, 1282, 1186, 1132, 1101, 1059, 1018 cm$^{-1}$
NMR (CDCl$_3$, δ): 2.00–5.30 (9H, m), 6.70–8.50 (7H, m)
MASS (APCI): 451 (M+H)$^+$ (free)

(12) (2R)-2-(4-Chlorobenzyl)-1-[3-methoxy-5-(trifluoromethyl)benzoyl]piperazine hydrochloride IR (KBr): 1643, 1605, 1489, 1464, 1423, 1377, 1350, 1319, 1271, 1242, 1175, 1128, 1097, 1053 cm$^{-1}$
NMR (DMSO-d$_6$, δ): 2.00–5.40 (13H, m), 6.20–8.20 (7H, m)
MASS (APCI): 413 (M+H)$^+$ (free)

(13) (2R)-1-(3,5-Bis(trifluoromethyl)benzoyl]-2-[4-(trifluoromethyl)benzyl]piperazine NMR (CDCl$_3$, δ): 2.30–5.30 (9H, m), 7.26–7.88 (7H, m)
MASS (APCI): 485 (M+H)$^+$

(14) (2R)-1-[3-Methoxy-5-(trifluoromethyl)benzoyl]-2-[4-(trifluoromethyl)benzyl]piperazine IR (Neat): 2951, 1632, 1608 cm$^{-1}$
NMR (CDCl$_3$, δ): 2.70–5.10 (9H, m), 3.80 (3H, s), 6.72–7.87 (7H, m)
MASS (APCI): 447 (M+H)$^+$

(15) (2R)-1-[3-Methoxy-5-(trifluoromethyl)benzoyl]-2-(2-naphthylmethyl)piperazine $[\alpha]_D^{28.8}$: −46.15° (C=0.26, MeOH)
IR (Neat): 3740, 1630 cm$^{-1}$
NMR (CDCl$_3$, δ): 2.5–5.4 (9H, m), 3.55 (3H, s), 6.51 (1H, br s), 6.87 (1H, br s), 7.06 (1H, br s), 6.8–7.9 (7H, m)
MASS (APCI): 429 (M+H)$^+$

(16) (2R)-2-[(1H-Indol-3-yl)methyl]-1-[3-methoxy-5-(trifluoromethyl)benzoyl]piperazine IR (Neat): 3280, 1620, 1459, 1427 cm$^{-1}$
NMR (CDCl$_3$; δ): 2.60–3.00 (10H, m), 3.74 (3H, s), 6.70–7.40 (8H, m), 8.25–8.52 (1H, m)
MASS (APCI): 418 (M+H)$^+$

(17) (2R)-1-tert-Butoxycarbonyl-2-(3-hydroxy-4-methylbenzyl)piperazine

IR (KBr): 1674 cm$^{-1}$
NMR (CDCl$_3$, δ): 1.37 (9H, s), 2.20 (3H, s), 2.72–3.15 (8H, m), 3.90–3.93 (1H, m), 4.16 (1H, br s), 6.62 (1H, s), 6.68 (1H, d, J=7.6 Hz), 7.02 (1H, d, J=7.6 Hz)
MASS (APCI): 207 (M+H-Boc)$^+$

(18) (2R)-1-(tert-Butoxycarbonyl)-2-(4-chlorobenzyl)-piperazine $[\alpha]_D^{27.2}$: +23.33° (C=0.39, MeOH)
IR (Neat): 3340, 2980, 2870, 2830, 1690, 1410, 1370 cm$^{-1}$
NMR (CDCl$_3$, δ): 1.36 (9H, s), 2.6–3.2 (7H, m), 3.90 (1H, br), 4.18 (1H, br s), 7.15 (2H, d, J=8.4 Hz), 7.25 (2H, d, J=8.4 Hz)
MASS (APCI): 311 (M+H)$^+$ Preparation 43

The following compounds were obtained according to a similar manner to that of Preparation 41.

(1) (2R)-1-[3-Trifluoromethyl-5-(methylthio)benzoyl]-2-[4-chloro-3-(tert-butyldimethylsilyloxy)benzyl]-4-benzylpiperazine IR (Neat): 1645, 1490, 1420, 1300, 1170, 1130 cm$^{-1}$
NMR (CDCl$_3$, δ): 0.15 (6H, s), 1.00 (9H, s), 1.95–5.02 (11H, m), 2.48 (3H, s), 6.20–8.25 (11H, m)
MASS (APCI): 649 (M+H)$^+$, 615

(2) (2R)-4-Benzyl-2-(4-fluoro-3-methoxybenzyl)-1-[3-methoxy-5-(trifluoromethyl)benzoyl]piperazine IR (Neat): 1738, 1643, 1628, 1616, 1604, 1516, 1464, 1454, 1417, 1371, 1342, 1273, 1099, 1055 cm$^{-1}$
NMR (CDCl$_3$, δ): 0.60–5.20 (17H, m), 6.00–7.50 (11H, m)
MASS (APCI): 517 (M+H)$^+$ (3) (2R)-4-Benzyl-1-[3-methoxy-5-(trifluoromethyl)benzoyl]-2-[3-methoxy-4-(trifluoromethyl)benzyl]piperazine IR (Neat): 2811, 1643, 1280, 1180, 1137 cm$^{-1}$
NMR (CDCl$_3$, δ): 2.20–5.20 (17H, m), 6.40–7.50 (11H, m)
MASS (APCI): 567 (M+H)$^+$ (4) (2R)-4-Benzyl-2-(4-fluorobenzyl)-1-[3-methoxy-5-(trifluoromethyl)benzoyl]piperazine IR (Neat): 1639, 1509, 1460, 1423, 1344, 1128, 1010 cm$^{-1}$
NMR (CDCl$_3$, δ): 2.07 (1H, br), 2.73–4.91 (8H, m), 6.57–7.53 (12H, m)
MASS: 487 (M+H)$^+$ (5) (2R)-4-Benzyl-1-[3,5-bis(trifluoromethyl)benzoyl]-2-(4-chlorobenzyl)piperazine IR (Neat): 1738, 1676, 1647, 1628, 1618, 1498, 1454, 1417, 1387, 1273, 1084, 1068 cm$^{-1}$
NMR (CDCl$_3$, δ): 0.60–5.20 (11H, m), 6.40–8.70 (12H, m)
MASS (APCI): 541 (M+H)$^+$ (6) (2R)-4-Benzyl-2-(4-chlorobenzyl)-1-[3-methoxy-5-(trifluoromethyl)benzoyl]piperazine IR (Neat): 1707, 1678, 1643, 1630, 1618, 1604, 1516, 1496, 1489, 1477, 1454, 1417, 1392, 1375, 1342, 1317 cm$^{-1}$
NMR (CDCl$_3$, δ): 0.60–5.20 (14H, m), 6.40–8.20 (12H, m)
MASS (APCI): 503 (M+H)$^+$ (7) (2R)-4-Benzyl-1-[3,5-bis(trifluoromethyl)benzoyl]-2-[4-(trifluoromethyl)benzyl]piperazine IR (Neat): 2950, 2800, 1765, 1740, 1640 cm$^{-1}$
NMR (DMSO-d$_6$, δ): 1.70–4.30 (11H, m), 7.13 (1H, d, J=7.8 Hz), 7.20–7.70 (10H, m), 8.13 (1H, d, J=7.8 Hz)
MASS (APCI): 575 (M+H)$^+$ (8) (2R)-4-Benzyl-1-[3-methoxy-5-(trifluoromethyl)benzoyl]-2-[4-(trifluoromethyl)benzyl]piperazine IR (Neat): 2945, 2812, 1643 cm$^{-1}$
NMR (CDCl$_3$, δ): 2.04–5.10 (11H, m), 3.81 (3H, s), 6.73–7.93 (12H, m)
MASS (APCI): 537 (M+H)$^+$ (9) (2R)-4-Benzyl-1-[3-methoxy-5-(trifluoromethyl)benzoyl]-2-(2-naphthylmethyl)piperazine

[α]$_D^{28.8}$: −18.34° (C=0.35, MeOH)
IR (Neat): 3740, 1640 cm$^{-1}$
NMR (CDCl$_3$, δ): 1.9–2.4 (2H, m), 2.6–4.0 (11H, m), 4.4–5.2 (1H, m), 6.4–7.9 (15H, m)
MASS (APCI): 519 (M+H)$^+$

(10) (2R)-4-Benzyl-2-[(1H-indol-3-yl)methyl]-1-[3-methoxy-5-(trifluoromethyl)benzoyl]piperazine IR (Neat): 3280, 1620, 1459 cm$^{-1}$
NMR (CDCl$_3$, δ): 2.00–5.20 (14H, m), 6.60–7.60 (13H, m), 7.90 (1H, br s)
MASS (APCI): 508 (M+H)$^+$ Preparation 44

To a solution of 4-fluoro-3-methoxybenzaldehyde (5 g) in methanol (25 ml) was added dropwise sodium borohydride (368 mg) in 0.1N sodium hydroxide aqueous solution (5 ml) in water bath and the whole was stirred for 1 hour. After the mixture was evaporated under reduced pressure, ethyl acetate and water were added thereto. The organic layer was separated and the water layer was further extracted with ethyl acetate. The combined organic layer was dried over magnesium sulfate and concentrated in vacuo to give 4-fluoro-3-methoxybenzyl-alcohol (5.22 g) as an oil.

IR (Neat): 1610, 1516, 1462, 1417, 1315, 1277, 1149, 1115, 1032 cm$^{-1}$
NMR (CDCl$_3$, δ): 1.75 (1H, br s), 3.90 (3H, s), 4.64 (2H, s), 6.70–7.20 (3H, m)

Preparation 45

The following compounds were obtained according to a similar manner to that of Preparation 26.

(1) 4-Fluoro-3-methoxybenzyl chloride

IR (Neat): 1608, 1516, 1462, 1417, 1325, 1284, 1271, 1219, 1155, 1119, 1032 cm$^{-1}$
NMR (CDCl$_3$, δ): 3.91 (3H, s), 4.55 (2H, s), 6.70–7.20 (3H, m)

(2) 3-Methoxy-4-(trifluoromethyl)benzyl chloride

IR (Neat): 1606, 1459, 1272, 1174 cm$^{-1}$
NMR (CDCl$_3$, δ): 3.91 (3H, s), 4.73 (2H, s), 6.95 (1H, dd, J=0.6 and 8.0 Hz), 7.04 (1H, d, J=0.6 Hz), 7.53 (1H, d, J=8.0 Hz)

Preparation 46

The following compound was obtained according to a similar manner to that of Preparation 24.

(2R)-1-[3,5-Bis(trifluoromethyl)benzoyl]-2-(4-fluoro-3-methoxybenzyl)piperazine

IR (Neat): 1641, 1633, 1626, 1514, 1475, 1462, 1452, 1446, 1435, 1423, 1417, 1385, 1340, 1336, 1273, 1095, 1063, 1045 cm$^{-1}$ NMR (CDCl$_3$, δ): 0.60–5.40 (12H, m), 6.20–8.60 (6H, m)
MASS (APCI): 465 (M+H)$^+$ Preparation 47

The following compound was obtained according to a similar manner to that of Preparation 17 followed by a similar manner to that of Preparation 18.

3,4-Difluorophenyl-D-alanine methyl ester hydrochloride

IR (KBr): 3400, 1735, 1610, 1235 cm$^{-1}$
NMR (DMSO-d$_6$, δ): 3.16 (2H, d, J=6.6 Hz), 3.70 (3H, s), 4.33 (1H, t, J=6.6 Hz), 7.05–7.52 (3H, m), 8.65 (3H, s)
MASS (APCI): 216 (M+H)$^+$ (free)

Preparation 48

28% Sodium methoxide in methanol (50 ml) was added to a solution of 3-fluoro-4-(trifluoromethyl)benzoic acid (20.8 g) in dimethylsulfoxide (200 ml). The mixture was stirred at 90° C. for 3.5 hours. After cooling at room temperature, the resulting mixture was poured into ice-water (1.5 l) and made acidic with diluted hydrochloric acid. After being stirred for 30 minutes, the resulting precipitates were collected by filtration and air-dried to give a colorless powder of 3-methoxy-4-(trifluoromethyl)benzoic acid (22.95 g).

mp: 203–204° C.
IR (KBr): 3500–3150, 2700–2300, 1637, 1606, 1459, 1272, 1174 cm$^{-1}$
NMR (DMSO-d$_6$, δ): 3.95 (3H, s), 7.61–7.77 (3H, m), 13.45 (1H, s)

Preparation 49

Lithium aluminum hydride (4.53 g) was added by small portions to an ice-cooled solution of 3-methoxy-4-(trifluoromethyl)benzoic acid (23.3 g) in tetrahydrofuran (400 ml) under nitrogen atmosphere, and the mixture was stirred at room temperature for 2 hours. After being cooled with ice, 2N sodium hydroxide (2 ml) was added to the mixture under nitrogen atmosphere. The resulting precipitates were filtered off and washed with tetrahydrofuran, and the filtrate and washings were combined and evaporated under reduced pressure to give a crude oil. The oil was purified by column chromatography on silica gel using a mixture of dichloromethane and methanol (40:1) to give 3-methoxy-4-(trifluoromethyl)benzyl alcohol (20 g) as a colorless oil.

IR (Neat): 3500–3150, 2700–2300, 1637, 1606, 1459, 1272, 1174 cm$^{-1}$
NMR (CDCl$_3$, δ): 2.01 (1H, t, J=4.6 Hz), 3.88 (3H, s), 4.72 (2H, d, J=4.6 Hz), 6.95 (1H, dd, J=0.4 and 8.0 Hz), 7.04 (1H, d, J=0.4 Hz) 7.52 (1H, d, J=8.0 Hz)

Preparation 50

A solution of 5-bromo-2-fluorotoluene (6 g) in ethyl ether (10 ml) and a catalytic amount of iodine were added to a suspension of magnesium (960 mg) in ethyl ether (10 ml) under nitrogen atmosphere and the whole was refluxed for 30 minutes. After cooling, a solution of ethyl orthoformate (5.4 g) in ethyl ether (20 ml) was added to the mixture and the whole was stirred overnight. Sulfuric acid (10%, 20 ml) was added to the mixture and the organic layer was separated, washed with brine, dried over sodium sulfate, and evaporated. The residue was purified by column chromatography on silica gel with a mixture of hexane and ethyl acetate (10:1) as eluent to give 4-fluoro-3-methylbenzaldehyde as an oil.

IR (Neat): 1695, 1590, 1495, 1280, 1245, 1110 cm$^{-1}$
NMR (CDCl$_3$, δ): 2.36 (3H, s), 7.10–7.84 (3H, m), 9.93 (1H, s)

The obtained compound was dissolved in a mixture of methanol and tetrahydrofuran and sodium borohydride was added to the solution. After 1 hour of stirring, the solvent was removed and water was added to the residue. The mixture was made acidic with 10% sulfuric acid, extracted with ethyl acetate, washed with brine, dried over sodium sulfate, and evaporated in vacuo to give 4-fluoro-3-methyl-benzylalcohol (1.33 g) as an oil.

IR (Neat): 3300, 1500, 1250 cm$^{-1}$

NMR (CDCl$_3$, δ): 2.28 (3H, s), 4.62 (2H, s), 6.93–7.26 (3H, m)

Preparation 51

Carbon tetrabromide (3.08 g) was added portion wisely to a solution of 4-fluoro-3-methylbenzylalcohol (1.3 g) and triphenylphosphine (2.9 g) in methylene chloride (50 ml) and the mixture was stirred for 1 hour. The solution was washed successively with saturated aqueous sodium hydrogen carbonate solution and brine, dried over sodium sulfate, and evaporated in vacuo. The residue was triturated with hexane and the resulting precipitate was removed by filtration. The filtrate was evaporated in vacuo and the residue was purified by column chromatography on silica gel with hexane as eluent to give 4-fluoro-3-methylbenzylbromide (1.28 g) as an oil.

IR (Neat): 1500, 1250, 1200 cm$^{-1}$

NMR (CDCl$_3$, δ): 2.26 (3H, s), 4.45 (2H, s), 6.91–7.26 (3H, m)

Preparation 52

The following compound was obtained according to a similar manner to that of Preparation 50.

3-Fluoro-4-methylbenzylalcohol

IR (Neat): 3350, 1580, 1510, 1420, 1250 cm$^{-1}$

Preparation 53

The following compound was obtained by a similar manner to that of Preparation 51 followed by a similar manner to that of Preparation 27.

2-Acetylamino-2-(3-fluoro-4-methylbenzyl)malonic acid diethyl ester

IR (Nujol): 3250, 1740, 1630, 1510, 1360 cm$^{-1}$

NMR (DMSO-d$_6$, δ): 1.20 (6H, t, J=7.0 Hz), 1.94 (3H, s), 2.19 (3H, s), 3.40 (2H, s), 4.10 (4H, q, J=7.0 Hz), 6.67–7.23 (3H, m), 8.13 (1H, s)

MASS (APCI): 340 (M+H)$^+$

Preparation 54

The following compounds were obtained according to a similar manner to that of the first half of Preparation 21.

(1) (2R)-4-Benzyl-2-[4-chloro-3-methoxybenzyl]piperazine dihydrochloride mp: 225–230° C. (decomp.)

IR (KBr): 3398, 1460, 1419, 1246, 1030 cm$^{-1}$

NMR (DMSO-d$_6$, δ): 2.80–4.60 (11H, m), 3.87 (3H, s), 6.86 (1H, d, J=8.1 Hz), 7.10 (1H, s), 7.30–7.60 (6H, m), 9.20–10.80 (3H, br)

MASS (APCI): 331 (M+H)$^+$ (free)

(2) (3R)-1-Benzyl-3-(4-fluoro-3-methoxybenzyl)piperazine

IR (Neat): 1666, 1608, 1516, 1456, 1419, 1321, 1275, 1217, 1151, 1126, 1034 cm$^{-1}$ NMR (CDCl$_3$, δ): 0.60–3.20 (9H, m), 3.58 (2H, s), 3.86 (3H, s), 6.50–7.10 (3H, m), 7.10–7.60 (5H, m)

MASS (APCI): 315 (M+H)$^+$ (3) (2R)-4-Benzyl-2-[3-methoxy-4-(trifluoromethyl)benzoyl]-piperazine IR (Neat): 2938, 2809, 1614, 1583, 1506, 1459, 1421 cm$^{-1}$ NMR (CDCl$_3$, δ): 1.84–2.16 (2H, m), 2.50–3.01 (7H, m), 3.51 (2H, s), 3.88 (3H, s), 6.83–6.85 (2H, m), 7.25–7.33 (6H, m), 7.47 (1H, d, J=8.2 Hz)

MASS (APCI): 365 (M+H)$^+$ (4) (2R)-4-Benzyl-2-(4-fluoro-3-methylbenzyl)piperazine IR (Neat): 1500, 1450, 1320, 1245, 1205, 1120 cm$^{-1}$ NMR (DMSO-d$_6$, δ): 1.60–3.52 (14H, m), 6.95–7.40 (8H, m)

MASS (APCI): 299 (M+H)$^+$ (5) (2R)-4-Benzyl-2-(3-fluoro-4-methylbenzyl)piperazine IR (Neat): 1575, 1510, 1450, 1320, 1250, 1130, 1110 cm$^{-1}$ (6) (2R)-4-Benzyl-2-(4-fluorobenzyl)piperazine IR (Neat): 2937, 2807, 1508, 1450, 1326, 1135, 827, 742 cm$^{-1}$ NMR (CDCl$_3$, δ): 1.87 (1H, t, J=10.4 Hz), 2.14 (1H, dt, J=3.8 and 11.0 Hz), 2.35–2.94 (7H, m), 3.47 (1H, d, J=13.0 Hz), 3.53 (1H, d, J=13.0 Hz), 6.92–7.32 (9H, m)

MASS (APCI): 285 (M+H)$^+$ (7) (3R)-1-Benzyl-3-(4-chlorobenzyl)piperazine

IR (Neat): 1670, 1491, 1450, 1406, 1360, 1329, 1136, 1093, 1036, 1022 cm$^{-1}$

NMR (CDCl$_3$, δ): 1.70–3.80 (11H, m), 7.12 (2H, d, J=8.4 Hz), 7.20–7.60 (7H, m)

MASS (APCI): 301 (M+H)$^+$ (8) (3R)-1-Benzyl-3-[4-(trifluoromethyl)benzyl]piperazine IR (Neat): 2939, 2810, 1676, 1618 cm$^{-1}$ NMR (CDCl$_3$, δ): 1.89 (1H, t, J=10.5 Hz), 2.09 (1H, dt, J=3.9 and 11.0 Hz), 2.55–3.04 (7H, m), 3.49 (1H, d, J=13.0 Hz), 3.52 (1H, d, J=13.0 Hz), 7.25–7.32 (7H, m), 7.55 (2H, d, J=8.1 Hz)

MASS (APCI): 335 (M+H)$^+$ (9) (3R)-1-Benzyl-3-[4-(trifluoromethyl)benzyl]piperazine dihydrochloride mp: 212–225° C.

IR (KBr): 3398, 2673, 1458, 1331 cm$^{-1}$

NMR (DMSO-d$_6$, δ): 3.00–4.50 (11H, m), 7.43–7.76 (9H, m)

MASS (APCI): 335 (M+H)$^+$ (free)

Preparation 55

The following compounds were obtained according to a similar manner to that of the latter half of Preparation 21.

(1) (2R)-4-Benzyl-1-[3,5-bis(trifluoromethyl)benzoyl]-2-(4-fluoro-3-methoxybenzyl)piperazine IR (Neat): 1736, 1643, 1616, 1516, 1462, 1454, 1435, 1425, 1377, 1273, 1103, 1065, 1038 cm$^{-1}$
NMR (CDCl$_3$, δ): 0.60–5.20 (14H, m), 6.20–8.60 (11H, m)
MASS (APCI): 555 (M+H)$^+$ (2) (2R)-4-Benzyl-1-[3,5-bis(trifluoromethyl)benzoyl]-2-[3-methoxy-4-(trifluoromethyl)benzyl]piperazine IR (Neat): 1643, 1280, 1180, 1137 cm$^{-1}$
NMR (CDCl$_3$, δ): 2.20–5.20 (14H, m), 6.40–8.00 (11H, m)
MASS (APCI): 605 (M+H)$^+$ (3) (2R)-1-[3,5-Bis(trifluoromethyl)benzoyl]-2-(4-fluoro-3-methylbenzyl)-4-benzylpiperazine IR (Neat): 1640, 1500, 1430, 1380, 1350, 1275, 1130 cm$^{-1}$
NMR (DMSO-d$_6$, δ): 2.00–4.83 (14H, m), 6.60–8.21 (11H, m)
MASS (APCI): 539 (M+H)$^+$ (4) (2R)-1-[3,5-Bis(trifluoromethyl)benzoyl]-2-(3-fluoro-3-methylbenzyl)-4-benzylpiperazine IR (Neat): 1640, 1430, 1280, 1170, 1130 cm$^{-1}$
NMR (DMSO-d$_6$, δ): 2.00–4.90 (11H, m), 2.16 (3H, s), 6.53–8.24 (11H, m)
MASS (APCI): 539 (M+H)$^+$

EXAMPLE 9

The following compounds were obtained according to a similar manner to that of Example 1 using N,N-diisopropylethylamine instead of potassium carbonate as a base.

(1) (2R)-1-[3,5-Bis(trifluoromethyl)benzoyl]-2-(4-chloro-3-hydroxybenzyl)-4-[2-[(2S)-2-(methoxymethyl)morpholino]-ethyl]piperazine dihydrochloride mp: 160–169° C.
[α]$_D^{27}$: +10.0° (C=0.52, MeOH)
IR (KBr): 3500–3150, 2700–2300, 1644, 1423, 1282 cm$^{-1}$
NMR (DMSO-d$_6$, δ): 2.60–5.00 (25H, m), 6.30–7.25 (3H, m), 7.43 (1H, s), 7.79 (1H, s), 8.17–8.22 (1H, m), 10.13 (1H, br s), 11.00–12.00 (2H, m)
MASS (APCI): 624 (M+H)$^+$ (free)

(2) (2R)-1-[3,5-Bis(trifluoromethyl)benzoyl]-2-(4-fluoro-3-methoxybenzyl)-4-[2-[(2S)-2-(methoxymethyl)morpholino]-ethyl]piperazine dihydrochloride mp: 180–190° C.
[α]$_D^{26.7}$: +13.90° (C=0.5, MeOH)
IR (KBr): 1676, 1645, 1547, 1516, 1464, 1427, 1392, 1387, 1367, 1321, 1282, 1217, 1184, 1136, 1034 cm$^{-1}$
NMR (DMSO-d$_6$, δ): 2.00–5.40 (28H, m), 6.30–8.30 (6H, m)
MASS (APCI): 622 (M+H)$^+$ (free)

(3) (2R)-1-[3,5-Bis(trifluoromethyl)benzoyl]-2-[4-(trifluoromethyl)benzyl]-4-[2-[(2S)-2-(methoxymethyl)-morpholino]ethyl]piperazine dihydrochloride mp: 146–159° C.
[α]$_D^{26.8}$: +10.67° (C=0.239, MeOH)
IR (KBr): 3435, 2656, 2598, 2467, 1647, 1429, 1329, 1282, 1180, 1132, 1068 cm$^{-1}$
NMR (DMSO-d$_6$, δ): 2.66–5.32 (27H, m), 7.10–8.30 (7H, m)
MASS (APCI): 642 (M+H)$^+$ (free)

(4) (2R)-1-[3,5-Bis(trifluoromethyl)benzoyl]-2-[3-[(2-methoxyethoxy)methoxy]-4-methylbenzyl]-4-[2-(5,6,7,8-tetrahydro-1,6-naphthyridin-6-yl)ethyl]piperazine IR (Neat): 1670, 1643, 1583, 1508, 1452, 1446, 1435, 1429, 1381, 1358, 1350, 1336, 1277 cm$^{-1}$
NMR (CDCl$_3$, δ): 0.70–5.50 (31H, m), 6.20–8.60 (9H, m)
MASS (APCI): 695 (M+H)$^+$ (5) (2R)-1-[3,5-Bis(trifluoromethyl)benzoyl]-2-[4-chloro-3-hydroxybenzyl]-4-[4-(3,3-dimethylmorpholino)-2-butynyl]-piperazine dihydrochloride mp: 181–186° C.
[α]$_D^{27.1}$: +0.571° (C=0.175, MeOH)
IR (KBr): 3431, 2586, 1647, 1431, 1281, 1180, 1134 cm$^{-1}$
NMR (DMSO-d$_6$, δ): 1.32 (3H, s), 1.39 (3H, s), 2.60–5.20 (19H, m), 6.31–7.29 (3H, m), 7.54–8.21 (3H, m), 10.10 (1H, br)
MASS (APCI): 632 (M)$^+$ (free)

(6) (2R)-1-[3,5-Bis(trifluoromethyl)benzoyl]-2-[4-chloro-3-hydroxybenzyl]-4-[2-(cis-2,6-dimethylmorpholino)ethyl]-piperazine dihydrochloride mp: 172–175° C.
[α]$_D^{28.2}$: −4.43° (C=0.305, MeOH)
IR (KBr): 3431, 2999, 1647, 1429, 1281, 1182, 1140 cm$^{-1}$
NMR (DMSO-d$_6$, δ): 1.15 (6H, d, J=6.1 Hz), 2.60–5.20 (19H, m), 6.32–7.28 (3H, m), 7.42–8.24 (3H, m), 10.12 (1H, br)
MASS (APCI): 608 (M)$^+$ (free)

(7) (2R)-1-[3,5-Bis(trifluoromethyl)benzoyl]-2-[4-chloro-3-hydroxybenzyl]-4-[2-(4,4-difluoropiperidino)ethyl]-piperazine dihydrochloride mp: 166–170° C.
[α]$_D^{28.0}$: −4.25° (C=0.365, MeOH)
IR (KBr): 3435, 1647, 1429, 1281, 1182, 1140 cm$^{-1}$
NMR (DMSO-d$_6$, δ): 2.20–5.20 (21H, m), 6.32–7.24 (3H, m), 7.42–8.18 (3H, m), 10.10 (1H, br)
MASS (APCI): 614 (M+H)$^+$ (free)

(8) (2R)-1-[3,5-Bis(trifluoromethyl)benzoyl]-2-[4-chloro-3-hydroxybenzyl]-4-[2-(5,6,7,8-tetrahydro-1,6-naphthyridin-6-yl)ethyl]piperazine trihydrochloride mp: 237–243° C. (decomp.)
[α]$_D^{26.1}$: −19.1° (C=0.285, MeOH)
IR (KBr): 3433, 2561, 1645, 1427, 1281, 1185, 1136 cm$^{-1}$ NMR (DMSO-d$_6$, δ): 2.60–6.10 (19H, m), 6.30–7.20 (3H, m), 7.40–8.20 (3H, m), 7.76 (1H, dd, J=4.5 and 8.1 Hz), 8.14 (1H, d, J=8.1 Hz), 8.71 (1H, d, J=4.5 Hz), 10.20 (1H, br)

MASS (APCI): 627 (M)$^+$ (free)

(9) (2R)-1-[3-Methoxy-5-(trifluoromethyl)benzoyl]-2-[4-chloro-3-hydroxybenzyl]-4-[2-[(2S)-2-(methoxymethyl)-morpholino]ethyl]piperazine dihydrochloride mp: 160–168° C.

[α]$_D^{28.3}$: +14.83° (C=0.30, MeOH)

IR (KBr): 3431, 2586, 1641, 1606, 1462, 1425, 1174, 1130 cm$^{-1}$

NMR (DMSO-d$_6$, δ): 2.60–5.20 (25H, m), 3.82 (3H, s), 6.32–7.31 (6H, m), 10.11 (1H, br)

MASS (APCI): 586 (M)$^+$ (free)

(10) (2R)-1-[3-Methoxy-5-(trifluoromethyl)benzoyl]-2-(4-chloro-3-hydroxybenzyl)-4-[4-(3,3-dimethylmorpholino)-2-butynyl]piperazine dihydrochloride mp: 187–195° C.

[α]$_D^{26.9}$: +9.19° (C=0.37, MeOH)

IR (KBr): 3423, 1641, 1604, 1462, 1425, 1238, 1173, 1126 cm$^{-1}$

NMR (DMSO-d$_6$, δ): 1.33 (3H, s), 1.37 (3H, s), 2.80–5.20 (19H, m), 3.85 (3H, s), 6.30–7.30 (6H, m), 10.10 (1H, br)

MASS (APCI): 594 (M)$^+$ (free)

(11) (2R)-1-[3-Methoxy-5-(trifluoromethyl)benzoyl]-2-(4-chloro-3-hydroxybenzyl)-4-[2-(cis-2,6-dimethylmorpholino)ethyl]piperazine dihydrochloride mp: 177–182° C.

[α]$_D^{27.3}$: +9.71° (C=0.34, MeOH)

IR (KBr): 3425, 2613, 1641, 1606, 1462, 1425, 1174, 1132 cm$^{-1}$

NMR (DMSO-d$_6$, δ): 1.15 (6H, d, J=5.8 Hz), 2.60–5.20 (19H, m), 3.82 (3H, s), 6.31–7.32 (6H, m), 9.90 (1H, br)

MASS (APCI): 570 (M)$^+$ (free)

(12) (2R)-1-[3-Methoxy-5-(trifluoromethyl)benzoyl]-2-(4-chloro-3-hydroxybenzyl)-4-[2-(4,4-difluoropieridino)-ethyl]piperazine dihydrochloride mp: 178–182° C.

[α]$_D^{27.1}$: +5.48° (C=0.21, MeOH)

IR (KBr): 3435, 1641, 1606, 1464, 1425, 1173, 1134 cm$^{-1}$

NMR (DMSO-d$_6$, δ): 2.20–5.20 (21H, m), 3.83 (3H, s), 6.32–7.40 (6H, m), 10.17 (1H, br)

MASS (APCI): 576 (M)$^+$ (free)

(13) (2R)-1-[3-Methoxy-5-(trifluoromethyl)benzoyl]-2-(4-chloro-3-hydroxybenzyl)-4-[2-(5,6,7,8-tetrahydro-1,6-naphthyridin-6-yl)ethyl]piperazine trihydrochloride mp: 225–240° C. (decomp.)

[α]$_D^{28.3}$: −8.15° (C=0.27, MeOH)

IR (KBr): 3435, 1641, 1626, 1464, 1425, 1238, 1173, 1130 cm$^{-1}$

NMR (DMSO-d$_6$, δ): 2.60–5.20 (19H, m), 3.83 (3H, s), 6.30–7.40 (6H, m), 7.71 (1H, dd, J=4.6 and 7.6 Hz), 8.12 (1H, d, J=7.6 Hz), 8.71 (1H, d, J=4.6 Hz), 10.20 (1H, br)

MASS (APCI): 589 (M)$^+$ (free)

(14) (2R)-1-[3,5-Bis(trifluoromethyl)benzoyl]-2-(4-chloro-3-methoxybenzyl)-4-[2-[(2S)-2-(methoxymethyl)morpholino]-ethyl]piperazine dihydrochloride mp: 145–149° C.

[α]$_D^{27}$: +11.0° (C=0.5, MeOH)

IR (KBr): 3500–3150, 2700–2300, 1644, 1423, 1282 cm$^{-1}$

NMR (DMSO-d$_6$, δ): 2.60–5.00 (28H, m), 6.53–7.39 (3H, m), 7.45 (1H, s), 7.73 (1H, s), 8.19 (1H, m)

MASS (APCI): 638 (M+H)$^+$ (free)

(15) (2R)-1-[3-Trifluoromethyl-5-methylthiobenzoyl]-2-(4-chloro-3-tert-butyldimethylsilyloxybenzyl)-4-[2-(cis-2,6-dimethylmorpholino)ethyl]piperazine IR (Neat): 1680, 1630, 1490, 1420, 1130, 1085 cm$^{-1}$ NMR (CDCl$_3$, δ): 0.18 (6H, s), 1.01 (9H, s), 1.15 (6H, d, J=6.3 Hz), 1.75 (2H, t, J=10.6 Hz), 2.08–5.10 (20H, m), 6.30–8.08 (6H, m)

MASS (API-ES): 700 (M$^+$)

(16) (2R)-1-(3-Trifluoromethyl-5-methylthiobenzoyl)-2-(4-chloro-3-tert-butyldimethylsilyloxybenzyl)-4-[2-(5,6,7,8-tetrahydro-1,6-naphthylidin-6-yl)ethyl]-piperazine IR (Neat): 1635, 1490, 1420, 1295, 1170, 1130, 1105 cm$^{-1}$ NMR (CDCl$_3$, δ): 0.18 (6H, s), 1.01 (9H, s), 2.08–5.10 (22H, m), 6.30–8.48 (9H, m)

MASS (API-ES): 719 (M$^+$)

(17) (2R)-1-[3,5-Bis(trifluoromethyl)benzoyl]-2-[3-[(2-methoxyethoxy)methoxy]-4-methylbenzyl]-4-[3-(3-pyridyl)-2-propynyl]piperazine IR (Neat): 1643, 1583, 1508, 1466, 1452, 1431, 1377, 1358, 1331, 1277, 1086, 1018 cm$^{-1}$ NMR (CDCl$_3$, δ): 0.70–5.60 (23H, m), 6.20–8.90 (10H, m)

MASS (APCI): 650 (M+H)$^+$

(18) (2R)-1-[3,5-Bis(trifluoromethyl)benzoyl]-2-(4-fluoro-3-methoxybenzyl)-4-[4-(3,3-dimethylmorpholino)-2-butynyl]-piperazine dihydrochloride mp: 125–130° C.

[α]$_D^{26.8}$: +11.77° (C=0.31, MeOH)

IR (KBr): 3425, 2586, 1647, 1518, 1281, 1182, 1132 cm$^{-1}$

NMR (DMSO-d$_6$, δ): 1.33 (3H, s), 1.40 (3H, s), 2.70–5.20 (22H, m), 6.50–7.30 (3H, m), 7.50–8.21 (3H, m)

MASS (APCI): 630 (M+H)$^+$ (free)

(19) (2R)-1-[3,5-Bis(trifluoromethyl)benzoyl]-2-(4-fluoro-3-methoxybenzyl)-4-[2-(cis-2,6-dimethylmorpholino)ethyl]-piperazine dihydrochloride mp: 205.0–208.0° C.

[α]$_D^{26.9}$: +14.4° (C=0.25, MeOH)

IR (KBr): 3500–3150, 2700–2300, 1644, 1617, 1517, 1463, 1427, 1278, 1133 cm$^{-1}$

NMR (DMSO-d$_6$, δ): 2.60–5.20 (28H, m), 6.60–8.40 (6H, m)

MASS (APCI): 606 (M+H)$^+$ (free)

(20) (2R)-1-[3,5-Bis(trifluoromethyl)benzoyl]-2-(4-fluoro-3-methoxybenzyl)-4-[2-(4,4-difluoropiperidino)ethyl]-piperazine dihydrochloride mp: 240–243° C.
$[\alpha]_D^{28.3}$: +2.86° (C=0.315, MeOH)
IR (KBr): 3384, 2941, 2418, 1649, 1518, 1282, 1184, 1138 cm$^{-1}$
NMR (DMSO-d$_6$, δ): 2.20–5.20 (24H, m), 6.50–7.30 (3H, m), 7.43–8.20 (3H, m)
MASS (APCI): 612 (M+H)$^+$ (free)

(21) (2R)-1-[3,5-Bis(trifluoromethyl)benzoyl]-2-(4-fluoro-3-methoxybenzyl)-4-[2-(5,6,7,8-tetrahydro-1,6-naphthyridin-6-yl)ethyl]piperazine trihydrochloride mp: 175–185° C.
$[\alpha]_D^{27}$: −10.0° (C=0.16, MeOH)
IR (KBr): 3500–3150, 2700–2300, 1641, 1562, 1459, 1432, 1282 cm$^{-1}$
NMR (DMSO-d$_6$, δ): 2.60–5.20 (22H, m), 6.60–8.70 (9H, m)
MASS (APCI): 625 (M+H)$^+$ (free)

(22) (2R)-2-(4-Fluoro-3-methoxybenzyl)-4-[2-[(2S)-2-(methoxymethyl)morpholino]ethyl]-1-[3-methoxy-5-(trifluoromethyl)benzoyl]piperazine dihydrochloride $[\alpha]_D^{26.7}$: +29.52° (C=0.31, MeOH)
IR (KBr): 1643, 1635, 1618, 1606, 1518, 1462, 1419, 1273, 1169, 1132, 1103, 1041 cm$^{-1}$
NMR (DMSO-d$_6$, δ): 0.70–5.40 (31H, m), 6.30–7.50 (6H, m)
MASS (APCI): 584 (M+H)$^+$ (free)

(23) (2R)-4-[4-(3,3-Dimethylmorpholino)-2-butynyl]-2-(4-fluoro-3-methoxybenzyl)-1-[3-methoxy-5-(trifluoromethyl)benzoyl]piperazine dihydrochloride $[\alpha]_D^{28.0}$: +26.67° (C=0.24, MeOH)
IR (KBr): 1676, 1645, 1635, 1628, 1616, 1516, 1464, 1423, 1346, 1273, 1171, 1126, 1101, 1049 cm$^{-1}$
NMR (DMSO-d$_6$, δ): 1.10–5.30 (31H, m), 6.40–7.50 (6H, m)
MASS (APCI): 592 (M+H)$^+$ (free)

(24) (2R)-4-[2-(cis-2,6-Dimethylmorpholino)ethyl]-2-(4-fluoro-3-methoxybenzyl)-1-[3-methoxy-5-(trifluoromethyl)benzoyl]piperazine dihydrochloride $[\alpha]_D^{26.3}$: +23.54° (C=0.24, MeOH)
IR (KBr): 1645, 1612, 1516, 1464, 1423, 1398, 1352, 1315, 1275, 1213, 1173, 1130, 1092, 1055, 1036 cm$^{-1}$
NMR (DMSO-d$_6$, δ): 0.80–5.30 (31H, m), 6.30–7.50 (6H, m)
MASS (APCI): 568 (M+H)$^+$ (free)

(25) (2R)-4-[2-(4,4-Difluoropiperidino)ethyl]-2-(4-fluoro-3-methoxybenzyl)-1-[3-methoxy-5-(trifluoromethyl)benzoyl]piperazine dihydrochloride $[\alpha]_D^{26.4}$: +24.63° (C=0.27, MeOH)
IR (KBr): 2538, 2488, 1641, 1604, 1516, 1464, 1417, 1387, 1346, 1290, 1242, 1171, 1134, 1047, 1024 cm$^{-1}$
NMR (DMSO-d$_6$, δ): 1.70–5.40 (27H, m), 6.30–7.50 (6H, m)
MASS (APCI): 574 (M+H)$^+$ (free)

(26) (2R)-2-(4-Fluoro-3-methoxybenzyl)-1-[3-methoxy-5-(trifluoromethyl)benzoyl]-4-[2-(5,6,7,8-tetrahydro-1,6-naphthyridin-6-yl)ethyl]piperazine trihydrochloride $[\alpha]_D^{25.8}$: +5.22° (C=0.345, MeOH)
IR (KBr): 1643, 1635, 1630, 1516, 1464, 1423, 1350, 1317, 1275, 1173, 1128, 1051, 1038 cm$^{-1}$
NMR (DMSO-d$_6$, δ): 0.80–5.50 (25H, m), 6.20–8.70 (9H, m)
MASS (APCI): 587 (M+H)$^+$ (free)

(27) (2R)-1-[3,5-Bis(trifluoromethyl)benzoyl]-2-(4-fluoro-3-hydroxybenzyl)-4-[2-[(2S)-2-(methoxymethyl)morpholino]-ethyl]piperazine dihydrochloride mp: 156–168° C.
$[\alpha]_D^{27.6}$: +5.14° (C=0.36, MeOH)
IR (KBr): 3458, 1647, 1518, 1433, 1282, 1184, 1140 cm$^{-1}$
NMR (DMSO-d$_6$, δ): 2.60–5.20 (25H, m), 6.30–7.20 (3H, m), 7.43–8.23 (3H, m), 9.77 (1H, br)
MASS (APCI): 608 (M+H)$^+$ (free)

(28) (2R)-1-[3,5-Bis(trifluoromethyl)benzoyl]-2-(4-fluoro-3-hydroxybenzyl)-4-[4-(3,3-dimethylmorpholino)-2-butynyl]-piperazine dihydrochloride mp: 180–184° C.
$[\alpha]_D^{26.8}$: +2.20° (C=0.25, MeOH)
IR (KBr): 3435, 2931, 2584, 1645, 1435, 1281, 1182, 1136 cm$^{-1}$
NMR (DMSO-d$_6$, δ): 1.32 (3H, s), 1.39 (3H, s), 2.60–5.20 (19H, m), 6.30–7.20 (3H, m), 7.50–8.21 (3H, m), 9.76 (1H, br)
MASS (APCI): 616 (M+H)$^+$ (free)

(29) (2R)-1-[3,5-Bis(trifluoromethyl)benzoyl]-2-(4-fluoro-3-hydroxybenzyl)-4-[2-(cis-2,6-dimethylmorpholino)ethyl]-piperazine dihydrochloride mp: 170–195° C.
$[\alpha]_D^{27}$: +6.77° (C=0.27, MeOH)
IR (KBr): 3500–3150, 2700–2300, 1644, 1519, 1434, 1371, 1282, 1184 cm$^{-1}$
NMR (DMSO-d$_6$, δ): 0.80–5.20 (25H, m), 6.60–8.20 (7H, m), 11.40–11.80 (2H, br)
MASS (APCI): 592 (M+H)$^+$ (free)

(30) (2R)-1-[3,5-Bis(trifluoromethyl)benzoyl]-2-(4-fluoro-3-hydroxybenzyl)-4-[2-(4,4-difluoropiperidino)ethyl]-piperazine dihydrochloride mp: 190–200° C.
$[\alpha]_D^{27}$: +0.83° (C=0.3, MeOH)
IR (KBr): 3500–3150, 2700–2300, 1646, 1517, 1432, 1373, 1282, 1139 cm$^{-1}$
NMR (DMSO-d$_6$, δ): 2.60–5.20 (21H, m), 6.20–8.30 (7H, m), 9.00–10.40 (2H, br)
MASS (APCI): 598 (M+H)$^+$ (free)

(31) (2R)-1-[3,5-Bis(trifluoromethyl)benzoyl]-2-(4-fluoro-3-hydroxybenzyl)-4-[2-(5,6,7,8-tetrahydro-1,6-naphthyridin-6-yl)ethyl]piperazine trihydrochloride mp: 240.0–241.0° C.
$[\alpha]_D^{26}$: −11.66° (C=0.57, MeOH)
IR (KBr): 3500–3150, 2700–2300, 1641, 1517, 1432, 1282, 1137 cm$^{-1}$
NMR (DMSO-d$_6$, δ): 2.60–5.20 (19H, m), 6.20–8.80 (10H, m), 9.00–10.50 (2H, br)
MASS (APCI): 611 (M+H)$^+$ (free)

(32) (2R)-1-[3,5-Bis(trifluoromethyl)benzoyl]-2-(3,4-difluorobenzyl)-4-[2-[(2S)-2-(methoxymethyl)morpholino)-ethyl]piperazine dihydrochloride mp: 196–198° C.
$[\alpha]_D^{27}$: +8.3° (C=0.5, MeOH)
IR (KBr): 3365, 2590, 2475, 1645, 1520, 1440, 1280 cm$^{-1}$
NMR (DMSO-d$_6$, δ): 2.73–5.07 (22H, m), 3.27 (3H, s), 6.88–8.21 (6H, m)
MASS (APCI): 610 (M+H)$^+$ (free)

(33) (2R)-1-[3,5-Bis(trifluoromethyl)benzoyl]-2-(3,4-difluorobenzyl)-4-[4-(3,3-dimethylmorpholino)-2-butynyl]piperazine dihydrochloride $[\alpha]_D^{27}$: +4.2° (C=0.5, MeOH)
IR (KBr): 2435, 1645, 1520, 1430, 1280 cm$^{-1}$
NMR (DMSO-d$_6$, δ): 1.32 (3H, s), 1.38 (3H, s), 2.76–5.17 (19H, m), 6.79–8.26 (6H, m)
MASS (APCI): 618 (M+H)$^+$ (free)

(34) (2R)-1-[3,5-Bis(trifluoromethyl)benzoyl]-2-(3,4-difluorobenzyl)-4-[2-(cis-2,6-dimethylmorpholino)ethyl]-piperazine dihydrochloride mp: 223–228° C.
$[\alpha]_D^{27}$: +5.1° (C=0.5, MeOH)
IR (KBr): 3435, 3390, 2600, 2495, 1650, 1520, 1435, 1280 cm$^{-1}$
NMR (DMSO-d$_6$, δ): 1.45 (6H, d, J=6.0 Hz), 2.60–5.20 (19H, m), 6.80–8.28 (6H, m)
MASS (APCI): 594 (M+H)$^+$ (free)

(35) (2R)-1-[3,5-Bis(trifluoromethyl)benzoyl]-2-(3,4-difluorobenzyl)-4-[2-(4,4-difluoropiperidino)ethyl]-piperazine dihydrochloride $[\alpha]^{27}$: +9.1° (C=0.5, MeOH)
IR (KBr): 2380, 1645, 1520, 1430, 1280 cm$^{-1}$
NMR (DMSO-d$_6$, δ): 2.10–5.14 (21H, m), 6.78–8.26 (6H, m)
MASS (APCI): 600 (M+H)$^+$ (free)

(36) (2R)-1-[3,5-Bis(trifluoromethyl)benzoyl]-2-(3,4-difluorobenzyl)-4-(1-methyl-1H-pyrazol-4-yl)methyl)-piperazine hydrochloride mp: 230° C.
$[\alpha]_D^{27}$: −1.6° (C=0.5, MeOH)
IR (KBr): 2520, 2470, 1645, 1525, 1440, 1365, 1275 cm$^{-1}$
NMR (DMSO-d$_6$, δ): 2.72–5.12 (11H, m), 3.86 (3H, s), 6.74–8.31 (8H, m)
MASS (APCI): 547 (M+H)$^+$ (free)

(37) (2R)-1-[3,5-Bis(trifluoromethyl)benzoyl]-2-(3,4-difluorobenzyl)-4-(3-pyridylmethyl)piperazine dihydrochloride mp: 203–208° C.
$[\alpha]_D^{27}$: +5.3° (C=0.5, MeOH)
IR (KBr): 2560, 1640, 1520, 1430, 1370, 1280 cm$^{-1}$
NMR (DMSO-d$_6$, δ): 2.80–5.14 (11H, m), 6.72–9.10 (10H, m)
MASS (APCI): 544 (M+H)$^+$ (free)

(38) (2R)-1-[3,5-Bis(trifluoromethyl)benzoyl]-2-(3,4-difluorobenzyl)-4-[3-(3-pyridyl)propyl]piperazine dihydrochloride mp: 215–220° C.
$[\alpha]_D^{27}$: +2.6° (C=0.5, MeOH)
IR (KBr): 2650, 1645, 1550, 1520, 1430, 1280 cm$^{-1}$
NMR (DMSO-d$_6$, δ): 2.13–5.15 (15H, m), 6.78–8.95 (10H, m)
MASS (APCI): 572 (M+H)$^+$ (free)

(39) (2R)-1-[3,5-Bis(trifluoromethyl)benzoyl]-2-(3,4-difluorobenzyl)-4-[2-(5,6,7,8-tetrahydro-1,6-naphthyridin-6-yl)ethyl]piperazine trihydrochloride $[\alpha]_D^{27}$: −2.0° (C=0.5, MeOH)
IR (KBr): 2620, 1645, 1515, 1430, 1280 cm$^{-1}$
NMR (DMSO-d$_6$, δ): 2.59–5.17 (19H, m), 6.76–8.69 (9H, m)
MASS (APCI): 613 (M+H)$^+$ (free)

(40) (2R)-1-[3,5-Bis(trifluoromethyl)benzoyl]-2-[3-methoxy-4-(trifluoromethyl)benzyl]-4-[2-(cis-2,6-dimethyl-morpholino)ethyl]piperazine dihydrochloride mp: 160.0–170.0° C.
$[\alpha]_D^{27}$: +17.16° (C=0.44, MeOH)
IR (KBr): 3500–3150, 2700–2300, 1648, 1623, 1587, 1511, 1463, 1280, 1132 cm$^{-1}$
NMR (DMSO-d$_6$, δ): 2.60–5.20 (28H, m), 6.40–8.20 (6H, m)
MASS (APCI): 656 (M+H)$^+$ (free)

(41) (2R)-1-[3,5-Bis(trifluoromethyl)benzoyl]-2-[3-methoxy-4-(trifluoromethyl)benzyl]-4-[2-(5,6,7,8-tetrahydro-1,6-naphthyridin-6-yl)ethyl]piperazine trihydrochloride mp: 195–200° C.
$[\alpha]_D^{27}$: +1.76° (C=0.34, MeOH)
IR (KBr): 3500–3150, 2700–2300, 1646, 1625, 1511, 1465, 1427, 1369, 1280, 1130 cm$^{-1}$
NMR (DMSO-d$_6$, δ): 2.60–5.20 (22H, m), 6.60–8.80 (9H, m)
MASS (APCI): 675 (M+H)$^+$ (free)

(42) (2R)-1-[3-Methoxy-5-(trifluoromethyl)benzoyl]-2-[3-methoxy-4-(trifluoromethyl)benzyl]-4-[2-[(2S)-2-(methoxymethyl)morpholino]ethyl]piperazine dihydrochloride mp: 135–140° C.
$[\alpha]_D^{27}$: +20.3° (C=0.15, MeOH)
IR (KBr): 3500–3150, 2700–2300, 1644, 1623, 1463, 1423, 1321, 1128, 1045 cm$^{-1}$ NMR (DMSO-d$_6$, δ): 2.80–5.20 (31H, m), 6.60–8.20 (6H, m), 10.60–12.20 (2H, br)
MASS (APCI): 634 (M+H)$^+$ (free)

(43) (2R)-1-[3-Methoxy-5-(trifluoromethyl)benzoyl]-2-[3-methoxy-4-(trifluoromethyl)benzyl]-4-[2-(cis-2,6-dimethylmorpholino)ethyl]piperazine dihydrochloride mp: 125–135° C.
[α]$_D^{27}$: +35.0° (C=0.18, MeOH)
IR (KBr): 3500–3150, 2700–2300, 1644, 1623, 1511, 1463, 1423, 1351, 1274, 1128 cm$^{-1}$
NMR (DMSO-d$_6$, δ): 2.60–5.20 (31H, m), 6.50–8.20 (6H, m), 11.20–11.80 (2H, br)
MASS (APCI): 618 (M+H)$^+$ (free)

(44) (2R)-1-[3-Methoxy-5-(trifluoromethyl)benzoyl]-2-[3-methoxy-4-(trifluoromethyl)benzyl]-4-(2-(5,6,7,8-tetrahydro-1,6-naphthyridin-6-yl)ethyl]piperazine trihydrochloride mp: 190–200° C.
[α]$_D^{27}$: +7.5° (C=0.16, MeOH)
IR (KBr): 3500–3150, 2700–2300, 1623, 1614, 1511, 1463, 1321, 1126 cm$^{-1}$
NMR (DMSO-d$_6$, δ): 2.80–5.20 (25H, m), 6.60–8.80 (9H, m)
MASS (APCI): 637 (M+H)$^+$ (free)

(45) (2R)-1-[3,5-Bis(trifluoromethyl)benzoyl]-2-(3-fluoro-4-methylbenzyl)-4-[2-[(2S)-2-(methoxymethyl)morpholino]-ethyl]piperazine dihydrochloride mp: 148–160° C.
[α]$_D^{26.5}$: −2.25° (C=0.222, MeOH)
IR (KBr): 3435, 2661, 2593, 2465, 1645, 1514, 1429, 1363, 1324, 1282, 1184, 1140 cm$^{-1}$
NMR (DMSO-d$_6$, δ): 2.20 (3H, s), 2.64–5.28 (25H, m), 6.62–8.28 (6H, m)
MASS (APCI): 606 (M+H)$^+$ (free)

(46) (2R)-1-[3,5-Bis(trifluoromethyl)benzoyl]-2-(4-fluoro-3-methylbenzyl)-4-[2-[(2S)-2-(methoxymethyl)morpholino]-ethyl]piperazine dihydrochloride mp: 151–156° C.
[α]$_D^{27}$: +2.96° (C=0.355, MeOH)
IR (KBr): 3435, 2941, 1647, 1510, 1281, 1184, 1138 cm$^{-1}$
NMR (DMSO-d$_6$, δ): 2.10–2.21 (3H, m), 2.65–5.25 (25H, m), 6.70–8.30 (6H, m)
MASS (APCI): 606 (M+H)$^+$ (free)

(47) (2R)-1-[3,5-Bis(trifluoromethyl)benzoyl]-2-[3-[(2-methoxyethoxy)methoxy]-4-methylbenzyl]-4-[4-[(2S)-2-(methoxymethyl)morpholino]-2-butynyl]piperazine IR (Neat): 1643, 1583, 1510, 1452, 1446, 1433, 1379, 1277, 1095, 1014 cm$^{-1}$
NMR (CDCl$_3$, δ): 0.60–5.40 (37H, m), 6.20–8.20 (6H, m)
MASS (ESI): 716.3 (M+H)$^+$

(48) (2R)-1-[3,5-Bis(trifluoromethyl)benzoyl]-4-[4-(3,3-dimethylmorpholino)-2-butynyl]-2-[4-(trifluoromethyl)-benzyl]piperazine dihydrochloride mp: 110–130° C.
[α]$_D^{24}$: +9.20° (C=0.25, MeOH)
IR (KBr): 1647 cm$^{-1}$
NMR (DMSO-d$_6$, δ): 1.33–1.41 (6H, m), 2.80–5.30 (19H, m), 7.20–8.17 (7H, m)
MASS (APCI): 650 (M+H)$^+$ (free)

(49) (2R)-1-[3,5-Bis(trifluoromethyl)benzoyl]-4-[2-(cis-2,6-dimethylmorpholino)ethyl]-2-[4-(trifluoromethyl)benzyl]-piperazine dihydrochloride mp: 148–159° C.
[α]$_D^{27}$: +10.60° (C=0.25, MeOH)
IR (KBr): 3437, 1645, 1516, 1427 cm$^{-1}$
NMR (DMSO-d$_6$, δ): 1.15 (6H, d, J=6.1 Hz), 6.60–5.30 (19H, m), 7.25–8.19 (7H, m)
MASS (APCI): 626 (M+H)$^+$ (free)

(50) (2R)-1-[3,5-Bis(trifluoromethyl)benzoyl]-4-[2-(4,4-difluoropiperidino)ethyl]-2-[4-(trifluoromethyl)benzyl]-piperazine dihydrochloride mp: 209–253° C.
[α]$_D^{26}$: +15.60° (C=0.25, MeOH)
IR (KBr): 1647 cm$^{-1}$
NMR (DMSO-d$_6$, δ): 2.60–5.20 (21H, m), 7.21–8.19 (7H, m)
MASS (APCI): 632 (M+H)$^+$ (free)

(51) (2R)-1-[3,5-Bis(trifluoromethyl)benzoyl]-4-[(1-methyl-1H-pyrazol-4-yl)methyl]-2-[4-(trifluoromethyl)benzyl]-piperazine hydrochloride mp: 200–229° C.
[α]$_D^{24}$: +5.07° (C=0.25, MeOH)
IR (KBr): 1647 cm$^{-1}$
NMR (DMSO-d$_6$, δ): 2.84–5.20 (14H, m), 7.14–7.72 (7H, m), 7.94–7.96 (1H, m), 8.21 (1H, s)
MASS (APCI): 579 (M+H)$^+$ (free)

(52) (2R)-1-[3,5-Bis(trifluoromethyl)benzoyl]-4-[(3-pyridyl)-methyl]-2-[4-(trifluoromethyl)benzyl]piperazine dihydrochloride mp: 198–223° C.
[α]$_D^{27}$: +6.60° (C=0.25, MeOH)
IR (KBr): 1645 cm$^{-1}$
NMR (DMSO-d$_6$, δ): 2.80–5.20 (11H, m), 7.13–7.91 (7H, m), 8.34 (1H, s), 8.62 (1H, d, J=7.7 Hz), 8.87 (1H, d, J=5.2 Hz), 9.05 (1H, s)
MASS (APCI): 576 (M+H)$^+$ (free)

(53) (2R)-1-[3,5-Bis(trifluoromethyl)benzoyl]-4-[3-(3-pyridyl)-2-propynyl]-2-[4-(trifluoromethyl)benzyl]-piperazine mp: 142–143° C.
IR (KBr): 1643 cm$^{-1}$
NMR (DMSO-d$_6$, δ): 2.20–5.20 (11H, m), 7.19–7.64 (7H, m), 7.80–7.90 (1H, m), 8.16 (1H, br s), 8.55–8.58 (1H, m), 8.66 (1H, br s)
MASS (APCI): 600 (M+H)$^+$

(53) (2R)-1-[3,5-Bis(trifluoromethyl)benzoyl]-4-[3-(3-pyridyl)-2-propynyl]-2-[4-(trifluoromethyl)benzyl]-piperazine mp: 142–143° C.
IR (KBr): 1643 cm$^{-1}$
NMR (DMSO-d$_6$, δ): 2.20–5.20 (11H, m), 7.19–7.64 (7H, m), 7.80–7.90 (1H, m), 8.16 (1H, br s), 8.35–8.58 (1H, m), 8.66 (1H, br s)
MASS (APCI): 600 (M+H)$^+$

(54) (2R)-1-[3,5-Bis(trifluoromethyl)benzoyl]-4-[2-(5,6,7,8-tetrahydro-1,6-naphthyridin-6-yl)ethyl]-2-[4-(trifluoromethyl)benzyl]piperazine trihydrochloride mp: 174–180° C.
[α]$_D$$^{27}$: −2.80° (C=0.25, MeOH)
IR (KBr): 3438, 1645, 1516 cm$^{-1}$
NMR (DMSO-d$_6$, δ): 2.60–5.30 (19H, m), 7.20–8.67 (10H, m)
MASS (APCI): 645 (M+H)$^+$ (free)

(55) (2R)-4-[2-[(2S)-2-(Methoxymethyl)morpholino]ethyl]-1-[3-methoxy-5-(trifluoromethyl)benzoyl]-2-[4-(trifluoromethyl)benzyl]piperazine dihydrochloride mp: 126–155° C.
[α]$_D$$^{26}$: +20.60° (C=0.25, MeOH)
IR (KBr): 3460, 1645, 1464 cm$^{-1}$
NMR (DMSO-d$_6$, δ): 2.80–5.30 (25H, m), 3.82 (3H, s), 6.31–7.80 (7H, m)
MASS (APCI): 604 (M+H)$^+$ (free)

(56) (2R)-4-[4-(3,3-Dimethylmorpholino)-2-butynyl]-1-[3-methoxy-5-(trifluoromethyl)benzyol]-2-(4-(trifluoromethyl)benzyl]piperazine dihydrochloride mp: 158–165° C.
[α]$_D$$^{26}$: +19.93° (C=0.25, MeOH)
IR (KBr): 3430, 1645, 1516, 1462, 1421 cm$^{-1}$
NMR (DMSO-d$_6$, δ): 1.33 (3H, s), 1.38 (3H, s), 2.90–5.30 (19H, m), 3.83 (3H, s), 6.30–7.70 (7H, m)
MASS (APCI): 612 (M+H)$^+$ (free)

(57) (2R)-4-[2-(cis-2,6-Dimethylmorpholino)ethyl]-1-[3-methoxy-5-(trifluoromethyl)benzoyl]-2-[4-(trifluoromethyl)benzyl]piperazine dihydrochloride mp: 139–151° C.
[α]17: +19.00° (C=0.25, MeOH)
IR (KBr): 3435, 1645, 1464, 1423 cm$^{-1}$
NMR (DMSO-d$_6$, δ): 1.15 (6H, d, J=6.1 Hz), 2.60–5.30 (19H, m), 3.82 (3H, s), 6.30–7.80 (7H, m)
MASS (APCI): 588 (M+H)$^+$ (free)

(58) (2R)-4-[2-(4,4-Difluoropiperidino)ethyl]-1-[3-methoxy-5-(trifluoromethyl)benzoyl]-2-[4-(trifluoromethyl)benzyl]-piperazine dihydrochloride mp: ~230° C.
[α]$_D$$^{27}$: +19.80° (C=0.25, MeOH)
IR (KBr): 1643, 1464, 1421 cm$^{-1}$
NMR (DMSO-d$_6$, δ): 2.30–5.30 (21H, m), 3.80 (3H, s), 6.30–7.80 (7H, m)
MASS (APCI): 594 (M+H)$^+$ (free)

(59) (2R)-1-[3-Methoxy-5-(trifluoromethyl)benzoyl]-4-[3-(3-pyridyl)-2-propynyl]-2-[4-(trifluoromethyl)benzyl]-piperazine IR (Neat): 3585, 1637 cm$^{-1}$
NMR (DMSO-d$_6$, δ): 2.20–5.20 (11H, m), 3.82 (3H, s), 6.81–7.70 (9H, m), 8.55 (1H, d, J=3.5 Hz), 8.66 (1H, s)
MASS (APCI): 562 (M+H)$^+$

(60) (2R)-1-[3-Methoxy-5-(trifluoromethyl)benzoyl]-4-[2-(5,6,7,8-tetrahydro-1,6-naphthyridin-6-yl)ethyl]-2-[4-(trifluoromethyl)benzyl]piperazine trihydrochloride mp: 185–191° C.
[α]$_D$$^{27}$: +4.00° (C=0.25, MeOH)
IR (KBr): 1645, 1423 cm$^{-1}$
NMR (DMSO-d$_6$, δ): 2.90–5.30 (19H, m), 3.83 (3H, s), 6.30–7.80 (8H, m), 8.11 (1H, d, J=7.7 Hz), 8.70 (1H, d, J=4.7 Hz)
MASS (APCI): 607 (M+H)$^+$ (free)

(61) (2R)-1-[3,5-Bis(trifluoromethyl)benzoyl]-2-(4-chlorobenzyl)-4-[2-[(2S)-2-(methoxymethyl)morpholino]-ethyl]piperazine dihydrochloride mp: 90–120° C.
[α]$_D$$^{27.7}$: +5.18° (C=0.28, MeOH)
IR (KBr): 1707, 1693, 1676, 1645, 1547, 1539, 1516, 1498, 1489, 1477, 1464, 1454, 1427, 1392, 1387, 1367, 1281, 1182, 1138, 1101 cm$^{-1}$
NMR (DMSO-d$_6$, δ): 2.00–5.40 (25H, m), 6.80–8.40 (7H, m)
MASS (APCI): 608 (M+H)$^+$ (free)

(62) (2R)-1-[3,5-Bis(trifluoromethyl)benzoyl]-2-(4-chlorobenzyl)-4-[4-(3,3-dimethylmorpholino)-2-butynyl]-piperazine dihydrochloride mp: 120–150° C.
[α]$_D$$^{27.6}$: −0.69° (C=0.29, MeOH)
IR (KBr): 2578, 2515, 1645, 1496, 1489, 1431, 1362, 1319, 1281, 1217, 1182, 1136, 1099, 1066 cm$^{-1}$
NMR (DMSO-d$_6$, δ): 1.10–1.50 (6H, m), 2.60–5.30 (19H, m), 6.80–8.40 (7H, m)
MASS (APCI): 616 (M+H)$^+$ (free)

(63) (2R)-1-[3,5-Bis(trifluoromethyl)benzoyl]-4-[2-(cis-2,6-dimethylmorpholino)ethyl]-2-(4-chlorobenzyl)-piperazine dihydrochloride mp: 150–175° C. (decomp.)
[α]$_D$$^{27.4}$: −2.86° (C=0.28, MeOH)
IR (KBr): 1693, 1687, 1645, 1514, 1508, 1498, 1489, 1464, 1454, 1429, 1329, 1281, 1182, 1142, 1099, 1038 cm$^{-1}$
NMR (DMSO-d$_6$, δ): 1.15 (6H, d, J=6.1 Hz), 1.80–5.40 (19H, m), 6.80–8.30 (7H, m)
MASS (APCI): 592 (M+H)$^+$ (free)

(64) (2R)-1-[3,5-Bis(trifluoromethyl)benzoyl]-2-(4-chlorobenzyl)-4-[2-(4,4-difluoropiperidino)ethyl]-piperazine dihydrochloride mp: 250–255° C.
[α]$_D$$^{28.2}$: −3.52° (C=0.27, MeOH)

IR (KBr): 1707, 1693, 1678, 1647, 1628, 1547, 1539, 1516, 1498, 1464, 1454, 1425, 1367, 1279; 1176, 1140, 1101, 1061, 974 cm$^{-1}$

NMR (DMSO-d$_6$, δ): 1.80–5.40 (21H, m), 6.80–8.40 (7H, m)

MASS (APCI): 598 (M+H)$^+$ (free)

(65) (2R)-1-[3,5-Bis(trifluoromethyl)benzoyl]-2-(4-chlorobenzyl)-4-[2-(5,6,7,8-tetrahydro-1,6-naphthyridin-6-yl)ethyl]piperazine trihydrochloride mp: 172–203° C. (decomp.)
$[\alpha]_D^{27.4}$: −16.12° (C=0.245, MeOH)
IR (KBr): 1674, 1645, 1630, 1558, 1550, 1539, 1516, 1498, 1489, 1464, 1427, 1392, 1387, 1367, 1281, 1182, 1136, 1101, 1043 cm$^{-1}$ NMR (DMSO-d$_6$, δ): 1.10–5.60 (19H, m), 6.80–8.80 (10H, m)

MASS (APCI): 611 (M+H)$^+$ (free)

(66) (2R)-2-(4-Chlorobenzyl)-4-[2-[(2S)-2-(methoxymethyl)-morpholino]ethyl]-1-[3-methoxy-5-(trifluoromethyl)-benzoyl]piperazine dihydrochloride mp: 70–90° C.
$[\alpha]_D^{28.2}$: +13.00° (C=0.227, MeOH)
IR (KBr): 1643, 1606, 1514, 1508, 1496, 1423, 1387, 1350, 1315, 1271, 1242, 1174, 1130, 1097, 1051 cm$^{-1}$ NMR (DMSO-d$_6$, δ): 2.50–5.40 (28H, m), 6.30–7.60 (7H, m)

MASS (APCI): 570 (M+H)$^+$ (free)

(67) (2R)-2-(4-Chlorobenzyl)-4-[4-(3,3-dimethylmorpholino)-2-butynyl]-1-[3-methoxy-5-(trifluoromethyl)benzoyl]-piperazine dihydrochloride mp: 110–140° C.
$[\alpha]_D^{28.2}$: +8.96° (C=0.24, MeOH)
IR (KBr): 1676, 1645, 1539, 1535, 1516, 1498, 1464, 1423, 1348, 1317, 1271, 1242, 1173, 1126, 1097, 1049 cm$^{-1}$ NMR (DMSO-d$_6$, δ): 1.10–1.60 (6H, m), 2.60–5.40 (22H, m), 6.40–7.60 (7H, m)

MASS (APCI): 578 (M+H)$^+$ (free)

(68) (2R)-2-(4-Chlorobenzyl)-4-[2-(cis-2,6-dimethylmorpholino)ethyl]-1-[3-methoxy-5-(trifluoromethyl)benzoyl]piperazine dihydrochloride mp: 90–120° C.
$[\alpha]_D^{27.9}$: +10.80° (C=0.25, MeOH)
IR (KBr): 1676, 1645, 1606, 1516, 1498, 1464, 1423, 1387, 1381, 1377, 1350, 1317, 1271, 1242, 1209, 1174, 1130, 1095, 1051 cm$^{-1}$ NMR (DMSO-d$_6$, δ): 1.15 (6H, d, J=6.1 Hz), 2.40–5.40 (22H, m), 6.30–7.60 (7H, m)

MASS (APCI): 554 (M+H)$^+$ (free)

(69) (2R)-2-(4-Chlorobenzyl)-4-[2-(4,4-difluoropiperidino)-ethyl]-1-[3-methoxy-5-(trifluoromethyl)benzoyl]-piperazine dihydrochloride mp: 220–250° C.
$[\alpha]_D^{28.3}$: +13.18° (C=0.425, MeOH)
IR (KBr): 1641, 1635, 1604, 1539, 1516, 1498, 1464, 1417, 1344, 1292, 1269, 1242, 1174, 1138, 1097, 1047 cm$^{-1}$ NMR (DMSO-d$_6$, δ): 2.00–5.40 (24H, m), 6.30–7.60 (7H, m)

MASS (APCI): 560 (M+H)$^+$ (free)

(70) (2R)-2-(4-Chlorobenzyl)-1-[3-methoxy-5-(trifluoromethyl)benzoyl]-4-[2-(5,6,7,8-tetrahydro-1,6-naphthyridin-6-yl)ethyl)piperazine trihydrochloride mp: 140–170° C. $[\alpha]_D^{28.7}$: −6.11° (C=0.36, MeOH)
IR (KBr): 1645, 1635, 1630, 1516, 1498, 1464, 1417, 1350, 1315, 1271, 1240, 1207, 1174, 1128, 1097, 1053 cm$^{-1}$ NMR (DMSO-d$_6$, δ): 2.40–5.40 (22H, m), 6.30–8.90 (10H, m)

MASS (APCI): 573 (M+H)$^+$ (free)

(71) (2R)-1-[3,5-Bis(trifluoromethyl)benzoyl]-4-[4-(3,3-dimethylmorpholino)-2-butynyl]-2-(4-fluorobenzyl)piperazine dihydrochloride mp: 76.5–130.6° C.
$[\alpha]_D^{26.3}$: +7.53° (C=0.25, MeOH)
IR (KBr): 1644, 1513, 1430, 1282, 1182, 1133 cm$^{-1}$ NMR (DMSO-d$_6$, δ): 1.32, 1.39 (6H, 2 br s), 2.50–4.58 (19H, m), 6.99–8.20 (7H, m)

MASS: 600 (M+H)$^+$ (free)

(72) (2R)-1-[3,5-Bis(trifluoromethyl)benzoyl]-4-[2-(cis-2,6-dimethylmorpholino)ethyl]-2-(4-fluorobenzyl)piperazine dihydrochloride mp: 89.0–110.2° C.
$[\alpha]_D^{28}$: +7.80° (C=0.25, MeOH)
IR (KBr): 1644, 1513, 1282, 1182, 1137 cm$^{-1}$ NMR (DMSO-d$_6$, δ): 1.13 (6H, d, J=6.05 Hz), 2.73–4.55 (19H, m), 7.00–8.17 (7H, m)

MASS: 576 (M+H)$^+$ (free)

(73) (2R)-1-[3,5-Bis(trifluoromethyl)benzoyl]-4-[2-(4,4-difluoropiperidino)ethyl]-2-(4-fluorobenzyl)piperazine dihydrochloride mp: 264.0–270.6° C.
$[\alpha]_D^{26.6}$: +5.070 (C=0.25, MeOH)
IR (KBr): 1644, 1513, 1427, 1278, 1187, 1141 cm$^{-1}$ NMR (DMSO-d$_6$, δ): 2.30–5.00 (21H, m), 6.99–8.17 (7H, m)

MASS: 582 (M+H)$^+$ (free)

(74) (2R)-1-[3,5-Bis(trifluoromethyl)benzoyl]-2-(4-fluorobenzyl)-4-[3-(3-pyridyl)-2-propynyl]piperazine NMR (CDCl$_3$, δ): 2.42–4.96 (11H, m), 6.95–8.66 (11H, m)

MASS: 550 (M+H)$^+$

(75) (2R)-1-[3,5-Bis(trifluoromethyl)benzoyl]-2-(4-fluorobenzyl)-4-[2-(5,6,7,8-tetrahydro-1,6-naphthyridin-6-yl)ethyl]piperazine trihydrochloride mp: 155.5–170.1° C.
$[\alpha]_D^{28}$: −81.20° (C=0.50, MeOH)
IR (KBr): 1644, 1513, 1427, 1282, 1184, 1135 cm$^{-1}$ NMR (DMSO-d$_6$, δ): 2.60–4.85 (19H, m), 7.03–8.69 (11H, m)

MASS: 595 (M+H)$^+$ (free)

(76) (2R)-2-(4-Fluorobenzyl)-4-[2-[(2S)-2-(methoxymethyl)-morpholino]ethyl]-1-[3-methoxy-5-(trifluoromethyl)-benzoyl]piperazine dihydrochloride mp: 109.5–119.2° C.
$[\alpha]_D^{26.8}$: +24.73° (C=0.46, MeOH)
IR (KBr): 1643, 1513, 1463, 1423, 1172, 1130, 1101 cm$^{-1}$
NMR (DMSO-d$_6$, δ): 2.73–4.10 (24H, m), 3.26 (3H, s), 3.87 (3H, s), 6.45–7.41 (7H, m)
MASS: 554 (M+H)$^+$ (free)

(77) (2R)-4-[4-(3,3-Dimethylmorpholino)-2-butynyl]-2-(4-fluorobenzyl)-1-[3-methoxy-5-(trifluoromethyl)benzoyl]-piperazine dihydrochloride mp: 137.5–140.7° C.
$[\alpha]_D^{27.0}$: +15.18° (C=0.48, MeOH)
IR (KBr): 1643, 1465, 1423, 1348, 1126 cm$^{-1}$
NMR (DMSO-d$_6$, δ): 1.32 and 1.37 (6H, s), 1.37 (6H, s x2), 3.10–5.00 (19H, m), 3.83 (3H, s), 6.99–12.0 (8H, m)
MASS: 562 (M+H)$^+$ (free)

(78) (2R)-4-[2-(cis-2,6-Dimethylmorpholino)ethyl]-2-(4-fluorobenzyl)-1-[3-methoxy-5-(trifluoromethyl)benzoyl]-piperazine dihydrochloride mp: 70.3–85.2° C.
$[\alpha]_D^{27.2}$: +19.03° (C=0.49, MeOH)
IR (KBr): 1645, 1513, 1463, 1423, 1174, 1130 cm$^{-1}$
NMR (DMSO-d$_6$, δ): 1.03 and 1.14 (6H, d, J=6.1 Hz), 2.89–5.10 (19H, m), 3.83 (3H, s), 6.46–7.40 (7H, m)
MASS: 538 (M+H)$^+$ (free)

(79) (2R)-4-[2-(4,4-Difluoropiperidino)ethyl]-2-(4-fluorobenzyl)-1-[3-methoxy-5-(trifluoromethyl)benzoyl]-piperazine dihydrochloride mp: 258.4–261.4° C.
$[\alpha]_D^{27.3}$: +20.40° (C=0.43, MeOH)
IR (KBr): 1637, 1604, 1417, 1346, 1240, 1047, 970 cm$^{-1}$
NMR (DMSO-d$_6$, δ): 2.73–5.09 (21H, m), 3.82 (3H, s), 6.45–7.38 (7H, m)
MASS: 544 (M+H)$^+$ (free)

(80) (2R)-4-(4-Fluorobenzyl)-1-[3-methoxy-5-(trifluoromethyl)benzoyl]-4-[3-(3-pyridyl)-2-propynyl]-piperazine NMR (CDCl$_3$, δ): 2.38–5.06 (11H, m), 3.82 (3H, s), 6.41–8.66 (11H, m)
MASS: 512 (M+H)$^+$

(81) (2R)-2-(4-Fluorobenzyl)-1-[3-methoxy-5-(trifluoromethyl)benzoyl]-4-[2-(5,6,7,8-tetrahydro-1,6-naphthyridin-6-yl)ethyl]piperazine trihydrochloride mp: 148.7–152.3° C.
$[\alpha]D^{27.1}$: −0.737° (C=0.48, MeOH)
IR (KBr): 1643, 1635, 1514, 1464, 1421, 1350, 1173, 1128 cm$^{-1}$
NMR (DMSO-d$_6$, δ): 2.65–5.10 (19, m), 3.83 (3H, s), 6.50–8.69 (10H, m)
MASS: 557 (M+H)$^+$ (free)

(82) (2R)-1-[3,5-Bis(trifluoromethyl)benzoyl]-4-[2-(cis-2,6-dimethylmorpholino)ethyl]-2-(2-naphthylmethyl)-piperazine dihydrochloride mp: 168–195° C.
$[\alpha]D^{26.4}$: −27.26° (C=0.31, MeOH)
IR (KBr): 3410, 1640 cm$^{-1}$
NMR (DMSO-d$_6$, δ): 1.16 (6H, d, J=6.0 Hz), 2.6–5.3 (19H, m), 7.0–8.2 (10H, m)
MASS (APCI): 608 (M+H)$^+$ (free)

(83) (2R)-1-[3,5-Bis(trifluoromethyl)benzoyl]-4-[2-(4,4-difluoropiperidino)ethyl]-2-(2-naphthylmethyl) piperazine dihydrochloride mp: >250° C.
$[\alpha]_D^{27.3}$: −33.11° (C=0.37, MeOH)
IR (KBr): 3740, 2400, 1650 cm$^{-1}$
NMR (DMSO-d$_6$, δ): 2.9–5.4 (21H, m), 7.0–8.2 (10H, m)
MASS (APCI): 614 (M+H)$^+$ (free)

(84) (2R)-1-[3,5-Bis(trifluoromethyl)benzoyl]-2-(2-naphthylmethyl)-4-[2-(5,6,7,8-tetrahydro-1,6-naphthyridin-6-yl)ethyl]piperazine trihydrochloride mp: 189–194° C.
$[\alpha]_D^{28.1}$: −34.93° (C=0.28, MeOH)
IR (KBr): 3400, 1640 cm$^{-1}$
NMR (DMSO-d$_6$, δ): 2.9–5.4 (19H, m), 6.9–8.2 (12H, m), 8.66 (1H, d, J=4.4 Hz)
MASS (APCI): 627 (M+H)$^+$ (free)

(85) (2R)-4-[2-[(2S)-2-(Methoxymethyl)morpholino]ethyl]-1-[3-methoxy-5-(trifluoromethyl)benzoyl]-2-(2-naphthylmethyl)piperazine dihydrochloride mp: 134–140° C.
$[\alpha]_D^{28.5}$: +0.78° (C=0.35, MeOH)
IR (KBr): 3750, 1640 cm$^{-1}$
NMR (DMSO-d$_6$, δ): 2.8–5.4 (28H, m), 6.3–8.0 (10H, m)
MASS (APCI): 586 (M+H)$^+$ (free)

(86) (2R)-4-[4-(3,3-Dimethylmorpholino)-2-butynyl]-1-[3-methoxy-5-(trifluoromethyl)benzoyl]-2-(2-naphthylmethyl)piperazine dihydrochloride mp: 190–199° C.
$[\alpha]_D^{28.7}$: −2.16° (C=0.26, MeOH)
IR (KBr): 3750, 3400, 1640 cm$^{-1}$
NMR (DMSO-d$_6$, δ): 1.32 (3H, s), 1.37 (3H, s), 3.0–5.4 (22H, m), 6.3–8.0 (1H, m)
MASS (APCI): 594 (M+H)$^+$ (free)

(87) (2R)-4-[2-(cis-2,6-Dimethylmorpholino)ethyl]-1-[3-methoxy-5-(trifluoromethyl)benzoyl]-2-(2-naphthylmethyl)piperazine dihydrochloride mp: 188–193° C.
$[\alpha]_D^{28.5}$: −7.70° (C=0.31, MeOH)
IR (KBr): 3430, 3400, 1640 cm$^{-1}$
NMR (DMSO-d$_6$, δ): 1.16 (6H, d, J=6.0 Hz), 2.6–5.4 (22H, m), 6.3–8.0 (1H, m)
MASS (APCI): 570 (M+H)$^+$ (free)

(88) (2R)-4-[2-(4,4-Difluoropiperidino)ethyl]-1-[3-methoxy-5-(trifluoromethyl)benzoyl]-2-(2-naphthylmethyl)piperazine dihydrochloride mp: 243–260° C.
$[\alpha]_D^{28.7}$: −10.36° (C=0.28, MeOH)
IR (KBr): 3400, 1640 cm$^{-1}$
NMR (DMSO-d$_6$, δ): 2.2–5.4 (24H, m), 6.3–8.0 (10H, m)
MASS (APCI): 576 (M+H)$^+$ (free)

(89) (2R)-1-[3-Methoxy-5-(trifluoromethyl)benzoyl]-2-(2-naphthylmethyl)-4-[3-(3-pyridyl)-2-propynyl]piperazine $[\alpha]_D^{28.7}$: −5.37° (C=0.27, MeOH)
IR (KBr): 3740, 1640 cm$^{-1}$
NMR (DMSO-d$_6$, δ): 2.1–5.2 (14H, m), 6.5–8.0 (12H, m), 8.57 (1H, m), 8.64 (1H, s)
MASS (APCI): 544 (M+H)$^+$

(90) (2R)-1-[3-Methoxy-5-(trifluoromethyl)benzoyl]-2-(2-naphthylmethyl)-4-[2-(5,6,7,8-tetrahydro-1,6-naphthyridin-6-yl)ethyl]piperazine trihydrochloride mp: 173–183° C.
$[\alpha]_D^{27.9}$: −20.91° (C=0.26, MeOH)
IR (KBr): 3400, 1640 cm$^{-1}$
NMR (DMSO-d$_6$, δ): 2.8–5.4 (22H, m), 6.4–8.0 (11H, m), 8.03 (1H, d, J=8.5 Hz), 8.67 (1H, d, J=4.9 Hz)
MASS (APCI): 589 (M+H)$^+$ (free)

(91) (2R)-1-[3,5-Bis(trifluoromethyl)]-2-[(1H-indol-3-yl)-methyl]-4-[2-(5,6,7,8-tetrahydro-1,6-naphthyridin-6-yl)-ethyl]piperazine trihydrochloride mp: 190–200° C.
$[\alpha]_D^{27}$: −25.25° (C=0.2, MeOH)
IR (KBr): 3500–3150, 2700–2300, 1646, 1519, 1434, 1371, 1272, 1236 cm$^{-1}$
NMR (DMSO-d$_6$, δ): 2.60–5.20 (25H, m), 6.60–8.70 (11H, m), 11.17 (1H, s)
MASS (APCI): 616 (M+H)$^+$ (free)

(92) (2R)-2-[(1H-Indol-3-yl)methyl]-1-[3-methoxy-5-(trifluoromethyl)benzoyl]-4-[2-[(2R)-2-(methoxymethyl)-morpholino]ethyl]piperazine dihydrochloride mp: 200–210° C.
$[\alpha]_D^{25.6}$: +34.4° (C=0.27, MeOH)
IR (KBr): 3400–3000, 2900–2500, 1637, 1607, 1461, 1423 cm$^{-1}$
NMR (DMSO-d$_6$, δ): 2.81–5.20 (28H, m), 6.60–9.20 (8H, m), 10.98 (1H, s), 11.60–12.20 (2H, m)
MASS (APCI): 575 (M+H)$^+$ (free)

(93) (2R)-2-[(1H-Indol-3-yl)methyl]-1-[3-methoxy-5-(trifluoromethyl)benzoyl]-4-[4-(3,3-dimethylmorpholino)-2-butynyl]piperazine dihydrochloride mp: 190–200° C.
$[\alpha]_D^{25.6}$: +23.6° (C=0.25, MeOH)
IR (KBr): 3400–3000, 2900–2500, 1644, 1608, 1457, 1421 cm$^{-1}$
NMR (DMSO-d$_6$, δ): 1.32–1.37 (6H, m), 3.20–5.20 (22H, m), 6.60–8.00 (8H, m), 10.96 (1H, s), 12.00–12.40 (2H, m)
MASS (APCI): 583 (M+H)$^+$ (free)

(94) (2R)-2-[(1H-Indol-3-yl)methyl]-4-[2-(cis-2,6-dimethylmorpholino)ethyl]-1-[3-methoxy-5-(trifluoromethyl)benzoyl]piperazine dihydrochloride mp: 188–200° C.
$[\alpha]_D^{26}$: +28.4° (C=0.19, MeOH)
IR (KBr): 3500–3150, 2700–2300, 1637, 1606, 1459, 1272, 1174 cm$^{-1}$
NMR (DMSO-d$_6$, δ): 0.80–5.20 (28H, m), 6.60–8.20 (8H, m), 10.96 (1H, s), 11.40–11.80 (2H, br)
MASS (APCI): 559 (M+H)$^+$ (free)

(95) (2R)-4-[2-(4,4-Difluoropiperidino)ethyl]-2-[(1H-indol-3-yl)methyl]-1-[3-methoxy-5-(trifluoromethyl)benzoyl]-piperazine dihydrochloride mp: 130–140° C.
$[\alpha]_D^{25.6}$: +22.9° (C=0.22, MeOH)
IR (KBr): 3400–3000, 2900–2500, 1635, 1608, 1461, 1423 cm$^{-1}$
NMR (DMSO-d$_6$, δ): 2.20–5.20 (24H, m), 6.60–8.80 (8H, m), 10.97 (1H, s), 11.20–12.20 (2H, m)
MASS (APCI): 565 (M+H)$^+$ (free)

(96) (2R)-2-[(1H-Indol-3-yl)methyl]-1-[3-methoxy-5-(trifluoromethyl)benzoyl]-4-[(1-methyl-1H-pyrazol-4-yl)methyl]piperazine hydrochloride mp: 210–220° C.
$[\alpha]_D^{25.6}$: +18.58° (C=0.24, MeOH)
IR (KBr): 3400–3000, 2900–2500, 1639, 1609, 1459, 1419, 1321 cm$^{-1}$
NMR (DMSO-d$_6$, δ): 2.70–5.20 (17H, m), 6.50–8.80 (8H, m), 7.63 (1H, s), 7.94 (1H, s), 10.88–10.93 (1H, m), 11.59 (1H, br s)
MASS (APCI): 512 (M+H)$^+$ (free)

(97) (2R)-2-[(1H-Indol-3-yl)methyl]-1-[3-methoxy-5-(trifluoromethyl)benzoyl]-4-(3-pyridylmethyl)piperazine dihydrochloride mp: 190–200° C.
$[\alpha]_D^{25.6}$: +22.0° (C=0.34, MeOH)
IR (KBr): 3400–3000, 2900–2500, 1637, 1606, 1463, 1421 cm$^{-1}$
NMR (DMSO-d$_6$, δ): 2.80–5.50 (14H, m), 6.50–8.00 (8H, m), 7.74–7.92 (1H, m), 8.67 (1H, d, J=8.0 Hz), 8.86 (1H, d, J=4.4 Hz), 9.07 (1H, s), 10.87 (1H, br s), 12.00–12.40 (2H, m)
MASS (APCI): 509 (M+H)$^+$ (free)

(98) (2R)-2-[(1H-Indol-3-yl)methyl]-1-[3-methoxy-5-(trifluoromethyl)benzoyl]-4-[3-(3-pyridyl)propyl]-piperazine dihydrochloride mp: 135–145° C.
$[\alpha]_D^{26.3}$: +21.2° (C=0.29, MeOH)
IR (KBr): 3400–3000, 2900–2500, 1635, 1607, 1463, 1421 cm$^{-1}$
NMR (DMSO-d$_6$, δ): 2.20–5.20 (18H, m), 6.60–8.80 (11H, m), 11.80–12.00 (2H, m)
MASS (APCI): 537 (M+H)$^+$ (free)

(99) (2R)-2-[(1H-Indol-3-yl)methyl]-1-[3-methoxy-5-(trifluoromethyl)benzoyl]-4-[2-(5,6,7,8-tetrahydro-1,6-naphthyridin-6-yl)ethyl]piperazine trihydrochloride mp: 180–190° C.
$[\alpha]_D^{27}$: −8.3° (C=0.15, MeOH)
IR (KBr): 3500–3150, 1700–2300, 1637, 1631, 1461, 1348, 1238, 1172 cm$^{-1}$
NMR (DMSO-d$_6$, δ): 3.20–5.20 (22H, m), 6.60–8.20. (11H, m), 10.98 (1H, s)
MASS (APCI): 578 (M+H)$^+$ (free)

(100) 1-[3,5-Bis(trifluoromethyl)benzoyl]-2-(3-hydroxy-4-methylbenzyl)-4-[2-(4,4-difluoropiperidino)ethyl]-piperazine dihydrochloride mp: 250–255° C
IR (KBr): 3400–3000, 2900–2500, 1646, 1427, 1280 cm$^{-1}$
NMR (DMSO-d$_6$, δ): 2.08 (3H, s), 2.35–5.20 (21H, m), 6.05–8.20 (7H, m), 8.90–9.50 (2H, m)
MASS (APCI): 594 (M+H)$^+$ (free)

(101) (2R)-1-[3,5-Bis(trifluoromethyl)benzoyl]-2-[3-[(2-methoxyethoxy)methoxy]-4-methylbenzyl]-4-[2-[(2R)-2-(methoxymethyl)morpholino]ethyl]piperazine IR (Neat): 1643, 1508, 1435, 1381, 1354, 1331, 1279, 1130, 1101, 1012 cm$^{-1}$
NMR (CDCl$_3$, δ): 1.90–5.60 (37H, m), 6.20–8.20 (6H, m)
MASS (APCI): 692 (M+H)$^+$ (102) (2R)-1-[3,5-Bis(trifluoromethyl)benzoyl]-4-[2-[(3S,5S)-3,5-dimethylmorpholino]ethyl]-2-[3-[(2-methoxyethoxy)-methoxy]-4-methylbenzyl]piperazine IR (Neat): 1643, 1583, 1508, 1435, 1379, 1356, 1329, 1279, 1132, 1099, 1012 cm$^{-1}$
NMR (CDCl$_3$, δ): 1.01 (6H, d, J=6.4 Hz), 1.90–5.50 (31H, m), 6.20–8.20 (6H, m)
MASS (APCI): 676 (M+H)$^+$ (103) (2R)-1-[3,5-Bis(trifluoromethyl)benzoyl]-4-[2-(cis-3,5-dimethylmorpholino)ethyl]-2-[3-[(2-methoxyethoxy)-methoxy]-4-methylbenzyl]piperazine IR (Neat): 1643, 1583, 1508, 1452, 1435, 1406, 1379, 1356, 1325, 1277, 1099, 1012 cm$^{-1}$
NMR (CDCl$_3$, δ): 0.51–5.70 (37H, m), 6.10–8.20 (6H, m)
MASS (APCI): 676 (M+H)$^+$ (104) (2R)-1-[3,5-Bis(trifluoromethyl)benzoyl]-2-[3-[(2-methoxyethoxy)methoxy]-4-methylbenzyl]-4-[3-[(2S)-2-(methoxymethyl)morpholino]propyl]piperazine IR (Neat): 1643, 1583, 1508, 1437, 1406, 1379, 1354, 1331, 1279, 1097, 1014 cm$^{-1}$
NMR (CDCl$_3$, δ): 1.60–5.40 (39H, m), 6.30–7.90 (6H, m)
MASS (APCI): 706.3 (M+H)$^+$, 728.3 (M+Na)$^+$ (105) (2R)-1-[3,5-Bis(trifluoromethyl)benzoyl]-2-[3-[(2-methoxyethoxy)methoxy]-4-methylbenzyl]-4-[(E)-4-[(2S)-2-(methoxymethyl)morpholino]-2-butenyl]piperazine IR (Neat): 1643, 1510, 1454, 1435, 1406, 1379, 1352, 1331, 1281, 1134, 1101, 1012 cm$^{-1}$
NMR (CDCl$_3$, δ): 0.70–5.40 (37H, m), 6.30–7.90 (8H, m)
MASS (ESI): 718.3 (M+H)$^+$, 740.3 (M+Na)$^+$ (106) (2R)-1-[3,5-Bis(trifluoromethyl)benzoyl]-2-[3-[(2-methoxyethoxy)methoxy]-4-methylbenzyl]-4-[2-[4,5,6,7-tetrahydrothieno[3,2-c]pyridin-5-yl]ethyl]piperazine IR (Neat): 1678, 1645, 1628, 1618, 1510, 1477, 1462, 1454, 1435, 1427, 1385, 1381, 1275 cm$^{-1}$
NMR (CDCl$_3$, δ): 0.70–5.40 (31H, m), 6.20–8.20 (8H, m)
MASS (APCI): 700 (M+H)$^+$ (107) (2R)-1-[3,5-Bis(trifluoromethyl)benzoyl]-2-[3-[(2-methoxyethoxy)methoxy]-4-methylbenzyl]-4-[(quinolin-6-yl)methyl]piperazine IR (Neat): 1693, 1678, 1645, 1630, 1618, 1547, 1539, 1514, 1464, 1454, 1427, 1392, 1387, 1381, 1277 cm$^{-1}$
NMR (CDCl$_3$, δ): 0.70–5.50 (23H, m), 6.20–9.00 (12H, m)
MASS (APCI): 676 (M+H)$^+$ (108) (2R)-1-[3,5-Bis(trifluoromethyl)benzoyl]-2-[3-[(2-methoxyethoxy)methoxy]-4-methylbenzyl]-4-[(3-bromo-1,2,4-oxadiazol-5-yl)methyl]piperazine NMR (CDCl$_3$, δ): 2.19 (3H, s), 2.40–5.40 (15H, m), 3.38 (3H, s), 3.78 (2H, s), 6.30–8.00 (6H, m)
MASS (APCI): 695 (M+H)$^+$, 621, 609

EXAMPLE 10

The following compounds were obtained according to a similar manner to that of Example 1.

(1) (2R)-1-[3,5-Bis(trifluoromethyl)benzoyl]-2-[4-fluorobenzyl]-4-[2-[(2S)-2-(methoxymethyl)morpholino]-ethyl]piperazine dihydrochloride mp: 129–133° C.
$[\alpha]_D^{28.0}$: +6.96° (C=0.28, MeOH)
IR (KBr): 1645, 1516, 1281, 1182, 1138 cm$^{-1}$
NMR (DMSO-d$_6$, δ): 2.70–5.20 (25H, m), 7.00–8.22 (7H, m)
MASS (APCI): 592 (M+H)$^+$ (free)

(2) (2R)-1-[3,5-Bis(trifluoromethyl)benzoyl]-2-(2-naphthylmethyl)-4-[2-[(2S)-2-(methoxymethyl)morpholino]-ethyl]piperazine dihydrochloride mp: 145–148° C.
$[\alpha]_D^{28.9}$: −16.6° (C=0.49, MeOH)
IR (KBr): 1645, 1429, 1281, 1182, 1134 cm$^{-1}$
NMR (DMSO-d$_6$, δ): 2.80–5.40 (25H, m), 7.05–8.20 (10H, m)
MASS (APCI): 624 (M+H)$^+$ (free)

(3) 1-[3,5-Bis(trifluoromethyl)benzoyl]-2-[3-[(2-methoxyethoxy)methoxy]-4-methylbenzyl]-4-[4-[(2S,5S)-2-methoxymethyl-5-methylmorpholino]-2-butynyl]piperazine IR (KBr): 1643 cm$^{-1}$
NMR (CDCl$_3$, δ): 1.20 (3H, d, J=6.3 Hz), 2.19 (3H, br s), 1.92–2.12 (2H, m), 2.60–5.40 (25H, m), 3.36 (6H, s), 6.67–7.81 (6H, m)
MASS (ESI+): 730.3 (M+H)$^+$, 752 (M+Na)$^+$ (4) 1-[3,5-Bis(trifluoromethyl)benzoyl]-2-[3-[(2-methoxyethoxy)methoxy]-4-methylbenzyl]-4-[2-[(1R,4S)-3,3-dimethyl-2-oxa-5-azabicyclo[2.2.1]heptan-5-yl]-ethyl]piperazine IR (Neat): 1643, 1437 cm$^{-1}$
NMR (CDCl$_3$, δ): 1.10–1.12 (3H, m), 1.31 (3H, s), 1.60–1.75 (1H, m), 1.92 (1H, d, J=10.0 Hz), 2.20-(3H, s), 2.28 (1H, d, J=10.0 Hz), 2.20–4.60 (19H, m), 3.36 (3H, s), 4.43 (1H, br s), 5.00–5.40 (2H, m), 6.30–7.79 (6H, m)
MASS (APCI): 688 (M+H)$^+$

EXAMPLE 11

Sodium triacetoxyborohydride (0.3 g) was added in portions to a mixture of (2R)-1-[3,5-bis(trifluoromethyl)-benzoyl]-2-[3-[(2-methoxyethoxy)methoxy]-4-methylbenzyl]-piperazine (0.5 g) and 1-methyl-1H-pyrazole-4-carboxaldehyde (0.12 g) in dichloromethane (10 ml) and the whole was stirred at room temperature for 1 hour. The mixture was washed with sodium hydrogen carbonate aqueous solution, dried over magnesium sulfate and evaporated under reduced pressure. The residue was purified by column chromatography on silica gel using ethyl acetate as an eluent. The fractions containing the objective compound were collected and evaporated in vacuo to give (2R)-1-[3,5-bis(trifluoromethyl)benzoyl]-2-[3-[(2-methoxyethoxy)methoxy]-4-methylbenzyl]-4-[(1-methyl-1H-pyrazol-4-yl)methyl]piperazine (0.54 g) as an oil.
IR (Neat): 1641, 1579, 1508, 1435, 1381, 1352, 1329, 1277, 1097, 1088, 1014 cm$^{-1}$
NMR (CDCl$_3$, δ): 1.75–5.40 (26H, m), 6.25–7.95 (8H, m)
MASS (APCI): 629 (M+H)$^+$

EXAMPLE 12

The following compounds were obtained according to a similar manner to that of Example 11.

(1) (2R)-1-[3,5-Bis(trifluoromethyl)benzoyl]-2-[3-[(2-methoxyethoxy)methoxy]-4-methylbenzyl]-4-(3-pyridylmethyl)piperazine IR (Neat): 1643, 1583, 1508, 1431, 1379, 1356, 1352, 1331, 1279, 1097 cm$^{-1}$
NMR (CDCl$_3$, δ): 0.70–5.60 (23H, m), 6.20–8.80 (10H, m)
MASS (APCI): 626 (M+H)$^+$ (2) (2R)-1-[3,5-Bis(trifluoromethyl)benzoyl]-2-(4-chloro-3-hydroxybenzyl)-4-[(1-methyl-1H-pyrazol-4-yl)methyl]-piperazine hydrochloride mp: 159–163° C.
$[α]_D^{28}$: −5.25° (C=2.0, MeOH)
IR (KBr): 3398, 1647, 1427, 1281, 1178, 1138 cm$^{-1}$
NMR (DMSO-d$_6$, δ): 2.60–5.10 (11H, m), 3.85 (3H, s), 6.26–7.21 (3H, m), 7.51–8.23 (5H, m), 10.20 (1H, br)
MASS (APCI): 561 (M+H)$^+$ (free)

(3) (2R)-1-[3,5-Bis(trifluoromethyl)benzoyl]-2-(4-chloro-3-hydroxybenzyl)-4-(3-pyridylmethyl)piperazine dihydrochloride mp: 187–192° C.
$[α]_D^{27.3}$: −8.11° (C=0.185, MeOH)
IR (KBr): 3435, 1645, 1429, 1281, 1182, 1136 cm$^{-1}$
NMR (DMSO-d$_6$, δ): 2.60–6.10 (11H, m), 6.29–7.20 (3H, m), 7.47–8.24 (4H, m), 8.61–9.03 (3H, m), 10.13 (1H, br)
MASS (APCI): 558 (M+H)$^+$ (free)

(4) (2R)-1-[3,5-Bis(trifluoromethyl)benzoyl]-2-(4-chloro-3-hydroxybenzyl)-4-[3-(3-pyridyl)propyl]piperazine dihydrochloride mp: 65–70° C.
$[α]_D^{27.9}$: −7.68° (C=0.28, MeOH)
IR (KBr): 1647, 1427, 1279, 1180, 1136 cm$^{-1}$
NMR (DMSO-d$_6$, δ): 2.10–5.10 (15H, m), 6.30–7.29 (3H, m), 7.48 (1H, s), 7.84 (1H, s), 7.95–8.89 (5H, m), 10.20 (1H, br)
MASS (APCI): 586 (M+H)$^+$ (free)

(5) (2R)-1-[3-Methoxy-5-(trifluoromethyl)benzoyl]-2-(4-chloro-3-hydroxybenzyl)-4-[(1-methyl-1H-pyrazol-4-yl)methyl]piperazine hydrochloride mp: 140–150° C.
$[α]_D^{28.3}$: +4.17° (C=0.36, MeOH)
IR (KBr): 3411, 2600, 1641, 1604, 1462, 1423, 1240, 1173, 1128 cm$^{-1}$
NMR (DMSO-d$_6$, δ): 2.70–5.10 (11H, m), 3.85 (6H, s), 6.30–7.32 (6H, m), 7.60 (1H, s), 7.95 (1H, s), 10.18 (1H, br)
MASS • (APCI): 523 (M+H)$^+$ (free)

(6) (2R)-1-[3-Methoxy-5-(trifluoromethyl)benzoyl]-2-(4-chloro-3-hydroxybenzyl)-4-(3-pyridylmethyl)piperazine dihydrochloride mp: 215–224° C.
$[α]_D^{28.3}$: +7.60° (C=0.25, MeOH)
IR (KBr): 3400, 1639, 1606, 1464, 1425, 1173; 1128 cm$^{-1}$
NMR (DMSO-d$_6$, δ): 2.60–5.10 (11H, m), 3.84 (3H, s), 6.26–7.33 (6H, m), 7.92 (1H, dd, J=4.8 and 7.9 Hz), 8.65 (1H, d, J=7.9 Hz), 8.88 (1H, d, J=4.8 Hz), 9.04 (1H, s), 10.13 (1H, br)
MASS (APCI): 520 (M+H)$^+$ (free)

(7) (2R)-1-[3-Methoxy-5-(trifluoromethyl)benzoyl]-2-(4-chloro-3-hydroxybenzyl)-4-[3-(3-pyridyl)propyl]-piperazine dihydrochloride mp: 90–110° C.
$[α]_D^{28.3}$: +0.27° (C=0.185, MeOH)
IR (KBr): 2952, 2600, 1645, 1606, 1464, 1425, 1238, 1171, 1126 cm$^{-1}$
NMR (DMSO-d$_6$, δ): 2.10–5.20 (15H, m), 3.83 (3H, s), 6.30–7.33 (6H, m), 7.61 (1H, dd, J=4.2 and 8.0 Hz), 8.01 (1H, d, J=8.0 Hz), 8.58 (1H, d, J=4.2 Hz), 8.65 (1H, s), 10.20 (1H, br)
MASS (APCI): 548 (M)$^+$ (free)

(8) (2R)-1-[3,5-Bis(trifluoromethyl)benzoyl]-2-(4-fluoro-3-methoxybenzyl)-4-[(1-methyl-1H-pyrazol-4-yl)methyl]-piperazine hydrochloride mp: 127–135° C.
$[\alpha]_D^{28.1}$: +2.75° (C=0.20, MeOH)
IR (KBr): 3400, 1645, 1516, 1282, 1182, 1136 cm$^{-1}$
NMR (DMSO-d$_6$, δ): 2.80–5.20 (14H, m), 3.85 (3H, s) 6.40–7.30 (3H, m), 7.58–8.30 (5H, m)
MASS (APCI): 559 (M+H)$^+$ (free)

(9) (2R)-1-[3,5-Bis(trifluoromethyl)benzoyl]-2-(4-fluoro-3-methoxybenzyl)-4-(3-pyridylmethyl)piperazine dihydrochloride mp: 143–147° C.
$[\alpha]_D^{28.1}$: +0.889° (C=0.225, MeOH)
IR (KBr): 3400, 1645, 1516, 1282, 1182, 1134 cm$^{-1}$
NMR (DMSO-d$_6$, δ): 2.80–5.20 (14H, m), 6.40–7.30 (3H, m), 7.50–8.30 (4H, m), 8.65 (1H, d, J=8.3 Hz), 8.88 (1H, d, J=5.0 Hz), 9.08 (1H, s)
MASS (APCI): 556 (M+H)$^+$ (free)

(10) (2R)-1-[3,5-Bis(trifluoromethyl)benzoyl]-2-(4-fluoro-3-methoxybenzyl)-4-[3-(3-pyridyl)propyl]piperazine dihydrochloride mp: 125–130° C.
$[\alpha]_D^{27.7}$: +2.50° (C=0.18, MeOH)
IR (KBr): 3400, 1645, 1516, 1281, 1182, 1134 cm$^{-1}$
NMR (DMSO-d$_6$, δ): 2.00–5.20 (18H, m), 6.40–7.40 (3H, m), 7.50–8.50 (5H, m), 8.70–9.00 (2H, m)
MASS (APCI): 584 (M+H)$^+$ (free)

(11) (2R)-2-(4-Fluoro-3-methoxybenzyl)-1-[3-methoxy-5-(trifluoromethyl)benzoyl]-4-[(1-methyl-1H-pyrazol-4-yl)-methyl]piperazine hydrochloride $[\alpha]_D^{28}$: +23.27° (C=0.245, MeOH)
IR (KBr): 1741, 1707, 1693, 1678, 1645, 1628, 1616, 1562, 1547, 1516, 1464, 1423, 1344, 1317, 1273, 1242, 1215, 1169, 1126, 1051 cm$^{-1}$
NMR (DMSO-d$_6$, δ): 2.00–5.20 (20H, m), 6.30–8.00 (8H, m)
MASS (APCI): 521 (M+H)$^+$ (free)

(12) (2R)-2-(4-Fluoro-3-methoxybenzyl)-1-[3-methoxy-5-(trifluoromethyl)benzoyl]-4-(3-pyridylmethyl)piperazine dihydrochloride $[\alpha]_D^{28}$: +24.20° (C=0.345, MeOH)
IR (KBr): 1643, 1635, 1616, 1516, 1466, 1423, 1350, 1273, 1171, 1126, 1051 cm$^{-1}$
NMR (DMSO-d$_6$, δ): 0.80–5.30 (17H, m), 6.00–9.00 (10H, m)
MASS (APCI): 518 (M+H)$^+$ (free)

(13) (2R)-2-(4-Fluoro-3-methoxybenzyl)-1-[3-methoxy-5-(trifluoromethyl)benzoyl]-4-[3-(3-pyridyl)propyl]-piperazine dihydrochloride $[\alpha]_D^{27.1}$: +25.77° (C=0.26, MeOH)
IR (KBr): 1645, 1635, 1628, 1618, 1516, 1464, 1425, 1171, 1128, 1088, 1047 cm$^{-1}$
NMR (DMSO-d$_6$, δ): 1.60–5.30 (21H, m), 6.00–9.00 (10H, m)
MASS (APCI): 546 (M+H)$^+$ (free)

(14) (2R)-1-[3,5-Bis(trifluoromethyl)benzoyl]-2-(4-fluoro-3-hydroxybenzyl)-4-[(1-methyl-1H-pyrazol-4-yl)methyl]-piperazine hydrochloride mp: 160–170° C.
$[\alpha]_D^{27.6}$: −4.45° (C=0.55, MeOH)
IR (KBr): 1693, 1674, 1645, 1630, 1533, 1516, 1477, 1446, 1437, 1429, 1392, 1387, 1365, 1282, 1180, 1138, 1057 cm$^{-1}$
NMR (DMSO-d$_6$, δ): 0.80–5.20 (14H, m), 6.00–8.40 (8H, m)
MASS (APCI): 545 (M+H)$^+$ (free)

(15) (2R)-1-[3,5-Bis(trifluoromethyl)benzoyl]-2-(4-fluoro-3-hydroxybenzyl)-4-(3-pyridylmethyl)piperazine dihydrochloride mp: 50–60° C.
$[\alpha]_D^{27.6}$: −0.95° (C=0.37, MeOH)
IR (KBr): 1707, 1693, 1676, 1645, 1628, 1618, 1558, 1547, 1533, 1516, 1477, 1466, 1454, 1429, 1392, 1387, 1367, 1281, 1180, 1136 cm$^{-1}$
NMR (DMSO-d$_6$, δ): 0.80–5.20 (11H, m), 6.00–9.20 (10H, m)
MASS (APCI): 542 (M+H)$^+$ (free)

(16) (2R)-1-[3,5-Bis(trifluoromethyl)benzoyl]-2-(4-fluoro-3-hydroxybenzyl)-4-[3-(3-pyridyl)propyl] piperazine dihydrochloride mp: 80–95° C.
$[\alpha]_D^{26.5}$: −3.51° (C=0.285, MeOH)
IR (KBr): 1647, 1518, 1281, 1180, 1136 cm$^{-1}$
NMR (DMSO-d$_6$, δ): 2.00–5.20 (15H, m), 6.30–7.20 (3H, m), 7.40–8.40 (5H, m), 8.60–8.80 (2H, m), 9.78 (1H, br)
MASS (APCI): 570 (M+H)$^+$ (free)

(17) (2R)-1-[3,5-Bis(trifluoromethyl)benzoyl]-2-(4-chlorobenzyl)-4-[(1-methyl-1H-pyrazol-4-yl)methyl]-piperazine hydrochloride mp: 210–245° C. (decomp.)
$[\alpha]_D^{27.6}$: −8.83° (C=0.283, MeOH)
IR (KBr): 1647, 1516, 1508, 1498, 1464, 1454, 1446, 1427, 1362, 1281, 1182, 1138, 1057, 1020 cm$^{-1}$
NMR (DMSO-d$_6$, δ): 2.00–5.40 (14H, m), 6.80–8.30 (9H, m)
MASS (APCI): 545 (M+H)$^+$ (free)

(18) (2R)-1-[3,5-Bis(trifluoromethyl)benzoyl]-2-(4-chlorobenzyl)-4-(3-pyridylmethyl)piperazine dihydrochloride mp: 220–228° C. (decomp.)
$[\alpha]_D^{27.7}$: −5.58° (C=0.26, MeOH)
IR (KBr): 1643, 1495, 1489, 1468, 1429, 1363, 1319, 1284, 1279, 1186, 1136, 1053 cm$^{-1}$
NMR (DMSO-d$_6$, δ): 2.00–5.80 (11H, m), 6.70–9.10 (11H, m)
MASS (APCI): 542 (M+H)$^+$ (free)

(19) (2R)-1-[3,5-Bis(trifluoromethyl)benzoyl]-2-(4-chlorobenzyl)-4-[3-(3-pyridyl)propyl]piperazine dihydrochloride mp: 60–100° C.
$[\alpha]^{28.3}$: −5.74° (C=0.27, MeOH)

IR (KBr): 1645, 1551, 1514, 1498, 1468, 1429, 1363, 1319, 1281, 1184, 1136, 1103, 1039, 1024 cm$^{-1}$
NMR (DMSO-d$_6$, δ): 2.00–5.40 (15H, m), 6.80–9.00 (11H, m)
MASS (APCI): 570 (M+H)$^+$ (free)

(20) (2R)-2-(4-Chlorobenzyl)-1-[3-methoxy-5-(trifluoromethyl)benzoyl]-4-[(1-methyl-1H-pyrazol-4-yl)-methyl]piperazine hydrochloride mp: 70–100° C.
[α]$_D^{27.8}$: +1.84° (C=0.435, MeOH)
IR (KBr): 1693, 1641, 1635, 1628, 1604, 1550, 1547, 1539, 1516, 1498, 1466, 1437, 1414, 1352, 1269, 1169, 1128, 1092, 1051 cm$^{-1}$
NMR (DMSO-d$_6$, δ): 2.60–5.20 (17H, m), 6.50–8.10 (9H, m)
MASS (APCI): 507 (M+H)$^+$ (free)

(21) (2R)-2-(4-Chlorobenzyl)-1-[3-methoxy-5-(trifluoromethyl)benzoyl]-4-(3-pyridylmethyl)piperazine dihydrochloride mp: 60–80° C.
[α]$_D^{27.8}$: +10.56° (C=0.27, MeOH)
IR (KBr): 1643, 1610, 1496, 1466, 1421, 1373, 1350, 1315, 1271, 1242, 1174, 1130, 1097, 1049 cm$^{-1}$
NMR (DMSO-d$_6$, δ): 2.60–5.20 (14H, m), 6.40–9.20 (11H, m)
MASS (APCI): 504 (M+H)$^+$ (free)

(22) (2R)-2-(4-Chlorobenzyl)-1-[3-methoxy-5-(trifluoromethyl)benzoyl]-4-[3-(3-pyridyl)propyl]-piperazine dihydrochloride mp: 60–100° C.
[α]$_D^{28.3}$: +4.08° (C=0.245, MeOH)
IR (KBr): 1643, 1606, 1558, 1550, 1516, 1496, 1466, 1421, 1350, 1317, 1271, 1242, 1173, 1128, 1097, 1051 cm$^{-1}$
NMR (DMSO-d$_6$, δ): 1.80–5.40 (18H, m), 6.40–9.00 (11H, m)
MASS (APCI): 532 (M+H)$^+$ (free)

(23) (2R)-1-[3,5-Bis(trifluoromethyl)benzoyl]-2-(4-fluorobenzyl)-4-[(1-methyl-1H-pyrazol-4-yl)methyl]-piperazine hydrochloride mp: 143.3–146.4° C.
[α]$_D^{26.6}$: −5.60° (C=0.25, MeOH)
IR (KBr): 1647, 1513, 1427, 1282, 1182, 1135 cm$^{-1}$
NMR (DMSO-d$_6$, δ): 2.80–5.04 (14H, m), 6.96–8.23 (9H, m)
MASS: 529 (M+H)$^+$ (free)

(24) (2R)-1-[3,5-Bis(trifluoromethyl)benzoyl]-2-(4-fluorobenzyl)-4-(3-pyridylmethyl)piperazine dihydrochloride mp: 130.0–137.3° C.
[α]$_D^{26}$: −13.03° (C=0.33, MeOH)
IR (KBr): 1645, 1427, 1282, 1184, 1133 cm$^{-1}$
NMR (DMSO-d$_6$, δ): 2.84–5.01 (11H, m), 6.94–9.05 (11H, m)
MASS: 526 (M+H)$^+$ (free)

(25) (2R)-2-(4-Fluorobenzyl)-1-[3-methoxy-5-(trifluoromethyl)benzoyl]-4-[(1-methyl-1H-pyrazol-4-yl)-methyl]piperazine hydrochloride mp: 225.6–228.4° C.
[α]$_D^{27.5}$: +8.84° (C=0.25, MeOH)
IR (KBr): 1635, 1413, 1351, 1238, 1158, 1122, 1049 cm$^{-1}$
NMR (DMSO-d$_6$, δ): 2.85–5.03 (17H, m), 6.59–8.45 (9H, m)
MASS: 491 (M+H)$^+$ (free)

(26) (2R)-2-(4-Fluorobenzyl)-1-[3-methoxy-5-(trifluoromethyl)benzoyl]-4-(3-pyridylmethyl)piperazine dihydrochloride mp: 81.4–84.3° C.
[α]$_D^{27.1}$: +15.58° (C=0.50, MeOH)
IR (KBr): 1643, 1606, 1513, 1465, 1423, 1349, 1172, 1128 cm$^{-1}$
NMR (DMSO-d$_6$, δ): 2.95–5.00 (14H, m), 6.58–7.32 (7H, m), 7.80–9.03 (4H, m)
MASS: 488 (M+H)$^+$ (free)

(27) (2R)-1-[3,5-Bis(trifluoromethyl)benzoyl]-4-[(1-methyl-1H-pyrazol-4-yl)methyl]-2-(2-naphthylmethyl)piperazine hydrochloride mp: >250° C.
[α]$_D^{25.2}$: −19.62° (C=0.26, MeOH)
IR (KBr): 3400, 1640 cm$^{-1}$
NMR (DMSO-d$_6$, δ): 2.8–5.3 (11H, m), 3.78 (3H, s), 6.96 (1H, d, J=8.1 Hz), 7.4–8.2 (11H, m)
MASS (APCI): 561 (M+H)$^+$ (free)

(28) (2R)-1-[3,5-Bis(trifluoromethyl)benzoyl]-2-(2-naphthylmethyl)-4-(3-pyridylmethyl)piperazine dihydrochloride mp: 198–208° C.
[α]$_D^{24.8}$: −12.81° (C=0.26, MeOH)
IR (KBr): 3430, 2590, 1640 cm$^{-1}$
NMR (DMSO-d$_6$, δ): 3.0–5.2 (11H, m), 6.95 (1H, d, J=7.7 Hz), 7.4–8.0 (9H, m), 8.17 (1H, m), 8.54 (1H, d, J=8.0 Hz), 8.80 (1H, br s), 9.00 (1H, s)
MASS (APCI): 558 (M+H)$^+$ (free)

(29) (2R)-1-[3-Methoxy-5-(trifluoromethyl)benzoyl]-4-[(1-methyl-1H-pyrazol-4-yl)methyl]-2-(2-naphthylmethyl)-piperazine hydrochloride mp: 226–228° C.
[α]$_D^{27.2}$: −2.55° (C=0.28, MeOH)
IR (KBr): 3400, 1640 cm$^{-1}$
NMR (DMSO-d$_6$, δ): 2.9–5.3 (17H, m), 6.6–8.0 (12H, m)
MASS (APCI): 523 (M+H)$^+$ (free)

(30) (2R)-1-[3-Methoxy-5-(trifluoromethyl)benzoyl]-2-(2-naphthylmethyl)-4-(3-pyridylmethyl)piperazine dihydrochloride mp: 162–168° C.
[α]$_D^{27.6}$: −1.41° (C=0.29, MeOH)
IR (KBr): 3400, 1640 cm$^{-1}$
NMR (DMSO-d$_6$, δ): 2.8–5.3 (11H, m), 3.65 and 3.73 (3H, s), 6.5–8.0 (11H, m), 8.51 (1H, d, J=8.7 Hz), 8.80 (1H, m), 8.98 (1H, s)
MASS (APCI): 520 (M+H)$^+$ (free)

(31) (2R)-1-[3,5-Bis(trifluoromethyl)benzoyl]-2-[3-[(2-methoxyethoxy)methoxy]-4-methylbenzyl]-4-[2-(3-pyridyl)-ethyl]piperazine IR (Neat): 1674, 1643, 1581, 1547, 1510, 1429, 1381, 1356, 1350, 1333, 1279, 1132, 1097, 1012 cm$^{-1}$
NMR (CDCl$_3$, δ): 0.70–5.50 (25H, m), 6.20–8.80 (10H, m)
MASS (APCI): 640 (M+H)$^+$

(32) (2R)-1-[3,5-Bis(trifluoromethyl)benzoyl]-4-[2-[3,4-dihydro-2H-pyrido[3,2-b]-1,4-oxazin-4-yl]ethyl]-2-[3-[(2-methoxyethoxy)methoxy]-4-methylbenzyl]piperazine IR (Neat): 1678, 1645, 1628, 1618, 1510, 1477, 1462, 1454, 1435, 1427, 1385, 1381, 1275 cm$^{-1}$
NMR (CDCl$_3$, δ): 0.70–5.60 (29H, m), 6.20–8.00 (9H, m)
MASS (APCI): 697 (M+H)$^+$

(33) (2R)-1-[3,5-Bis(trifluoromethyl)benzoyl]-2-[3-[(2-methoxyethoxy)methoxy]-4-methylbenzyl]-4-[(1-trityl-1H-pyrazol-4-yl)methyl]piperazine $[α]_D^{27.2}$: −26.15° (C=0.260, MeOH)
IR (Neat): 1645, 1450, 1280, 1130, 1020 cm$^{-1}$
NMR (CDCl$_3$, δ): 1.86–5.40 (23H, m), 6.30–7.90 (23H, m)
MASS (API-ES): 857 (M$^+$)

(34) (2R)-1-[3-Methoxy-5-(trifluoromethyl)benzoyl]-4-[1-methyl-1H-pyrazol-4-ylmethyl]-2-[4-(trifluoromethyl)-benzyl]piperazine hydrochloride mp: 218–223° C.
$[α]_D^{27}$: +18.73° (C=0.25, MeOH)
IR (KBr): 3437, 3400, 1645 cm$^{-1}$
NMR (DMSO-d$_6$, δ): 2.80–5.30 (11H, m), 3.80 (3H, s), 3.85 (3H, s), 6.48–7.94 (9H, m)
MASS (APCI): 541 (M+H)$^+$ (free)

(35) (2R)-1-[3-Methoxy-5-(trifluoromethyl)benzoyl]-4-(3-pyridylmethyl)-2-[4-(trifluoromethyl)benzyl]piperazine dihydrochloride mp: 101–108° C.
$[α]_D^{27}$: +15.60° (C=0.25, MeOH)
IR (KBr): 3431, 1643, 1518 cm$^{-1}$
NMR (DMSO-d$_6$, δ): 2.80–5.20 (11H, m), 3.83 (3H, s), 6.42–7.90 (8H, m), 8.56 (1H, d, J=7.6 Hz), 8.84 (1H, d, J=5.2 Hz), 9.01 (1H, s)
MASS (APCI): 538 (M+H)$^+$ (free)

EXAMPLE 13

To a solution of (2R)-1-[3,5-bis(trifluoromethyl)-benzoyl]-2-(3-tert-butyldiphenylsilyloxy-4-methylbenzyl)-4-[2-[(2S)-2-(methoxymethyl)morpholino]ethyl]piperazine (651.9 mg) in tetrahydrofuran (6.5 ml) was added tetrabutylammonium fluoride (1M solution in tetrahydrofuran, 0.85 ml) at 5° C. After stirring at room temperature, the mixture was evaporated and purified with column chromatography (silica gel, 65 ml, methanol:dichloromethane=3:97) to give an oil (381.5 mg). The solution of the oil in methanol (3 ml) was added 2.17M hydrogen chloride in methanol (1.43 ml), and the mixture was concentrated to give (2R)-1-[3,5-bis(trifluoromethyl)benzoyl]-2-(3-hydroxy-4-methylbenzyl)-4-[2-[(2S)-2-(methoxymethyl)morpholino]ethyl]piperazine dihydrochloride as a solid. The solid was recrystallized with a mixture of acetone (4.55 ml) and water (13.9 μl) at room temperature and then 0° C. and dried under reduced pressure at 45° C. to give pure product (393.9 mg) as a powder.
mp: 206–224.5° C.
IR (KBr): 1635 cm$^{-1}$
NMR (D$_2$O, δ): 2.16 (3H, s), 2.60–5.30 (22H, m), 3.40 (3H, s), 6.30–8.10 (6H, m)
MASS (APCI): 604 (M+H)$^+$ (free)

EXAMPLE 14

The following compounds were obtained according to a similar manner to that of Example 13.

(1) (2R)-2-(3-Hydroxy-4-methylbenzyl)-4-[2-[(2S)-2-(methoxymethyl)morpholino]ethyl]-1-[3-nitro-5-(trifluoromethyl)benzoyl]piperazine dihydrochloride
mp: 181–185° C.
$[α]_D^{23}$: +24.00° (C=0.25, MeOH)
IR (KBr): 1641 cm$^{-1}$
NMR (DMSO-d$_6$, δ): 2.08 (3H, s), 2.80–5.10 (25H, m), 6.18–8.55 (6H, m)
MASS (APCI): 581 (M+H)$^+$ (free)

(2) (2R)-1-[3-Dimethylamino-5-(trifluoromethyl)benzoyl]-2-(3-hydroxy-4-methylbenzyl)-4-[2-[(2S)-2-(methoxymethyl)morpholino]ethyl]piperazine dihydrochloride mp: 182–186° C.
$[α]_D^{23}$: +27.00° (C=0.25, MeOH)
IR (KBr): 1643 cm$^{-1}$
NMR (DMSO-d$_6$, δ): 2.06 (3H, s), 2.94 (6H, br s), 2.70–5.20 (25H, m), 6.24–7.00 (6H, m)
MASS (APCI): 579 (M+H)$^+$ (free)

(3) (2R)-2-(3-Hydroxy-4-methylbenzyl)-4-[2-[(2S)-2-(methoxymethyl)morpholino]ethyl]-1-[3-methylamino-5-(trifluoromethyl)benzoyl]piperazine dihydrochloride mp: 159–170° C.
$[α]_D^{22}$: +23.60° (C=0.125, MeOH)
IR (KBr): 3433, 3400, 1643 cm$^{-1}$
NMR (DMSO-d$_6$, δ): 2.06 (3H, s), 2.68 (3H, br s), 2.80–5.10 (25H, m), 6.10–7.00 (6H, m)
MASS (APCI): 565.37 (M+H)$^+$ (free)

(4) (2R)-2-(3-Hydroxy-4-methylbenzyl)-4-[2-[(2S)-2-(methoxymethyl)morpholino]ethyl]-1-[3-(pyrrol-1-yl)-5-(trifluoromethyl)benzoyl]piperazine dihydrochloride mp: 159–170° C.
$[α]_D^{24}$: +1.20° (C=0.125, MeOH)
IR (KBr): 3433, 3400, 1636, 1494 cm$^{-1}$
NMR (DMSO-d$_6$, δ): 2.05 (3H, s), 2.80–5.10 (25H, m), 6.10–8.02 (10H, m)
MASS (APCI): 601.4 (M+H)$^+$ (free)

(5) (2R)-2-(3-Hydroxy-4-methylbenzyl)-4-[2-[(2S)-2-(methoxymethyl)morpholino]ethyl-1-[3-methoxy-5-(trifluoromethyl)benzoyl]piperazine dihydrochloride mp: 160–169° C.
$[α]_D^{24}$: +6.80° (C=0.125, MeOH)
IR (KBr): 3430, 3400, 1643, 1461 cm$^{-1}$ NMR (DMSO-d$_6$, δ): 2.07 (3H, s), 3.27 (3H, s), 3.93 (3H, br s), 2.40–4.10 (22H, m), 6.10–7.40 (6H, m)
MASS (APCI): 566 (M+H)$^+$ (free)

(6) (2R)-2-(3-Hydroxy-4-methylbenzyl)-4-[2-[(2S)-2-(methoxymethyl)morpholino]ethyl]-1-[3-methylthio-5-(trifluoromethyl)benzoyl]piperazine dihydrochloride mp: 154–168° C.
[α]$_D^{24}$: +5.87° (C=0.125, MeOH)
IR (KBr): 3431, 3400, 1639 cm$^{-1}$
NMR (DMSO-d$_6$, δ): 2.09 (3H, s), 3.27 (3H, s), 2.40–5.10 (25H, m), 6.17–7.60 (6H, m)
MASS (APCI): 582 (M+H)$^+$ (free)

(7) (2R)-2-(3-Hydroxy-4-methylbenzyl)-4-[2-[(2S)-2-(methoxymethyl)morpholino]ethyl]-1-[3-methylsulfonyl-5-(trifluoromethyl)benzoyl]piperazine dihydrochloride mp: 173.5–178.0° C.
[α]$_D^{25}$: −19.07° (C=0.125, MeOH)
IR (KBr): 3437, 3402, 1645 cm$^{-1}$
NMR (DMSO-d$_6$, δ): 2.08 (3H, s), 3.27 (3H, s), 3.37 (3H, s), 2.20–5.10 (22H, m), 6.21–8.31 (6H, m)
MASS (APCI): 614 (M+H)$^+$ (free)

(8) (2R)-1-[3-Dimethylsulfamoyl-5-(trifluoromethyl)benzoyl]-2-(3-hydroxy-4-methylbenzyl)-4-[2-[(2S)-2-(methoxymethyl)morpholino]ethyl]piperazine dihydrochloride mp: 153.5–160° C.
[α]$_D^{25}$: −15.60° (C=0.125, MeOH)
IR (KBr): 3400, 1643, 1516 cm$^{-1}$
NMR (DMSO-d$_6$, δ): 2.07 (3H, s), 2.66 (6H, s), 2.40–5.20 (25H, m), 6.18–8.01 (6H, m)
MASS (APCI): 643.36 (M+H)$^+$ (free)

(9) (2R)-2-(3-Hydroxy-4-methylbenzyl)-4-[2-[(2S)-2-(methoxymethyl)morpholino]ethyl]-1-[3-methylsulfamoyl-5-(trifluoromethyl)benzoyl]piperazine dihydrochloride mp: 120–187° C. [α]$_D^{25}$: −15.07° (C=0.125, MeOH)
IR (KBr): 1643 cm$^{-1}$
NMR (DMSO-d$_6$, δ): 2.07 (3H, s), 2.60–5.10 (28H, m), 6.17–8.10 (6H, m)
MASS (APCI): 629 (M+H)$^+$ (free)

(10) (2R)-2-(3-Hydroxy-4-methylbenzyl)-4-[2-[(2S)-2-(methoxymethyl)morpholino]ethyl]-1-[3-(1-pyrrolidinylsulfonyl)-5-(trifluoromethyl)benzoyl]-piperazine dihydrochloride mp: 125–177° C.
[α]$_D^{24}$: −11.10° (C=0.25, MeOH)
IR (KBr): 1645 cm$^{-1}$
NMR (DMSO-d$_6$, δ): 1.60–1.76 (4H, m), 2.07 (3H, s), 2.49–5.20 (29H, m), 6.20–8.02 (6H, m)
MASS (APCI): 669 (M+H)$^+$ (free)

(11) (2R)-2-(3-Hydroxy-4-methylbenzyl)-4-[2-[(2S)-2-(methoxymethyl)morpholino]ethyl]-1-[3-(morpholinosulfonyl)-5-(trifluoromethyl)benzoyl]-piperazine dihydrochloride mp: 130–175° C.
[α]$_D^{25}$: −8.60° (C=0.25, MeOH)
IR (KBr): 1645 cm$^{-1}$
NMR (DMSO-d$_6$, δ): 2.08 (3H, s), 2.60–5.10 (33H, m), 6.20–8.01 (6H, m)
MASS (APCI): 685 (M+H)$^+$ (free)

(12) (2R)-2-(3-Hydroxy-4-methylbenzyl)-4-[2-[(2S)-2-(methoxymethyl)morpholino]ethyl]-1-[3-(4-pyridyl)-5-(trifluoromethyl)benzoyl]piperazine trihydrochloride mp: 169–173° C.
[α]$_D^{28}$: −1.60° (C=0.125, MeOH)
IR (KBr): 1635 cm$^{-1}$
NMR (DMSO-d$_6$, δ): 1.91–2.04 (3H, m), 2.84–5.20 (25H, m), 6.17–8.37 (8H, m), 8.96 (2H, d, J=5.9 Hz)
MASS (APCI): 613 (M+H)$^+$ (free)

(13) (2R)-1-[3-Trifluoromethyl-5-(methylthio)benzoyl]-2-(4-chloro-3-hydroxybenzyl)-4-[2-(cis-2,6-dimethylmorpholino)ethyl]piperazine dihydrochloride mp: 162–178° C.
[α]$_D^{26.2}$: +6.42° (C=0.226, MeOH)
IR (KBr): 3400, 2665, 2600, 2488, 1643, 1425, 1331, 1311, 1174, 1130, 1043 cm$^{-1}$
NMR (DMSO-d$_6$-D$_2$O, δ): 1.17 (6H, d, J=6.2 Hz), 2.40–5.20 (21H, m), 6.26–7.70 (6H, m)
MASS (APCI): 586 (M+H)$^+$ (free), 552

(14) (2R)-1-[3-Trifluoromethyl-5-(methylthio)benzoyl]-2-(4-chloro-3-hydroxybenzyl)-4-[2-(5,6,7,8-tetrahydro-1,6-naphthyridin-6-yl)ethyl]piperazine trihydrochloride mp: 169–178° C.
[α]$_D^{26.4}$: −7.99° (C=0.263, MeOH)
IR (KBr): 3400, 2679, 2561, 1645, 1425, 1173, 1130, 1053 cm$^{-1}$
NMR (DMSO-d$_6$-D$_2$O, δ): 2.40–5.40 (22H, m), 6.20–8.80 (9H, m)
MASS (APCI): 605 (M+H)$^+$ (free), 571

(15) (2R)-1-[3-(2,5-Dimethylpyrrol-1-ylsulfonyl)-5-(trifluoromethyl)benzoyl]-2-(3-hydroxy-4-methylbenzyl)-4-[2-[(2S)-2-(methoxymethyl)morpholino]ethyl]piperazine IR (KBr): 1637 cm$^{-1}$
NMR (DMSO-d$_6$, δ): 2.05 (3H, s), 2.30 (6H, s), 1.78–4.80 (25H, m), 6.05 (2H, s), 6.00–9.17 (6H, m)
MASS (APCI): 693 (M+H)$^+$

(16) (2R)-1-[3,5-Bis(trifluoromethyl)benzoyl]-2-(3-hydroxy-4-methylbenzyl)-4-[(1-(2-hydroxyethyl)-1H-pyrazol-4-yl)-methyl]piperazine hydrochloride mp: 140–156° C.
[α]$_D^{22.3}$: −15.68° (C=0.204, MeOH)
IR (KBr): 3400, 1645, 1427, 1279, 1180, 1134 cm$^{-1}$ NMR (DMSO-d$_6$-D$_2$O, δ): 2.02–5.20 (18H, m), 6.14–8.26 (8H, m)

MASS (APCI): 571 (M+H)$^+$ (free)

EXAMPLE 15

The following compounds were obtained according to a similar manner to that of Example 3.

(1) (2R)-1-[3,5-Bis(trifluoromethyl)benzoyl]-2-(3-hydroxy-4-methylbenzyl)-4-[(1-methyl-1H-pyrazol-4-yl)methyl]-piperazine hydrochloride mp: 160–180° C.
[α]$_D$$^{27.0}$: −13.28° (C=0.32, MeOH)
IR (KBr): 2976, 1643, 1446, 1427, 1381, 1363, 1323, 1281, 1217, 1182, 1142, 1088, 1049 cm$^{-1}$
NMR (DMSO-d$_6$, δ): 1.60–5.20 (17H, m), 5.90–8.30 (8H, m)
MASS (APCI): 541 (M+H)$^+$ (free)

(2) (2R)-1-[3,5-Bis(trifluoromethyl)benzoyl]-2-(3-hydroxy-4-methylbenzyl)-4-(3-pyridylmethyl)piperazine dihydrochloride mp: 110–130° C.
[α]$_D$$^{27.0}$: −7.75° (C=0.4, MeOH)
IR (KBr): 1643, 1558, 1550, 1541, 1516, 1464, 1454, 1427, 1365, 1319, 1281, 1242, 1184, 1138, 1053 cm$^{-1}$
NMR (DMSO-d$_6$, δ): 1.70–5.80 (14H, m), 6.00–9.50 (1H, m)
MASS (APCI): 538 (M+H)$^+$ (free)

(3) (2R)-1-[3,5-Bis(trifluoromethyl)benzoyl]-2-(3-hydroxy-4-methylbenzyl)-4-[2-(5,6,7,8-tetrahydro-1,6-naphthyridin-6-yl)ethyl]piperazine trihydrochloride mp: 255–270° C.
[α]D$^{25.1}$: −22.88° (C=0.295, MeOH)
IR (KBr): 1643, 1635, 1562, 1550, 1516, 1462, 1427, 1365, 1327, 1282, 1244, 1184, 1138, 1041, 1003 cm$^{-1}$
NMR (DMSO-d$_6$, δ): 0.80–5.40 (22H, m), 6.00–8.80 (9H, m)
MASS (APCI): 607 (M+H)$^+$ (free)

(4) (2R)-1-[3,5-Bis(trifluoromethyl)benzoyl]-2-(3-hydroxy-4-methylbenzyl)-4-[(Z)-3-(3-pyridyl)-2-propenyl]-piperazine dihydrochloride mp: 85–130° C.
[α]$_D$$^{22.9}$: +2.86° (C=0.28, MeOH)
IR (KBr): 1643, 1550, 1516, 1462, 1427, 1362, 1325, 1282, 1184, 1136, 1045, 1001 cm$^{-1}$
NMR (DMSO-d$_6$, δ): 0.70–5.20 (14H, m), 6.00–10.00 (12H, m)
MASS (APCI): 564 (M+H)$^+$ (free)

(5) (2R)-1-[3,5-Bis(trifluoromethyl)benzoyl]-2-(3-hydroxy-4-methylbenzyl)-4-[4-[(2S)-2-(methoxymethyl)-morpholino]-2-butynyl]piperazine IR (KBr): 1741, 1707, 1693, 1678, 1645, 1562, 1558 1547, 1539, 1516, 1454, 1141, 1109 cm$^{-1}$
NMR (DMSO-d$_6$, δ): 0.70–5.00 (28H, m), 6.00–8.20 (6H, m)
MASS (APCI): 628 (M+H)$^+$ (6) 1-[3,5-Bis(trifluoromethyl)benzoyl]-2-(3-hydroxy-4-methylbenzyl)-4-[4-[(2S,5S)-2-methoxymethyl-5-methylmorpholino]-2-butynyl]piperazine dihydrochloride mp: 110–135° C.
[α]$_D$$^{29}$: +3.40° (C=0.25, MeOH)
IR (KBr): 1645 cm$^{-1}$
NMR (DMSO-d$_6$, δ): 1.16 (3H, d, J=6.2 Hz), 2.08 (3H, br s), 3.25 (3H, s), 2.52–5.20 (21H, m), 6.17–8.20 (6H, m)
MASS (APCI): 642 (M+H)$^+$ (free)

(7) 1-[3,5-Bis(trifluoromethyl)benzoyl]-2-(3-hydroxy-4-methylbenzyl)-4-[2-[(1R,4S)-3,3-dimethyl-2-oxa-5-azabicyclo[2.2.1]heptan-5-yl]ethyl]piperazine dihydrochloride mp: 173–185° C.
[α]$_D$$^{27}$: +14.20° (C=0.25, MeOH)
IR (KBr): 3400, 2981, 1643 cm$^{-1}$
NMR (DMSO-d$_6$, δ): 1.18 (3H, s), 1.49 (3H, s), 2.09 (3H, s), 2.20–5.10 (19H, m), 6.20–8.25 (6H, m)
MASS (APCI): 600 (M+H)$^+$ (free)

(8) (2R)-1-[3,5-Bis(trifluoromethyl)benzoyl]-2-(3-hydroxy-4-methylbenzyl)-4-[2-[(2R)-2-(methoxymethyl)-morpholino]ethyl]piperazine dihydrochloride mp: 225–235° C.
[α]$_D$$^{26.6}$: −13.02° (C=0.315, MeOH)
IR (KBr): 1645, 1516, 1454, 1425, 1365, 1321, 1281, 1190, 1134, 1001 cm$^{-1}$
NMR (DMSO-d$_6$, δ): 2.08 (3H, s), 2.50–5.20 (25H, m), 6.00–8.30 (6H, m)
MASS (APCI): 604 (M+H)$^+$ (free)

(9) (2R)-1-[3,5-Bis(trifluoromethyl)benzoyl]-4-[2-[(3S,5S)-3,5-dimethylmorpholino]ethyl]-2-(3-hydroxy-4-methylbenzyl)piperazine dihydrochloride mp: 240–250° C.
[α]$_D$$^{26.7}$: +10.24° (C=0.21, MeOH)
IR (KBr): 1645, 1516, 1454, 1427, 1387, 1365, 1327, 1281, 1184, 1136, 1041 cm$^{-1}$
NMR (DMSO-d$_6$, δ): 1.00–1.60 (6H, m), 2.08 (3H, s), 2.30–5.20 (19H, m), 6.10–8.30 (6H, m)
MASS (APCI): 588 (M+H)$^+$ (free)

(10) (2R)-1-[3,5-Bis(trifluoromethyl)benzoyl]-4-[2-(cis-3,5-dimethylmorpholino)ethyl]-2-(3-hydroxy-4-methylbenzyl)piperazine dihydrochloride mp: 210–220° C.
[α]$_D$$^{25.2}$: −9.81° (C=0.26, MeOH)
IR (KBr): 1676, 1643, 1533, 1516, 1454, 1425, 1387, 1367, 1327, 1281, 1236, 1182, 1134, 1057 cm$^{-1}$
NMR (DMSO-d$_6$, δ): 0.80–5.30 (28H, m), 6.10–8.40 (6H, m)
MASS (APCI): 588 (M+H)$^+$ (free)

(11) (2R)-1-[3,5-Bis(trifluoromethyl)benzoyl]-2-(3-hydroxy-4-methylbenzyl)-4-[3-[(2S)-2-(methoxymethyl)-morpholino]propyl]piperazine dihydrochloride mp: 150–170° C.
[α]$_D$$^{25}$: −10.50° (C=0.30, MeOH)

IR (KBr): 1678, 1655, 1649, 1531, 1514, 1454, 1446, 1429, 1392, 1387, 1365, 1327, 1321, 1282, 1186, 1136 cm$^{-1}$

NMR (DMSO-d$_6$, δ): 1.60–5.30 (30H, m), 5.90–8.50 (6H, m)

MASS (APCI): 618 (M+H)$^+$ (free)

(12) (2R)-1-[3,5-Bis(trifluoromethyl)benzoyl]-2-(3-hydroxy-4-methylbenzyl)-4-[(E)-4-[(2S)-2-(methoxymethyl)-morpholino]-2-butenyl]piperazine dihydrochloride mp: 50–70° C.

[α]$_D^{25}$: −4.79° (C=0.24, MeOH)

IR (KBr): 1772, 1739, 1678, 1514, 1498, 1454, 1429, 1363, 1325, 1282, 1186, 1134 cm$^{-1}$

NMR (DMSO-d$_6$, δ): 1.80–5.20 (30H, m), 5.70–8.40 (6H, m)

MASS (APCI): 630 (M+H)$^+$ (free)

(13) (2R)-1-[3,5-Bis(trifluoromethyl)benzoyl]-2-(3-hydroxy-4-methylbenzyl)-4-[2-(3-pyridyl)ethyl]piperazine dihydrochloride mp: 90–120° C.

[α]$_D^{26.9}$: −4.19° (C=0.215, MeOH)

IR (KBr): 1643, 1550, 1516, 1466, 1454, 1427, 1365, 1327, 1281, 1184, 1138 cm$^{-1}$

NMR (DMSO-d$_6$, δ): 0.70–5.20 (16H, m), 6.00–8.90 (10H, m)

MASS (APCI): 552 (M+H)$^+$ (free)

(14) (2R)-1-[3,5-Bis(trifluoromethyl)benzoyl]-2-(3-hydroxy-4-methylbenzyl)-4-[2-[4,5,6,7-tetrahydrothieno[3,2-c]-pyridin-5-yl]ethyl]piperazine dihydrochloride mp: 245–265° C.

[α]$_D^{27.9}$: −2.78° (C=0.27, MeOH)

IR (KBr): 1693, 1674, 1645, 1547, 1533, 1516, 1454, 1427, 1365, 1329, 1281, 1182, 1138, 1041 cm$^{-1}$

NMR (DMSO-d$_6$, δ): 1.60–5.50 (22H, m), 6.00–8.40 (8H, m)

MASS (APCI): 612 (M+H)$^+$ (free)

(15) (2R)-1-[3,5-Bis(trifluoromethyl)benzoyl]-4-[2-[3,4-dihydro-2H-pyrido[3,2-b]-1,4-oxazin-4-yl]ethyl]-2-(3-hydroxy-4-methylbenzyl)piperazine dihydrochloride mp: 190–200° C.

[α]$_D^{26.9}$: +6.79° (C=0.265, MeOH)

IR (KBr): 1641, 1618, 1566, 1454, 1427, 1281, 1184, 1132, 1066, 1032 cm$^{-1}$

NMR (DMSO-d$_6$, δ): 0.70–5.60 (20H, m), 6.00–8.40 (9H, m)

MASS (APCI): 609 (M+H)$^+$ (free)

(16) (2R)-1-[3,5-Bis(trifluoromethyl)benzoyl]-2-(3-hydroxy-4-methylbenzyl)-4-[6-quinolylmethyl]piperazine dihydrochloride mp: 170–200° C.

[α]$_D^{25.8}$: −28.54° (C=0.247, MeOH)

IR (KBr): 1724, 1707, 1645, 1514, 1454, 1427, 1385, 1365, 1311, 1281, 1180, 1136 cm$^{-1}$

NMR (DMSO-d$_6$, δ): 0.70–5.10 (15H, m), 6.00–9.40 (12H, m)

MASS (APCI): 588 (M+H)$^+$ (free)

EXAMPLE 16

The following compounds were obtained according to a similar manner to that of Preparation 41.

(1) (2R)-1-[3,5-Bis(trifluoromethyl)benzoyl]-2-(3-tert-butyldiphenylsilyloxy-4-methylbenzyl)-4-[2-[(2S)-2-(methoxymethyl)morpholino]ethyl]piperazine NMR (CDCl$_3$, δ): 1.09 (9H, s), 1.89–4.90 (22H, m), 2.35 (3H, s), 3.38 (3H, s), 6.10–7.92 (16H, m)

MASS (ESO+): 842.4 (M+H)$^+$ (2) (2R)-2-(3-tert-Butyldiphenylsilyloxy-4-methylbenzyl)-4-[2-[(2S)-2-(methoxymethyl)morpholino)ethyl]-1-[3-nitro-5-(trifluoromethyl)benzoyl]piperazine IR (Neat): 1641 cm$^{-1}$ NMR (CDCl$_3$, δ): 1.09 (9H, s), 2.37 (3H, s), 1.89–4.80 (22H, m), 3.35 (3H, s), 6.00–8.40 (16H, m)

MASS (ESI+): 819.3 (M+H)$^+$ (3) (2R)-2-(3-tert-Butyldiphenylsilyloxy-4-methylbenzyl)-1-[3-dimethylamino-5-(trifluoromethyl)benzoyl]-4-[2-[(2S)-2-(methoxymethyl)morpholino]ethyl]piperazine IR (KBr): 1641, 1608 cm$^{-1}$ NMR (CDCl$_3$, δ): 1.50 (9H, s), 2.25 (3H, br s), 2.95 (6H, br s), 3.35 (3H, s), 1.80–4.80 (22H, m), 6.05–7.80 (16H, m)

MASS (ESI+): 817.4 (M+H)$^+$ (4) (2R)-2-(3-tert-Butyldiphenylsilyloxy-4-methylbenzyl)-4-[2-[(2S)-2-(methoxymethyl)morpholino]ethyl]-1-[3-methylamino-5-(trifluoromethyl)benzoyl]piperazine IR (KBr): 1614 cm$^{-1}$ NMR (DMSO-d$_6$, δ): 1.03 (9H, s), 1.70–4.80 (28H, m), 2.26 (3H, br s), 6.00–7.70 (16H, m)

MASS (ESI+): 803.4 (M+H)$^+$, 825.3 (M+Na)$^+$ (5) (2R)-2-(3-tert-Butyldiphenylsilyloxy-4-methylbenzyl)-4-[2-[(2S)-2-(methoxymethyl)morpholino]ethyl]-1-[3-(1-pyrrolyl)-5-(trifluoromethyl)benzoyl]piperazine IR (KBr): 1643 cm$^{-1}$ NMR (DMSO-d$_6$, δ): 1.00–1.04 (9H, m), 1.70–4.80 (28H, m), 6.00–8.00 (20H, m)

MASS (ESI+): 839.4 (M+H)$^+$, 861.4 (M+Na)$^+$ (6) (2R)-2-(3-tert-Butyldiphenylsilyloxy-4-methylbenzyl)-4-[2-[(2S)-2-(methoxymethyl)morpholino]ethyl]-1-[3-methoxy-5-(trifluoromethyl)benzoyl]piperazine IR (KBr): 2939, 1643, 1512, 1462, 1423 cm$^{-1}$ NMR (DMSO-d$_6$, δ): 1.04 (9H, s), 2.22 (3H, s), 1.71–4.60 (28H, m), 5.99–7.75 (16H, m)

MASS (ESI+): 804.4 (M+H)$^+$, 826.3 (M+Na)$^+$ (7) (2R)-2-(3-tert-Butyldiphenylsilyloxy-4-methylbenzyl)-4-[2-[(2S)-2-(methoxymethyl)morpholino]ethyl]-1-[3-methylthio-5-(trifluoromethyl)benzoyl]piperazine IR (KBr): 2933, 1641, 1510, 1421 cm$^{-1}$
NMR (DMSO-d$_6$, δ): 1.04 (9H, s), 2.29 (3H, s), 3.18 (3H, s), 1.70–4.70 (25H, m), 6.00–7.80 (16H, m)
MASS (ESI+): 820.3 (M+H)$^+$, 842.3 (M+Na)$^+$ (8) (2R)-2-(3-tert-Butyldiphenylsilyloxy-4-methylbenzyl)-4-[2-[(2S)-2-(methoxymethyl)morpholino]ethyl]-1-(3-methylsulfonyl-5-(trifluoromethyl)benzoyl]piperazine IR (KBr): 1643 cm$^{-1}$
NMR (CDCl$_{300}$, δ): 1.03 (9H, br s), 1.72–4.60 (28H, m), 2.28 (3H, br s), 6.02–8.28 (16H, m)
MASS (ESI+): 852.3 (M+H)$^+$, 874.3 (M+Na)$^+$ (9) (2R)-2-(3-tert-Butyldiphenylsilyloxy-4-methylbenzyl)-1-[3-dimethylsulfamoyl-5-(trifluoromethyl)benzoyl]-4-[2-[(2S)-2-(methoxymethyl)morpholino]ethyl]piperazine IR (KBr): 1639 cm$^{-1}$
NMR (DMSO-d$_6$, δ): 1.04 (9H, s), 1.71–4.70 (31H, m), 2.28 (3H, br s), 6.04–8.00 (16H, m)
MASS (ESI+): 881.4 (M+H)$^+$, 904.3 (M+Na)$^+$

(10) (2R)-2-(3-tert-Butyldiphenylsilyloxy-4-methylbenzyl)-4-[2-[(2S)-2-(methoxymethyl)morpholino]ethyl]-1-[3-methylsulfamoyl-5-(trifluoromethyl)benzoyl]piperazine IR (KBr): 1643 cm$^{-1}$
NMR (DMSO-d$_6$, δ): 1.04–1.05 (9H, m), 1.70–4.60 (28H, m), 2.28 (3H, br s), 6.03–8.07 (16H, m)
MASS (ESI+): 867.3 (M+H)$^+$

(11) (2R)-2-(3-tert-Butyldiphenylsilyloxy-4-methylbenzyl)-4-[2-[(2S)-2-(methoxymethyl)morpholino]ethyl]-1-[3-(pyrrolidinosulfonyl)-5-(trifluoromethyl)benzoyl]-piperazine IR (KBr): 1643 cm$^{-1}$
NMR (CDCl$_3$, δ): 1.09 (9H, s), 1.75–1.82 (4H, m), 2.35 (3H, s), 2.05–4.80 (29H, m), 6.00–8.65 (16H, m)
MASS (ESI+): 907 (M+H)$^+$

(12) (2R)-2-(3-tert-Butyldiphenylsilyloxy-4-methylbenzyl)-4-[2-[(2S)-2-(methoxymethyl)morpholino]ethyl]-1-[3-(morpholinosulfonyl)-5-(trifluoromethyl)benzoyl]-piperazine IR (KBr): 1645 cm$^{-1}$
NMR (CDCl$_3$, δ): 1.09 (9H, s), 2.35 (3H, s), 2.46–4.80 (33H, m), 6.00–8.56 (16H, m)
MASS (ESI+): 923.4 (M+H)$^+$

(13) (2R)-2-(3-tert-Butyldiphenylsilyloxy-4-methylbenzyl)-4-[2-[(2S)-2-(methoxymethyl)morpholino]ethyl]-1-[3-(4-pyridyl)-5-(trifluoromethyl)benzoyl]piperazine IR (KBr): 1645 cm$^{-1}$
NMR (CDCl$_3$, δ): 0.99–1.02 (9H, m), 1.80–4.80 (28H, m), 6.00–8.16 (18H, m), 8.70 (2H, d, J=5.6 Hz)
MASS (ESI+): 851.4 (M+H)$^+$, 873.3 (M+Na)$^+$

(14) (2R)-2-(4-Chlorobenzyl)-4-[2-(cis-2,6-dimethylmorpholino)ethyl]-1-[3-nitro-5-(trifluoro-methyl)benzoyl]piperazine dihydrochloride mp: 133.3–136.2° C.
[α]$_D^{26}$: +5.62° (C=0.61, MeOH)
IR (KBr): 1645, 1547, 1327, 1182, 1143 cm$^{-1}$
NMR (DMSO-d$_6$, δ): 1.02 and 1.14 (6H, d, J=6.2 Hz), 2.71–4.53 (19H, m), 6.95–8.52 (7H, m)
MASS: 569 (M$^+$) (free)

(15) (2R)-2-(4-Chlorobenzyl)-4-[2-(cis-2,6-dimethylmorpholino)ethyl]-1-[3-methylamino-5-(trifluoromethyl)benzoyl]piperazine dihydrochloride mp: 245.6–248.7° C.
[α]$_D^{26.4}$: +21.44° (C=0.26, MeOH)
IR (KBr): 1612, 1494, 1427, 1182, 1143, 1095 cm$^{-1}$
NMR (DMSO-d$_6$, δ): 1.15 (6H, d, J=6.0 Hz), 2.68 (3H, s), 3.20–4.30 (19H, m), 6.14–7.47 (7H, m)
MASS: 553 (M$^+$) (free)

(16) (2R)-2-(4-Chlorobenzyl)-1-[3-dimethylamino-5-(trifluoromethyl)benzoyl]-4-[2-(cis-2,6-dimethylmorpholino)ethyl]piperazine dihydrochloride mp: 148.2–153.3° C.
[α]$_D^{26.6}$: +19.82° (C=0.36, MeOH)
IR (KBr): 1645, 1464, 1425, 1182, 1138 cm$^{-1}$
NMR (DMSO-d$_6$, δ): 1.15 (6H, d, J=6.0 Hz), 2.94 (0.6H, s), 3.40–4.20 (19H, m), 6.20–7.38 (7H, m)
MASS: 567 (M$^+$) (free)

(17) (2R)-2-(4-Chlorobenzyl)-4-[2-(cis-2,6-dimethylmorpholino)ethyl]-1-[3-methylthio-5-(trifluoromethyl)benzoyl]piperazine dihydrochloride mp: 138.4–142.5° C.
[α]$_D^{26.6}$: +7.55° (C=0.26, MeOH)
IR (KBr): 1643, 1417, 1330, 1176, 1128, 1099 cm$^{-1}$
NMR (DMSO-d$_6$, δ): 1.02 and 1.15 (6H, d, J=6.2 Hz), 2.54 (3H, s), 2.71–3.99 (19H, m), 6.69–7.91 (7H, m)
MASS: 570 (M$^+$) (free)

(18) (2R)-2-(4-Chlorobenzyl)-4-[2-(cis-2,6-dimethylmorpholino)ethyl]-1-[3-methanesulfonyl-5-(trifluoromethyl)benzoyl]piperazine dihydrochloride mp: 138.4–142.5° C.
[α]$_D^{26.7}$: +7.55° (C=0.26, MeOH)
IR (KBr): 1645, 1462, 1423, 1328, 1303, 1182, 1144 cm$^{-1}$
NMR (DMSO-d$_6$, δ): 1.16 (6H, d, J=6.1 Hz), 2.55–4.05 (19H, m), 3.38 (3H, s), 6.98–8.32 (7H, m)
MASS: 602 (M$^+$) (free)

(19) (2R)-2-(4-Chlorobenzyl)-4-[2-(cis-2,6-dimethylmorpholino)ethyl]-1-[3-dimethylaminosulfonyl-5-(trifluoromethyl)benzoyl]piperazine dihydrochloride mp: 209.6–213.7° C.
[α]$_D^{26.5}$: +4.44° (C=0.31, MeOH)
IR (KBr): 1645, 1461, 1423, 1344, 1173, 1146, 1103 cm$^{-1}$
NMR (DMSO-d$_6$, δ): 1.17 (6H, d, J=6.0 Hz), 2.66 (6H, s), 3.00–4.46 (19H, m), 7.03–8.00 (7H, m)
MASS: 631 (M$^+$) (free)

(20) (2R)-2-(4-Chlorobenzyl)-4-[2-(cis-2,6-dimethylmorpholino)ethyl]-1-[3-(1-pyrrolyl)-5-(trifluoromethyl)benzoyl]piperazine dihydrochloride mp: 152.7–157.9° C.
$[\alpha]_D^{26.2}$: +5.96° (C=0.55, MeOH)
IR (KBr): 1345, 1496, 1178, 1130 cm$^{-1}$
NMR (DMSO-d$_6$, δ): 1.15 (6H, d, J=5.9 Hz), 2.70–4.20 (19H, m), 6.34 (2H, s), 6.96–7.91 (9H, m)
MASS: 589 (M$^+$) (free)

(21) (2R)-2-(4-Chlorobenzyl)-4-[2-(cis-2,6-dimethylmorpholino)ethyl]-1-[3-(4-pyrrolyl)-5-(trifluoromethyl)benzoyl]piperazine trihydrochloride mp: 287.7–289.1° C.
$[\alpha]_D^{26.9}$: −3.00° (C=0.36, MeOH)
IR (KBr): 1641, 1635, 1427, 1270, 1178, 1130 cm$^{-1}$
NMR (DMSO-d$_6$, δ): 1.08 (6H, d, J=6.0 Hz), 2.73–5.15 (19H, m), 6.94–8.97 (11H, m)
MASS: 601 (M$^+$) (free)

(22) (2R)-2-(4-Chlorobenzyl)-1-[3-chloro-5-(trifluoromethyl)benzoyl]-4-[2-(cis-2,6-dimethylmorpholino)ethyl]piperazine dihydrochloride mp: 136.4–141.0° C.
$[\alpha]_D^{26.8}$: +1.06° (C=0.45, MeOH)
IR (KBr): 1644, 1417, 1326, 1178, 1135, 1095 cm$^{-1}$
NMR (DMSO-d$_6$, δ): 1.02 and 1.15 (6H, d, J=6.1 Hz), 2.60–4.12 (19H, m), 6.93–7.96 (7H, m)
MASS: 560 (M+H)$^+$ (free)

(23) (2R)-2-(4-Chlorobenzyl)-4-[2-(cis-2,6-dimethylmorpholino)ethyl]-1-[3-fluoro-5-(trifluoromethyl)benzoyl]piperazine dihydrochloride mp: 80.1–82.5° C.
$[\alpha]_D^{27.0}$: +3.54° (C=0.30, MeOH)
IR (KBr): 1645, 1427, 1344, 1178, 1136, 1091 cm$^{-1}$
NMR (DMSO-d$_6$, δ): 1.16 (6H, d, J=6.1 Hz), 2.60–4.53 (19H, m), 6.78–7.78 (7H, m)
MASS: 542 (M$^+$) (free)

(24) (2R)-2-(4-Chlorobenzyl)-4-[2-(cis-2,6-dimethylmorpholino)ethyl]-1-[3-methyl-5-(trifluoromethyl)benzoyl]piperazine dihydrochloride mp: 82.3–88.2° C.
$[\alpha]_D^{26.5}$: +4.05° (C=0.315, MeOH)
IR (KBr): 1643, 1635, 1425, 1174, 1128 cm$^{-1}$
NMR (DMSO-d$_6$, δ): 1.15 (6H, d, J=6.1 Hz), 2.32–4.10 (22H, m), 6.68–7.57 (7H, m)
MASS: 539 (M+H)$^+$ (free)

(25) (2R)-2-(4-Chlorobenzyl)-1-[3,5-dichlorobenzoyl]-4-[2-(cis-2,6-dimethylmorpholino)ethyl]piperazine dihydrochloride mp: 140.1–143.8° C.
$[\alpha]_D^{25.7}$: +3.25° (C=0.55, MeOH)
IR (KBr): 1643, 1452, 1446, 1409, 1330, 1277, 1092, 1036 cm$^{-1}$
NMR (DMSO-d$_6$, δ): 1.15 (6H, d, J=6.2 Hz), 2.72–4.15 (19H, m), 6.56–7.64 (7H, m)
MASS: 524 (M$^+$) (free)

(26) (2R)-2-(4-Chlorobenzyl)-1-[3-nitro-5-(trifluoromethyl)-benzoyl]-4-[2-(5,6,7,8-tetrahydro-1,6-naphthyridin-6-yl)ethyl]piperazine trihydrochloride mp: 221–228° C.
$[\alpha]_D^{27.2}$: −11.50° (C=0.30, MeOH)
IR (KBr): 3430, 3400, 1640, 1550, 1470, 1420 cm$^{-1}$
NMR (DMSO-d$_6$, δ): 2.6–5.2 (19H, m), 6.8–8.8 (10H, m)
MASS: (APCI): 588 (M+H)$^+$ (free)

(27) (2R)-2-(4-Chlorobenzyl)-1-[3-methylamino-5-(trifluoromethyl)benzoyl]-4-[2-(5,6,7,8-tetrahydro-1,6-naphthyridin-6-yl)ethyl]piperazine trihydrochloride mp: 199–245° C.
$[\alpha]_D^{27.1}$: +2.31° (C=0.26, MeOH)
IR (KBr): 3430, 3400, 1630, 1510, 1460, 1430 cm$^{-1}$
NMR (DMSO-d$_6$, δ): 2.69 (3H, s), 2.8–5.3 (19H, m), 6.41 (1H, s), 6.83 (1H, s), 6.9–7.5 (5H, m), 7.71 (1H, dd, J=5, 8 Hz), 8.11 (1H, d, J=8 Hz), 8.70 (1H, d, J=5 Hz)
MASS (APCI): 572 (M+H)$^+$ (free)

(28) (2R)-2-(4-Chlorobenzyl)-1-[3-methylthio-5-(trifluoromethyl)benzoyl]-4-[2-(5,6,7,8-tetrahydro-1,6-naphthyridin-6-yl)ethyl]piperazine trihydrochloride mp: 182–195° C.
$[\alpha]_D^{26.8}$: −9.58° (C=0.24, MeOH)
IR (KBr): 3430, 3400, 1640, 1460, 1420 cm$^{-1}$
NMR (DMSO-d$_6$, δ): 2.55 (3H, s), 2.6–5.2 (19H, m), 6.6–8.7 (10H, m)
MASS (APCI): 589 (M+H)$^+$ (free)

(29) (2R)-2-(4-Chlorobenzyl)-1-[3-methanesulfonyl-5-(trifluoromethyl)benzoyl]-4-[2-(5,6,7,8-tetrahydro-1,6-naphthyridin-6-yl)ethyl]piperazine trihydrochloride mp: 198–213° C.
$[\alpha]_D^{26.8}$: −13.71° (C=0.28, MeOH)
IR (KBr): 3430, 3400, 1640, 1460, 1420 cm$^{-1}$
NMR (DMSO-d$_6$, δ): 2.6–5.2 (19H, m), 3.39 (3H, s), 6.9–8.2 (8H, m), 8.33 (1H, s), 8.67 (1H, d, J=5 Hz)
MASS: 621 (M+H)$^+$ (free)

(30) (2R)-2-(4-Chlorobenzyl)-1-[3-dimethylsulfamoyl-5-(trifluoromethyl)benzoyl]-4-[2-(5,6,7,8-tetrahydro-1,6-naphthyridin-6-yl)ethyl]piperazine trihydrochloride mp: 209–226° C.
$[\alpha]_D^{26.8}$: −8.38° (C=0.24, MeOH)
IR (KBr): 3740, 1680, 1640, 1520, 1460 cm$^{-1}$
NMR (DMSO-d$_6$, δ): 2.67 (6H, s), 2.8–5.2 (19H, m), 6.9–8.7 (10H, m)
MASS: 650 (M+H)$^+$ (free)

(31) (2R)-2-(4-Chlorobenzyl)-1-[3-(1-pyrrolyl)-5-(trifluoromethyl)benzoyl]-4-[2-(5,6,7,8-tetrahydro-1,6-naphthyridin-6-yl)ethyl]piperazine trihydrochloride mp: 184–191° C.
$[\alpha]_D^{26.7}$: −12.13° (C=0.40, MeOH)
IR (KBr): 3400, 1640, 1500, 1430 cm$^{-1}$ NMR (DMSO-d$_6$, δ): 2.8–5.3 (19H, m), 6.2–8.7 (14H, m)
MASS: 608 (M+H)$^+$ (free)

(32) (2R)-2-(4-Chlorobenzyl)-1-[3-(4-pyridyl)-5-(trifluoromethyl)benzoyl]-4-[2-(5,6,7,8-tetrahydro-1,6-naphthyridin-6-yl)ethyl]piperazine tetrahydrochloride mp: 206–217° C.
$[α]_D^{25.8}$: −20.08° (C=0.27, MeOH)
IR (KBr): 3430, 3400, 1640, 1510, 1430 cm$^{-1}$
NMR (DMSO-d$_6$, δ): 2.7–6.2 (19H, m), 6.8–8.1 (8H, m), 8.10 (1H, d, J=8.5 Hz), 8.41 (2H, d, J=6.5 Hz), 8.70 (1H, d, J=4.4 Hz), 9.04 (2H, d, J=6.5 Hz)
MASS (API-ES): 620 (M+H)$^+$ (free)

(33) (2R)-2-(4-Chlorobenzyl)-1-[3-chloro-5-(trifluoromethyl)benzoyl]-4-[2-(5,6,7,8-tetrahydro-1,6-naphthyridin-6-yl)ethyl]piperazine trihydrochloride mp: 130.6–135.7° C.
$[α]_{Dhub\ 26.6}$: −12.12° (C=0.60, MeOH)
IR (KBr): 1643, 1635, 1417, 1326, 1321, 1178, 1135 cm$^{-1}$
NMR (DMSO-d$_6$, δ): 2.79–4.78 (19H, m), 7.02–8.66 (10H, m)
MASS: 577 (M$^+$) (free)

(34) (2R)-2-(4-Chlorobenzyl)-1-[3-fluoro-5-(trifluoromethyl)benzoyl]-4-[2-(5,6,7,8-tetrahydro-1,6-naphthyridin-6-yl)ethyl]piperazine trihydrochloride mp: 127.3–130.9° C.
$[α]_D^{26.4}$: −10.20° (C=0.51, MeOH)
IR (KBr): 1643, 1635, 1629, 1425, 1178, 1135 cm$^{-1}$
NMR (DMSO-d$_6$, δ): 2.80–4.60 (19H, m), 6.80–8.63 (10H, m)
MASS: 561 (M$^+$) (free)

(35) (2R)-2-(4-Chlorobenzyl)-1-[3-methyl-5-(trifluoromethyl)benzoyl]-4-[2-(5,6,7,8-tetrahydro-1,6-naphthyridin-6-yl)ethyl]piperazine trihydrochloride mp: 102.5–110.4° C.
$[α]_D^{26.8}$: −13.35° (C=0.310, MeOH)
IR (KBr): 1643, 1635, 1423, 1419, 1173, 1128 cm$^{-1}$
NMR (DMSO-d$_6$, δ): 2.35 (2H, m), 2.51–4.49 (20H, m), 7.03–8.69 (10H, m)
MASS: 557 (M$^+$) (free)

(36) (2R)-2-(4-Chlorobenzyl)-1-[3-dimethylamino-5-(trifluoromethyl)benzoyl]-4-[2-(5,6,7,8-tetrahydro-1,6-naphthyridin-6-yl)ethyl]piperazine trihydrochloride mp: 209–214° C.
$[α]_D^{27.1}$: +1.51° (C=0.27, MeOH)
IR (KBr): 3430, 3400, 1640, 1500, 1460, 1420 cm$^{-1}$
NMR (DMSO-d$_6$, δ): 2.8–5.3 (19H, m), 2.95 (6H, s), 6.1–7.5 (7H, m), 7.65 (1H, dd, J=5, 8 Hz), 8.05 (1H, d, J=8 Hz), 8.67 (1H, d, J=5 Hz)
MASS: 586 (M+H)$^+$ (free)

(37) (2R)-2-(3-tert-Butyldiphenylsilyloxy-4-methylbenzyl)-1-[3-(2,5-dimethylpyrrol-1-ylsulfonyl)-5-(trifluoromethyl)benzoyl]-4-[2-[(2S)-2-(methoxymethyl)-morpholino]ethyl]piperazine IR (KBr): 1643 cm$^{-1}$
NMR (DMSO-d$_6$, δ): 1.04 (9H, s), 2.30 (6H, br s), 2.30 (3H, br s), 1.91–4.60 (25H, m), 6.05 (2H, s), 6.60–7.98 (16H, m)
MASS (ESI+): 931.3 (M+H)$^+$

EXAMPLE 17

The following compounds were obtained according to a similar manner to that of Example 11 followed by a similar manner to that of Example 3.

(1) 1-[3,5-Bis(trifluoromethyl)benzoyl]-2-(3-hydroxy-4-methylbenzyl)-4-[(E)-3-(3-pyridyl)-2-propenyl]-piperazine dihydrochloride mp: 60–80° C.
IR (KBr): 1707, 1693, 1676, 1645, 1628, 1550, 1539, 1516, 1477, 1464, 1454, 1427, 1392, 1365, 1281, 1182, 1136, 1049 cm$^{-1}$
NMR (DMSO-d$_6$, δ): 1.90–5.60 (16H, m), 6.10–9.10 (10H, m)
MASS (APCI): 564 (M+H)$^+$ (free)

(2) 1-[3,5-Bis(trifluoromethyl)benzoyl]-2-(3-hydroxy-4-methylbenzyl)-4-[1-methyl-1H-pyrazol-4-yl)methyl]-piperazine hydrochloride IR (KBr): 1707, 1693, 1676, 1645, 1562, 1550, 1547, 1533, 1516, 1454, 1427, 1392, 1363, 1319, 1281, 1182, 1138, 1057 cm$^{-1}$
NMR (DMSO-d$_6$, δ): 1.60–5.20 (17H, m), 5.90–8.30 (8H, m)
MASS (APCI): 541 (M+H)$^+$ (free)

(3) (2R)-1-[3,5-Bis(trifluoromethyl)benzoyl]-2-(3-hydroxy-4-methylbenzyl)-4-[(2-aminothiazol-4-yl)methyl]-piperazine dihydrochloride mp: 205–215° C.
$[α]_D^{27}$: −12.13° (C=0.40, MeOH)
IR (KBr): 3500–3000, 2700–2300, 1639, 1428, 1280 cm$^{-1}$
NMR (DMSO-d$_6$, δ): 2.07 (3H, s), 2.60–5.20 (11H, m), 6.20–8.20 (7H, m), 8.00–9.00 (2H, m)
MASS (APCI): 559 (M+H)$^+$ (free)

(4) (2R)-1-[3,5-Bis(trifluoromethyl)benzoyl]-2-(3-hydroxy-4-methylbenzyl)-4-[(5-amino-1,2,4-thiadiazol-3-yl)-methyl]piperazine dihydrochloride mp: 177–182° C.
$[α]_D^{27}$: −31.5° (C=0.18, MeOH)
IR (KBr): 3500–3000, 2700–2300, 1644, 1278 cm$^{-1}$
NMR (DMSO-d$_6$, δ): 2.07 (3H, s), 2.60–5.20 (11H, m), 6.20–8.20 (8H, m), 8.00–9.00 (2H, m)
MASS (APCI): 560 (M+H)$^+$ (free), 447

(5) (2R)-1-[3,5-Bis(trifluoromethyl)benzoyl]-2-(3-hydroxy-4-methylbenzyl)-4-[[2-(dimethylamino)thiazol-4-yl]-methyl]piperazine dihydrochloride mp: 162–165° C.
$[\alpha]_D^{27}$: −17.6° (C=0.5, MeOH)
IR (KBr): 3500–3000, 2700–2300, 1639, 1427, 1365, 1280 cm$^{-1}$
NMR (DMSO-d$_6$, δ): 1.80–1.90 (6H, m), 2.07 (3H s), 2.60–5.20 (11H, m), 4.50–5.80 (2H, m), 5.90–8.20 (7H, m)
MASS (APCI): 587 (M+H)$^+$ (free)

(6) (2R)-1-[3,5-Bis(trifluoromethyl)benzoyl]-2-(3-hydroxy-4-methylbenzyl)-4-[[3-(methylamino)-1,2,4-oxadiazol-5-yl]methyl]piperazine dihydrochloride mp: 145–160° C.
$[\alpha]_D^{26}$: −23.1° (C=0.55, MeOH)
IR (KBr): 3500–3150, 2700–2300, 1644, 1428, 1363, 1280 cm$^{-1}$
NMR (DMSO-d$_6$, δ): 2.07 (3H, s), 2.66–5.20 (14H, m), 6.10–8.30 (7H, m)
MASS (APCI): 558 (M+H)$^+$ (free)

EXAMPLE 18

The following compound was obtained according to a similar manner to that of Example 1 followed by a similar manner to that of Example 3.

1-[3,5-Bis(trifluoromethyl)benzoyl]-4-[2-[(2S)-5,5-dimethyl-2-(methoxymethyl)morpholino]ethyl]-2-(3-hydroxy-4-methylbenzyl)piperazine dihydrochloride mp: 150–180° C.
IR (KBr): 1707, 1693, 1678, 1645, 1628, 1562, 1547, 1539, 1533, 1516, 1477, 1464, 1454, 1427, 1392, 1367, 1281, 1182, 1138 cm$^{-1}$
NMR (DMSO-d$_6$, δ): 1.10–1.60 (6H, m), 2.08 (3H, s), 2.30–5.20 (23H, m), 6.10–8.30 (6H, m), 9.15 (1H, br s)
MASS (APCI): 632 (M+H)$^+$ (free)

EXAMPLE 19

A solution of (2R)-1-[3,5-bis(trifluoromethyl)benzoyl]-2-(3-hydroxy-4-methylbenzyl)-4-[4-[(2S)-2-(methoxymethyl)-morpholino]-2-butynyl]piperazine (0.33 g) in methanol (10 ml) was hydrogenated over Lindlar catalyst (63 mg). After removal of catalyst by filtration, the filtrate was evaporated under reduced pressure. The residue was purified by column chromatography on silica gel using methanol/dichloromethane (1:9) as an eluent. The fractions containing the objective compound were collected and evaporated in vacuo to give (2R)-1-[3,5-bis(trifluoromethyl)-benzoyl]-2-(3-hydroxy-4-methylbenzyl)-4-[(Z)-4-[(2S)-2-(methoxymethyl)morpholino]-2-butenyl]piperazine (0.22 g) as an oil.

IR (Neat): 1707, 1693, 1678, 1645, 1635, 1547, 1539, 1535, 1516, 1464, 1454, 1423, 1417, 1405, 1387 cm$^{-1}$
NMR (CDCl$_3$, δ): 0.60–5.20 (28H, m), 5.40–5.90 (2H, m), 6.10–8.10 (6H, m)
MASS (APCI): 630 (M+H)$^+$

EXAMPLE 20

The following compound was obtained according to a similar manner to that of Example 19.

(2R)-1-[3,5-Bis(trifluoromethyl)benzoyl]-2-[3-[(2-methoxyethoxy)methoxy]-4-methylbenzyl]-4-[(Z)-3-(3-pyridyl)-2-propenyl]piperazine IR (Neat): 1670, 1641, 1585, 1550, 1510, 1431, 1379, 1350, 1329, 1279, 1130, 1101, 1012 cm$^{-1}$
NMR (CDCl$_3$, δ): 0.70–5.50 (23H, m), 5.70–6.10 (1H, m), 6.10–8.80 (11H, m)
MASS (APCI): 652 (M+H)$^+$

EXAMPLE 21

The following compounds were obtained according to a similar manner to that of Example 8.

(1) (2R)-1-[3,5-Bis(trifluoromethyl)benzoyl]-4-[3-(3-pyridyl)propyl]-2-[4-(trifluoromethyl)benzyl]piperazine dihydrochloride mp: 64–74° C.
$[\alpha]_D^{27}$: +7.47° (C=0.5, MeOH)
IR (KBr): 1645 cm$^{-1}$
NMR (DMSO-d$_6$, δ): 2.10–2.40 (2H, m), 2.80–5.40 (13H, m), 7.19–7.69 (6H, m), 7.97–8.03 (1H, m), 8.19–8.22 (1H, m), 8.42–8.58 (1H, m), 8.81 (1H, d, J=5.5 Hz), 8.90–9.00 (1H, m)
MASS (APCI): 604 (M+H)$^+$ (free)

(2) (2R)-1-[3-Methoxy-5-(trifluoromethyl)benzoyl]-4-[3-(3-pyridyl)propyl]-2-[4-(trifluoromethyl)benzyl]piperazine dihydrochloride mp: 70–80° C.
$[\alpha]_D^{27}$: +19.49° (C=0.0065, MeOH)
IR (KBr): 1643, 1466, 1423 cm$^{-1}$
NMR (DMSO-d$_6$, δ): 2.10–2.40 (2H, m), 2.80–5.30 (13H, m), 3.82 (3H, s), 6.41–7.70 (7H, m), 7.97 (1H, dd, J=5.5 and 8.0 Hz), 8.45 (1H, d, J=8.0 Hz), 8.79 (1H, d, J=5.5 Hz), 8.88 (1H, s)
MASS (APCI): 566 (M+H)$^+$ (free)

(3) (2R)-1-[3,5-Bis(trifluoromethyl)benzoyl]-2-(4-fluoro-benzyl)-4-[3-(3-pyridyl)propyl]piperazine dihydrochloride mp: 110.2–117.5° C.
$[\alpha]_D^{28}$: +19.46° (C=0.34, MeOH)
IR (KBr): 1644, 1513, 1280, 1184, 1135 cm$^{-1}$
NMR (DMSO-d$_6$, δ): 1.03 (2H, d, J=6.07 Hz), 2.23 (2H, m), 2.86–5.05 (11H, m), 6.99–8.85 (11H, m)
MASS: 554 (M+H)$^+$ (free)

(4) (2R)-2-(4-Fluorobenzyl)-1-[3-methoxy-5-(trifluoromethyl)benzoyl]-4-[3-(3-pyridyl)propyl]-piperazine dihydrochloride mp: 111.5–118.3° C.
$[\alpha]^{27.3}$: +11.3° (C=0.26, MeOH)
IR (KBr): 1643, 1511, 1465, 1421, 1049 cm$^{-1}$
NMR (DMSO-d$_6$, δ): 2.21 (1H, br), 2.88–5.41 (18H, m), 6.56–8.86 (11H, m), 11.5 (1H, br)
MASS: 516 (M+H)$^+$ (free)

(5) (2R)-1-[3-Methoxy-5-(trifluoromethyl)benzoyl]-2-(2-naphthylmethyl)-4-[3-(3-pyridyl)propyl]piperazine dihydrochloride $[\alpha]_D^{28.2}$: −9.96° (C=0.24, MeOH)
IR (KBr): 3400, 1640 cm$^{-1}$ NMR (DMSO-d$_6$, δ): 2.1–2.4 (2H, m), 2.7–5.3 (13H, m), 3.61 and 3.71 (3H, s), 6.5–8.9 (14H, m)

MASS: 548 (M+H)$^+$ (free)

EXAMPLE 22

To a solution of (2R)-1-[3,5-bis(trifluoromethyl)-benzoyl]-2-[3-[(2-methoxyethoxy)methoxy]-4-methylbenzyl]-4-[(1-trityl-1H-pyrazol-4-yl)methyl]piperazine (1.184 g) in 1,4-dioxane (118 ml) was added 1N hydrochloric acid (71 ml) and the resulting mixture was stirred at 40° C. for 7 hours. After cooling, the pH of the mixture was adjusted to 7 with 4N sodium hydroxide solution and sodium chloride was added to the mixture. The organic layer was separated, dried over magnesium sulfate, and evaporated in vacuo. The residue was purified by column chromatography on silica gel with a mixture of methylene chloride and methanol (30:1) as eluent to give (2R)-1-[3,5-bis(trifluoromethyl)benzoyl]-2-[3-[(2-methoxyethoxy)methoxy]-4-methylbenzyl]-4-[(1H-pyrazol-4-yl)-methyl]piperazine (575 mg).

IR (Neat): 3250, 1645, 1280, 1130 cm$^{-1}$

NMR (CDCl$_3$, δ): 1.95–5.22 (23H, m), 6.24–7.90 (8H, m)

MASS (APCI): 615 (M+H)$^+$ (free)

EXAMPLE 23

A mixture of (2R)-1-[3,5-bis(trifluoromethyl)benzoyl]-2-[3-[(2-methoxyethoxy)methoxy]-4-methylbenzyl]-4-[(1H-pyrazol-4-yl)methyl]piperazine (254 mg), 2-bromoethanol (259 mg), potassium carbonate (228 mg) and tetrabutyl ammonium bromide (13 mg) in N,N-dimethylformamide (2.5 ml) was stirred at 100° C. for 2 days. After cooling, the mixture was evaporated in vacuo and water and ethyl acetate were added to the residue. The organic layer was separated, washed with brine, dried over magnesium sulfate and evaporated in vacuo. The residue was purified by column chromatography on alumina with a mixture of methylene chloride and methanol (100:1) as eluent to give (2R)-1-[3,5-bis(trifluoromethyl)-benzoyl]-2-[3-[(2-methoxyethoxy)methoxy]-4-methylbenzyl]-4-[[1-(2-hydroxyethyl)-1H-pyrazol-4-yl]methyl]piperazine (185 mg).

IR (Neat): 3400, 1640, 1440, 1280, 1135 cm$^{-1}$

NMR (CDCl$_3$, δ): 1.84–5.38 (27H, m), 6.30–7.90 (8H, m)

MASS (APCI): 659 (M+H)$^+$ (free)

EXAMPLE 24

(2R)-1-[3,5-Bis(trifluoromethyl)benzoyl]-2-(3-hydroxy-4-methylbenzyl)-4-[4-[(2S)-2-(methoxymethyl)morpholino]-2-butynyl]piperazine (0.05 g) in ethyl acetate (5 ml) was treated with 4N hydrogen chloride in ethyl acetate (1 ml) and the mixture was concentrated under reduced pressure. After the residue was triturated with a mixture of dichloromethane and diisopropyl ether, the organic solvents were removed under reduced pressure to give (2R)-1-[3,5-bis(trifluoromethyl)benzoyl]-2-(3-hydroxy-4-methylbenzyl)-4-[4-[(2S)-2-(methoxymethyl)morpholino]-2-butynyl]piperazine dihydrochloride (0.05 g) as a powder.

mp: 110–130° C.

[α]$_D^{25.5}$: −7.89° (C=0.40, MeOH)

IR (KBr): 1687, 1645, 1516, 1454, 1429, 1362, 1327, 1281, 1184, 1138 cm$^{-1}$

NMR (DMSO-d$_6$, δ): 1.70–5.30 (28H, m), 6.00–8.40 (6H, m)

MASS (APCI): 628 (M+H)$^+$ (free)

EXAMPLE 25

The following compound was obtained according to a similar manner to that of Example 24.

(2R)-1-[3,5-Bis(trifluoromethyl)benzoyl]-2-(3-hydroxy-4-methylbenzyl)-4-[(Z)-4-[(2S)-2(methoxymethyl)morpholino]-2-butenyl]piperazine dihydrochloride mp: 180–200° C.

[α]$_D^{25.6}$: +0.49° (C=0.205, MeOH)

IR (KBr): 1693, 1687, 1645, 1531, 1516, 1454, 1427, 1363, 1321, 1281, 1184, 1140, 1003 cm$^{-1}$

NMR (DMSO-d$_6$, δ): 0.80–5.30 (30H, m), 5.80–8.40 (6H, m)

MASS (APCI): 630 (M+H)$^+$ (free)

EXAMPLE 26

To a stirred suspension of 2-[3-methoxy-4-(trifluoromethyl)benzyl]piperazine dihydrobromide (109 mg), potassium iodide (109 mg) and N,N-diisopropylethylamine (0.26 ml) in N,N-dimethylformamide (4 ml) was added (2R)-4-(2-chloroethyl)-2-(methoxymethyl)morpholine hydrochloride (29 mg) at 5° C. under nitrogen atmosphere and the mixture was gradually warmed to room temperature overnight. To the above stirred suspension was added 3,5-bis(trifluoromethyl)-benzoyl chloride (118 mg) at 5° C. and the mixture was stirred for 1 hour at the same temperature. The mixture was extracted with ethyl acetate and the extract was washed with water, and dried over magnesium sulfate. The usual work up followed by flash chromatography on silica gel with a mixture of dichloromethane and methanol (60:1) gave the product, which was dissolved in ethyl acetate and treated with 4N hydrogen chloride in ethyl acetate to give 1-[3,5-bis(trifluoromethyl)benzoyl]-2-[3-methoxy-4-(trifluoromethyl)benzyl]-4-[2-[(2S)-2-(methoxymethyl)-morpholino]ethyl]piperazine dihydrochloride (22 mg) as a powder.

NMR (DMSO-d$_6$, δ): 2.80–5.20 (28H, m), 6.60–8.50 (8H, m)

MASS (APCI): 672 (M+H)$^+$ (free)

EXAMPLE 27

(2R)-1-[3,5-Bis(trifluoromethyl)benzoyl]-2-[3-[(2-methoxyethoxy)methoxy]-4-methylbenzyl]-4-[(3-bromo-1,2,4-oxadiazol-5-yl)methyl]piperazine (250 mg) was dissolved with 2M ammonia in tetrahydrofuran (10 ml). After being stored at room temperature for one day, the solution was evaporated under reduced pressure. The residue was partitioned between ethyl acetate and brine. The organic layer was separated and washed with brine, dried over magnesium sulfate and concentrated under reduced pressure. The residue was purified by column chromatography on silica gel using a mixture of dichloromethane and methanol (30:1). The fractions containing the objective compound were collected and evaporated under reduced pressure and treated with 4N hydrogen chloride in ethyl acetate to give (2R)-1-[3,5-bis(trifluoromethyl)benzoyl]-2-(3-hydroxy-4-methylbenzyl)-4-[(3-amino-1,2,4-oxadiazol-5-yl)methyl]piperazine dihydrochloride (40 mg).

mp: 160–170° C.

[α]$_D^{26}$: −20.1° (C=0.38, MeOH)

IR (KBr): 3500–3150, 2700–2300, 1635, 1428, 1280 cm$^{-1}$

NMR (DMSO-d$_6$, δ): 2.07 (3H, s), 2.60–5.20 (13H, m), 6.10–8.20 (7H, m), 8.60–9.40 (2H, m)

MASS (APCI): 544 (M+H)$^+$ (free)

EXAMPLE 28

The following compounds were obtained according to a similar manner to that of Example 27.

(2R)-1-[3,5-Bis(trifluoromethyl)benzoyl]-2-(3-hydroxy-4-methylbenzyl)-4-[[3-(dimethylamino)-1,2,4-oxadiazol-5-yl]-methyl]piperazine dihydrochloride mp: 140–150° C.

[α]$_D^{27}$: −20.14° (C=0.35, MeOH)

IR (KBr): 3500–3000, 2700–2300, 1635, 1606, 1430 cm$^{-1}$

NMR (DMSO-d$_6$, δ): 2.07 (3H, s), 2.92 (3H, s), 2.94 (3H, s), 2.60–5.20 (11H, m), 6.10–8.20 (7H, m), 8.60–9.60 (2H, m)

MASS (APCI): 572 (M+H)$^+$ (free)

EXAMPLE 29

(2R)-1-[3,5-Bis(trifluoromethyl)benzoyl]-2-(3-hydroxy-4-methylbenzyl)-4-[2-[(2S)-2-(methoxymethyl)morpholino]-ethyl]piperazine dihydrochloride (0.50 g) was partitioned between ethyl acetate and saturated aqueous sodium hydrogen carbonate solution, and the organic layer was separated, washed with brine, dried over magnesium sulfate, and evaporated in vacuo to give (2R)-1-[3,5-bis(trifluoromethyl)benzoyl]-2-(3-hydroxy-4-methylbenzyl)-4-[2-[(2S)-2-(methoxymethyl)morpholino]ethyl]piperazine (0.437 mg). A solution of the obtained compound in methylene chloride was added 4-(dimethylamino)pyridine (9 mg) and trifuric anhydride (0.22 ml) successively with ice-bath cooling under nitrogen atmosphere. After stirring for 1 hour, saturated aqueous sodium hydrogen carbonate solution was added to the mixture, and the organic layer was separated and the aqueous layer was extracted with methylene chloride. The combined organic layer was washed with brine, dried over magnesium sulfate and silica gel (1.1 g), and evaporated in vacuo to give (2R)-1-[3,5-bis(trifluoromethyl)benzoyl]-2-(4-methyl-3-trifluoromethanesulfonyloxybenzyl)-4-[2-[(2S)-2-(methoxymethyl)morpholino]ethyl]piperazine (358 mg) as an oil.

IR (Neat): 1645, 1425, 1280, 1210, 1135 cm$^{-1}$

NMR (CDCl$_{3O}$, δ): 1.90–5.14 (28H, m), 6.60–8.20 (6H, m)

MASS (APCI): 736 (M+H)$^+$

EXAMPLE 30

A mixture of (2R)-1-[3,5-bis(trifluoromethyl)benzoyl]-2-(4-methyl-3-trifluoromethanesulfonyloxybenzyl)-4-[2-[(2S)-2-(methoxymethyl)morpholino]ethyl]piperazine (0.10 g), benzophenone imine (30.5 mg), cesium carbonate (62 mg), palladium acetate (3 mg), and 2,2'-bis(diphenylphosphino)-1,1'-binaphthyl (12.7 mg) in toluene was stirred at 80° C. under nitrogen atmosphere for 22 hours. After cooling, water and ethyl acetate were added to the mixture and the organic layer was separated, washed with brine, dried over sodium sulfate, and evaporated in vacuo. The residue was purified by column chromatography on silica gel (NH-DM1020, Fuji Silysia Chemical Ltd.) with a mixture of hexane and ethyl acetate (3:1) as eluent to give (2R)-1-[3,5-bis(trifluorometh yl)benzoyl]-2-[3-(diphenylmethyleneamino)-4-methylbenzyl]-4-[2-[(2S)-2-(methoxymethyl)morpholino]ethyl]piperazine (75 mg) as an oil.

[α]$_D^{23.7}$: −63.51° (C=0.222, MeOH)

IR (Neat): 2620, 1625, 1435 cm$^{-1}$

NMR (CDCl$_3$, δ): 1.86–4.84 (28H, m), 6.00–7.95 (16H, m)

MASS (APCI): 767 (M+H)$^+$

EXAMPLE 31

A solution of (2R)-1-[3,5-bis(trifluoromethyl)benzoyl]-2-[3-(diphenylmethyleneamino)-4-methylbenzyl]-4-[2-[(2S)-2-(methoxymethyl)morpholino]ethyl]piperazine (65 mg) in methanol was subjected to hydrogenolysis (3 atm hydrogen pressure) using 10% palladium on carbon (6 mg, 50% wet) at 50° C. for 16 hours. After cooling, the mixture was filtered and the filtrate was evaporated in vacuo. Ethyl acetate and water were added to the residue and the organic layer was separated, dried over magnesium sulfate, and evaporated in vacuo. The residue was purified by column chromatography on silica gel (NH-DM1020, Fuji Silysis Chemical Ltd.) with a mixture of hexane and ethyl acetate (1:1) as eluent to give (2R)-1-[3,5-bis(trifluoromethyl)benzoyl]-2-(3-amino-4-methylbenzyl)-4-[2-[(2S)-2-(methoxymethyl)morpholino]ethyl]-piperazine (18 mg). To a solution of the obtained compound in methanol was added 4N hydrogen chloride in ethyl acetate (0.05 ml) and the mixture was evaporated in vacuo to give (2R)-1-[3,5-bis(trifluoromethyl)benzoyl]-2-(3-amino-4-methylbenzyl)-4-[2-((2S)-2-(methoxymethyl)morpholino]ethyl]-piperazine trihydrochloride (20 mg).

mp: 180–186° C.

[α]$_D^{24.4}$: +9.41° (C=0.085, MeOH)

IR (KBr): 3435, 2600, 1645, 1514, 1454, 1429, 1365, 1282, 1182, 1105 cm$^{-1}$

NMR (D$_2$O, δ): 2.20–5.35 (28H, m), 6.80–8.30 (6H, m)

MASS (APCI): 604 (M+H)$^+$ (free)

EXAMPLE 32

A mixture of (2R)-1-[3,5-bis(trifluoromethyl)benzoyl]-2-(3-amino-4-methylbenzyl)-4-[2-[(2S)-2-(methoxymethyl)-morpholino]ethyl]piperazine (0.10 g), succinimide (30 mg) and formalin (28 mg) in ethanol (0.5 ml) was stirred at 100° C. for 24 hours. After cooling, the mixture was evaporated in vacuo and the residue of the following compound was used to the next reaction without purification:

(2R)-1-[3,5-bis(trifluoromethyl)benzoyl]-2-[4-methyl-3-[[(2,5-dioxopyrrolidino)methyl]amino]benzyl]-4-[2-[(2S)-2-(methoxymethyl)morpholino] ethyl]piperazine IR (Neat): 1705, 1640, 1280, 1130 cm$^{-1}$ NMR (CDCl$_3$, δ): 1.50–5.20 (34H, m), 6.02–7.90 (6H, m)

MASS (API-ES): 714 (M$^+$) (free)

EXAMPLE 33

A solution of (2R)-1-[3,5-bis(trifluoromethyl)benzoyl]-2-[4-methyl-3-[[(2,5-dioxopyrrolidino)methyl]amino]benzyl]-4-[2-[(2S)-2-(methoxymethyl)morpholino]ethyl]piperazine (0.14 g) in dimethylsulfoxide (0.42 ml) was added sodium borohydride (10 mg) and the whole was stirred at 80° C. for 15 hours. After cooling, water and ethyl acetate were added to the mixture. The organic layer was separated, washed with brine, dried over sodium sulfate and evaporated in vacuo. The residue was purified by column chromatography on silica gel with a mixture of methylene chloride and methanol (30:1 to 10:1) as eluent to give (2R)-1-[3,5-bis(trifluoromethyl)-benzoyl]-2-[4-methyl-3-(methylamino)benzyl]-4-[2-[(2S)-2-(methoxymethyl)morpholino]ethyl]piperazine (37 mg) and (2R)-1-[3,5-bis(trifluoromethyl)benzoyl]-2-[4-methyl-3-[[(5-hydroxy-2-oxopyrrolidino)methyl]amino]benzyl]-4-[2-[(2S)-2-(methoxymethyl)morpholino]ethyl]piperazine (45 mg), respectively. Each compound was converted to its trihydrochloride in a conventional manner.

(2R)-1-[3,5-Bis(trifluoromethyl)benzoyl]-2-[4-methyl-3-(methylamino)benzyl]-4-[2-[(2S)-2-(methoxymethyl)-morpholino]ethyl]piperazine trihydrochloride mp: 156–163° C.
$[\alpha]_D^{25.9}$: -1.790 (C=0.003, MeOH)
IR (KBr): 3425, 2669, 2605, 2451, 1647, 1516, 1462, 1429, 1281, 1134, 1105 cm$^{-1}$
NMR (D$_2$O, δ): 2.05–5.57 (31H, m), 6.74–8.25 (6H, m)
MASS (APCI): 617 (M+H)$^+$ (free), 581

(2R)-1-[3,5-Bis(trifluoromethyl)benzoyl]-2-[4-methyl-3-[[(5-hydroxy-2-oxopyrrolidino)methyl]amino]benzyl]-4-[2-[(2S)-2-(methoxymethyl)morpholino]ethyl]piperazine trihydrochloride mp: 163–176° C.
IR (KBr): 3400, 2586, 2443, 1647, 1454, 1427, 1369, 1281, 1174, 1134, 1103 cm$^{-1}$
NMR (D$_2$O, δ): 1.70–6.50 (35H, m), 6.70–8.30 (6H, m)
MASS (APCI): 716 (M+H)$^+$ (free)

EXAMPLE 34

The following compounds were obtained according to a similar manner to that of Example 30.

(1) (2R)-1-[3,5-Bis(trifluoromethyl)benzoyl]-2-(4-methyl-3-pyrrolidinobenzyl)-4-[2-[(2S)-2-(methoxymethyl)-morpholino]ethyl]piperazine trihydrochloride mp: 160–165° C.
$[\alpha]_D^{24.6}$: +20.83° (C=0.108, MeOH)
IR (KBr): 3438, 2665, 2586, 2482, 1645, 1516, 1454, 1429, 1282, 1182, 1138, 1105 cm$^{-1}$
NMR (D$_2$O, δ): 2.05–5.50 (36H, m), 6.74–8.30 (6H, m)
MASS (APCI): 657 (M+H)$^+$ (free), 588

(2) (2R)-1-[3,5-Bis(trifluoromethyl)benzoyl]-2-(4-methyl-3-morpholinobenzyl)-4-[2-[(2S)-2-(methoxymethyl)-morpholino]ethyl]piperazine trihydrochloride mp: 150–170° C.
$[\alpha]_D^{24.7}$: -4.48° (C=0.067, MeOH)
IR (KBr): 3437, 2667, 2576, 2457, 1645, 1514, 1454, 1429, 1282, 1182, 1136 cm$^{-1}$
NMR (D$_2$O, δ): 2.15–5.50 (36H, m), 6.74–8.30 (6H, m)
MASS (APCI): 673 (M+H)$^+$ (free), 588

EXAMPLE 35

To a solution of (2R)-1-[3,5-bis(trifluoromethyl)-benzoyl]-2-(3-amino-4-methylbenzyl)-4-[2-[(2S)-2-(methoxymethyl)morpholino]ethyl]piperazine (132 mg) in methylene chloride was added 4-(dimethylamino)pyridine (2 mg) and trifluoroacetic anhydride (0.05 ml) successively and the mixture was stirred at room temperature overnight. The mixture was evaporated in vacuo and to the residue was added ethyl acetate and water. The organic layer was separated, washed with brine, dried over magnesium sulfate, and evaporated in vacuo. The residue was purified by column chromatography on silica gel with a mixture of methylene chloride and methanol (25:1) as eluent to give (2R)-1-[3,5-bis(trifluoromethyl)benzoyl]-2-[4-methyl-3-(trifluoroacetylamino)benzyl]-4-[2-[(2S)-2-(methoxymethyl)-morpholino]ethyl]piperazine (134 mg).

MASS (APCI): 699 (M+H)$^+$

EXAMPLE 36

To a solution of (2R)-1-[3,5-bis(trifluoromethyl)-benzoyl]-2-[4-methyl-3-(trifluoroacetylamino)benzyl]-4-[2-[(2S)-2-(methoxymethyl)morpholino]ethyl]piperazine (131 mg) in tetrahydrofuran (2 ml) was added sodium hydride (10 mg) and the resulting mixture was stirred for 20 minutes. Methyl iodide (28 mg) was added to the mixture and the whole was stirred at room temperature overnight. Brine was added to the mixture and the organic layer was separated, dried over magnesium sulfate, and evaporated in vacuo. The residue was purified by HPLC to give (2R)-1-[3,5-bis(trifluoromethyl)benzoyl]-2-[4-methyl-3-(N-methyl-N-trifluoroacetylamino)benzyl]-4-[2-[(2S)-2-(methoxymethyl)-morpholino]ethyl]piperazine (31 mg) as an oil. The obtained compound was converted to its dihydrochloride in a conventional manner.

$[\alpha]_D^{27.3}$: -10.94° (C=0.032, MeOH)
IR (KBr): 3425, 1695, 1647, 1282, 1207, 1180, 1140, 1101 cm$^{-1}$
NMR (DMSO-d$_6$, δ): 1.95–5.32 (31H, m), 6.75–8.34 (6H, m)
MASS (APCI): 713 (M+H)$^+$ (free)

EXAMPLE 37

A suspension of (2R)-1-[3-(2,5-dimethylpyrrol-1-ylsulfonyl)-5-(trifluoromethyl)benzoyl]-2-(3-hydroxy-4-methylbenzyl)-4-[2-[(2S)-2-(methoxymethyl)morpholino]ethyl]-piperazine (160.6 mg) in 6N hydrochloric acid (10 ml) was stirred at 70° C. for 2 hours. The mixture was poured into saturated aqueous sodium hydrogen carbonate solution (150 ml) and extracted with ethyl acetate (50 ml×3). The combined extracts were washed with brine, dried over magnesium sulfate, and evaporated under reduced pressure to give an oil (163.4 mg). The oil was dissolved in ethyl acetate (1.6 ml), then 4N hydrogen chloride in ethyl acetate (0.17 ml) and hexane (50 ml) was added successively to the solution at room temperature. The resulting powder was collected by filtration and dried under reduced pressure to give (2R)-2-(3-hydroxy-4-methylbenzyl)-4-[2-[(2S)-2-(methoxymethyl)-morpholino]ethyl]-1-[3-sulfamoyl-5-(trifluoromethyl)benzoyl]-piperazine dihydrochloride (149.3 g) as a powder.

mp: 166–206° C.
$[\alpha]_D^{25}$: -11.93° (C=0.25, MeOH)
IR (KBr): 3431, 3402, 1641 cm$^{-1}$
NMR (DMSO-d$_6$, δ): 2.08 (3H, s), 2.60–5.20 (25H, m), 6.18–9.20 (6H, m)
MASS (APCI): 615 (M+H)$^+$ (free)

Preparation 56

To a solution of (3R)-1-benzyl-3-(3-hydroxy-4-methylbenzyl)piperazine (840 mg) in a mixture of 1,4-dioxane (7.5 ml), water (5 ml), and 1N hydrochloric acid (2.8 ml) was added successively a solution of di-tert-butyl dicarbonate (740 mg) in 1,4-dioxane (2.5 ml) and 2N sodium hydroxide solution (1.9 ml) at 0° C. After stirring at 0° C. for 1 hour, a solution of di-tert-butyl dicarbonate (123 mg) in 1,4-dioxane was added to the solution, and stirred at 0° C. for 2 hours. The mixture was adjusted to pH 7–8 by 1N hydrochloric acid (0.99 ml) and extracted with dichloromethane (×3). The combined extracts were washed with brine, dried over magnesium sulfate, and evaporated under reduced pressure to give an oil (1.74 g), which was purified with column chromatography (silica gel, 50 ml, ethyl acetate: hexane (1:5–1:4)) to give (2R)-4-benzyl-1-tert-butoxycarbonyl-2-(3-hydroxy-4-methylbenzyl)piperazine (1.08 g) as a foam.

IR (Neat): 1664 cm$^{-1}$

NMR (CDCl$_3$, δ): 1.40 (9H, s), 1.92 (1H, dd, J=3.8 and 11.4 Hz), 2.15 (3H, s), 2.05–2.20 (1H, m), 2.64–3.10 (4H, m), 3.19 (1H, dt, J=3.5 and 12.6 Hz), 3.25 (1H, d, J=12.8 Hz), 3.59 (1H, d, J=12.8 Hz), 3.80–4.15 (2H, m), 4.77 (1H, br s), 6.15 (1H, br s), 6.55 (1H, d, J=7.5 Hz), 6.91 (1H, d, J=7.5 Hz), 7.26–7.37 (5H, m)

MASS (APCI): 397 (M+H)$^+$

Preparation 57

To a solution of (2R)-1-tert-butoxycarbonyl-2-(3-hydroxy-4-methylbenzyl)piperazine (7.73 g) and 4-dimethylaminopyridine (620 mg) in dichloromethane (90 ml) was added successively triethylamine (15.82 ml) and tert-butyldiphenylsilyl chloride (26.24 ml) at room temperature. After stirring under reflux for 27.5 hours, water (200 ml) was added to the mixture, and the mixture was extracted with dichloromethane (100 ml, 50 ml×2). The combined organic extracts were washed successively with water and brine, dried over magnesium sulfate, and evaporated under reduced pressure to give crude oil. The oil was purified with column chromatography (silica gel, 500 ml, methanol:dichloromethane 5:95) to give (2R)-1-tert-butoxycarbonyl-2-(3-tert-butyldiphenylsilyloxy-4-methylbenzyl)piperazine (12.07 g) as a solid.

mp: 64.5–65.5° C.

IR (KBr): 2962, 2933, 1693 cm$^{-1}$

NMR (CDCl$_3$, δ): 1.07–1.09 (9H, m), 1.26–1.50 (9H, m), 2.00–3.80 (9H, m), 2.36 (3H, s), 6.13–6.20 (1H, m), 6.67 (1H, d, J=7.6 Hz), 7.03 (1H, d, J=7.6 Hz), 7.26–7.34 (6H, m), 7.65–7.73 (4H, m)

MASS (APCI): 545 (M+H)$^+$

Preparation 58

The following compounds were obtained by a similar manner to that of Example 1 using N,N-diisopropylethylamine instead of potassium carbonate as a base.

(1) (2R)-1-tert-Butoxycarbonyl-2-(3-tert-butyldiphenylsilyloxy-4-methylbenzyl)-4-[2-((2S)-2-methoxymethylmorpholino)ethyl]piperazine IR (Neat): 1695 cm$^{-1}$ NMR (CDCl$_3$, δ): 1.10 (9H, s), 1.21 (9H, s), 1.60–3.00 (17H, m), 2.34 (3H, s), 3.37 (3H, s), 3.37–4.00 (5H, m), 6.23 (1H, s), 6.64 (1H, d, J=7.6 Hz), 7.38 (1H, d, J=7.6 Hz), 7.34–7.42 (6H, m), 7.66–7.73 (4H, m)

MASS (ESI): 702.5 (M+H)$^+$ (2) (2R)-1-(tert-Butoxycarbonyl)-2-(4-chlorobenzyl)-4-[2-(cis-2,6-dimethylmorpholino)ethyl]piperazine IR (Neat): 1693, 1410, 1367, 1087 cm$^{-1}$ NMR (CDCl$_3$, δ): 1.16 (6H, d, J=6.3 Hz), 1.38 (9H, s), 1.76 (1H, t, J=11.0 Hz), 2.03 (2H, m), 2.51 (4H, m), 2.60–3.20 (8H, m), 3.50–4.15 (4H, m), 7.12–7.27 (4H, m)

MASS: 452 (M$^+$)

(3) (2R)-1-(tert-Butoxycarbonyl)-2-(4-chlorobenzyl)-4-[2-(5,6,7,8-tetrahydro-1,6-naphthyridin-6-yl)ethyl]-piperazine

[α]$_D^{27.2}$: +4.89° (C=0.32, MeOH)

IR (Neat): 2970, 2930, 2810, 1690, 1580 cm$^{-1}$

NMR (CDCl$_3$, δ): 1.39 (9H, s), 1.9–2.2 (2H, m), 2.4–3.3 (13H, m), 3.67 (2H, s), 3.8–4.3 (2H, m), 7.07 (1H, dd, J=4.7 and 7.6 Hz), 7.13 (2H, d, J=8.4 Hz), 7.22 (2H, d, J=8.4 Hz), 7.33 (1H, d, J=7.6 Hz), 8.40 (1H, d, J=4.7 Hz)

MASS (APCI): 471 (M+H)$^+$

Preparation 59

To a solution of (2R)-1-tert-butoxycarbonyl-2-(3-tert-butyldiphenylsilyloxy-4-methylbenzyl)-4-[2-[(2S)-2-methoxymethylmorpholino]ethyl]piperazine (13.43 g) in dichloromethane (67.0 ml) was added trifluoroacetic acid (67.0 ml) at 0° C. After stirring at room temperature for 30 minutes, the mixture was concentrated and was added dropwise saturated aqueous sodium hydrogen carbonate solution. After stirring at room temperature for 30 minutes, the mixture was extracted with dichloromethane (100 ml×1, 50 ml×2). The combined extracts were dried over magnesium sulfate and evaporated under reduced pressure to give (2R)-2-(3-tert-butyldiphenylsilyloxy-4-methylbenzyl)-4-[2-[(2S)-2-methoxymethylmorpholino]ethyl]piperazine (11.63 g) as a brown oil.

IR (Neat): 1676, 1614, 1579 cm$^{-1}$

NMR (CDCl$_3$, δ): 1.10 (9H, s), 1.60–2.80 (17H, m), 2.36 (3H, s), 3.37 (3H, s), 3.37–3.41 (2H, m), 3.60–3.95 (3H, m), 6.22 (1H, d, J=1.4 Hz), 6.60 (1H, dd, J=1.4 and 7.6 Hz), 7.06 (1H, d, J=7.6 Hz), 7.31–7.42 (6H, m), 7.68–7.73 (4H, m)

MASS (APCI): 602 (M+H)$^+$

Preparation 60

To a solution of (2R)-2-(3-tert-butyldiphenylsilyloxy-4-methylbenzyl)-4-[2-[(2S)-2-(methoxymethyl)morpholino]ethyl]-piperazine (9.38 g) in ethyl acetate (40 ml) was added 4N hydrogen chloride in ethyl acetate (11.7 ml) at 0° C. and then added dropwise hexane (200 ml). After stirring at room temperature for 2 hours, the mixture was cooled at 0° C. The resulting precipitates were collected by filtration, washed with hexane, and dried under reduced pressure to give (2R)-2-(3-tert-butyldiphenylsilyloxy-4-methylbenzyl)-4-[2-[(2S)-2-(methoxymethyl)morpholino]ethyl]piperazine trihydrochloride (10.75 g) as a powder.

mp: 173–185° C.

IR (KBr): 3398, 2935, 1647, 1510 cm$^{-1}$

NMR (DMSO-d$_6$, δ): 1.07 (9H, s), 2.31 (3H, s), 1.80–4.30 (25H, m), 6.15 (1H, br s), 6.70 (1H, d, J=7.7 Hz), 7.17 (1H, d, J=7.7 Hz), 7.42–7.50 (6H, m), 7.65–7.70 (4H, m)

NMR (D$_2$O, δ): 1.03 (9H, s), 2.27 (3H, s), 2.90–4.20 (22H, m), 3.39 (3H, s), 6.32 (1H, s), 6.80–6.87 (1H, m), 7.19 (1H, d, J=7.8 Hz), 7.37–7.76 (10H, m)

MASS (APCI): 602 (M+H)$^+$ (free)

Preparation 61

N,O-Dimethylhydroxylamine hydrochloride (5.37 g) was added to a mixture of 3-methoxy-4-(trifluoromethyl)benzoic acid (11.0 g), 1-hydroxybenzotriazole (6.76 g), 1-(3-dimethylaminopropyl)-3-ethylcarbodiimide hydrochloride (9.59 g) and N,N-diisopropylethylamine (9.6 ml) in dichloromethane (200 ml), and the whole was stirred at room temperature for 18 hours. Saturated aqueous sodium hydrogen carbonate solution was added to the mixture and the organic layer was separated, dried over magnesium sulfate, and evaporated in vacuo. The residue was purified by column chromatography on silica gel with 25% of ethyl acetate in hexane as an eluent to give 3-methoxy-N-methoxy-N-methyl-4-(trifluoromethyl)-benzamide (12.0 g) as a colorless oil.

NMR (CDCl$_3$, δ): 3.38 (3H, s), 3.56 (3H, s), 3.94 (3H, s), 7.28 (2H, m), 7.60 (1H, d, J=8.3 Hz)

MASS (APCI): 264 (M+H)$^+$

Preparation 62

To a stirred solution of 3-methoxy-N-methoxy-N-methyl-4-(trifluoromethyl)benzamide (2.63 g) in dry tetrahydrofuran (26 ml) was added lithium aluminum hydride (380 mg) at −40° C. under nitrogen atmosphere. After 1 hour of stirring at 5° C., 2N sodium hydroxide was added to the mixture. The insoluble materials were removed by filtration through Celite® and washed with ethyl acetate. The filtrate and washing were combined and evaporated under reduced pressure to give crude 3-methoxy-4-(trifluoromethyl)benzaldehyde as a colorless oil.

To a stirred mixture of crude 3-methoxy-4-(trifluoromethyl)-benzaldehyde and 1,4-diacetylpiperazine-2,5-dione (1.98 g) in a mixture of N,N-dimethylformamide (10 ml) and tert-butanol (10 ml) was added potassium tert-butoxide (1.12 g) at 5° C. The mixture was stirred for 18 hours at room temperature. Water (30 ml) and ethyl acetate (100 ml) were added to the mixture and the organic layer was separated, and the aqueous layer was extracted with ethyl acetate. The combined extract was washed with water, dried over magnesium sulfate, and evaporated in vacuo. The residue was purified by column chromatography on silica gel with 50% of ethyl acetate in hexane as an eluent to give 1-acetyl-3-[[3-methoxy-4-(trifluoromethyl)phenyl]methylene]piperazine-2,5-dione (2.11 g) as a powder.

NMR (DMSO-d$_6$, δ): 3.33 (3H, s), 3.90 (3H, s), 4.37 (2H, s), 6.98 (1H, s), 7.26 (1H, d, J=8.1 Hz), 7.38 (1H, s), 7.63 (1H, d, J=8.1 Hz), 10.55 (1H, s)

MASS (APCI): 343 (M+H)$^+$

Preparation 63

A solution of 1-acetyl-3-[[3-methoxy-4-(trifluoromethyl)phenyl]methylene]piperazine-2,5-dione (1.8 g) in tetrahydrofuran (50 ml) was hydrogenated over 10% palladium-carbon (50% wet, 180 mg) for 5 hours at atmospheric pressure. After removal of the catalyst by filtration, the filtrate was added hydrazine monohydrate (395 mg). The mixture was stirred for 1.5 hours at room temperature and concentrated under reduced pressure. The residue was triturated with isopropyl ether (12 ml) and the precipitates were collected by filtration, and washed with isopropyl ether to give 3-[3-methoxy-4-(trifluoromethyl)benzyl]piperazine-2,5-dione (1.29 g) as a powder.

NMR (DMSO-d$_6$, δ): 2.94–3.19 (3H, m), 3.51 (1H, m), 3.84 (3H, s), 4.15 (1H, m), 6.90 (1H, d, J=7.9 Hz), 7.08 (1H, s), 7.52 (1H, d, J=7.9 Hz), 7.99 (1H, m), 8.20 (1H, m)

MASS (APCI): 303 (M+H)$^+$

Preparation 64

To a stirred suspension of 3-[3-methoxy-4-(trifluoromethyl)benzyl]piperazine-2,5-dione (1.2 g) in tetrahydrofuran (100 ml) was added borane-tetrahydrofuran complex (1M in tetrahydrofuran, 39.7 ml) by syringe under nitrogen atmosphere at room temperature and the mixture was heated under reflux for 18 hours. After cooling, the reaction mixture was filtered, and the filtrate was slowly added 12% hydrogen bromide in acetic acid (16 ml). To the mixture was added isopropyl ether (300 ml) and the whole was stirred for 1 hour at 5° C. The resulting precipitates were collected by filtration and dried under reduced pressure to give 2-[3-methoxy-4-(trifluoromethyl)benzyl]piperazine dihydrobromide (1.73 mg) as a powder.

NMR (DMSO-d$_6$, δ): 2.70–3.90 (9H, m), 3.92 (3H, s), 6.50 (1H, m), 7.03 (1H, d, J=7.9 Hz), 7.25 (1H, s), 7.62 (1H, d, J=7.9 Hz), 8.10 (1H, br s), 9.07 (2H, br s)

MASS (APCI): 275 (M+H)$^+$ (free)

Preparation 65

The following compound was obtained according to a similar manner to that of Preparation 56.

(2R)-4-Benzyl-1-(tert-butoxycarbonyl)-2-(4-chlorobenzyl)piperazine mp: 139–140° C.

$[α]_D^{26.8}$: −2.96° (C=0.27, MeOH)

IR (KBr): 3740, 2970, 2810, 1700, 1650 cm$^{-1}$

NMR (CDCl$_3$, δ): 1.38 (9H, s), 1.9–2.2 (2H, m), 2.58 (1H, d, J=11.5 Hz), 2.7–3.3 (4H, m), 3.32 (1H, d, J=12.9 Hz), 3.56 (1H, d, J=12.9 Hz), 3.7–4.3 (2H, m), 6.93 (2H, d, J=8.2 Hz), 7.12 (2H, d, J=8.2 Hz), 7.33 (5H, s)

MASS (APCI): 401 (M+H)$^+$

Preparation 66

The following compounds were obtained according to a similar manner to that of Preparation 59.

(1) (2R)-2-(4-Chlorobenzyl)-4-[2-(cis-2,6-dimethylmorpholino)ethyl]piperazine trihydrochloride IR (KBr): 1645, 1454, 1425, 1120, 1086 cm$^{-1}$ NMR (DMSO-d$_6$, δ): 1.11 (6H, d, J=6.2 Hz), 2.59–4.60 (19H, m), 7.34 (2H, d, J=8.5 Hz), 7.44 (2H, d, J=8.5 Hz), 9.47–10.0 (1H, br), 9.50 (0.5H, br), 10.5 (0.5H, br)

MASS: 352 (M$^+$)

(2) (2R)-2-(4-Chlorobenzyl)-4-[2-(5,6,7,8-tetrahydro-1,6-naphthyridin-6-yl)ethyl]piperazine tetrahydrochloride $[α]_D^{27.2}$: +13.10° (C=0.35, MeOH)

IR (KBr): 3400, 1640, 1630, 1550, 1520 cm$^{-1}$

NMR (DMSO-d$_6$, δ): 2.8–6.2 (16H, m), 4.53 (2H, s), 7.34 (2H, d, J=8 Hz), 7.43 (2H, d, J=8 Hz), 7.80 (1H, dd, j=5 and 8 Hz), 8.23 (1H, d, J=8 Hz), 8.75 (1H, d, J=5 Hz), 9.7–10.0 (1H, br), 10.1–10.3 (1H, br)

MASS (APCI): 371 (M+H)$^+$

Preparation 67

To a 3-chlorosulfonyl-5-(trifluoromethyl)benzoic acid (0.4 g) was added 28% ammonia aqueous solution (5.0 ml) at 0° C. The mixture was stirred at 0° C., and then allowed to stand at room temperature overnight. The mixture was concentrated to dryness, and then 1N hydrochloric acid (5 ml) was added to the mixture, and stirred at 0° C. for 30 minutes. The resulted powder was collected by filtration and dried under reduced pressure to give 3-sulfamoyl-5-(trifluoromethyl)benzoic acid (299.4 mg) as a pale yellow powder.

mp: 244–246° C.

IR (KBr): 1713 cm$^{-1}$

NMR (DMSO-d$_6$, δ): 7.73 (2H, s), 8.34 (1H, s), 8.37 (1H, s), 8.62 (1H, s)

MASS (ESI–): 268.1 (M–H)

Preparation 68

To a solution of 3-sulfamoyl-5-(trifluoromethyl)benzoic acid (200 mg) and 2,5-hexanedione (0.26 ml) in toluene (1 ml) was added p-toluenesulfonic acid monohydrate (28 mg), and the mixture was stirred under reflux with Dean-Stark Trap for 24 hours. Then 2,5-hexanedione (0.26 ml) and p-toluenesulfonic acid monohydrate (30 mg) was added to the mixture, and the mixture was stirred under the same condition for 24 hours. The mixture was evaporated and purified with column chromatography (silica gel, 50 ml, methanol:dichloromethane (5:95–20:80)) to give 3-[(2,5-dimethylpyrrol-1-yl)-sulfonyl]-5-(trifluoromethyl)benzoic acid (280 mg) as a crude solid. The solid was dissolved in a mixture of 1N sodium hydroxide aqueous solution (10 ml) and water (20 ml), and then adjusted to pH 1–2 with 1N hydrochloric acid (20 ml). The resulting powder was collected by filtration and dried under reduced pressure to give pure product (191.1 mg).

mp: 150–153° C.

IR (KBr): 1701 cm$^{-1}$

NMR (DMSO-d$_6$, δ): 2.33 (6H, s), 6.07 (2H, s), 8.13 (1H, s), 8.23 (1H, s), 8.46 (1H, s)

MASS (APCI): 348 (M+H)$^+$

Preparation 69

A solution of a mixture of 3-chlorosulfonyl-5-trifluoromethylbenzoic acid (0.5 g) and pyrrolidine (0.72 ml) in dichloromethane (5 ml) was stirred at room temperature overnight. After evaporation to dryness, water (50 ml) was added to the residue and adjusted to pH 1.0 by 1N hydrochloric acid. The resulting precipitates were collected by filtration, and dried under reduced pressure at 45° C. to give 3-(pyrrolidinosulfonyl)-5-(trifluoromethyl)benzoic acid (0.514 g) as a powder.

mp: 198–199° C.

IR (KBr): 1697 cm$^{-1}$

NMR (DMSO-d$_6$, δ): 1.64–1.77 (4H, m), 3.18–3.29 (4H, m), 8.28 (1H, s), 8.45 (1H, s), 8.46 (1H, s)

MASS (APCI): 324 (M+H)$^+$

Preparation 70

The following compounds were obtained according to a similar manner to that of Preparation 69.

(1) 3-(Morpholinosulfonyl)-5-(trifluoromethyl)benzoic acid mp: 210–213° C.

IR (KBr): 1707 cm$^{-1}$

NMR (DMSO-d$_6$, δ): 2.96–3.01 (4H, m), 3.62–3.67 (4H, m), 8.22 (1H, s), 8.41 (1H, s), 8.48 (1H, s)

MASS (ESI–): 338.1 (M–H)

(2) 3-Methylsulfamoyl-5-(trifluoromethyl)benzoic acid mp: 194–197° C.

IR (KBr): 1705 cm$^{-1}$

NMR (DMSO-d$_6$, δ): 2.46 (3H, s), 7.84–7.94 (1H, m), 8.28 (1H, s), 8.41 (1H, s), 8.55 (1H, s)

NMR (CD$_3$OD, δ): 2.57 (3H, s), 8.29 (1H, s), 8.48 (1H, s), 8.65 (1H, s)

MASS (ESI–): 282 (M–H)

(3) 3-Dimethylsulfamoyl-5-(trifluromethyl)benzoic acid mp: 145–155° C.

IR (KBr): 1705 cm$^{-1}$

NMR (DMSO-d$_6$, δ): 2.70 (6H, s), 8.24 (1H, s), 8.42 (1H, s), 8.46 (1H, s)

MASS (APCI): 298 (M+H)$^+$

Preparation 71

A solution of 3-amino-5-(trifluoromethyl)benzoic acid (2.0 g) and 2,5-dimethoxytetrahydrofuran (1.52 ml) in a mixture of acetic acid (10 ml) and 1,4-dioxane (10 ml) was stirred at 100° C. for 2 hours. After cooling to room temperature, the mixture was concentrated and purified with column chromatography (silica gel, 50 ml, methanol:dichloromethane=10:90) to give crude solid. The solid was recrystallized from ethyl acetate (5.0 ml) and hexane (200 ml) to give 3-(pyrrol-1-yl)-5-(trifluoromethyl)-benzoic acid (1.72 g) as a powder.

mp: 191–192.5° C.

IR (KBr): 1705, 1614, 1496 cm$^{-1}$

NMR (CDCl$_3$, δ): 6.43 (2H, s), 7.19 (2H, s), 7.87 (1H, s), 8.22 (1H, s), 8.31 (1H, s)

MASS (ESI–): 254 (M–H), 509.1 (2M–1)

Preparation 72

To a solution of 3-iodo-5-(trifluoromethyl)benzoic acid (2.32 g) and triethylamine (1.13 ml) in dichloromethane (20 ml) was added dropwise a solution of ethyl chloroformate (1.4 ml) in dichloromethane (2.0 ml) over 10 minutes at –30° C., and the mixture was stirred at –30° C. for 1 hour. 2-Amino-2-methyl-1-propanol was added dropwise to the mixture over 5 minutes at –30° C., and the mixture was stirred at –30° C. for 30 minutes and then at room temperature for 1 hour. The mixture was quenched with aqueous ammonium chloride solution at 0° C., and extracted with dichloromethane (X2). The combined organic extracts were washed successively with saturated aqueous sodium hydrogen carbonate solution, 1N hydrochloric acid and brine, and then dried over magnesium sulfate, evaporated, and purified with column chromatography (silica gel, ethyl acetate:hexane=20:80) to give N-(2-hydroxy-1,1-dimethylethyl)-3-iodo-5-(trifluoromethyl)benzamide (2.10 g) as an oil.

IR (Neat): 3400, 1640, 1550 cm$^{-1}$

NMR (CDCl$_3$, δ): 1.44 (6H, s), 3.69 (2H, d, J=5.9 Hz), 4.02 (1H, t, J=5.9 Hz), 7.93 (1H, d, J=0.6 Hz), 8.05 (1H, d, J=0.6 Hz), 8.22 (1H, s)

NMR (DMSO-d$_6$, δ): 3.33 (6H, s), 3.53 (2H, d, J=5.7 Hz), 4.81 (1H, t, J=5.7 Hz), 8.12 (1H, s), 8.22 (1H, s), 8.45 (1H, s)

MASS (ESI+): 410.1 (M+Na)$^+$

Preparation 73

To N-(2-hydroxy-1,1-dimethylethyl)-3-iodo-5-(trifluromethyl)benzamide (2.11 g) was added thionyl chloride (1.29 ml), and the mixture was stirred at room temperature for 4 hours. The mixture was concentrated under reduced pressure, quenched with saturated aqueous sodium hydrogen carbonate solution, and extracted with ethyl acetate (X2). The combined extracts were dried over magnesium sulfate, evaporated, and purified with column chromatography (silica gel, ethyl acetate:hexane=2.5:97.5) to give 2-[3-iodo-5-(trifluoromethyl)phenyl]-4,4-dimethyl-4,5-dihydrooxazole (1.66 g) as a solid.

mp: 73–74.5° C.
IR (KBr): 2968, 1645, 1566 cm$^{-1}$
NMR (CDCl$_3$, δ): 1.39 (6H, s), 4.14 (2H, s), 8.03 (1H, d, J=0.7 Hz), 8.16 (1H, d, J=0.7 Hz), 8.48 (1H, s)
MASS (APCI): 370 (M+H)$^+$

Preparation 74

To a solution of 2-[3-iodo-5-(trifluromethyl)phenyl]-4,4-dimethyl-4,5-dihydrooxazole (2.11 g) and triisopropyl borate (1.26 g) in tetrahydrofuran (21 ml) was added dropwise butyllithium (1.6 M in hexane) at −70° C. After stirring for 4 hours, the mixture was quenched with 2N hydrochloric acid and extracted with ethyl acetate. The combined extracts were washed with brine, dried over magnesium sulfate, and evaporated in vacuo to give 3-(4,4-dimethyl-4,5-dihydrooxazol-2-yl)-5-(trifluoromethyl)phenylboroic acid (1.65 g) as a yellow oil. This oil was used immediately in the next reaction without further purification because of its instability.

Preparation 75

To a suspension of 3-(4,4-dimethyl-4,5-dihydrooxazol-2-yl)-5-(trifluoromethyl)phenylboroic acid (0.58 g) and 4-bromopyridine hydrochloride (0.39 g) in a mixture of sodium carbonate aqueous solution (2M, 6 ml) and 1,2-dimethoxyethane (4 ml) was added tetrakis(triphenylphosphine)palladium (0.116 g) under nitrogen atmosphere. After stirring at 80° C. for 12 hours, the mixture was quenched with water and extracted with ethyl acetate twice. The combined extracts were dried over magnesium sulfate, evaporated, and purified with column chromatography (silica gel, ethyl acetate:hexane=1:3–2:1–1:2) to give 4-[3-(4,4-dimethyl-4,5-dihydrooxazol-2-yl)-5-(trifluoromethyl)phenyl]pyridine (0.61 g) as a syrup.

IR (KBr): 2972, 1651, 1597, 1446 cm$^{-1}$
NMR (CDCl$_3$, δ): 1.42 (6H, s), 4.14 (2H, s), 7.57 (2H, d, J=6.2 Hz), 7.96 (1H, s), 8.28 (1H, s), 8.40 (1H, s), 8.72 (2H, d, J=6.2 Hz)
MASS (ESI+): 321.1 (M+H)$^+$

Preparation 76

A mixture of 4-[3-(4,4-dimethyl-4,5-dihydrooxazol-2-yl)-5-(trifluoromethyl)phenyl]pyridine (0.60 g) and 6N hydrochloric acid (6 ml) was stirred at 90° C. for 5 hours. After cooling to room temperature, the mixture was concentrated. Small amount of water was added to the residue and the appeared crystals were gathered by filtration and dried under reduced pressure to give 5-(4-pyridinyl)-3-(trifluoromethyl) benzoic acid hydrochloride (0.33 g) as a powder. The second crystals were obtained from mother liquid similarly (0.1 g).

mp: ~230° C.
IR (KBr): 2534, 1703, 1641, 1608, 1514 cm$^{-1}$
NMR (DMSO-d$_6$, δ): 8.36 (1H, s), 8.50 (2H, d, J=6.7 Hz), 8.60 (1H, s), 8.69 (1H, s), 9.01 (2H, d, J=6.7 Hz)
MASS (ESI+): 268.2 (M+H)$^+$

Preparation 77

The following compound was obtained according to a similar manner to that of Preparation 11.

2-Benzylamino-2-methyl-1-propanol

NMR (CDCl$_3$, δ): 1.14 (6H, s), 3.34 (2H, s), 3.67 (2H, s), 7.20–7.34 (5H, m)
MASS (APCI): 180 (M+H)$^+$

Preparation 78

The following compound was obtained according to a similar manner to that of Preparation 12.

2-Methyl-[2-[N-benzyl-N-[(2S)-2-hydroxy-3-methoxypropyl]amino]-1-propanol

IR (Neat): 3400, 2973, 2881, 1643, 1454 cm$^{-1}$
NMR (CDCl$_3$, δ): 1.03 (3H, s), 1.13 (3H, s), 2.49 (1H, dd, J=3.5 and 14.0 Hz), 2.79 (1H, dd, J=9.2 and 14.0 Hz), 3.28 (3H, s), 2.92–3.32 (3H, m), 3.38–3.48 (1H, m), 3.48–3.61 (2H, m), 4.02 (1H, d, J=15.3 Hz), 7.17–7.41 (5H, m)
MASS (APCI): 268 (M+H)$^+$ Preparation 79

The following compounds were obtained according to a similar manner to that of Preparation 13.

(1) (2S)-1-[N-Benzyl-N-(2-chloro-1,1-dimethylethyl)amino]-3-methoxy-2-propanol

IR (Neat): 2933, 1645, 1456 cm$^{-1}$
NMR (CDCl$_3$, δ): 1.08–1.53 (6H, m), 2.46–4.10 (9H, m), 3.34 (3H, s), 7.23–7.40 (5H, m)
MASS (APCI): 286 (M+H)$^+$ (2) (1R,4S)-3,3-Dimethyl-5-(2-chloroethyl)-2-oxa-5-azabicyclo[2.2.1]heptane hydrochloride IR (KBr): 2945, 2603, 1514, 1462 cm$^{-1}$
NMR (DMSO-d$_6$, δ): 1.16 (3H, s), 1.45 (3H, s), 2.20–2.40 (2H, m), 3.21 (1H, d, J=11.9 Hz), 3.40–3.80 (3H, m), 3.90–4.15 (2H, m), 4.31 (1H, s), 4.56 (1H, s)
MASS (APCI): 190 (M+H)$^+$ (free)

Preparation 80

The following compound was obtained according to a similar manner to that of Preparation 14.

(2S)-4-Benzyl-5,5-dimethyl-2-(methoxymethyl)morpholine

NMR (CDCl$_3$, δ): 1.10 (3H, s), 1.12 (3H, s), 2.21 (1H, dd, J=10.5 and 11.7 Hz), 2.37 (1H, dd, J=3.0 and 11.7 Hz), 3.00 (1H, d, J=13.8 Hz), 3.32 (3H, s), 3.24–3.56 (4H, m), 3.61–3.71 (1H, m), 4.02 (1H, d, J=13.8 Hz), 7.20–7.36 (5H, m)
MASS (APCI): 250 (M+H)$^+$ Preparation 81

The following compounds were obtained according to a similar manner to that of Preparation 15.

(1) (2S)-5,5-Dimethyl-2-(methoxymethyl) morpholine hydrochloride

IR (Neat): 3398, 2947, 1458, 1390 cm$^{-1}$
NMR (CDCl$_3$, δ): 1.26 (3H, s), 1.33 (3H, s), 2.90–3.00 (2H, m), 3.27 (3H, s), 3.35–3.50 (2H, m), 3.49–3.64 (2H, m), 3.82–3.94 (1H, m)
MASS (APCI): 1.60 (M+H)$^+$ (free)

(2) (1R,4S)-3,3-Dimethyl-2-oxa-5-azabicyclo[2.2.1] heptane hydrochloride mp: 237–238° C.
IR (KBr): 2895, 2727, 1587, 1464 cm$^{-1}$ NMR (DMSO-d$_6$, δ): 1.11 (3H, s), 1.31 (3H, s), 1.92 (1H, d, J=11.3 Hz), 2.28 (1H, d, J=11.3 Hz), 3.00–3.15 (2H, m), 4.08 (1H, s), 4.53 (1H, s)

MASS (APCI): 128 (M+H)$^+$ (free)

Preparation 82

The following compounds were obtained according to a similar manner to that of Preparation 7.

(1) (2S)-5,5-Dimethyl-4-(2-hydroxyethyl)-2-(methoxymethyl)-morpholine

IR (KBr): 3433, 2970, 2875, 1458, 1365 cm$^{-1}$

NMR (CDCl$_3$, δ): 0.98 (3H, s), 1.06 (3H, s), 2.12 (1H, ddd, J=2.2, 3.2 and 12.9 Hz), 2.31 (1H, dd, J=10.8 and 11.8 Hz), 2.63 (1H, dd, J=2.8 and 11.8 Hz), 2.96 (1H, ddd, J=5.3, 10.7 and 12.9 Hz), 3.39 (3H, s), 3.33–3.60 (6H, m), 3.60–3.80 (1H, m)

MASS (APCI): 204 (M+H)$^+$ (2) (1R,4S)-3,3-Dimethyl-5-(2-hydroxyethyl)-2-oxa-5-azabicyclo[2.2.1]heptane IR (KBr): 3433, 2978, 1460 cm$^{-1}$ NMR (CDCl$_3$, δ): 1.13 (3H, s), 1.34 (3H, s), 1.63 (1H, dd, J=1.7 and 10.2 Hz), 1.99 (1H, ddd, J=1.1, 1.1 and 10.2 Hz), 2.32 (1H, dd, J=1.7 and 10.4 Hz), 2.52 (1H, ddd, J=4.1, 5.4 and 12.3 Hz), 2.85 (1H, ddd, J=4.8, 6.8 and 12.3 Hz), 2.98 (1H, br s), 3.00 (1H, d, J=10.4 Hz), 3.40–3.75 (2H, m), 4.38 (1H, br s)

MASS (APCI): 172 (M+H)$^+$ (3) 4,4-Difluoro-1-(2-hydroxyethyl)piperidine

NMR (CDCl$_3$, δ): 1.85–2.05 (5H, m), 2.55–2.65 (6H, m), 3.62 (2H, t, J=5.3 Hz)

MASS (APCI): 166 (M+H)$^+$

Preparation 83

Methylmagnesium bromide (0.93 M in tetrahydrofuran, 120 ml) was added to a solution of N-benzyl-trans-4-hydroxy-L-proline methyl ester (5.0 g) in tetrahydrofuran (50 ml) with dry ice acetone bath cooling under nitrogen atmosphere and the whole was stirred for 30 minutes. Saturated ammonium chloride aqueous solution was added to the mixture and the organic layer was separated, washed with brine, dried over sodium sulfate, and evaporated in vacuo to give (2S,4R)-1-benzyl-2-(1-hydroxy-1-methylethyl)-4-hydroxypyrrolidine (5.0 g) as an oil.

IR (Neat): 3400, 1455, 1370, 1120 cm$^{-1}$

NMR (CDCl$_3$-D$_2$O, δ): 1.15 (3H, s), 1.30 (3H, s), 1.80–2.02 (2H, m), 2.52–2.66 (1H, m), 3.02 (1H, dd, J=11.9 and 3.8 Hz), 3.15 (1H, d, J=8.0 Hz), 3.92 (1H, d, J=13.6 Hz), 4.17 (1H, d, J=13.6 Hz), 4.32–4.45 (1H, m), 7.15–7.44 (5H, m)

MASS (APCI): 236 (M+H)$^+$

Preparation 84

To a solution of triethylamine (4.32 ml) and (2S,4R)-1-benzyl-2-(1-hydroxy-1-methylethyl)-4-hydroxypyrrolidine (4.87 g) in dichloromethane (50 ml) was added methanesulfonyl chloride (2.4 ml) at 0° C. After stirring at room temperature for 4 hours, the mixture was quenched with water and extracted with ethyl acetate (×2). The combined extracts were washed with brine, dried over magnesium sulfate, evaporated under reduced pressure, and purified with column chromatography (silica gel, 500 ml, methanol:dichloromethane=4:96) to give (2S,4R)-1-benzyl-2-(1-hydroxy-1-methylethyl)-4-(methanesulfonyloxy)pyrrolidine (3.34 g) as a pale yellow solid.

IR (Neat): 3431, 3402, 1647, 1458 cm$^{-1}$

NMR (CDCl$_3$, δ): 1.15 (3H, s), 1.32 (3H, s), 2.04–2.35 (2H, m), 2.93–3.21 (3H, m), 3.02 (3H, s), 3.89 (1H, d, J=13.9 Hz), 4.13 (1H, d, J=13.9 Hz), 5.14 (1H, br s), 7.23–7.35 (5H, m)

MASS (APCI): 314 (M+H)$^+$

Preparation 85

To a solution of (2S,4R)-1-benzyl-2-(1-hydroxy-1-methylethyl)-4-(methanesulfonyloxy)pyrrolidine (3.65 g) in N,N-dimethylformamide (36 ml) was added sodium hydride (1.12 g, 60% in mineral oil) at 0° C. The mixture was stirred at room temperature for 2.5 hours and allowed to stand overnight. The mixture was quenched with methanol (20 ml), then stirred for 30 minutes, and evaporated. The residue was added water (300 ml) and extracted with ethyl acetate (100 ml×3). The combined extracts were washed successively with water and brine. The organic layer was dried over magnesium sulfate, evaporated, and purified with column chromatography (silica gel, 125 ml, ethyl acetate:hexane=5:95–20:80) to give (1R,4S)-2-benzyl-3,3-dimethyl-2-oxa-5-azabicyclo[2.2.1]-heptane (2.32 g) as a colorless oil.

IR (Neat): 2978, 1676, 1647 cm$^{-1}$

NMR (CDCl$_3$, δ): 1.08 (3H, s), 1.40 (3H, s), 1.73 (1H, dd, J=1.9 and 10.1 Hz), 1.92 (1H, ddd, J=1.1, 1.1 and 10.1 Hz), 2.30 (1H, dd, J=1.6 and 10.5 Hz), 2.92 (1H, br s), 2.98 (1H, d, J=10.5 Hz), 3.62 (1H, d, J=13.6 Hz), 3.77 (1H, d, J=13.6 Hz), 4.36 (1H, br s), 7.19–7.42 (5H, m)

MASS (APCI): 218 (M+H)$^+$

Preparation 86

The following compound was obtained according to a similar manner to that of Example 1.

(2S,5S)-4-(4-Chloro-2-butynyl)-2-methoxymethyl-5-methylmorpholine

IR (Neat): 2877, 1454, 1381, 1327 cm$^{-1}$

NMR (CDCl$_3$, δ): 1.20 (3H, d, J=6.3 Hz), 1.94–2.14 (2H, m), 2.69–2.79 (2H, m), 3.35 (2H, t, J=2.0 Hz), 3.38 (3H, s), 3.38–3.51 (2H, m), 3.68–3.81 (2H, m), 4.17 (2H, t, J=2.0 Hz)

MASS (APCI): 232 (M+H)$^+$

Preparation 87

To a solution of 3,4-dihydro-2H-pyrido[3,2-b]-1,4-oxazine (0.4 g) in N,N-dimethylformamide (5 ml) was added sodium hydride (60% oil suspension; 0.24 g) in portions. After a few minutes, a solution of 2-chloromethyl-1,3-dioxolane (0.43 g) in N,N-dimethylformamide (2 ml) was added dropwise to the mixture. After stirring for 2 hours, the mixture was poured into a mixed solvent of water and ethyl acetate. The organic layer was separated, washed with water twice, dried over magnesium sulfate and concentrated under reduced pressure. The residue was purified by column chromatography on silica gel using a mixed solvent of ethyl acetate and hexane (1:1) as an eluent to give 3,4-dihydro-4-[(1,3-dioxolan-2-yl)methyl]-2H-pyrido[3,2-b]-1,4-oxazine (0.28 g) as an oil.

NMR (CDCl$_3$, δ): 3.30–4.40 (10H, m), 5.10 (1H, t, J=4.4 Hz), 6.49 (1H, dd, J=4.9 and 7.6 Hz), 6.91 (1H, dd, J=1.5 and 7.6 Hz), 7.73 (1H, dd, J=1.5 and 4.9 Hz)

MASS (APCI): 223 (M+H)$^+$

Preparation 88

A solution of 3,4-dihydro-4-[(1,3-dioxolan-2-yl)methyl]-2H-pyrido[3,2-b]-1,4-oxazine (0.13 g) in acetone (10 ml) and water (1 ml) was heated under reflux in the presence of p-toluenesulfonic acid (2.24 g) for 3 days. The mixture was concentrated in vacuo and the residue was poured into aqueous saturated sodium hydrogen carbonate solution. The water layer was extracted with ethyl acetate three times and the combined organic layers were dried over magnesium sulfate and concentrated in vacuo. The residue was purified by column chromatography on silica gel using a mixed solvent of methanol and dichloromethane (1:10) as an eluent. The fractions containing the objective compound were collected and evaporated under reduced pressure to give 2-[3,4-dihydro-2H-pyrido[3,2-b]-1,4-oxazin-4-yl]acetaldehyde (0.09 g) as an oil.

NMR (CDCl$_3$, δ): 3.56 (2H, t, J=4.5 Hz), 4.00–4.40 (4H, m), 6.57 (1H, dd, J=5.5 and 8 Hz), 6.97 (1H, dd, J=1.4 and 8.0 Hz), 7.69 (1H, dd, J=1.4 and 5.5 Hz), 9.73 (1H, s)

MASS (APCI): 179 (M+H)$^+$

Preparation 89

A mixture of 4,5,6,7-tetrahydrothieno[3,2-c]pyridine (0.86 g), 2-bromoethanol (0.66 g), potassium carbonate (2.58 g) and potassium iodide (3.10 g) in N,N-dimethylformamide (20 ml) was stirred at 70° C. for 2 hours. After cooling, ethyl acetate and water were added thereto. The organic layer was separated, washed with water twice, dried over magnesium sulfate and evaporated under reduced pressure. The residue was purified by column chromatography on silica gel using a mixed solvent of methanol and dichloromethane (1:10) as an eluent. The fractions containing the objective compound were collected and evaporated under reduced pressure to give 5-(2-hydroxyethyl)-4,5,6,7-tetrahydrothieno[3,2-c]pyridine (0.53 g) as an oil.

IR (Neat): 1664, 1456, 1441, 1406, 1360, 1327, 1111, 1065, 1043 cm$^{-1}$

NMR (DMSO-d$_6$, δ): 2.60–3.10 (6H, m), 3.50–3.90 (4H, m), 6.74 (1H, d, J=5.1 Hz), 7.10 (1H, d, J=5.1 Hz)

MASS (APCI): 184 (M+H)$^+$

Preparation 90

To a solution of 5-(2-hydroxyethyl)-4,5,6,7-tetrahydrothieno[3,2-c]pyridine (0.49 g) in dichloromethane (20 ml) was added dropwise thionyl chloride (0.39 ml). The mixture was stirred at 40° C. for 1.5 hours. After the mixture was evaporated under reduced pressure, the residue was triturated with diisopropyl ether. The resulting powder was collected by filtration, washed with diisopropyl ether and dried in vacuo to give 5-(2-chloroethyl)-4,5,6,7-tetrahydrothieno[3,2-c]pyridine hydrochloride (0.44 g).

mp: 205–215° C.

IR (KBr): 2667, 2576, 2544, 2467, 2397, 1693, 1645, 1547, 1539, 1516, 1452, 1437, 1184, 1155, 1086, 1066 cm$^{-1}$

NMR (DMSO-d$_6$, δ): 2.80–4.80 (10H, m), 6.91 (1H, d, J=5.2 Hz), 7.49 (1H, d, J=5.2 Hz)

MASS (ESI): 202.2 (M+H)$^+$ (free)

Preparation 91

The following compounds were obtained according to a similar manner to that of Preparation 90.

(1) 1-(2-Chloroethyl)-4,4-difluoropiperidine hydrochloride mp: 158–159° C.

IR (KBr): 2700–2300, 1477, 1388 cm$^{-1}$

NMR (DMSO-d$_6$, δ): 2.20–2.60 (4H, m), 3.00 (4H, m), 3.55 (2H, t, J=7.0 Hz), 4.07 (2H, t, J=7.0 Hz)

(2) (2S)-4-(2-Chloroethyl)-5,5-dimethyl-2-(methoxymethyl)-morpholine hydrochloride IR (KBr): 1562, 1558, 1547, 1539, 1516, 1498, 1464, 1456, 1198, 1180, 1126, 1105, 1041 cm$^{-1}$ NMR (DMSO-d$_6$, δ): 1.41 (3H, s), 1.54 (3H, s), 2.60–4.70 (14H, m)

MASS (APCI): 222 (M+H)$^+$ (free)

Preparation 92

The following compounds were obtained by a similar manner to that of Preparation 7 followed by a similar manner to that of Preparation 90.

(1) (3S,5S)-4-(2-Chloroethyl)-3,5-dimethylmorpholine hydrochloride mp: 190–195° C. (decomp.)

IR (KBr): 1516, 1454, 1398, 1371, 1342, 1250, 1205, 1153, 1132, 1103, 1074, 1024 cm$^{-1}$

NMR (DMSO-d$_6$, δ): 0.90–1.50 (6H, m), 3.00–4.50 (10H, m)

MASS (APCI): 178 (M+H)$^+$ (free)

(2) cis-4-(2-Chloroethyl)-3,5-dimethylmorpholine hydrochloride mp: 70–80° C. (decomp.)

IR (KBr): 2559, 2478, 2407, 1477, 1466, 1454, 1429, 1390, 1146, 1120, 1074, 1030 cm$^{-1}$

NMR (DMSO-d$_6$, δ): 1.27 (6H, d, J=6.1 Hz), 3.20–4.40 (10H, m), 11.58 (1H, br s)

MASS (APCI): 178 (M+H)$^+$ (free)

(3) (2R)-4-(2-Chloroethyl)-2-(methoxymethyl)morpholine hydrochloride mp: 150–155° C. (decomp.)

[α]$_D^{27.5}$: −9.69° (C=0.485, MeOH)

IR (KBr): 2673, 2590, 2476, 1516, 1477, 1454, 1400, 1201, 1132, 1107, 1084 cm$^{-1}$

NMR (DMSO-d$_6$, δ): 2.80–3.20 (2H, m), 3.28 (3H, s), 3.30–4.40 (11H, m)

MASS (APCI): 194 (M+H)$^+$ (free)

Preparation 93

A mixture of (2S)-2-(methoxymethyl)morpholine hydrochloride (0.5 g), 1-bromo-3-chloropropane (1.47 ml) and potassium carbonate (2.06 g) in N,N-dimethylformamide (6 ml) was stirred at room temperature for 1 hour. After ethyl acetate and water were added to the mixture, the organic layer was separated, washed with water twice, dried over magnesium sulfate and evaporated under reduced pressure. The residue was purified by column chromatography on silica gel using ethyl acetate as an eluent. The fractions containing the objective compound were collected and evaporated under reduced pressure. The resulting oil was treated with 4N hydrogen chloride in ethyl acetate to give (2S)-4-(3-chloropropyl)-2-(methoxymethyl)morpholine hydrochloride (0.44 g).

mp: 165–170° C. (decomp.)

IR (KBr): 1547, 1539, 1516, 1454, 1192, 1142, 1111, 1092, 1066 cm$^{-1}$

NMR (DMSO-d$_6$, δ): 2.10–2.40 (2H, m), 2.70–4.20 (16H, m), 11.53 (1H, br s)

MASS (APCI): 208 (M+H)$^+$ (free)

Preparation 94

The following compounds were obtained according to a similar manner to that of Preparation 93.

(1) (2S)-4-[(E)-4-Chloro-2-butynyl]-2-(methoxymethyl)-morpholine hydrochloride

IR (Neat): 1722, 1450, 1400, 1360, 1286, 1255, 1201, 1136, 1090, 1030 cm$^{-1}$

NMR (DMSO-d$_6$, δ): 2.60–3.60 (10H, m), 3.60–4.20 (4H, m), 4.28 (2H, d, J=5.9 Hz), 5.80–6.30 (2H, m), 11.87 (1H, br s)

MASS (APCI): 220 (M+H)$^+$ (free)

(2) (2S)-4-[4-Chloro-2-butynyl]-2-(methoxymethyl)-morpholine hydrochloride mp: 70–75° C. (decomp.)
IR (KBr): 1516, 1464, 1454, 1427, 1398, 1273, 1194, 1136, 1086, 1032 cm$^{-1}$
NMR (DMSO-d$_6$, δ): 2.60–4.80 (16H, m)
MASS (APCI): 218 (M+H)$^+$ (free)

Preparation 95

The following compound was obtained according to a similar manner to that of Preparation 27.

2-Acetylamino-2-(4-benzyloxy-3-methoxybenzyl) malonic acid diethyl ester mp: 105–106° C.
IR (KBr): 3224, 2977, 1752, 1635, 1519, 1301, 1236 cm$^{-1}$
NMR (CDCl$_3$, δ): 1.29 (6H, t, J=7.2 Hz), 2.02 (3H, s), 3.58 (2H, s), 3.82 (3H, s), 4.12–4.32 (4H, m), 5.11 (2H, s), 6.48 (1H, dd, J=2.0 and 8.1 Hz), 6.55 (1H, d, J=2.0 Hz), 6.56 (1H, s), 6.76 (1H, d, J=8.1 Hz), 7.29–7.40 (5H, m)
MASS (APCI): 444 (M+H)$^+$, 402, 354

Preparation 96

The following compound was obtained according to a similar manner to that of Preparation 28.

(D,L)-N-Acetyl-4-benzyloxy-3-methoxy-DL-phenylalanine mp: 125.0–130.0° C.
IR (KBr): 3316, 3200–2500, 1714, 1652, 1544 cm$^{-1}$
NMR (DMSO-d$_6$, δ): 1.79 (3H, s), 2.76 (1H, dd, J=9.6 and 13.7 Hz), 2.96 (1H, dd, J=4.8 and 13.7 Hz), 3.74 (3H, s), 4.35–4.37 (1H, m), 5.02 (2H, s), 6.71 (1H, dd, J=1.8 and 8.2 Hz), 6.86 (1H, d, J=1.8 Hz), 6.92 (1H, d, J=8.2 Hz), 7.31–7.45 (5H, m), 8.15 (1H, d, J=8.0 Hz), 12.63 (1H, br s)
MASS (APCI): 344 (M+H)$^+$, 302

Preparation 97

(D)-N-Acetyl-4-benzyloxy-3-methoxy-D-phenylalanine

[α]$_{Dhub\ 26}$: −14.3° (C=0.5, DMF)
mp: 148.0–149.0° C.
IR (KBr): 3324, 3200–2700, 1741, 1616, 1550, 1513, 1398 cm$^{-1}$
NMR (DMSO-d$_6$, δ): 1.79 (3H, s), 2.76 (1H, dd, J=9.2 and 13.9 Hz), 2.97 (1H, dd, J=4.8 and 13.9 Hz), 3.74 (3H, s), 4.31–4.42 (1H, m), 5.02 (2H, s), 6.71 (1H, dd, J=1.8 and 8.2 Hz), 6.86 (1H, d, J=1.8 Hz), 6.92 (1H, d, J=8.2 Hz), 7.28–7.45 (5H, m), 8.14 (1H, d, J=8.2 Hz), 12.85 (1H, br s)
MASS (APCI): 344 (M+H)$^+$, 372

Preparation 98

The following compound was obtained according to a similar manner to that of Preparation 17.

4-Hydroxy-3-methoxy-D-phenylalanine hydrochloride mp: 188–200° C.
IR (KBr): 3500–3150, 2700–2300, 1739, 1589, 1488 cm$^{-1}$
NMR (D$_2$O, δ): 3.13 (1H, dd, J=7.6 and 14.6 Hz), 3.28 (1H, dd, J=5.8 and 14.6 Hz), 3.85 (3H, s), 4.28 (1H, dd, J=5.8 and 7.6 Hz), 6.77–6.95 (3H, m)
MASS (APCI): 212 (M+H)$^+$, (free)

Preparation 99

Di-tert-butyl dicarbonate (2.55 g) was added to a solution of 4-hydroxy-3-methoxy-D-phenylalanine hydrochloride (2.2 g) and triethylamine (2.9 ml) in a mixture of acetone (25 ml) and water (25 ml). After being stirred at room temperature for 5 hours, the reaction mixture was diluted with water and extracted with ethyl acetate. The organic layer was separated, dried over magnesium sulfate and evaporated under reduced pressure to give N-tert-butyloxycarbonyl-4-hydroxy-3-methoxy-D-phenylalanine (2.6 g) as an oil.

NMR (CDCl$_3$, δ): 1.42 (9H, s), 2.82–3.20 (2H, m), 3.83 (3H, s), 4.20–5.50 (2H, m), 6.56–6.68 (2H, m), 6.83 (1H, d, J=8.5 Hz), 7.23 (1H, s)
MASS (APCI): 212 (M+H-Boc)$^+$, 195

Preparation 100

Benzyl bromide (2.34 ml, 19.8 ml) was added to a solution of N-tert-butyloxycarbonyl-4-hydroxy-3-methoxy-D-phenylalanine (3.44 g) and N,N-diisopropylethylamine (3.85 ml) in N,N-dimethylformamide (20 ml). After being stirred at room temperature for 6 hours, the reaction mixture was diluted with water and extracted with ethyl acetate. The organic layer was separated, dried over magnesium sulfate and evaporated under reduced pressure. The residue was purified by column chromatography on silica gel using a mixture of hexane and ethyl acetate (4:1) to give (2R)-2-(tert-butyloxycarbonylamino)-3-(4-hydroxy-3-methoxyphenyl)propionic acid benzyl ester (2.98 g) as colorless powders.

IR (KBr): 3438, 3378, 2700–2300, 1725, 1683, 1521, 1488 cm$^{-1}$
NMR (CDCl$_3$, δ): 1.41 (9H, s), 3.03 (2H, d, J=5.8 Hz), 3.76 (3H, s), 4.45–4.55 (1H, m), 4.95–5.05 (1H, m), 5.09 (1H, d, J=12.5 Hz), 5.18 (1H, d, J=12.5 Hz), 5.53 (1H, s), 6.56–6.68 (2H, m), 6.76 (1H, d, J=8.0 Hz), 7.25–7.36 (5H, m)
MASS (APCI): 302 (M+H-Boc)$^+$

Preparation 101

4N Hydrogen chloride in 1,4-dioxane solution (9 ml) was added to an ice-cooled solution of (2R)-2-(tert-butyloxycarbonylamino)-3-(4-hydroxy-3-methoxyphenyl)propionic acid benzyl ester (2.90 g) in dichloromethane (29 ml). After being stirred at the same temperature for 2 hours, the mixture was concentrated under reduced pressure to give (2R)-2-amino-3-(4-hydroxy-3-methoxyphenyl)propionic acid benzyl ester hydrochloride (2.8 g) as an oil.

NMR (DMSO-d$_6$, δ): 3.00–3.10 (2H, m), 3.70 (3H, s), 4.31 (1H, t, J=6.2 Hz), 5.18 (2H, s), 6.54 (1H, dd, J=1.7 and 8.0 Hz), 6.68 (1H, d, J=8.0 Hz), 6.81 (1H, d, J=1.7 Hz), 7.29–7.39 (5H, m), 8.57 (3H, br s), 8.97 (1H, s)
MASS (APCI): 301 (M+H)$^+$ (free)

Preparation 102

The following compound was obtained according to a similar manner to that of Preparation 19.

(2R)-2-[N-(Chloroacetyl)amino]-3-(4-hydroxy-3-methoxyphenyl)propionic acid benzyl ester Preparation 103

The following compound was obtained according to a similar manner to that of the first half of Preparation 20.

(2R)-2-[N-[(Benzylamino)acetyl]amino]-3-(4-hydroxy-3-methoxyphenyl)propionic acid benzyl ester Preparation 104

The following compound was obtained according to a similar manner to that of the second half of Preparation 20.

(3R)-1-Benzyl-3-(4-hydroxy-3-methoxybenzyl)piperazine-2,5-dione $[\alpha]_D^{26}$: =5.2° (C=0.5, DMF)
mp: 225.0–226.0° C.
IR (KBr): 3335, 1677, 1515, 1463, 1276, 1185 cm$^{-1}$
NMR (DMSO-d$_6$, δ): 2.73 (1H, d, J=17.2 Hz), 2.78 (1H, dd, J=4.6 and 13.6 Hz), 3.04 (1H, dd, J=4.6 and 13.6 Hz), 3.42 (1H, d, J=17.2 Hz), 3.66 (3H, s), 4.28 (1H, m), 4.27 (1H, d, J=14.6 Hz), 4.47 (1H, d, J=14.6 Hz), 6.43 (1H, dd, J=1.8 and 8.0 Hz), 6.54 (1H, d, J=8.0 Hz), 6.67 (1H, d, J=1.8 Hz), 7.05–7.31 (5H m), 8.31 (1H, br s), 8.84 (1H, s)
MASS (APCI): 341 (M+H)$^+$ Preparation 105

Lithium aluminum hydride (614 mg) was added to a suspension of (3R)-1-benzyl-3-(4-hydroxy-3-methoxybenzyl)piperazine-2,5-dione (1.1 g) in tetrahydrofuran (40 ml) at room temperature. After being stirred under reflux for 5 hours, the reaction mixture was treated with 2N sodium hydroxide (5 ml) under nitrogen atmosphere. The whole mixture was diluted with water (40 ml) and thereto 3,5-bis(trifluoromethyl)benzoyl chloride (1.6 ml) was added dropwise under ice-cooling. After being stirred for 30 minutes, the resulting mixture was extracted with ethyl acetate. The organic layer was separated, dried over magnesium sulfate and evaporated under reduced pressure. The residue was purified by column chromatography on silica gel using a mixture of hexane and ethyl acetate (4:1) to give the objective (2R)-4-benzyl-1-[3,5-bis(trifluoromethyl)benzoyl]-2-(4-hydroxy-3-methoxybenzyl)piperazine and its 3,5-bis(trifluoromethyl)benzoate, which was converted to the objective compound by treatment with a mixture of 1N sodium hydroxide and methanol.

NMR (CDCl$_3$, δ): 2.20–4.55 (14H, m), 6.20–7.90 (12H, m)
MASS (APCI): 553 (M+H)$^+$

Preparation 106

Trifluoromethane sulfonic acid anhydride (5.25 ml) was added dropwise over 30 minutes to an ice-cooled solution of (2R)-4-benzyl-1-[3,5-bis(trifluoromethyl)benzoyl]-2-(4-hydroxy-3-methoxybenzyl)piperazine (14.3 g) and 4-(dimethylamino)pyridine (0.47 g) and 2,6-lutidine (3.6 ml) in dichloromethane (150 ml) below 10° C. After being stirred at the same temperature for 2 hours, the reaction mixture was poured into water. The pH of the whole mixture was adjusted to 7 with diluted hydrochloric acid and the organic layer was separated, dried over magnesium sulfate and evaporated under reduced pressure. The residue was purified by column chromatography on silica gel using a mixture of toluene and ethyl acetate (100:1–5:1) to give the objective trifluoromethanesulfonic acid 4-[[(2R)-1-[3,5-bis(trifluoromethyl)benzoyl]-4-benzylpiperazin-2-yl]methyl]-2-methoxyphenyl ester as an oil.

Preparation 107

Carbon monoxide was introduced by bubbling to a mixture of trifluoromethanesulfonic acid 4-[[(2R)-1-[3,5-bis(trifluoromethyl)benzoyl]-4-benzylpiperazin-2-yl]methyl]-2-methoxyphenyl ester (15.0 g), palladium acetate (150 mg), 1,3-bis(diphenylphosphino)propane (275 mg) and triethylamine (4.28 ml) in a mixed solvent of methanol (30 ml) and N,N-dimethylformamide (75 ml) at room temperature for 1 hour. The mixture was warmed to 70° C. and stirred under carbon monoxide atmosphere for 3 hours. The resulting mixture was filtered through Celite® and the residue was washed with ethyl acetate. The filtrate and washings were combined and evaporated under reduced pressure. The residue was dissolved into ethyl acetate and the solution was washed with water and brine successively, dried over magnesium sulfate, and evaporated under reduced pressure. The residue was purified by column chromatography on silica gel using a mixed solvent of toluene and hexane as eluent. The fractions containing the objective compound was collected and evaporated under reduced pressure to give a syrup, which was treated with 4N hydrogen chloride in ethyl acetate to give a powder of 4-[[(2R)-1-[3,5-bis(trifluoromethyl)benzoyl]-4-benzylpiperazin-2-yl]methyl]-2-methoxybenzoic acid methyl ester hydrochloride (7.71 g).

mp: 100–102° C.
IR (KBr): 3335, 1720, 1648, 1614, 1459, 1427, 1185 cm$^{-1}$
NMR (DMSO-d$_6$, δ): 2.95–5.20 (11H, m), 3.41 (3H, s), 3.75 (3H, s), 6.40–8.25 (11H, m), 11.50–11.80 (1H, m)
MASS (API-ES): 617 (M+Na, free)$^+$, 595 (M+H, free)$^+$ Preparation 108

The following compound was obtained according to a similar manner to that of Preparation 22.

4-[[(2R)-1-[3,5-Bis(trifluoromethyl)benzoyl]-4-benzylpiperazin-2-yl]methyl]-2-hydroxybenzoic acid methyl ester IR (Neat): 1677, 1643, 1438, 1280 cm$^{-1}$
NMR (CDCl$_3$, δ): 2.00–5.10 (11H, m), 3.93 (3H, s), 6.20–7.90 (11H, m), 10.71 (1H, br s)
MASS (API-ES): 603 (M+Na)$^+$, 581 (M+H)$^+$ Preparation 109 tert-Butyldimethylsilyl chloride (2.34 g) was added to a solution of 4-[[(2R)-1-[3,5-bis(trifluoromethyl)benzoyl]-piperazin-2-yl]methyl]-2-hydroxybenzoic acid methyl ester (2.56 g), 4-(dimethylamino)pyridine (126 mg) and triethylamine (2.51 ml) in dichloromethane (50 ml) at room temperature. After stirring at room temperature for 15 hours, additional triethylamine (2.51 ml) and tert-butyldimethylsilyl chloride (2.34 g) were added and the whole mixture was stirred for further 1 day. Water (200 ml) was added to the mixture, and the resulting mixture was extracted with dichloromethane. The organic extracts were washed with water and brine successively, dried over magnesium sulfate, and evaporated under reduced pressure to give crude oil. The oil was purified by column chromatography on silica gel using a mixed solvent of dichloromethane and methanol to give 4-[[(2R)-1-[3,5-bis(trifluoromethyl)benzoyl]piperazin-2-yl]-methyl]-2-(tert-butyldimethylsilyloxy)benzoic acid methyl ester (1.72 g).

IR (Neat): 2955, 1727, 1639, 1436, 1280 cm$^{-1}$

NMR (CDCl$_3$, δ): 0.10–0.30 (6H, m), 1.00 (9H, s), 2.80–5.10 (9H, m), 3.85 (3H, s), 6.30–7.90 (6H, m)

MASS (APCI): 605 (M+H)$^+$, 573, 491

Preparation 110

To a solution of (2R)-2-tert-butoxycarbonylamino-3-(4-methoxyphenyl)propionic acid (5.14 g) in dichloromethane (50 ml) was added triethylamine (8.49 ml), N-benzylglycine benzyl ester hydrochloride (5.08 g), and 2-chloro-1-methylpyridinium iodide (4.89 g) under ice-bath cooling. After being stirred at room temperature 90 minutes, the reaction mixture was concentrated under reduced pressure, and ethyl acetate (50 ml) and water (50 ml) were added to the residue with stirring, adjusted pH 1 with diluted hydrochloric acid. The organic layer was separated, washed with brine, dried over magnesium sulfate, and concentrated under reduced pressure. The resulting residue was purified by column chromatography on silica gel (100 g) using a mixed solvent of toluene and ethyl acetate (10:1). The fractions containing the objective compound were collected and evaporated under reduced pressure to give N-benzyl-N-(benzyloxycarbonylmethyl)-(2R)-2-(tert-butoxycarbonylamino)-3-(4-methoxyphenyl)propionamide (8.57 g) as a syrup.

[α]$_D^{24.0}$: +6.60° (C=0.50, MeOH)

IR (Neat): 3300, 1740, 1700, 1650, 1240 cm$^{-1}$

NMR (DMSO-d$_6$, δ): 1.27 and 1.31 (9H, s, s), 2.76 (2H, m), 3.69 and 3.70 (3H, s, s), 3.95–4.90 (5H, m), 5.13 (2H, m), 6.70–7.36 (15H, m)

MASS (APCI): 533 (M+H)$^+$

Preparation 111

4N Hydrogen chloride in 1,4-dioxane solution (48 ml) was added dropwise to a solution of N-benzyl-N-benzyloxycarbonylmethyl-(2R)-2-(tert-butoxycarbonylamino)-3-(4-methoxyphenyl)propionamide (8.48 g) in dichloromethane (48 ml) under ice-bath cooling. After being stirred for 2 hours at the same temperature, the reaction mixture was concentrated under reduced pressure. The residue was added to aqueous sodium bicarbonate solution (50 ml) and dichloromethane (50 ml), and the organic layer was separated, washed with brine, dried over sodium sulfate, and evaporated under reduced pressure to give a powder of (3R)-1-benzyl-3-(4-methoxybenzyl)piperazine-2,5-dione (3.65 g).

[α]$_D^{27.9}$: −38.6° (C=0.50, MeOH)

IR (Nujol): 3250, 1680, 1640, 1245 cm$^{-1}$

NMR (DMSO-d$_6$, δ): 2.60 (1H, d, J=17 Hz), 2.80 (1H, dd, J=4.7 and 14 Hz), 3.09 (1H, dd, J=3.8 and 14 Hz), 3.46 (1H, d, J=17 Hz), 3.67 (3H, s), 4.11 (1H, d, J=14 Hz), 4.22 (1H, br), 4.65 (1H, d, J=14 Hz), 6.63 (2H, d, J=8.7 Hz), 6.93 (2H, d, J=8.7 Hz), 7.10–7.40 (5H, m), 8.30 (1H, br)

MASS (APCI): 325 (M+H)$^+$

Preparation 112

Under nitrogen atmosphere, to a suspension of lithium aluminum hydride (0.85 g) in tetrahydrofuran (65 ml) was added (3R)-1-benzyl-3-(4-methoxybenzyl)piperazine-2,5-dione (3.65 g) portionwise under ice-bath cooling. The reaction mixture was refluxed with stirring for one hour. After cooling, it was quenched by sequential addition of water (0.85 ml), 15% aqueous sodium hydroxide (0.85 ml), and water (2.5 ml) and the whole was stirred at room temperature for 30 minutes. The resulting insoluble material was removed by filtration, and the filtrate was added to a mixture of ethyl acetate (50 ml) and brine (70 ml). The organic layer was separated, dried over magnesium sulfate, and concentrated under reduced pressure to give (2R)-2-(4-methoxybenzyl)-4-benzylpiperazine (3.51 g) as a syrup.

IR (Neat): 3250, 1240 cm$^{-1}$

NMR (DMSO-d$_6$, δ): 1.60–2.00 (4H, m), 2.40–2.90 (5H, m), 3.30–3.50 (2H, m), 3.70 (3H, s), 6.81 (2H, d, J=8.6 Hz), 7.07 (2H, d, J=8.6 Hz), 7.15–7.40 (6H, m)

MASS (APCI): 297 (M+H)$^+$

Preparation 113

To a solution of 3,5-bis(trifluoromethyl)benzoic acid (3.04 g) and pyridine (0.030 ml) in tetrahydrofuran (9 ml) was added dropwise oxalyl chloride. (1.80 g) over 5 minutes, and the reaction mixture was heated at 55° C. with stirring for one hour. After cooling, the solution was added dropwise to a solution of (2R)-2-(4-methoxybenzyl)-4-benzylpiperazine (3.47 g) and triethylamine (3.55 g) in dichloromethane (35 ml) below 5C over 30 minutes under nitrogen atmosphere. The reaction mixture was stirred at room temperature for one hour, and concentrated under reduced pressure. To the residue were added ethyl acetate (40 ml) and water (20 ml) with stirring. The organic layer was separated, washed with brine, and dried over magnesium sulfate. After removal of the solvent by evaporation, the resulting residue was purified by column chromatography on silica gel (70 g) using a mixed solvent of toluene and ethyl acetate (5:1). The fractions containing the objective compound were collected and evaporated under reduced pressure to give (2R)-1-[3,5-bis(trifluoromethyl)benzoyl]-2-(4-methoxybenzyl)-4-benzylpiperazine (5.03 g) as syrup.

[α]$_D^{28.0}$: −21.4° (C=0.50, MeOH)

IR (Neat): 1740, 1640, 1270 cm$^{-1}$

NMR (DMSO-d$_6$, δ): 1.70–2.40 (3H, m), 2.60–3.80 (11H, m), 6.60–7.60 (10H, m), 7.65–8.55 (2H, m)

MASS (APCI): 537 (M+H)$^+$

Preparation 114

To a solution of (2R)-1-[3,5-bis(trifluoromethyl)-benzoyl]-2-(4-methoxybenzyl)-4-benzylpiperazine (4.90 g) in ethanol (50 ml) were added water (5 ml), ammonium formate (1.44 g), and 10% palladium on activated carbon [50% wet] (0.49 g) under nitrogen atmosphere. The reaction mixture was heated at 60° C. with stirring for 2 hours. Insoluble material was removed by filtration, and the filtrate was concentrated under reduced pressure. Ethyl acetate (40 ml) and water (40 ml) were added to the residue, and the organic layer was separated, washed with brine, and dried over magnesium sulfate. After removal of the solvent by evaporation, the resulting residue was purified by column chromatography on silica gel (70 g) using a mixed solvent of ethyl acetate and methanol (10:1). The fractions containing the objective compound were collected and evaporated under reduced pressure to give (2R)-1-[3,5-bis(trifluoromethyl)benzoyl]-2-(4-methoxybenzyl)piperazine (3.18 g) as syrup.

[α]$^{28.1}$: −32.6° (C=0.50, MeOH)

IR (Neat): 3300, 1630, 1280 cm$^{-1}$

NMR (DMSO-d$_6$, δ): 2.40–3.55 (9H, m), 3.72 (3H, s), 6.70–8.45 (7H, m)

MASS (APCI): 447 (M+H)$^+$

Preparation 115

The following compounds were obtained according to a similar manner to that of Preparation 56.

(1) (2R)-4-Benzyl-1-(tert-butoxycarbonyl)-2-[4-(trifluoromethyl)benzyl]piperazine NMR (CDCl$_3$, δ): 1.36 (9H, s), 1.98 (1H, dd, J=11.5 and 3.7 Hz), 2.10 (1H, td, J=12.0 and 3.4 Hz), 2.58 (1H, d, J=11.5 Hz), 2.83–3.13 (3H, m), 3.20 (1H, td, J=12.8 and 3.4

Hz), 3.26 (1H, d, J=12.8 Hz), 3.58 (1H, d, J=12.8 Hz), 3.80–4.30 (2H, m), 7.12 (2H, d, J=7.7 Hz), 7.26–7.42 (7H, m)

MASS (APCI): 435 (M+H)$^+$ (2) (2R)-4-Benzyl-2-(4-fluoro-3-methoxybenzyl)-1-(tert-butoxycarbonyl)piperazine IR (Neat): 1516, 1458, 1400, 1327, 1275, 1217, 1169 cm$^{-1}$ NMR (CDCl$_3$, δ): 1.39 (9H, s), 1.95–2.13 (2H, m), 2.60–3.24 (5H, m), 3.32–3.57 (2H, m), 3.79 (3H, s), 3.90–4.14 (2H, m), 6.52–7.35 (8H, m)

MASS (APCI): 415 (M+H)$^+$ (3) (2R)-4-Benzyl-1-(tert-butoxycarbonyl)-2-[4-chloro-3-(tert-butyldimethylsilyloxy)benzyl]piperazine IR (Neat): 1695, 1480, 1415, 1250, 1170 cm$^{-1}$ (4) (3S,4S)-1-(tert-Butoxycarbonyl)pyrrolidine-3,4-diol mp: 156–158° C.
IR (KBr): 3398, 3334, 1662, 1431, 1174, 1122, 1082, 985 cm$^{-1}$ NMR (DMSO-d$_6$, δ): 1.42 (9H, s), 3.10 (2H, br d, J=11.3 Hz), 3.25–3.44 (2H, m), 3.86 (2H, br s), 5.05 (2H, d, J=3.2 Hz)

MASS (ES+): 429.3 (2M+Na)$^+$, 226.2 (M+Na)$^+$ (free)

Preparation 116

The following compounds were obtained according to a similar manner to that of Preparation 37.

(1) 4-[[(2R)-1-[3,5-Bis(trifluoromethyl)benzoyl]piperazin-2-yl]methyl]-2-hydroxybenzoic acid methyl ester IR (Neat): 3083, 1677, 1639, 1438, 1280 cm$^{-1}$ (2) (2R)-1-[3,5-Bis(trifluoromethyl)benzoyl]-2-[3-(tert-butyldimethylsilyloxy)-4-chlorobenzyl]piperazine mp: 95–97° C.
IR (KBr): 1954, 1628, 1481, 1437 cm$^{-1}$
NMR (CDCl$_3$, δ): 0.17 (3H, s), 0.20 (3H, s), 1.01 (9H, s), 2.50–5.10 (9H, m), 6.30–7.70 (5H, m), 7.87 (1H, s)
MASS (APCI): 581 (M+H)$^+$ (3) (2R)-2-[3-(tert-Butyldimethylsilyloxy)-4-chlorobenzyl]-1-[3-chloro-5-(trifluoromethyl)benzoyl]piperazine IR (Neat): 2954, 2933, 1635, 1483, 1419 cm$^{-1}$
NMR (CDCl$_3$, δ): 0.18 (3H, s), 0.21 (3H, s), 1.02 (9H, s), 2.50–5.20 (9H, m), 6.20–7.70 (6H, m)
MASS (APCI): 547 (M+H)$^+$ (4) (2R)-1-(tert-Butoxycarbonyl)-2-[4-chloro-3-(tert-butyldimethylsilyloxy)benzyl]piperazine NMR (DMSO-d$_6$, δ): 0.99 (9H, s), 1.24 (9H, s), 2.15 (6H, s), 2.20–4.10 (9H, m), 6.78–7.33 (3H, m)
MASS (APCI): 441 (M+H)$^+$ Preparation 117

The following compounds were obtained according to a similar manner to that of Preparation 24.

(1) (2R)-1-(tert-Butoxycarbonyl)-2-[4-(trifluoromethyl)-benzyl]piperazine mp: 61–62° C.
IR (KBr): 2981, 2952, 1682, 1417, 1330 cm$^{-1}$
NMR (CDCl$_3$, δ): 1.33 (9H, s), 2.67–4.40 (9H, m), 7.35 (2H, d, J=8.0 Hz), 7.54 (2H, d, J=8.0 Hz)
MASS (ESI): 345.3 (M+H)$^+$, 289.2 (M–Bu)$^+$ (2) (2R)-2-(4-Fluoro-3-methoxybenzyl)-1-(tert-butoxycarbonyl)piperazine IR (Neat): 1689, 1515, 1414, 1273, 1165, 1115 cm$^{-1}$
NMR (CDCl$_3$, δ): 1.38 (9H, s), 2.70–3.14 (8H, m), 3.87 (3H, s), 3.88–4.18 (2H, m), 6.74–7.26 (3H, m)
MASS (APCI): 225 (M–Boc+1)$^+$, 269 (M–tBu+1)$^+$ (3) (2R)-1-[3-(Dimethylsulfamoyl)-5-(trifluoromethyl)-benzoyl]-2-[4-(trifluoromethyl)benzyl]piperazine IR (KBr): 2956, 1639, 1462, 1423, 1329 cm$^{-1}$
NMR (CDCl$_3$, δ): 2.60–5.20 (9H, m), 2.72 (6H, s), 7.00–7.60 (5H, m), 7.67 (1H, s), 8.00 (1H, s)
MASS (APCI): 524 (M+H)$^+$ (4) (2R)-1-[3-Methylsulfonyl-5-(trifluoromethyl)benzoyl]-2-[4-(trifluoromethyl)benzyl]piperazine hydrochloride mp: 94.5–101° C.
IR (KBr): 3433, 1645 cm$^{-1}$
NMR (DMSO-d$_6$, δ): 2.80–5.30 (12H, m), 7.00–8.31 (7H, m)
MASS (APCI): 495 (M+H)$^+$ (free)

(5) (2R)-2-(3-tert-Butyldimethylsilyloxy-4-methylbenzyl)-1-[3-methoxy-5-(trifluoromethyl)benzoyl]piperazine IR (KBr): 2956, 2935, 1641, 1606 cm$^{-1}$
NMR (CDCl$_3$, δ): 0.14, 0.17 (6H, s), 0.99 (9H, s), 2.15 (3H, s), 2.50–5.20 (9H, m), 3.81 (3H, s), 6.75–7.13 (6H, m)
MASS (APCI): 523 (M+H)$^+$ Preparation 118

The following compounds were obtained according to a similar manner to that of Example 1 using N,N-diisopropylethylamine instead of potassium carbonate as a base.

(1) (2R)-1-(tert-Butoxycarbonyl)-4-[2-(5,6,7,8-tetrahydro-1,6-naphthyridin-6-yl)ethyl]-2-[4-(trifluoromethyl)-benzyl]piperazine IR (KBr): 2974, 2935, 2814, 1693 cm$^{-1}$
NMR (CDCl$_3$, δ): 1.35 (9H, s), 2.04–2.17 (2H, m), 2.50–4.30 (17H, m), 7.07 (1H, dd, J=4.8 and 7.6 Hz), 7.27–7.34 (3H, m), 7.50 (2H, d, J=8.0 Hz), 8.40 (1H, d, J=4.8 Hz)
MASS (APCI): 505 (M+H)$^+$ (2) (2R)-1-(tert-Butoxycarbonyl)-4-[2-(cis-2,6-dimethylmorpholino)ethyl]-2-[4-(trifluoromethyl)benzyl]-piperazine IR (Neat): 2974, 1693, 1680 cm$^{-1}$
NMR (CDCl$_3$, δ): 1.19, 1.20 (6H, d, J=6.2 Hz), 1.32 (9H, s), 2.02–2.21 (4H, m), 2.71–3.31 (11H, m), 3.90–4.50 (4H, m), 7.34 (2H, d, J=7.9 Hz), 7.54 (2H, d, J=7.9 Hz)
MASS (APCI): 486 (M+H)$^+$ (3) (2R)-1-(tert-Butoxycarbonyl)-4-[2-[(2S)-2-(methoxymethyl)morpholino]ethyl]-2-[4-(trifluoromethyl)-benzyl]piperazine IR (Neat): 3438, 2816, 1691 cm$^{-1}$
NMR (CDCl$_3$, δ): 1.33 (9H, s), 2.02–4.30 (22H, m), 3.37 (3H, s), 7.35 (2H, d, J=8.0 Hz), 7.54 (2H, d, J=8.0 Hz)
MASS (APCI): 502 (M+H)$^+$ (4) (2R)-2-(4-Fluoro-3-methoxybenzyl)-1-(tert-butoxycarbonyl)-4-[2-(cis-2,6-dimethylmorpholino)ethyl]-piperazine IR (Neat): 1515, 1458, 1414, 1367, 1323, 1115, 1086 cm$^{-1}$
NMR (CDCl$_3$, δ): 1.14 (6H, d, J=1.2 Hz), 1.40 (9H, s), 1.70–2.10 (4H, m), 2.36–3.20 (12H, m), 3.61–4.18 (3H, m), 3.88 (3H, s), 6.74–7.02 (3H, m)
MASS (APCI): 466 (M+H)$^+$ (5) (2R)-2-(4-Fluoro-3-methoxybenzyl)-1-(tert-butoxycarbonyl)-4-[2-[(2S)-2-(methoxymethyl)morpholino]-ethyl]piperazine IR (Neat): 1516, 1456, 1414, 1273, 1165, 1111, 1036 cm$^{-1}$
NMR (CDCl$_3$, δ): 1.40 (9H, s), 1.90–4.25 (22H, m), 3.38 (3H, s), 3.87 (3H, s), 6.69–7.27 (3H, m)
MASS: 482 (M+H)$^+$ (6) (2R)-2-(4-Fluoro-3-methoxybenzyl)-1-(tert-butoxycarbonyl)-4-[2-(5,6,7,8-tetrahydro-1,6-naphthyridin-6-yl)ethyl]piperazine NMR (DMSO-d$_6$, δ): 1.40 (9H, s), 1.99–2.15 (2H, m), 2.51–3.18 (14H, m), 3.67–4.18 (3H, m), 3.86 (3H, s), 6.73–8.40 (6H, m)
MASS: 485 (M+H)$^+$ (7) (2R)-1-(tert-Butoxycarbonyl)-2-(4-chloro-3-hydroxybenzyl)-4-[2-[(2S)-2-(methoxymethyl)morpholino]-ethyl]piperazine Preparation 119
The following compounds were obtained according to a similar manner to that of Preparation 41.

(1) (2R)-4-Benzyl-1-[3-(dimethylsulfamoyl)-5-(trifluoro-methyl)benzoyl]-2-[4-(trifluoromethyl)benzyl]piperazine IR (Neat): 1645, 1456, 1419, 1319 cm$^{-1}$
NMR (CDCl$_3$, δ): 2.00–2.40 (2H, m), 2.70–5.10 (9H, m), 2.73 (6H, s), 6.90–7.60 (10H, m), 7.73 (1H, s), 8.01 (1H, s)
MASS (APCI): 614 (M+H)$^+$ (2) (2R)-4-Benzyl-1-[3-methylsulfonyl-5-(trifluoromethyl)benzoyl]-2-[4-(trifluoromethyl)benzyl]piperazine NMR (CDCl$_3$, δ): 2.00–2.40 (2H, m), 2.70–3.71 (8H, m), 3.06 (3H, s), 4.50–5.10 (1H, m), 6.80–7.60 (10H, m), 7.86 (1H, s), 8.19 (1H, s)
MASS (APCI): 585 (M+H)$^+$ (3) (2R)-1-[3,5-Bis(trifluoromethyl)benzoyl]-4-benzyl-2-[3-(tert-butyldimethylsilyloxy)-4-chlorobenzyl]piperazine IR (Neat): 2935, 2860, 2812, 1645, 1483, 1423 cm$^{-1}$
NMR (CDCl$_3$, δ): 0.10–0.30 (6H, br), 1.00 (9H, s), 1.80–5.10 (11H, m), 6.20–8.00 (10H, m), 7.87 (1H, s)
MASS (APCI): 671 (M+H)$^+$ (4) (2R)-4-Benzyl-2-[3-(tert-butyldimethylsilyloxy)-4-chlorobenzyl]-1-[3-chloro-5-(trifluoromethyl)benzoyl]-piperazine IR (Neat): 2935, 1641, 1483, 1417 cm$^{-1}$
NMR (CDCl$_3$, δ): 0.10–0.30 (6H, br), 1.01 (9H, s), 1.80–5.00 (11H, m), 6.20–7.70 (10H, m), 7.59 (1H, s)
MASS (APCI): 637 (M+H)$^+$ (5) (2R)-4-Benzyl-2-[3-(tert-butyldimethylsilyloxy)-4-methylbenzyl]-1-[3-methoxy-5-(trifluoromethyl)benzoyl]-piperazine IR (KBr): 1643, 1464, 1421, 1267 cm$^{-1}$
NMR (CDCl$_3$, δ): 0.09 (6H, br s), 0.98 (9H, s), 2.04–2.21 (2H, m), 2.14 (3H, s), 2.60–5.10 (12H, m), 6.24–7.36 (11H, m)
MASS (APCI): 613 (M+H)$^+$ Preparation 120
The following compounds were obtained according to a similar manner to that of Preparation 59.

(1) (2R)-4-[2-(5,6,7,8-Tetrahydro-1,6-naphthyridin-6-yl)-ethyl]-2-[4-(trifluoromethyl)benzyl]piperazine tetrahydrochloride NMR (DMSO-d$_6$, δ): 3.03–4.00 (19H, m), 7.57 (2H, d, J=8.1 Hz), 7.75 (2H, d, J=8.1 Hz), 7.85 (1H, dd, J=7.7 and 5.6 Hz), 8.29 (1H, d, J=7.7 Hz), 8.78 (1H, d, J=5.6 Hz)
MASS (APCI): 405 (M+H)$^+$ (free)

(2) (2R)-4-[2-(cis-2,6-Dimethylmorpholino)ethyl]-2-[4-(trifluoromethyl)benzyl]piperazine trihydrochloride mp: >250° C.
IR (KBr): 2563, 2426, 1456, 1327 cm$^{-1}$
NMR (CDCl$_3$, δ): 1.11 (6H, d, J=6.2 Hz), 2.59–4.50 (19H, m), 7.56 (2H, d, J=8.1 Hz), 7.75 (2H, d, J=8.1 Hz)
MASS (APCI): 386 (M+H)$^+$ (free)

(3) (2R)-4-[2-[(2S)-2-(Methoxymethyl)morpholino]ethyl]-2-[4-(trifluoromethyl)benzyl]piperazine trihydrochloride mp: 80–95° C.
IR (KBr): 1695, 1516 cm$^{-1}$
NMR (DMSO-d$_6$, δ): 2.80–4.60 (25H, m), 7.56 (2H, d, J=8.1 Hz), 7.75 (2H, d, J=8.1 Hz)
MASS (APCI): 402 (M+H)$^+$ (free)

(4) (2R)-2-(4-Fluoro-3-methoxybenzyl)-4-[2-(cis-2,6-dimethylmorpholino)ethyl]piperazine trihydrochloride IR (KBr): 1610, 1517, 1452, 1425, 1367, 1326, 1274 cm$^{-1}$
NMR (DMSO-d$_6$, δ): 1.11 (6H, d, J=6.0 Hz), 2.49–4.40 (21H, m), 3.86 (3H, s), 6.87–7.24 (3H, m), 9.55–10.06 (2H, m)
MASS: 366 (M+H)$^+$ (free)

(5) (2R)-2-(4-Fluoro-3-methoxybenzyl)-4-[2-[(2S)-2-(methoxymethyl)morpholino]ethyl]piperazine trihydrochloride IR (KBr): 3465, 3435, 3400, 1615, 1515, 1455, 1270, 1235 cm$^{-1}$
NMR (DMSO-d$_6$, δ): 2.65–4.20 (22H, m), 3.27 (3H, s), 3.86 (3H, s), 6.82–7.23 (3H, m)
MASS (APCI): 382 (M+H)$^+$ (free)

(6) (2R)-2-(4-Fluoro-3-methoxybenzyl)-4-[2-(5,6,7,8-tetrahydro-1,6-naphthyridin-6-yl)ethyl]piperazine tetrahydrochloride IR (KBr): 1515, 1464, 1269, 1153, 1095 cm$^{-1}$
NMR (CDCl$_3$, δ): 2.60–4.50 (22H, m), 3.84 (3H, s), 6.85–10.0 (8H, m)
MASS: 385 (M+H)$^+$ (free)

(7) (2R)-2-(4-Chloro-3-hydroxybenzyl)-4-[2-[(2S)-2-(methoxy-methyl)morpholino]ethyl]piperazine trihydrochloride IR (KBr): 1645, 1450, 1425, 1370, 1236, 1140 cm$^{-1}$
NMR (DMSO-d$_6$, δ): 2.64–4.50 (22H, m), 3.27 (3H, s), 6.71–7.32 (3H, s)
MASS (APCI): 384 (M+H)$^+$ (free)

(8) (3S,4S)-3,4-Dimethoxypyrrolidine hydrochloride mp: 168° C.
IR (KBr): 3464, 2900–2350, 1198, 1109, 1065, 1024 cm$^{-1}$
NMR (DMSO-d$_6$, δ): 3.05–3.35 (4H, m), 3.31 (6H, s), 4.00 (2H, d, J=3.5 Hz), 9.67 (2H, br s)
MASS (APCI): 132 (M+H)$^+$ (free)

Preparation 121

2-Bromoethanol (310 mg) was added to a solution of (2R)-1-[3,5-bis(trifluoromethyl)benzoyl]-2-[4-(trifluoromethyl)-benzyl]piperazine (1 g) in acetonitrile (10 ml). The reaction mixture was stirred at 70° C. for 19 hours. The mixture was filtered, and the residue on filter was washed with dichloromethane twice. The filtrate and combined washings were concentrated in vacuo. The residue was purified by silica gel column chromatography eluted with methanol in dichloromethane (2% then 5%) to give (2R)-1-[3,5-bis(trifluoromethyl)benzoyl]-4-(2-hydroxyethyl)-2-[4-(trifluoromethyl)benzyl]piperazine (927 mg) as an amorphous powder.

IR (Neat): 3462, 3435, 2949, 2817, 1637, 1439 cm$^{-1}$
NMR (CDCl$_3$, δ): 2.1–5.2 (14H, m), 6.9–8.0 (7H, m)
MASS (APCI): 529 (M+H)$^+$ Preparation 122

The following compound was obtained according to a similar manner to that of Preparation 121.

(2R)-1-[3,5-Bis(trifluoromethyl)benzoyl]-2-(4-fluoro-3-methoxybenzyl)-4-(2-hydroxyethyl)piperazine IR (Neat): 2945, 2817, 1639, 1518, 1442 cm$^{-1}$
NMR (CDCl$_3$, δ): 2.20–5.10 (13H, m), 4.52 (3H, s), 6.30–7.89 (6H, m)
MASS (APCI): 509 (M+H)$^+$ Preparation 123

The following compounds were obtained according to a similar manner to that of Preparation 9.

(1) (2R)-1-[3,5-Bis(trifluoromethyl)benzoyl]-4-(2-chloroethyl)-2-[4-(trifluoromethyl)benzyl]piperazine hydrochloride IR (KBr): 3437, 3429, 2561, 1649, 1427 cm$^{-1}$
NMR (DMSO-d$_6$, δ): 2.20–5.40 (13H, m), 7.10–8.30 (7H, m)
MASS (APCI): 547 (M+H)$^+$ (free)

(2) (2R)-1-[3,5-Bis(trifluoromethyl)benzoyl]-4-(2-chloroethyl)-2-(4-fluoro-3-methoxybenzyl)piperazine hydrochloride mp: 75–79° C.
IR (KBr): 1647, 1518, 1427 cm$^{-1}$
NMR (DMSO-d$_6$, δ): 2.75–5.20 (13H, m), 4.49 (3H, s), 6.50–8.23 (6H, m)
MASS (APCI): 527 (M+H)$^+$ (free)

Preparation 124

The following compound was obtained according to a similar manner to that of Preparation 57.

(2R)-4-Benzyl-2-[3-(tert-butyldimethylsilyloxy)-4-methylbenzyl]piperazine

IR (Neat): 2952, 2933, 2856, 1504 cm$^{-1}$
NMR (DMSO-d$_6$, δ): 0.21 (6H, s), 1.02 (9H, s), 1.66–2.00 (2H, m), 2.13 (3H, s), 2.49–2.85 (4H, m), 3.37–3.41 (5H, m), 6.63 (1H, s), 6.69 (1H, d, J=7.6 Hz), 7.05 (1H, d, J=7.6 Hz), 7.25–7.40 (5H, m)
MASS (ESI+): 411.4 (M+H)$^+$ Preparation 125

A solution of (2S,4R)-1-benzyl-4-hydroxy-2-(hydroxymethyl)pyrrolidine (1.49 g) in N,N-dimethylformamide (10 ml) was added to a suspension of sodium hydride (60% dispersion in mineral oil, 689 mg) in N,N-dimethylformamide (5 ml) dropwise at ambient temperature. The reaction mixture was stirred at the same temperature for 1 hour. To the reaction mixture was added methyl iodide (2.55 g) in N,N-dimethylformamide (3 ml) dropwise. After stirring at ambient temperature for 2 hours, the reaction mixture was poured into ice water, and the whole was extracted with ethyl acetate twice. The combined organic layer was washed successively with a mixture of saturated aqueous sodium bicarbonate solution and 5% aqueous sodium thiosulfate solution, and saturated aqueous sodium chloride solution, dried over magnesium sulfate, and concentrated in vacuo. The residue was purified by silica gel column chromatography eluted with methanol in dichloromethane 1% then 2% to give (2S,4R)-1-benzyl-4-methoxy-2-(methoxymethyl) pyrrolidine (1.07 g) as an oil.

IR (Neat): 2877, 2817, 1452 cm$^{-1}$
NMR (CDCl$_3$, δ): 1.79–2.02 (2H, m), 2.26 (1H, dd, J=9.9 and 5.6 Hz), 2.88–3.01 (1H, m), 3.19–3.49 (4H, m), 3.25 (3H, s), 3.35 (3H, s), 3.86 (1H, m), 4.10 (1H, d, J=13.1 Hz), 7.20–7.33 (5H, m)
MASS (APCI): 236 (M+H)$^+$ Preparation 126
The following compounds were obtained according to a similar manner to that of Preparation 15.

(1) (2S,4R)-4-Methoxy-2-(methoxymethyl) pyrrolidine

IR (Neat): 3342, 2881, 1668, 1444 cm$^{-1}$
NMR (CDCl$_3$, δ): 1.55 (1H, m), 1.93 (1H, dd, J=13.6 and 7.1 Hz), 2.88–3.09 (2H, m), 3.24–3.52 (3H, m), 3.29 (3H, s), 3.36 (3H, s), 3.89 (1H, m)
MASS (APCI): 146 (M+H)$^+$ (2) (3S,4S)-Pyrrolidine-3,4-diol hydrochloride mp: 69–73° C.
IR (KBr): 3400, 1622, 1442, 1238, 1109, 1030, 989 cm$^{-1}$
NMR (DMSO-d$_6$-D$_2$O, δ): 3.05 (2H, d, J=12.1 Hz), 3.28 (2H, dd, J=12.1 and 3.2 Hz), 4.10 (2H, d, J=3.2 Hz)
MASS (APCI): 104 (M+H)$^+$ (free)

(3) cis-2,6-Dimethoxymethylpiperidine hydrochloride mp: 200–202° C.
IR (KBr): 3402, 2941, 2821, 2735, 1645, 1516, 1456 cm$^{-1}$
NMR (DMSO-d$_6$, δ): 1.30–1.90 (6H, m), 3.10–3.40 (2H, m), 3.30 (6H, s), 3.54 (4H, d, J=5.3 Hz)
MASS (APCI): 1.74 (M+H)$^+$ (free)

(4) cis-3,5-Dimethoxymethylpiperidine hydrochloride mp: 220–222° C.
IR (KBr): 2939, 2806, 2783, 1460, 1392 cm$^{-1}$
NMR (DMSO-d$_6$, δ): 0.99 (1H, q, J=12.4 Hz), 1.69 (1H, m), 1.90–2.25 (2H, m), 2.50 (2H, t, J=12.3 Hz), 3.10–3.40 (6H, m), 3.23 (6H, s)
MASS (APCI): 174 (M+H)$^+$ (free)

(5) cis-2,6-Dimethoxymethylmorpholine hydrochloride

IR (Neat): 2935, 2819, 1595, 1513, 1456 cm$^{-1}$
NMR (CDCl$_3$, δ): 2.73 (2H, t, J=12.0 Hz), 3.18 (2H, d, J=12.0 Hz), 3.35 (6H, s), 3.35–3.46 (4H, m), 3.92–4.05 (2H, m)
MASS (APCI): 176 (M+H)$^+$ (free)

(6) 2,2-Dimethoxymethylmorpholine hydrochloride

IR (Neat): 2935, 2522, 1594, 1454 cm$^{-1}$
NMR (CDCl$_3$, δ): 2.92–3.00 (4H, m), 3.29 (6H, s), 3.46 (2H, d, J=10.2 Hz), 3.51 (2H, d, J=10.2 Hz), 3.81–3.86 (2H, m)
MASS (APCI): 176 (M+H)$^+$ (free)

(7) 8-Oxa-3-azabicyclo[3.2.1]octane hydrochloride mp: 205–207.5° C.
IR (KBr): 2920, 2792, 1591, 1442 cm$^{-1}$
NMR (DMSO-d$_6$, δ): 1.85–2.18 (4H, m), 2.97–3.08 (4H, m), 4.39–4.40 (2H, m)
MASS (APCI): 114 (M+H)$^+$ (free)

Preparation 127
The following compounds were obtained according to a similar manner to that of Preparation 89.

(1) (2S,4R)-1-(2-Hydroxyethyl)-4-methoxy-2-(methoxymethyl)-pyrrolidine

IR (Neat): 3400, 2881, 1660, 1458, 1379 cm$^{-1}$
NMR (CDCl$_3$, δ): 1.77 (1H, m), 2.00 (1H, m), 2.45 (1H, dd, J=10.4, 4.5 Hz), 2.62 (1H, dt, J=12.7, 3.7 Hz), 2.95–3.11 (2H, m), 3.29–3.45 (3H, m), 3.30 (3H, s), 3.36 (3H, s), 3.50–3.70 (2H, m), 3.90 (1H, m)
MASS (APCI): 190 (M+H)$^+$ (2) 2,2-Dimethyl-4-(2-hydroxyethyl)morpholine IR (Neat): 2972, 2941, 1458, 1387 cm$^{-1}$
NMR (CDCl$_3$, δ): 1.26 (6H, s), 2.31 (2H, s), 2.45–2.54 (4H, m), 3.63 (2H, t, J=5.1 Hz), 3.77 (2H, t, J=5.1 Hz)
MASS (APCI): 160 (M+H)$^+$ (3) (3S,4S)-1-(2-Bromoethyl)-3,4-dimethoxypyrrolidine hydrochloride Preparation 128
The following compounds were obtained according to a similar manner to that of Preparation 90.

(1) (2S,4R)-1-(2-Chloroethyl)-4-methoxy-2-(methoxymethyl)-pyrrolidine hydrochloride IR (Neat): 3400, 2939, 1645, 1450 cm$^{-1}$
NMR (DMSO-d$_6$, δ): 1.80 (1H, m), 2.23 (1H, m), 3.26 (3H, s), 3.32 (3H, s), 3.20–4.20 (10H, m)
MASS (APCI): 208 (M+H)$^+$ (free)

(2) 2,2-Dimethyl-4-(2-chloroethyl)morpholine hydrochloride mp: 180–185° C.
IR (KBr): 2978, 2677, 2630, 2584, 1456 cm$^{-1}$
NMR (DMSO-d$_6$, δ): 1.18 (3H, s), 1.44 (3H, s), 2.80–3.10 (2H, m), 3.30–3.91 (6H, m), 4.10 (2H, t, J=6.9 Hz)
MASS (APCI): 178 (M+H)$^+$ (free)

(3) (3S,4S)-1-(2-Chloroethyl)-3,4-dimethoxypyrrolidine hydrochloride

IR (Neat): 3400, 2563, 2440, 1637, 1460, 1113 cm$^{-1}$
NMR (DMSO-d$_6$, δ): 3.20–3.86 (6H, m), 3.32 (6H, s), 3.92–4.16 (4H, m), 11.44 (1H, s)
MASS (APCI): 194 (M+H)$^+$ (free)

Preparation 129
A solution of 3-dimethylamino-1H-pyrrolo[3,2-b]pyridine (1.53 g) and hexamethylenetetramine (1.22 g) in 6.68 g of 66% propionic acid was added dropwise to a refluxing solution of 2.44 g of hexamethylenetetramine in 8.92 g of the same solvent. The addition was carried out over a period of one hour and the solution was refluxed 3.5 hours more. The solution was concentrated in vacuo and thereto water (30 ml), ethyl acetate (25 ml), and tetrahydrofuran (20 ml) were added. The organic layer was separated, dried over sodium sulfate, and concentrated under reduced pressure.

The resulting residue was purified by column chromatography on silica gel (12 g) using a mixed solvent of dichloromethane and methanol (0.15:1). The fractions containing the objective compound were collected and evaporated under reduced pressure to give a powder of 3-formyl-1H-pyrrolo[3,2-b]pyridine (0.45 g).

mp: 230° C. (decomp.)

IR (KBr): 2744, 1658, 1466, 1408, 1142, 1113, 777 cm$^{-1}$

NMR (DMSO-d$_6$, δ): 7.27 (1H, dd, J=4.6 and 8.3 Hz), 7.92 (1H, d, J=8.3 Hz), 8.44 (1H, s), 8.50 (1H, d, J=4.6 Hz), 10.19 (1H, s), 12.38 (1H, s)

MASS (APCI): 147 (M+H)$^+$

Preparation 130

The following compounds were obtained according to a similar manner to that of Preparation 125.

(1) (3S,4S)-1-(tert-Butoxycarbonyl)-3,4-dimethoxypyrrolidine

IR (Neat): 1690, 1410, 1365, 1165, 1100 cm$^{-1}$

NMR (CDCl$_3$, δ): 1.45 (9H, s), 3.37 (6H, s), 3.30–3.56 (4H, m), 3.72–3.85 (2H, m)

MASS (APCI): 132 (M−Boc+H)$^+$ (2) cis-2,6-Dimethoxymethyl-1-benzylpiperidine

IR (Neat): 2924, 2883, 1489, 1450 cm$^{-1}$

NMR (CDCl$_3$, δ): 1.30–1.85 (6H, m), 2.68–2.78 (2H, m), 3.13 (6H, s), 3.18 (2H, dd, J=9.6, 6.2 Hz), 3.35 (2H, dd, J=9.6, 4.4 Hz), 3.84 (2H, s), 7.17–7.42 (5H, m)

MASS (APCI): 264 (M+H)$^+$ (3) cis-3,5-Dimethoxymethyl-1-benzylpiperidine

IR (Neat): 2920, 2829, 1454, 1389 cm$^{-1}$

NMR (CDCl$_3$, δ): 0.68 (1H, q, J=12.2 Hz), 1.61 (2H, t, J=11.1 Hz), 1.78 (1H, m), 1.85–2.20 (2H, m), 2.90–3.05 (2H, m), 3.19 (4H, d, J=6.2 Hz), 3.29 (6H, s), 3.52 (2H, s), 7.20–7.32 (5H, m)

MASS (APCI): 264 (M+H)$^+$

Preparation 131

A solution of (S)-methyl glycidyl ether (10 g) and benzylamine (3.62 g) in methanol (50 ml) was stirred at 55° C. for 2 hours. To the mixture was added (S)-methyl glycidyl ether (1 g), and the mixture was stirred at 55° C. for 2 hours, and then evaporated under reduced pressure. Toluene was added to the residue and evaporated under reduced pressure to give (2S)-1-[N-benzyl-N-[(2S)-2-hydroxy-3-methoxypropyl]amino]-3-methoxypropan-2-ol (8.84 g) as a pale yellow oil.

IR (Neat): 3430, 3402, 2889, 1454 cm$^{-1}$

NMR (CDCl$_3$, δ): 2.52–2.70 (4H, m), 3.34 (6H, s), 3.26–3.44 (4H, m), 3.61 (1H, d, J=13.7 Hz), 3.81–3.92 (2H, m), 3.84 (1H, d, J=13.7 Hz), 7.20–7.33 (5H, m)

MASS (APCI): 284 (M+H)$^+$

Preparation 132

A mixture of triphenylphosphine (10.2 g), diethyl azodicarboxylate (6.12 ml), and (2S)-1-[N-benzyl-N-[(2S)-2-hydroxy-3-methoxypropyl]amino]-3-methoxypropan-2-ol (7.34 g) in tetrahydrofuran (70 ml) was stirred at 0° C. for 5 hours. To the mixture was added successively triphenylphosphine (2.04 g) and diethyl azodicarboxylate (1.2 ml), and the mixture was stirred at 0° C. for 3 hours. The mixture was poured into water and extracted with dichloromethane (×3). The combined extracts were washed with brine, dried over sodium sulfate, and evaporated. Isopropyl ether (50 ml) was added to the residue and stirred at room temperature for 30 minutes. The insoluble precipitate was filtered off, and the solution was evaporated and purified twice with column chromatography (1st: silica gel 800 ml, ethyl acetate:isopropyl ether=2:8–3:7) (2nd: silica gel 300 ml, ethyl acetate:isopropyl ether 3:97–10.90) to give 4-benzyl-cis-2,6-dimethoxymethylmorpholine (2.65 g) as an oil.

IR (Neat): 2883, 1514, 1458, 1099 cm$^{-1}$

NMR (CDCl$_3$, δ): 1.93 (2H, t, J=11.0 Hz), 2.77 (2H, d, J=11.0 Hz), 3.34 (6H, s), 3.36–3.50 (4H, m), 3.51 (2H, s), 3.75–3.87 (2H, m), 7.25–7.32 (5H, m)

MASS (APCI): 266 (M+H)$^+$

Preparation 133

To a solution of N-benzylethanolamine (302 g) in a mixture of water (8.92 ml) and toluene (1510 ml) and diglyme (151 ml) was added dropwise sulfuric acid (128 ml) over 30 minutes, and the mixture was stirred under reflux for 6 hours. After cooled to room temperature, to the mixture was added methanol (300 ml), and then the mixture was stirred for 1 hour. The precipitate was filtered and washed with methanol (300 ml×4), and dried to give 2-(N-benzylamino)ethyl hydrogen sulfate (352.6 g) as a white powder.

MASS (APCI): 232 (M+H)$^+$

Elemental Analysis Calcd. for C$_9$H$_{13}$N$_1$O$_4$S:

Calcd. C, 46.74%, H, 5.67%, N, 6.06%

Found. C, 46.42%, H, 5.63%, N, 5.93%

Preparation 134

To a solution of 2-(N-benzylamino)ethyl hydrogen sulfate (28 g) in a mixture of water (36.3 ml) and 40% sodium hydroxide aqueous solution (12.1 ml) was added 2,2-bis(methoxymethyl)oxirane (16.0 g) at room temperature over 30 minutes. After stirring at room temperature for 87 hours, 40% sodium hydroxide aqueous solution (73 ml) was added dropwise to the mixture over 20 minutes. The mixture was stirred at room temperature for 1 hour and at 40° C. for 20 hours, and extracted with ethyl acetate (100 ml×3). The organic layer was extracted with 1N hydrochloric acid (×6). The combined extracts were neutralized with sodium hydroxide, and then added sodium chloride, and extracted with ethyl acetate (100 ml×3). The combined extracts were washed with brine, dried over magnesium sulfate, and evaporated under reduced pressure to give 4-benzyl-2,2-dimethoxymethylmorpholine (31.79 g) as an orange oil.

IR (Neat): 2922, 2877, 2812, 1454 cm$^{-1}$

NMR (CDCl$_3$, δ): 2.38–2.44 (4H, m), 3.27–3.45 (4H, m), 3.37. (6H, s), 3.65 (2H, d, J=9.6 Hz), 3.77–3.84 (2H, m), 7.20–7.34 (5H, m)

MASS (APCI): 266 (M+H)$^+$

Preparation 135

A mixture of 2,5-bis(hydroxymethyl)tetrahydrofuran bis (p-toluenesulfonate) (10 g) and benzylamine (9.7 g) was stirred at 70° C. for 24 hours. To the mixture was added a solution of sodium hydroxide (1.85 g) in methanol (30 ml). After stirring at room temperature for 30 minutes, the mixture was filtered. The filtrate was evaporated, added dichloromethane, and filtered. The filtrate was evaporated under reduced pressure, and purified with column chromatography (silica gel, 250 ml, ethyl acetate:hexane=1:4) to give 3-benzyl-8-oxa-3-azabicyclo[3.2.1]octane (4.05 g) as an oil.

IR (Neat): 2951, 2800, 1452 cm$^{-1}$

NMR (CDCl$_3$, δ): 1.78–2.07 (4H, m), 2.33 (2H, dd, J=11.1 and 1.8 Hz), 2.54 (2H, br d, J=11.1 Hz), 3.45 (2H, s), 4.25–4.28 (2H, m), 7.18–7.34 (5H, m)

MASS (APCI): 204 (M+H)$^+$

EXAMPLE 38

(1) (2R)-1-[3,5-Bis(trifluoromethyl)benzoyl]-4-[2-(2,2-dimethylmorpholino)ethyl]-2-[4-(trifluoromethyl)benzyl]-piperazine dihydrochloride $[\alpha]_D^{26}$: +11.00° (C=0.25, MeOH)
mp: 215–231° C.
IR (KBr): 3438, 1645, 1329, 1281 cm$^{-1}$
NMR (DMSO-d$_6$, δ): 1.25, 1.33 (6H, s), 2.60–5.30 (19H, m), 7.21–8.19 (7H, m)
MASS (APCI): 626 (M+H)$^+$ (free)

(2) (2R)-1-[3,5-Bis(trifluoromethyl)benzoyl]-4-[2-[(2S,5S)-2-methoxymethyl-5-methylmorpholino]ethyl]-2-[4-(trifluoromethyl)benzyl]piperazine dihydrochloride $[\alpha]_D^{26}$: +12.33° (C=0.25, MeOH)
mp: 142–182° C.
IR (KBr): 1647, 1281 cm$^{-1}$
NMR (DMSO-d$_6$, δ): 1.16 (3H, d, J=6.2 Hz), 2.70–5.30 (24H, m), 7.21–8.19 (7H, m)
MASS (APCI): 656 (M+H)$^+$ (free)

(3) (2R)-1-[3,5-Bis(trifluoromethyl)benzoyl]-4-[2-(cis-2,6-dimethoxymethylmorpholino)ethyl]-2-[4-(trifluoromethyl)-benzyl]piperazine dihydrochloride $[\alpha]_D^{24}$: +9.00° (C=0.25, MeOH)
mp: 130–138° C.
IR (KBr): 3437, 1647, 1427, 1329, 1282 cm$^{-1}$
NMR (DMSO-d$_6$, δ): 2.80–5.30 (29H, m), 7.21–8.18 (7H, m)
MASS (APCI): 686 (M+H)$^+$ (free)

(4) (2R)-1-[3,5-Bis(trifluoromethyl)benzoyl]-4-[2-(2,2-dimethoxymethylmorpholino)ethyl]-2-[4-(trifluoromethyl)-benzyl]piperazine dihydrochloride $[\alpha]_D^{26}$: +5.27° (C=0.25, MeOH)
mp: 123–149° C.
IR (KBr): 3435, 1647 cm$^{-1}$
NMR (DMSO-d$_6$, δ): 2.70–5.30 (29H, m), 7.21–8.19 (7H, m)
MASS (APCI): 686 (M+H)$^+$ (free)

(5) (2R)-1-[3,5-Bis(trifluoromethyl)benzoyl]-4-[2-(8-oxa-3-azabicyclo[3.2.1]octan-3-yl)ethyl]-2-[4-(trifluoromethyl)benzyl]piperazine dihydrochloride $[\alpha]_D^{25}$: +11.67° (C=0.25, MeOH)
mp: 232–250° C.
IR (KBr): 3438, 1645, 1281 cm$^{-1}$
NMR (DMSO-d$_6$, δ): 1.91–2.27 (4H, m), 2.80–5.40 (19H, m), 7.21–8.19 (7H, m)
MASS (APCI): 624 (M+H)$^+$ (free)

(6) (2R)-1-[3,5-Bis(trifluoromethyl)benzoyl]-4-[2-(2,2-dimethylmorpholino)ethyl]-2-(4-fluoro-3-methoxybenzyl)piperazine dihydrochloride $[\alpha]_D^{26}$: +9.73° (C=0.25, MeOH)
mp: 152–162° C.
IR (KBr): 3438, 1645, 1516, 1282 cm$^{-1}$
NMR (DMSO-d$_6$, δ): 1.30 (6H, br s), 2.60–5.30 (22H, m), 6.40–8.20 (6H, m)
MASS (APCI): 606 (M+H)$^+$ (free)

(7) (2R)-1-[3,5-Bis(trifluoromethyl)benzoyl]-4-[2-[(2S,5S)-2-methoxymethyl-5-methylmorpholino]ethyl]-2-(4-fluoro-3-methoxybenzyl)piperazine dihydrochloride $[\alpha]_D^{24}$: +12.33° (C=0.25, MeOH)
mp: 140–164° C.
IR (KBr): 3437, 1645, 1282 cm$^{-1}$
NMR (DMSO-d$_6$, δ): 1.16 (3H, d, J=6.1 Hz), 2.70–5.30 (27H, m), 6.50–8.20 (6H, m)
MASS (APCI): 636 (M+H)$^+$ (free)

(8) (2R)-1-[3,5-Bis(trifluoromethyl)benzoyl]]-4-[2-(cis-2,6-dimethoxymethylmorpholino)ethyl]-2-(4-fluoro-3-methoxybenzyl)piperazine dihydrochloride $[\alpha]_D^{26}$: +10.60° (C=0.25, MeOH)
mp: 148–156° C.
IR (KBr): 1645, 1516, 1281 cm$^{-1}$
NMR (DMSO-d$_6$, δ): 2.60–5.20 (32H, m), 6.40–8.20 (6H, m)
MASS (APCI): 666 (M+H)$^+$ (free)

(9) (2R)-1-[3,5-Bis(trifluoromethyl)benzoyl]-4-[2-(2,2-dimethoxymethylmorpholino)ethyl]-2-(4-fluoro-3-methoxybenzyl)pipeazine dihydrochloride $[\alpha]_D^{23}$: +6.60° (C=0.25, MeOH)
mp: 132–150° C.
IR (KBr): 3437, 1645, 1516, 1282 cm$^{-1}$
NMR (DMSO-d$_6$, δ): 2.60–5.30 (32H, m), 6.45–8.20 (6H, m)
MASS (APCI): 666 (M+H)$^+$ (free)

(10) (2R)-1-[3,5-Bis(trifluoromethyl)benzoyl]-4-[2-(8-oxa-3-azabicyclo[3.2.1]octan-3-yl)ethyl]-2-(4-fluoro-3-methoxybenzyl)piperazine dihydrochloride $[\alpha]_D^{23}$: +13.20° (C=0.25, MeOH)
mp: 163–178° C.
IR (KBr): 3431, 1645, 1518, 1427, 1282 cm$^{-1}$
NMR (DMSO-d$_6$, δ): 1.91–2.30 (4H, m), 2.70–5.30 (22H, m), 6.45–8.25 (6H, m)
MASS (APCI): 604 (M+H)$^+$ (free)

EXAMPLE 39

The following compounds were obtained according to a similar manner to that of Example 1 using N,N-diisopropylethylamine instead of potassium carbonate as a base.

(1) 4-[[(2R)-1-[3,5-Bis(trifluoromethyl)benzoyl]-4-[2-[(2S)-2-(methoxymethyl)morpholino]ethyl]piperazin-2-yl]-methyl]-2-(tert-butyldimethylsilyloxy)benzoic acid methyl ester IR (Neat): 1677, 1643, 1438, 1280 cm$^{-1}$
NMR (CDCl$_3$, δ): 0.10–0.30 (6H, m), 0.99 (9H, s), 2.00–5.10 (22H, m), 3.38 (3H, s), 3.87 (3H, s), 6.30–7.90 (6H, m)
MASS (APCI): 784 (M+Na)$^+$, 763 (M+H)$^+$ (2) (2R)-1-[3,5-Bis(trifluoromethyl)benzoyl]-2-(4-methoxybenzyl)-4-[2-[(2S)-2-(methoxymethyl)morpholino]-ethyl]piperazine dihydrochloride $[\alpha]_D^{25}$: −5.16° (C=0.32, MeOH)
mp: 146–149° C.
IR (KBr): 1645, 1282, 1182, 1136 cm$^{-1}$ NMR (DMSO-d$_6$, δ): 2.60–5.20 (28H, m), 6.75–6.90 (4H, m), 7.29–8.21 (3H, m)
MASS (APCI): 604 (M+H)$^+$ (free)

(3) (2R)-2-[3-(tert-Butyldimethylsilyloxy)-4-methyl-benzyl]-1-[3-methoxy-5-(trifluoromethyl)benzoyl]-4-[2-(5,6,7,8-tetrahydro-1,6-naphthyridin-6-yl)ethyl]piperazine IR (Neat): 2935, 1641, 1464, 1421 cm$^{-1}$
NMR (CDCl$_3$, δ): 0.13 (6H, br s), 0.99 (9H, s), 2.15 (3H, s), 2.10–5.10 (19H, m), 3.81 (3H, s), 6.20–7.10 (7H, m), 7.32 (1H, d, J=6.7 Hz), 8.40 (1H, d, J=3.8 Hz)
MASS (APCI): 683 (M+H)$^+$ (4) (2R)-2-[3-(tert-Butyldimethylsilyloxy)-4-methyl-benzyl]-4-[4-(3,3-dimethylmorpholino)-2-butynyl]-1-[3-methoxy-5-(trifluoromethyl)benzoyl]piperazine IR (Neat): 2952, 1645, 1510 cm$^{-1}$
NMR (CDCl$_3$, δ): 0.14 (6H, br s), 0.99 (9H, s), 1.05 (6H, s), 2.15 (3H, s), 2.20–5.20 (19H, m), 3.81 (3H, s), 6.20–7.58 (6H, m)
MASS (APCI): 688 (M+H)$^+$ (5) (2R)-1-[3-(Dimethylsulfamoyl)-5-(trifluoromethyl)-benzoyl]-4-[2-(5,6,7,8-tetrahydro-1,6-naphthyridin-6-yl)ethyl]-2-[4-(trifluoromethyl)benzyl]piperazine trihydrochloride $[α]_D^{26}$: +1.33° (C=0.25, MeOH)
mp: 190–194° C.
IR (KBr): 3398, 1647 cm$^{-1}$
NMR (DMSO-d$_6$, δ): 2.66 (6H, s), 2.80–5.30 (19H, m), 6.90–8.71 (10H, m)
MASS (APCI): 684 (M+H)$^+$ (free)

(6) (2R)-1-[3-Methylsulfonyl-5-(trifluoromethyl)benzoyl]-2-[4-(trifluoromethyl)benzyl]-4-[2-(5,6,7,8-tetrahydro-1,6-naphthyridin-6-yl)ethyl]piperazine trihydrochloride $[α]_D^{26}$: −2.33° (C=0.25, MeOH)
mp: 192–197° C.
IR (KBr): 3433, 3400, 1647 cm$^{-1}$
NMR (DMSO-d$_6$, δ): 2.70–5.30 (22H, m), 7.05–8.68 (10H, m)
MASS (APCI): 655 (M+H)$^+$ (free)

(7) (2R)-1-[3,5-Bis(trifluoromethyl)benzoyl]-4-[2-[(2R)-2-(methoxymethyl)morpholino]ethyl]-2-[4-(trifluoromethyl)-benzyl]piperazine dihydrochloride $[α]_D^{26.5}$: +5.18° (C=0.28, MeOH)
mp: 188–194° C.
IR (KBr): 3438, 1645, 1516, 1464, 1456 cm$^{-1}$
NMR (DMSO-d$_6$, δ): 2.50–5.30 (22H, m), 3.27 (3H, s), 7.10–8.30 (7H, m)
MASS (API-ES positive): 642 (M+H)$^+$ (free)

(8) (2R)-1-[3,5-Bis(trifluoromethyl)benzoyl]-4-[2-[(2S,4R)-4-methoxy-2-(methoxymethyl)pyrrolidino]ethyl]-2-[4-(trifluoromethyl)benzyl]piperazine dihydrochloride $[α]_D^{26.7}$: −17.430 (C=0.23, MeOH)
mp: 56.59° C.
IR (KBr): 3438, 1647, 1427 cm$^{-1}$
NMR (DMSO-d$_6$, δ): 1.70–5.40 (21H, m), 3.29 (3H, s), 3.35 (3H, s), 7.10–7.80 (6H, m), 8.19 (1H, br s)
MASS (APCI): 656 (M+H)$^+$ (free)

(9) (2R)-1-[3,5-Bis(trifluoromethyl)benzoyl]-4-[2-[(3S,4S)-3,4-dimethoxypyrrolidino]ethyl]-2-[4-(trifluoromethyl)-benzyl]piperazine dihydrochloride $[α]_D^{23.1}$: +5.94° (C=0.202, MeOH)
mp: 203–208° C.
IR (KBr): 3437, 2565, 2440, 1647, 1429, 1331, 1282, 1178, 1128, 1066 cm$^{-1}$
NMR (DMSO-d$_6$, δ): 2.76–5.32 (25H, m), 7.10–8.26 (7H, m)
MASS (APCI): 642 (M+H)$^+$ (free)

(10) (2R)-1-[3,5-Bis(trifluoromethyl)benzoyl]-2-(4-fluoro-3-methoxybenzyl)-4-[2-[(2S,4R)-4-methoxy-2-(methoxy-methyl)pyrrolidino]ethyl]piperazine dihydrochloride $[α]_D^{26.6}$: −12.27° (C=0.30, MeOH)
mp: 128–134° C.
IR (KBr): 3437, 3400, 1645, 1516 cm$^{-1}$
NMR (DMSO-d$_6$, δ): 1.70–5.30 (21H, m), 3.29 (3H, s), 3.35 (3H, s), 3.57 (3H, s), 6.40–8.30 (6H, m)
MASS (APCI): 636 (M+H)$^+$ (free)

(11) (2R)-1-[3,5-Bis(trifluoromethyl)benzoyl]-2-(4-fluoro-3-methoxybenzyl)-4-[2-[(2R)-2-(methoxymethyl)morpholino]-ethyl]piperazine dihydrochloride $[α]_D^{26.8}$: +6.24° (C=0.33, MeOH)
mp: 139–148° C.
IR (KBr): 3438, 1644, 1516, 1464, 1427 cm$^{-1}$
NMR (DMSO-d$_6$, δ): 2.60–5.30 (25H, m), 3.27 (3H, s), 6.40–8.30 (6H, m)
MASS (APCI): 622 (M+H)$^+$ (free)

(12) (2R)-1-[3,5-Bis(trifluoromethyl)benzoyl]-4-[2-[(3S,4S)-3,4-dimethoxypyrrolidino]ethyl]-2-(4-fluoro-3-methoxybenzyl)piperazine dihydrochloride $[α]_D^{23.5}$: +8.05° (C=0.205, MeOH)
mp: 112–120° C.
IR (KBr): 3431, 2561, 2436, 1645, 1516, 1464, 1427, 1282, 1182, 1134, 1034 cm$^{-1}$
NMR (DMSO-d$_6$, δ): 2.65–5.24 (28H, m), 6.44–8.30 (6H, m)
MASS (APCI): 622 (M+H)$^+$ (free)

(13) (2R)-1-[3,5-Bis(trifluoromethyl)benzoyl]-2-(4-chloro-3-hydroxybenzyl)-4-[2-[(2R)-2-(methoxymethyl)morpholino]-ethyl]piperazine dihydrochloride $[α]_D^{26.5}$: −11.28° (C=0.27, MeOH)
mp: 204–214° C.
IR (KBr): 1645, 1539, 1516 cm$^{-1}$
NMR (DMSO-d$_6$, δ): 2.50–5.20 (22H, m), 3.27 (3H, s), 6.30–8.30 (6H, m), 9.90–10.30 (1H, br)
MASS (API-ES positive): 624 (M+H)$^+$ (free)

(14) (2R)-1-[3,5-Bis(trifluoromethyl)benzoyl]-2-(4-chloro-3-hydroxybenzyl)-4-[2-[(2S,4R)-4-methoxy-2-(methoxy-methyl)pyrrolidino]ethyl]piperazine dihydrochloride $[\alpha]_D^{26.4}$: −25.54° (C=0.33, MeOH)
mp: 95–105° C.
IR (KBr): 3400, 1645, 1516, 1429 cm$^{-1}$
NMR (DMSO-d$_6$, δ): 1.70–5.30 (21H, m), 3.28 (3H, s), 3.35 (3H, s), 6.20–8.30 (6H, m), 10.07–11.26 (1H, br)
MASS (APCI): 638 (M+H)$^+$ (free)

(15) (2R)-1-[3,5-Bis(trifluoromethyl)benzoyl]-2-(4-chloro-3-hydroxybenzyl)-4-[2-[(3S,4S)-3,4-dimethoxypyrrolidino]-ethyl]piperazine dihydrochloride $[\alpha]_D^{23.8}$: −6.49° (C=0.23, MeOH)
mp: 150–155° C.
IR (KBr): 3398, 2600, 2436, 1645, 1429, 1281, 1180, 1136, 1107, 1047 cm$^{-1}$
NMR (DMSO-d$_6$, δ): 2.55–5.15 (25H, m), 6.24–8.30 (6H, m)
MASS (APCI): 624 (M+H)$^+$ (free)

(16) (2R)-2-[3-(tert-Butyldimethylsilyloxy)-4-chlorobenzyl]-1-[3-chloro-5-(trifluoromethyl)benzoyl]-4-[2-(cis-2,6-dimethylmorpholino)ethyl]piperazine IR (Neat): 2935, 1641, 1417 cm$^{-1}$
NMR (CDCl$_3$, δ): 0.18 (6H, br s), 1.02 (9H, s), 1.16 (6H, d, J=6.3 Hz), 1.76 (2H, t, J=10.7 Hz), 2.00–5.10 (17H, m), 6.30–7.50 (5H, m), 7.61 (1H, s)
MASS (APCI): 688 (M+H)$^+$

(17) (2R)-2-[3-(tert-Butyldimethylsilyloxy)-4-chlorobenzyl]-1-[3-chloro-5-(trifluoromethyl)benzoyl]-4-[2-(5,6,7,8-tetrahydro-1,6-naphthyridin-6-yl)ethyl]piperazine IR (KBr): 2954, 2935, 1643, 1419 cm$^{-1}$
NMR (DMSO-d$_6$, δ): 0.00–0.07 (6H, br), 0.83 (9H, s), 1.70–5.00 (19H, m), 6.20–8.10 (8H, m), 8.18 (1H, d, J=4.7 Hz)
MASS (API-ES positive): 707 (M+H)$^+$

EXAMPLE 40

The following compound was obtained by reacting (2R)-4-(2-chloroethyl)-1-[3,5-bis(trifluoromethyl)benzoyl]-2-[4-(trifluoromethyl)benzyl]piperazine hydrochloride with (2S)-2-(hydroxymethyl)pyrrolidine with a reaction condition similar to that of Example 1 using N,N-diisopropylethylamine instead of potassium carbonate as a base.

(2R)-1-[3,5-Bis(trifluoromethyl)benzoyl]-4-[2-[(2S)-2-(hydroxymethyl)pyrrolidino]ethyl]-2-[4-(trifluoromethyl)-benzyl]piperazine dihydrochloride $[\alpha]_D^{24.0}$: +6.43° (C=0.28, MeOH)
mp: 221–224° C.
IR (KBr): 1643, 1516, 1427 cm$^{-1}$
NMR (DMSO-d$_6$, δ): 1.65–2.30 (4H, m), 2.60–5.40 (19H, m), 7.10–8.30 (7H, m)
MASS (APCI): 612 (M+H)$^+$ (free)

EXAMPLE 41

The following compounds were obtained according to a similar manner to that of Example 40.

(1) (2R)-1-[3,5-Bis(trifluoromethyl)benzoyl]-4-[2-(cis-2,6-dihydroxymethylpiperidino)ethyl]-2-[4-(trifluoromethyl)-benzyl]piperazine dihydrochloride $[\alpha]_D^{24.2}$: +10.36° (C=0.14, MeOH)
mp: 164–167° C.
IR (KBr): 3396, 3369, 1645, 1516, 1427 cm$^{-1}$
NMR (DMSO-d$_6$, δ): 1.30–2.10 (6H, m), 2.40–5.60 (21H, m), 7.00–8.30 (7H, m)
MASS (APCI): 656 (M+H)$^+$ (free)

(2) (2R)-1-(3,5-Bis(trifluoromethyl)benzoyl]-4-[2-(cis-2,6-dimethoxymethylpiperidino)ethyl]-2-[4-(trifluoromethyl)-benzyl]piperazine dihydrochloride $[\alpha]_D^{23.1}$: +5.12° (C-0.21, MeOH)
mp: 147–151° C.
IR (KBr): 1645, 1516, 1454, 1427 cm$^{-1}$
NMR (DMSO-d$_6$, δ): 1.40–2.00 (6H, m), 2.80–5.30 (25H, m), 7.10–8.40 (7H, m)
MASS (APCI): 684 (M+H)$^+$ (free)

(3) (2R)-1-[3,5-Bis(trifluoromethyl)benzoyl]-4-[2-(cis-3,5-dimethoxymethylpiperidino)ethyl]-2-[4-(trifluoromethyl)-benzyl]piperazine dihydrochloride $[\alpha]_D^{23.4}$: +8.28° (C=0.32, MeOH)
mp: 157–160° C.
IR (KBr): 3438, 1647, 1464, 1427 cm$^{-1}$
NMR (DMSO-d$_6$, δ): 1.05 (1H, q, J=12.4 Hz), 1.70 (1H, m), 2.10–5.40 (23H, m), 3.24 (6H, s), 7.10–8.30 (7H, m)
MASS (APCI): 684 (M+H)$^+$ (free)

(4) (2R)-1-[3,5-Bis(trifluoromethyl)benzoyl]-4-[2-[(3S,4S)-3,4-dihydroxypyrrolidino]ethyl]-2-[4-(trifluoromethyl)-benzyl]piperazine dihydrochloride $[\alpha]_D^{23.9}$: +7.37° (C=0.29, MeOH)
mp: 154–159° C.
IR (KBr): 3398, 3369, 1645, 1427 cm$^{-1}$
NMR (DMSO-d$_6$, δ): 2.20–5.40 (21H, m), 7.1–8.3 (7H, m)
MASS (APCI): 614 (M+H)$^+$ (free)

(5) (2R)-1-[3,5-Bis(trifluoromethyl)benzoyl]-2-(4-fluoro-3-methoxybenzyl)-4-[2-[(2S)-2-(hydroxymethyl)pyrrolidino]-ethyl]piperazine dihydrochloride $[\alpha]_D^{24.1}$: +4.76° (C=0.25, MeOH)
mp: 198–201° C.
IR (KBr): 1645, 1516, 1464, 1425 cm$^{-1}$
NMR (DMSO-d$_6$, δ): 1.60–5.40 (23H, m), 3.59 (3H, s), 6.40–8.30 (6H, m)
MASS (APCI): 592 (M+H)$^+$ (free)

(6) (2R)-1-[3,5-Bis(trifluoromethyl)benzoyl]-4-[2-(cis-2,6-dihydroxymethylpiperidino)ethyl]-2-(4-fluoro-3-methoxybenzyl)piperazine dihydrochloride $[\alpha]_D^{24.3}$: +11.33° (C=0.27, MeOH)
mp: 159–161° C.
IR (KBr): 3367, 1645, 1516, 1464, 1427 cm$^{-1}$ NMR (DMSO-d$_6$, δ): 1.40–2.00 (6H, m), 2.60–5.30 (24H, m), 6.40–8.30 (6H, m)
MASS (APCI): 636 (M+H)$^+$ (free)

(7) (2R)-1-[3,5-Bis(trifluoromethyl)benzoyl]-4-[2-(cis-3,5-dimethoxymethylpiperidino)ethyl]-2-(4-fluoro-3-methoxybenzyl)piperazine dihydrochloride

[α]$_D^{23.7}$: +9.45° (C=0.28, MeOH)
mp: 150–156° C.
IR (KBr): 3438, 2939, 1645, 1518, 1464, 1427 cm$^{-1}$
NMR (DMSO-d$_6$, δ): 1.05 (1H, q, J=12.3 Hz), 1.70 (1H, m), 2.10–5.30 (26H, m), 3.24 (6H, s), 6.40–8.30 (6H, m)
MASS (APCI): 664 (M+H)$^+$ (free)

EXAMPLE 42

The following compounds were obtained according to a similar manner to that of Example 13.

(1) (2R)-2-(3-Hydroxy-4-methylbenzyl)-1-[3-methoxy-5-(trifluoromethyl)benzoyl]-4-[2-(5,6,7,8-tetrahydro-1,6-naphthyridin-6-yl)ethyl]piperazine trihydrochloride

[α]$_D^{27}$: −17.11° (C=0.15, MeOH)
mp: 192–208° C.
IR (KBr): 1643, 1628, 1464 cm$^{-1}$
NMR (DMSO-d$_6$, δ): 2.06 (3H, s), 2.60–5.10 (22H, m), 6.20–7.30 (6H, m), 7.62–7.69 (1H, m), 8.05 (1H, d, J=7.8 Hz), 8.67 (1H, d, J=4.0 Hz)
MASS (APCI): 569 (M+H)$^+$ (free)

(2) (2R)-4-[4-(3,3-Dimethylmorpholino)-2-butynyl]-2-(3-hydroxy-4-methylbenzyl)-1-(3-methoxy-5-(trifluoromethyl)benzoyl]piperazine dihydrochloride

[α]$_D^{27}$: +13.87° (C=0.25, MeOH)
mp: 181–188° C.
IR (KBr): 1645, 1464, 1425 cm$^{-1}$
NMR (DMSO-d$_6$, δ): 1.25–1.32 (6H, m), 2.07 (3H, s), 2.70–5.20 (22H, m), 6.20–7.29 (6H, m)
MASS (APCI): 574 (M+H)$^+$ (free)

(3) (2R)-2-(4-Chloro-3-hydroxybenzyl)-1-[3-chloro-5-(trifluoromethyl)benzoyl]-4-[2-(cis-2,6-dimethylmorpholino)ethyl]piperazine dihydrochloride

[α]$_D^{26.5}$: −12.04° (C=0.25, MeOH)
mp: 196–199° C.
IR (KBr): 3398, 1643, 1514, 1456, 1425 cm$^{-1}$
NMR (DMSO-d$_6$, δ): 1.15 (6H, d, J=6.1 Hz), 2.60–5.20 (19H, m), 6.30–8.10 (6H, m), 10.08 (1H, br s)
MASS (APCI): 574 (M+H)$^+$ (free)

(4) (2R)-2-(4-Chloro-3-hydroxybenzyl)-1-[3-chloro-5-(trifluoromethyl)benzoyl]-4-[2-(5,6,7,8-tetrahydro-1,6-naphthyridin-6-yl)ethyl]piperazine trihydrochloride

[α]$_D^{26.5}$: −20.57° (C=0.28, MeOH)
mp: 200–204° C.
IR (KBr): 3430, 3400, 1645, 1514, 1464, 1425 cm$^{-1}$
NMR (DMSO-d$_6$, δ): 2.60–5.20 (19H, m), 6.30–8.10 (8H, m), 8.63 (1H, d, J=4.6 Hz), 10.09 (1H, br)
MASS (APCI): 593 (M+H)$^+$ (free)

EXAMPLE 43

The following compounds were obtained according to a similar manner to that of Example 41.

(1) (2R)-2-(4-Chlorobenzyl)-4-[2-[(2S)-2-(methoxymethyl)-morpholino]ethyl]-1-[3-(4-pyridyl)-5-(trifluoromethyl)-benzoyl]piperazine trihydrochloride

[α]$_D^{27}$: +1.5° (C=0.5, MeOH)
IR (KBr): 1645, 1510, 1460, 1425, 1270, 1240, 1175, 1135 cm$^{-1}$
NMR (DMSO-d$_6$, δ): 2.62–5.15 (22H, m), 3.28 (3H, s), 6.16–9.01 (11H, m)
MASS (APCI): 617 (M)$^+$ (free)

(2) (2R)-2-(4-Chlorobenzyl)-4-[2-[(2S)-2-(methoxymethyl)-morpholino]ethyl]-1-[3-methyl-5-(trifluoromethyl)-benzoyl]piperazine dihydrochloride

[α]$_D^{27}$: +10.9° (C=0.5, MeOH)
mp: 148–151° C.
IR (KBr): 1645, 1510, 1465, 1425, 1270, 1230 cm$^{-1}$
NMR (DMSO-d$_6$, δ): 2.33 (3H, s), 3.28 (3H, s), 2.66–5.24 (22H, m), 6.16–7.70 (7H, m)
MASS (APCI): 554 (M)$^+$ (free)

(3) (2R)-2-(4-Chlorobenzyl)-1-[3-cyclopentylsulfonyl-5-(trifluoromethyl)benzoyl]-4-[2-[(2S)-2-(methoxymethyl)-morpholino]ethyl]piperazine dihydrochloride

[α]$_D^{27}$: +12.1° (C=0.5, DMF)
mp: >230° C.
IR (KBr): 1650, 1465, 1425, 1335, 1305, 1235, 1135 cm$^{-1}$
NMR (DMSO-d$_6$, δ): 1.45–1.93 (9H, m), 2.80–5.20 (22H, m), 3.27 (3H, s), 6.14–8.30 (7H, m)
MASS (APCI): 672 (M)$^+$ (free)

(4) (2R)-2-(4-Chlorobenzyl)-4-[2-[(2S)-2-(methoxymethyl)-morpholino]ethyl]-1-[3-methylthio-5-(trifluoromethyl)-benzoyl]piperazine dihydrochloride

[α]$_D^{27}$: +13.3° (C=0.5, MeOH)
mp: 140–146° C.
IR (KBr): 1625, 1415, 1320, 1270, 1225, 1175 cm$^{-1}$
NMR (DMSO-d$_6$, δ): 2.54 (3H, s), 2.66–5.20 (22H, m), 3.27 (3H, s), 6.66–7.64 (7H, m)
MASS (APCI): 586 (M)$^+$ (free)

(5) (2R)-2-(4-Chlorobenzyl)-1-[3-chloro-5-(trifluoromethyl)-benzoyl]-4-[2-[(2S)-2-(methoxymethyl)morpholino]ethyl]-piperazine dihydrochloride

[α]$_D^{27}$: +7.0° (C=0.5, MeOH)
mp: 148–153° C.
IR (KBr): 1645, 1460, 1420, 1315, 1270, 1230, 1175 cm$^{-1}$
NMR (DMSO-d$_6$, δ): 2.66–5.20 (22H, m), 3.28 (3H, s), 6.02–8.00 (7H, m)
MASS (APCI): 574 (M)$^+$ (free)

(6) (2R)-2-(4-Chlorobenzyl)-1-[3-fluoro-5-(trifluoromethyl)-benzoyl]-4-[2-[(2S)-2-(methoxymethyl)morpholino]ethyl]-piperazine dihydrochloride $[\alpha]_D^{27}$: +10.0° (C=0.5, MeOH)
mp: 199–204° C.
IR (KBr): 1645, 1425, 1235, 1175, 1135 cm$^{-1}$
NMR (DMSO-d$_6$, δ): 2.70–5.16 (22H, m), 3.28 (3H, s), 6.16–7.90 (7H, m)
MASS (APCI): 558 (M)$^+$ (free)

(7) (2R)-1-[3-Methylthio-5-(trifluoromethyl)benzoyl]-2-[4-(trifluoromethyl)benzyl]-4-[2-[(2S)-2-(methoxymethyl)-morpholino]ethyl]piperazine dihydrochloride $[\alpha]_D^{22}$: +21.93° (C=0.25, MeOH)
mp: 153–170° C.
IR (KBr): 3433, 1645 cm$^{-1}$
NMR (DMSO-d$_6$, δ): 2.54 (3H, s), 2.70–5.30 (25H, m), 6.50–7.80 (7H, m)
MASS (APCI): 620 (M+H)$^+$ (free)

(8) (2R)-1-[3-Chloro-5-(trifluoromethyl)benzoyl]-2-[4-(trifluoromethyl)benzyl]-4-[2-[(2S)-2-(methoxymethyl)-morpholino]ethyl]piperazine dihydrochloride $[\alpha]_D^{22}$: +29.60° (C=0.21, MeOH)
mp: 168–173° C.
IR (KBr): 3433, 1647 cm$^{-1}$
NMR (DMSO-d$_6$, δ): 2.80–5.30 (25H, m), 6.87–8.00 (7H, m)
MASS (APCI): 608 (M+H)$^+$ (free)

(9) (2R)-1-[3-Fluoro-5-(trifluoromethyl)benzoyl]-4-[2-[(2S)-2-(methoxymethyl)morpholino]ethyl]-2-[4-(trifluoromethyl)benzyl]piperazine dihydrochloride $[\alpha]_D^{27}$: +17.47° (C=0.25, MeOH)
mp: 173–176° C.
IR (KBr): 1647 cm$^{-1}$
NMR (DMSO-d$_6$, δ): 2.80–5.30 (25H, m), 6.70–7.90 (7H, m)
MASS (APCI): 592 (M+H)$^+$ (free)

(10) (2R)-4-[2-[(2S)-2-(Methoxymethyl)morpholino]ethyl]-1-[3-(4-pyridyl)-5-(trifluoromethyl)benzoyl]-2-[4-(trifluoromethyl)benzyl]piperazine trihydrochloride $[\alpha]_D^{26}$: +13.60° (C=0.25, MeOH)
mp: 81–91° C.
IR (KBr): 3435, 1643 cm$^{-1}$
NMR (DMSO-d$_6$, δ): 2.80–5.30 (25H, m), 6.88–8.98 (11H, m)
MASS (APCI): 651 (M+H)$^+$ (free)

(11) (2R)-4-[2-(cis-2,6-Dimethylmorpholino)ethyl]-1-[3-methylthio-5-(trifluoromethyl)benzoyl]-2-[4-(trifluoromethyl)benzyl]piperazine dihydrochloride $[\alpha]_D^{27}$: +19.00° (C=0.25, MeOH)
mp: 154–156° C.
IR (KBr): 3435, 1647 cm$^{-1}$
NMR (DMSO-d$_6$, δ): 1.15 (6H, d, J=6.1 Hz), 2.54 (3H, s), 2.60–5.30 (19H, m), 6.50–7.70 (7H, m)
MASS (APCI): 604 (M+H)$^+$ (free)

(12) (2R)-4-[2-(cis-2,6-Dimethylmorpholino)ethyl]-1-[3-methylsulfonyl-5-(trifluoromethyl)benzoyl]-2-[4-(trifluoromethyl)benzyl]piperazine dihydrochloride $[\alpha]_D^{25}$: +12.60° (C=0.25, MeOH)
mp: 188–195° C.
IR (KBr): 1647 cm$^{-1}$
NMR (DMSO-d$_6$, δ): 1.15 (6H, d, J=6.1 Hz), 2.60–5.30 (22H, m), 7.00–8.32 (7H, m)
MASS (APCI): 636 (M+H)$^+$ (free)

(13) (2R)-4-[2-(cis-2,6-Dimethylmorpholino)ethyl]-1-[3-(4-pyridyl)-5-(trifluoromethyl)benzoyl]-2-[4-(trifluoromethyl)benzyl]piperazine trihydrochloride $[\alpha]_D^{26}$: +8.40° (C=0.25, MeOH)
mp: 135–145° C.
IR (KBr): 3433, 3402, 1641 cm$^{-1}$
NMR (DMSO-d$_6$, δ): 1.15 (6H, d, J=6.2 Hz), 2.60–5.30 (19H, m), 6.80–9.02 (11H, m)
MASS (APCI): 635 (M+H)$^+$ (free)

(14) (2R)-1-[3-Methylthio-5-(trifluoromethyl)benzoyl]-4-[2-(5,6,7,8-tetrahydro-1,6-naphthyridin-6-yl)ethyl]-2-[4-(trifluoromethyl)benzyl]piperazine dihydrochloride $[\alpha]_D^{27}$: +1.53° (C=0.25, MeOH)
mp: 190–210° C.
IR (KBr): 3431, 1643 cm$^{-1}$
NMR (DMSO-d$_6$, δ): 2.54 (3H, s), 2.80–5.30 (19H, m), 6.50–8.71 (10H, m)
MASS (APCI): 623 (M+H)$^+$ (free)

(15) (2R)-1-[3-(4-Pyridyl)-5-(trifluoromethyl)benzoyl]-4-[2-(5,6,7,8-tetrahydro-1,6-naphthyridin-6-yl)ethyl]-2-[4-(trifluoromethyl)benzyl]piperazine tetrahydrochloride $[\alpha]_D^{26}$: −5.73° (C=0.25, MeOH)
mp: 205–218° C.
IR (KBr): 3400, 1641 cm$^{-1}$
NMR (DMSO-d$_6$, δ): 2.60–5.30 (19H, m), 6.85–9.02 (14H, m)
MASS (APCI): 654 (M+H)$^+$ (free)

(16) (2R)-2-(4-Fluoro-3-methoxybenzyl)-4-[2-(cis-2,6-dimethylmorpholino)ethyl]-1-[3-methylthio-5-(trifluoromethyl)benzoyl]piperazine dihydrochloride $[\alpha]_D^{27.3}$: +23.47° (C=0.36, MeOH)
mp: 62.5–82.4° C.
IR (KBr): 1645, 1518, 1421, 1176, 1126 cm$^{-1}$
NMR (DMSO-d$_6$, δ): 1.15 (6H, d, J=6.1 Hz), 2.60–4.20 (27H, m), 6.50–7.56 (6H, m)
MASS: 584 (M+H)$^+$ (free)

(17) (2R)-2-(4-Fluoro-3-methoxybenzyl)-4-[2-(cis-2,6-dimethylmorpholino)ethyl]-1-[3-(4-pyridyl)-5-(trifluoromethyl)benzoyl]piperazine trihydrochloride $[\alpha]_D^{27.4}$: +14.30° (C=0.37, MeOH)
mp: 137.6–142.5° C.
IR (KBr): 1641, 1515, 1425, 1270, 1176, 1145, 1132 cm$^{-1}$
NMR (DMSO-d$_6$, δ): 1.14 (6H, d, J=6.0 Hz), 2.60–4.20 (25H, m), 6.52–8.90 (10H, m)
MASS (APCI): 615 (M+H)$^+$ (free)

(18) (2R)-2-(4-Fluoro-3-methoxybenzyl)-1-[3-methylthio-5-(trifluoromethyl)benzoyl]-4-[2-(5,6,7,8-tetrahydro-1,6-naphthyridin-6-yl)ethyl]piperazine trihydrochloride $[\alpha]_D^{27.4}$: −3.51° (C=0.39, MeOH)
mp: 143.3–147.5° C.
IR (KBr): 1645, 1516, 1417, 1173, 1126 cm$^{-1}$
NMR (DMSO-d$_6$, δ): 3.80–5.20 (28H, m), 6.53–8.68 (9H, m)
MASS (APCI): 603 (M+H)$^+$ (free)

(19) (2R)-2-(4-Fluoro-3-methoxybenzyl)-1-[3-(4-pyridyl)-5-(trifluoromethyl)benzoyl]-4-[2-(5,6,7,8-tetrahydro-1,6-naphthyridin-6-yl)ethyl]piperazine tetrahydrochloride $[\alpha]_D^{27.9}$: −9.07° (C=0.46, MeOH)
mp: 236.8–248.5° C.
IR (KBr): 1641, 1635, 1516, 1423, 1273, 1130 cm$^{-1}$
NMR (DMSO-d$_6$, δ): 2.65–5.10 (26H, m), 6.51–9.00 (13H, m)
MASS: 634 (M+H)$^+$ (free)

(20) (2R)-2-(4-Fluoro-3-methoxybenzyl)-4-[2-[(2S)-2-(methoxymethyl)morpholino]ethyl]-1-[3-(4-pyridyl)-5-(trifluoromethyl)benzoyl]piperazine trihydrochloride $[\alpha]_D^{28}$: +32.5° (C=0.5, MeOH)
IR (KBr): 1645, 1515, 1425, 1270, 1235 cm$^{-1}$
NMR (DMSO-d$_6$, δ): 2.66–5.24 (25H, m), 3.27 (3H, s), 6.45–8.93 (10H, m)
MASS (APCI): 631 (M+H)$^+$ (free)

(21) (2R)-1-[3-Chloro-5-(trifluoromethyl)benzoyl]-2-(4-fluoro-3-methoxybenzyl)-4-[2-[(2S)-2-(methoxymethyl)-morpholino]ethyl]piperazine dihydrochloride $[\alpha]_D^{28}$: +25.4° (C=0.5, MeOH)
mp: 139–142° C.
IR (KBr): 1645, 1515, 1460, 1420, 1315, 1270, 1230 cm$^{-1}$
NMR (DMSO-d$_6$, δ): 2.72–5.21 (22H, m), 3.29 (3H, s), 3.44 (3H, s), 6.17–8.00 (6H, m)
MASS (APCI): 588 (M)$^+$ (free)

(22) (2R)-2-(4-Fluoro-3-methoxybenzyl)-4-[2-[(2S)-2-(methoxymethyl)morpholino]ethyl]-1-[3-methylthio-5-(trifluoromethyl)benzoyl]piperazine dihydrochloride $[\alpha]_D^{8}$: +28.1° (C=0.5, MeOH)
mp: 132–135° C.
IR (KBr): 1645, 1515, 1460, 1420, 1315, 1270, 1230, 1130 cm$^{-1}$
NMR (DMSO-d$_6$, δ): 2.54 (3H, s), 2.73–5.27 (22H, m), 3.28 (3H, s), 3.41 (3H, s), 6.15–7.83 (6H, m)
MASS (APCI): 600 (M+H)$^+$ (free)

(23) (2R)-2-(4-Fluoro-3-methoxybenzyl)-1-[3-fluoro-5-(trifluoromethyl)benzoyl]-4-[2-[(2S)-2-(methoxymethyl)-morpholino]ethyl]piperazine dihydrochloride $[\alpha]_D^{27}$: +21.4° (C=0.5, MeOH)
IR (KBr): 1640, 1515, 1465, 1425, 1345, 1275, 1230, 1135 cm$^{-1}$
NMR (DMSO-d$_6$, δ): 2.76–5.20 (22H, m), 3.29 (3H, s), 3.42 (3H, s), 6.16–7.86 (6H, m)
MASS (APCI): 572 (M+H)$^+$ (free)

EXAMPLE 44

The following compounds were obtained according to a similar manner to that of the second half of Preparation 21.

(1) (2R)-2-(4-Chloro-3-hydroxybenzyl)-1-[3-chloro-5-(trifluoromethyl)benzoyl]-4-[2-[(2S)-2-(methoxymethyl)-morpholino]ethyl]piperazine dihydrochloride $[\alpha]_D^{28}$: +6.1° (C=0.5, MeOH)
IR (KBr): 1645, 1510, 1425, 1235, 1175 cm$^{-1}$
NMR (DMSO-d$_6$, δ): 2.55–5.10 (22H, m), 3.27 (3H, s), 6.31–8.03 (6H, m), 10.07 (1H, br s)
MASS (APCI): 590 (M)$^+$ (free)

(2) (2R)-2-(4-Chloro-3-hydroxybenzyl)-4-[2-[(2S)-2-(methoxymethyl)morpholino]ethyl]-1-[3-methylthio-5-(trifluoromethyl)benzoyl]piperazine dihydrochloride $[\alpha]_D^{8}$: +15.0° (C=0.5, MeOH)
mp: 169–174° C.
IR (KBr): 3475, 3420, 1640, 1425, 1320, 1270, 1230, 1135 cm$^{-1}$
NMR (DMSO-d$_6$, δ): 2.54 (3H, s), 2.56–5.10 (22H, m), 3.27 (3H, s), 6.29–7.69 (6H, m), 10.10 (1H, br s)
MASS (APCI): 602 (M)$^+$ (free)

(3) (2R)-2-(4-Chloro-3-hydroxybenzyl)-1-[3-fluoro-5-(trifluoromethyl)benzoyl]-4-[2-[(2S)-2-(methoxymethyl)-morpholino]ethyl]piperazine dihydrochloride $[\alpha]_D^{27}$: +7.6° (C=0.5, MeOH)
mp: 176–178° C.
IR (KBr): 1645, 1510, 1460, 1425, 1235, 1175 cm$^{-1}$
NMR (DMSO-d$_6$, δ): 2.52–4.98 (22H, m), 3.28 (3H, s), 6.34–7.77 (7H, m)
MASS (APCI): 574 (M)$^+$ (free)

EXAMPLE 45

The following compounds were obtained according to a similar manner to that of Example 11.

(1) (2R)-1-[3,5-Bis(trifluoromethyl)benzoyl]-2-(4-chloro-3-hydroxybenzyl)-4-[(1H-pyrrolo[3,2-b]pyridin-3-yl)-methyl]piperazine dihydrochloride $[\alpha]_D^{25.0}$: +5.42° (C=0.60, MeOH)
mp: 208–211° C.
IR (KBr): 1647, 1281, 1180, 1138 cm$^{-1}$
NMR (DMSO-d$_6$, δ): 2.60–5.10 (11H, m), 6.26–7.20 (3H, m), 7.43–7.82 (3H, m), 8.18–8.72 (4H, m), 10.08 (1H, br), 13.11 (1H, s)
MASS (APCI): 597 (M+H)$^+$ (free)

(2) (2R)-1-[3,5-Bis(trifluoromethyl)benzoyl]-2-(4-chloro-3-hydroxybenzyl)-4-[(1H-pyrrolo[2,3-b]pyridin-3-yl)-methyl]piperazine dihydrochloride $[\alpha]_D^{24.9}$: −0.90° (C=0.50, MeOH)
mp: 197–200° C.
IR (KBr): 1647, 1281, 1180, 1136 cm$^{-1}$ NMR (DMSO-$d_6$, δ): 2.60–5.20 (11H, m), 6.24–7.40 (4H, m), 7.45 (1H, s), 7.76 (1H, s), 7.95–8.55 (4H, m), 11.60 (1H, br), 12.45 (1H, s)

MASS (APCI): 597 (M+H)$^+$ (free)

EXAMPLE 46

1M Methylmagnesium iodide in diethyl ether solution (3.15 ml) was added to a solution of 4-[[(2R)-1-[3,5-bis (trifluoromethyl)benzoyl]-4-[2-[(2S)-2-(methoxymethyl)-morpholino]ethyl]piperazin-2-yl]methyl]-2-(tert-butyldimethylsilyloxy)benzoic acid methyl ester (0.8 g) in toluene (8 ml). After being stirred at 45° C. for 4 hours, the mixture was quenched with saturated aqueous ammonium chloride solution and the whole was extracted with ethyl acetate. The organic layer was separated, washed with water and brine successively, dried over magnesium sulfate, and evaporated under reduced pressure to give crude oil. The oil was purified by column chromatography on silica gel using a mixed solvent of dichloromethane and methanol (40:1) to give (2R)-1-[3,5-bis(trifluoromethyl)benzoyl]-2-[3-(tert-butyldimethyl-silyloxy)-4-(1-hydroxy-1-methylethyl)benzyl]-4-[2-[(2S)-2-(methoxymethyl)morpholino]ethyl]piperazine (0.333 g)

IR (Neat): 1643, 1438, 1280 cm$^{-1}$

NMR (CDCl$_3$, δ): 0.10–0.50 (6H, m), 1.03 (9H, s), 1.58 (6H, s), 2.00–5.10 (22H, m), 3.38 (3H, s), 6.30–7.90 (6H, m)

MASS (API-ES): 784 (M+Na)$^+$, 763 (M+H)$^+$

EXAMPLE 47

Methanesulfonyl chloride (0.115 ml) was added to an ice-cooled solution of (2R)-1-[3,5-bis(trifluoromethyl)benzoyl]-2-[3-(tert-butyldimethylsilyloxy)-4-(1-hydroxy-1-methylethyl)benzyl]-4-[2-[(2S)-2-(methoxymethyl)morpholino]-ethyl]piperazine (0.76 g) and triethylamine (0.35 ml) in dichloromethane (9 ml). After being stirred at the same temperature for 2 hours, the mixture was washed with water. The organic layer was separated, washed with brine, dried over magnesium sulfate and evaporated under reduced pressure to give a mixture of the mesylated and unmesylated compound. The mixture was dissolved into methanol without further purification and the solution was hydrogenated over 20% palladium hydroxide-charcoal (0.1 g) at room temperature at 3 atmosphere for 5 hours. The reaction mixture was filtered through Celite® and washed with methanol. The filtrate and washing were combined and evaporated under reduced pressure. The resulting syrup was dissolved in tetrahydrofuran (6.5 ml) and thereto tetrabutylammonium fluoride (1M solution of tetrahydrofuran, 0.1 ml) was added below 10° C. After stirring at room temperature, the mixture was evaporated under reduced pressure and the residue was purified by column chromatography using a mixed solvent of dichloromethane and methanol (40:1) to give an oil. The oil was treated with 4N hydrogen chloride in ethyl acetate to give a powder of (2R)-1-[3,5-bis(trifluoromethyl)benzoyl]-2-[3-hydroxy-4-(1-methylethyl)benzyl]-4-[2-[(2S)-2-(methoxymethyl)morpholino]-ethyl]piperazine dihydrochloride (150 mg).

[α]$_D^{26}$: -1.25° (C=0.2, MeOH)

mp: 218–228° C.

IR (KBr): 3500–3150, 2700–2300, 1644, 1498, 1461, 1282, 1174 cm$^{-1}$

NMR (DMSO-$d_6$, δ): 1.00–1.30 (6H m), 2.60–5.10 (26H, m), 6.20–8.20 (6H, m), 9.22 (1H, br s)

MASS (APCI): 632 (M+H)$^+$ (free)

The invention claimed is:

1. A compound of the formula:

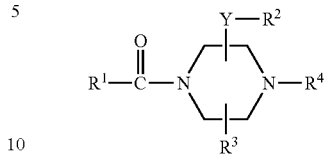

or a pharmaceutically acceptable salt thereof;

wherein

Y is $C_1$–$C_4$ alkylene;

$R^1$ is bis [mono (or di or tri) halo ($C_1$–$C_4$) alkyl]phenyl;

$R^2$ is phenyl which is substituted with hydroxy and a substituent(s) selected from the group consisting of $C_1$–$C_4$ alkyl, mono (or di or tri) halo($C_1$–$C_4$) alkyl, halogen, $C_1$–$C_4$ alkoxy and hydroxy;

$R^3$ hydrogen; and $R^4$ is (2,6-dimethylmorpholino) ($C_1$–$C_4$) alkyl; (2-methoxymethylmorpholino) ($C_1$–$C_4$)alkyl; (3-methoxymethylmorpholino) ($C_1$–$C_4$) alkyl; or (2-methoxymethyl-5-methylmorpholino) ($C_1$–$C_4$) alkyl.

2. The compound of claim 1, which is selected from the group consisting of:

(1) 1-[3,5-Bis(trifluoromethyl)benzoyl]-2-(3-hydroxy-4-methylbenzyl)-4-[2-[(3R)-3-(methoxymethyl)morpholino]-ethyl]piperazine, (2) 1-[3,5-Bis(trifluoromethyl)benzoyl]-4-[2-(cis-2,6-dimethylmorpholino)ethyl]-2-(3-hydroxy-4-methylbenzyl)piperazine, (3) 1-[3,5-Bis(trifluoromethyl)benzoyl]-2-(3-hydroxy-4-methylbenzyl)-4-[2-[(2S,5S) -2-methoxymethyl-5-methylmorpholino]ethyl]piperazine, (4) 1-[3,5-Bis(trifluoromethyl)benzoyl]-4-[2-[(2S)-2-(methoxymethyl)morpholino]ethyl]-2-(3-hydroxy-4-methylbenzyl)piperazine, and (5) (2R)-1-[3,5-Bis(trifluoromethyl)benzoyl]-4-[2-[(2S)-2-(methoxymethyl)morpholino]ethyl]-2-(3-hydroxy-4-methylbenzyl)piperazine;

or a pharmaceutically acceptable salt thereof.

3. A process for the preparation of the compound, or a salt thereof, of claim 1, which comprises, reacting a compound of the formula (II), or a salt thereof:

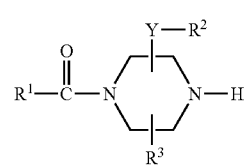

(II)

with a compound of the formula (III), or a salt thereof:

W$_1$—R$^4$ (III)

wherein W$_1$ is a leaving group, to give a compound of the formula (I), or a salt thereof:

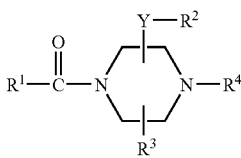

(I)

wherein

Y is $C_1$–$C_4$ alkylene;

$R^1$ is bis [mono (or di or tri) halo ($C_1$–$C_4$) alkyl]phenyl;

$R^2$ is phenyl which is substituted with hydroxy and a substituent(s) selected from the group consisting of $C_1$–$C_4$ alkyl, mono (or di or tri) halo($C_1$–$C_4$) alkyl, halogen, $C_1$–$C_4$ alkoxy and hydroxy;

$R^3$ is hydrogen; and $R^4$ is (2,6-dimethylmorpholino) ($C_1$–$C_4$) alkyl; (2-methoxymethylmorpholino) ($C_1$–$C_4$)alkyl; (3-methoxymethylmorpholino) ($C_1$–$C_4$) alkyl; or (2-methoxymethyl-5-methylmorpholino) ($C_1$–$C_4$) alkyl.

4. The compound of claim 1, which is (2R)-1-[3,5-Bis(trifluoromethyl)benzoyl]-4-[2-[(2S)-2-(methoxymethyl)morpholino]ethyl]-2-(3-hydroxy-4-methylbenzyl)piperazine, or a pharmaceutically acceptable salt thereof.

5. The compound of claim 1, which is (2R)-1-[3,5-Bis(trifluoromethyl)benzoyl]-4-[2-[(2S)-2-(methoxymethyl)morpholino]ethyl]-2-(3-hydroxy-4-methylbenzyl)piperazine dihydrochloride.

6. A compound wherein the compound is (2R)-1-[3,5-Bis(trifluoromethyl)benzoyl]-2-[4-chloro-3-hydroxybenzyl]-4-[2-(cis-2,6-dimethylmorpholino)ethyl]piperazine, or a pharmaceutically acceptable salt thereof.

7. A compound, wherein the compound is (2R)-1-[3,5-Bis(trifluoromethyl)benzoyl]-2-[4-chloro-3-hydroxybenzyl]-4-[2-(cis-2,6-dimethylmorpholino)ethyl]piperazine dihydrochloride.

8. A pharmaceutical composition which comprises:
the compound of claim 1 or a pharmaceutically acceptable salt thereof, and a pharmaceutical acceptable carrier.

9. A method for treating at least one tachykinin-mediated disease selected from the group consisting of asthma, emesis, an anxiety disorder, pollakiuria, urinary incontinence and irritable bowel syndrome, in a subject in need thereof, which comprises:
administering to subject in need thereof the compound of claim 1 or a pharmaceutically acceptable salt thereof, in an amount sufficient to treat the at least one disease.

10. The method of claim 9, wherein said disease is asthma.

11. The method of claim 9, wherein said disease is emesis.

12. The method of claim 9, wherein said disease is an anxiety disorder.

13. The method of claim 9, wherein said disease is pollakiuria.

14. The method of claim 9, wherein said disease is urinary incontinence.

15. The method of claim 9, wherein said disease is irritable bowel syndrome.

* * * * *

UNITED STATES PATENT AND TRADEMARK OFFICE
CERTIFICATE OF CORRECTION

PATENT NO.         : 7,166,598 B2                                      Page 1 of 1
APPLICATION NO.    : 10/968473
DATED              : January 23, 2007
INVENTOR(S)        : Take et al.

It is certified that error appears in the above-identified patent and that said Letters Patent is hereby corrected as shown below:

On the title page, Item (63), the Related U.S. Application Data is incorrect. Item (63) should read:

-- Related U.S. Application Data
(63) Continuation of Application No. 09/857,869, filed as Application No. PCT/JP99/06943 on Dec. 10, 1999, now abandoned. --

Signed and Sealed this

Third Day of April, 2007

JON W. DUDAS
*Director of the United States Patent and Trademark Office*